(12) United States Patent
Senger et al.

(10) Patent No.: US 8,311,790 B2
(45) Date of Patent: Nov. 13, 2012

(54) REVERSE ENGINEERING GENOME-SCALE METABOLIC NETWORK RECONSTRUCTIONS FOR ORGANISMS WITH INCOMPLETE GENOME ANNOTATION AND DEVELOPING CONSTRAINTS USING PROTON FLUX STATES AND NUMERICALLY-DETERMINED SUB-SYSTEMS

(75) Inventors: Ryan S. Senger, Blacksburg, VA (US); Eleftherios Papoutsakis, Newark, DE (US)

(73) Assignee: University of Delaware, Newark, DE (US)

( * ) Notice: Subject to any disclaimer, the term of this patent is extended or adjusted under 35 U.S.C. 154(b) by 569 days.

(21) Appl. No.: 12/422,772

(22) Filed: Apr. 13, 2009

(65) Prior Publication Data

US 2009/0259451 A1    Oct. 15, 2009

Related U.S. Application Data

(60) Provisional application No. 61/123,791, filed on Apr. 11, 2008.

(51) Int. Cl.
*G06F 19/12* (2011.01)
(52) U.S. Cl. .......................................................... 703/11
(58) Field of Classification Search ........................ None
See application file for complete search history.

(56) References Cited

U.S. PATENT DOCUMENTS

| | | | |
|---|---|---|---|
| 4,649,112 A * | 3/1987 | Datta et al. .................... | 435/136 |
| 2003/0224363 A1 | 12/2003 | Park et al. | |
| 2003/0228567 A1 | 12/2003 | Famili et al. | |

OTHER PUBLICATIONS

Huang, L., Forsberg, C. W. & Gibbins, L. N. Influence of external pH and fermentation products on clostridium acetobutylicum intracellular pH and cellular distribution of fermentation products. Applied and Environmental Microbiology 51, 1230-1234 (1986).*

Michels, P. A. M., Michels, J. P. J., Boonstra, J. & Konings, W. N. Generation of an electrochemical proton gradient in bacteria by the excretion of metabolic end products. FEMS Microbiology Letters 5, 357-364 (1979).*

Alberty R.A., Thermodynamics of the Mechanism of the Nitrogenase Reaction, Biophysical Chemistry, (2005), vol. 114, pp. 115-120.

(Continued)

*Primary Examiner* — Marjorie Moran
*Assistant Examiner* — Soren Harward
(74) *Attorney, Agent, or Firm* — RatnerPrestia

(57) ABSTRACT

A genome-scale metabolic network reconstruction for *Clostridium acetobutylicum* (ATCC 824) was created using a new semi-automated reverse engineering algorithm. This invention includes algorithms and software that can reconstruct genome-scale metabolic networks for cell-types available through the Kyoto Encyclopedia of Genes and Genomes. This method can also be used to complete partial metabolic networks and cell signaling networks where adequate starting information base is available. The software may use a semi-automated approach which uses a priori knowledge of the cell-type from the user. Upon completion, the program output is a genome-scale stoichiometric matrix capable of cell growth in silico. The invention also includes methods for developing flux constraints and reducing the number of possible solutions to an under-determined system by applying specific proton flux states and identifying numerically-determined sub-systems. Although the model-building and analysis tools described in this invention were initially applied to *C. acetobutylicum*, the novel algorithms and software can be applied universally.

15 Claims, 16 Drawing Sheets

OTHER PUBLICATIONS

Alasker K.V, et al., Transcriptional Program of Early Sporulation and Stationary-Phase Events in Clostridium acetobutylicum. Journal of Bacteriology, (2005), 187, vol. 20, pp. 7103-7318.

Alasker K.V. et al, Transcriptional analysis of spo0A Overexpression in Clostridium acetoubutylicum and its Effect on the cell's response to butanol stress, J Bacteriol, (2004) vol. 186, No. 7, pp. 1959-1971.

Atrih A., et al., Analysis of the role of bacterial endospore cortex structure in resistance properties and demonstration of its conversation amongst species, J Appl. Microbiol, (2001), vol. 91, No. 2, pp. 364-372.

Baer S.H., et al., Effect of Butanol Challenge and Temperature on Lipid Composition and Membrane Fluidity of Butanol-tolerant *Clostridium acetobutylicum, Appl. Environ Microbiol*, (1987), vol. 53, No. 12, pp. 2854-2861.

Bairoch A., The Enzyme database in 2000. Nucleic Acids Res, (2000), vol. 28, No. 1, pp. 304-305.

Baitaluk M., et al., BiologicalNetworks: visualization and analysis tool for systems biology. (2006) Nucleic Acids Res, vol. 34, (2006) (Web Server Issue), pp. W466-W471.

Baumbach J., et al., CoryneRegNet: An Ontology-based Data Warehouse of Corynebacterial Transcription Factors and Regulatory Networks, (2006), BMC Genomics, vol. 7, No. 24.

Becker S.A. et al., Genome-scale reconstruction of the metabolic network in *Staphylococcus aureus N315: an initial draft to the two-dimensional annotation*, (2005), BMC Microbiol 5:8.

Beste D.J.V., et al., GSMN-TB: a web-based genome-scale network model of Myobacterium tuberculosis metabolism, Genome Biol, (2007), vol. 8, Issue 5, Article R89.

Billheimer J.T., et al., Ornithine delta-transaminase activity in *Esherichia coli*—its identity with Acetylornithine delta-Transaminase, J. Bacteriol, (1976), vol. 127, No. 3, pp. 1315-1323.

Blattner F.R., et al., The Complete Genome Sequence of *Escherichia Coli* K-12, Science, vol. 277, (1997), pp. 1453-1462.

Bleakley K., et al., Supervised Reconstruction of Biological Networks with Local Models. Bioinformatics, (2007), vol. 23, No. 13, pp. i57-i65.

Borden, J.R., et al., Dynamics of Genomic-library Enrichment and Identification of Solvent Tolerance Genes for Clostridium Acetobutylicum, Appl. Environ Microbiol, (2007), vol. 73, No. 9, pp. 3061-3068.

Borodina I. et al., Genome-scale analysis of *Streptomyces coelicolor* A3(2) metabolism, Genome Res, (2005), vol. 15, No. 6, pp. 820-829.

Borodina I. et al., From Genomes to in Silico cells via metabolic networks, Current Opinion Biotechnol, (2005), vol. 16, No. 3, pp. 350-355.

Boynton, Z.L. et al., Intracellular Concentrations of Coenzyme A and Its Derivatives from *Clostridium acetobutylicum* ATCC 824 and their Roles in Enzyme Regulation, Appl. Environ Microbiol, (1994), vol. 60, No. 1, pp. 39-44.

Breitling R. et al., New surveyor tools for charting microbial metabolic maps, Nat Rev. Microbiol, (2008), 6(2):156-61.

Bro C., et al. In silico aided metabolic engineering of *Saccharomyces cerevisiae* for improved bioethanol production, Metabolic Engineering., (2006), vol. 8, No. 2, pp. 102-111.

Busch W., et al., The transporter Classification(TC) System, 2002, Critical Reiews in Biochemistry and Molecular Biology, (2002), vol. 37, No. 5, pp. 287-337.

Cakir T. et al., Integration of Metabolome Data with Metabolic Networks Reveals Reporter Reactions, Molecular Systems Biology, (2006), vol. 2, No. 50.

Caspi, R., et al. MetaCyc: A Multiorganism Database of Metabolic pathways and Enzymes. Nucleic Acids Res 34 (Nucleic Acids Res (Database issue), (2006), vol. 34, pp. D511-D516.

Choi, H.S. et al., Incorporating Metabolic flux Ratios into Constraint-based flux Analysis by Using Artificial Metabolites and Converging Ratio Determinants, J. Biotechnol, (2007), vol. 129, pp. 696-705.

Covert M.W. et al., Regulation of Gene Expression in Flux Balance Modes of Metabolism, J. Theor Biol, (2001), vol. 213, No. 1, pp. 73-88.

Covert. M. W. et al., Identifying Constraints that Govern Cell Behavior: A Key to Converting Conceptual to Computational Models in Biology, Biotechnol Bioeng, (2003), vol. 84, No. 7, pp. 763-772.

Covert. M. W. et al., Metabolic Modeling of Microbial Strains in Silico, Trends in Biochemical Sciences (2001), vol. 26, No. 3, pp. 179-186.

Cummins et al., Taxonomy of Clostridia—Wall Composition and DNA Homologies in *Clostridium Butyricum* and Butyric Acid-producing Clostridia, Journal of General Microbiology, (1971), vol. 67, pp. 33-46.

Da Fontoura Costa et al., Analyzing Trails in Complex Networks, Physical Review E, (2007), vol. 76, pp. 046106-1-046106-12.

Dandekar T. et al., A Method for Classifying Metabolites in Topological Pathway Analysis based on Minimization of Pathway Number, BioSystems, (2003), vol. 70, No. pp. 255-270.

Das A, et al., Purification and Reconstitution into Proteoliposomes of the $F_1F_0$ ATP Synthase from the Obligately Anaerobic gram-positive bacterium Clostridium Thermoautotrophicum. Journal of Bacteriology (1997), vol. 179, No. 5, pp. 1714-1720.

David H. et al., Reconstruction of the Central Carbon Metabolism of Aspergillus Niger, Eur J Biochem, (2003), vol. 270, No. 21, pp. 4243-4253.

Demain A.L. et al., Cellulase, Clostridia, and Ethanol. Microbiol Mol Biol Rev, (2005), vol. 69, No. 1, pp. 124-154.

Desai R.P. et al., Stoichiometric Modeling of Clostridium Acetobutylicum Fermentations with Non-linear Constraints. J Biotechnol, (1999), vol. 71, pp. 191-205.

Desai R.P. et al., Metabolic flux Analysis Elucidates the Importance of the Acid-formation Pathways in Regulating Solvent Production by Clostridium Acetobutylicum, Metab Eng, (1999), vol. 1, No. 3, pp. 206-213.

Dills S.S. et al., Carbohydrate Transport in Bacteria. Microbiol Rev. (1980), vol. 44, No. 3, pp. 385-418.

Dougherty D. P. et al., Semi-mechanistic Partial Buffer Approach to Modeling pH, the Buffer Properties, and the Distribution of Ionic Species in Complex Solutions. J Agric Food Chem, (2006), vol. 54, No. 16, pp. 6021-6029.

Duarte N.C. et al., Global Reconstruction of the Human Metabolic Network Based on Genomic and Bibliomic data, Proc Natl Acad Sci U S A, (2007), vol. 104, No. 6, pp. 1777-1782.

Duarte N. C. et al., Reconstruction and Validation of *Saccharomyces cerevisiae* iND750, a fully Compartmentalized Genome-scale Metabolic model, Genome Res, (2004), vol. 14, No. 7, pp. 1298-1309.

Dworkin J. et al., Developmental commitment in a Bacterium Cell (2005), vol. 121, No. 3, pp. 401-409.

Edwards J.S. et al., Metabolic Flux Analysis. In: Lee Sy, Papoutsakis Et, editors. Metabolic Engineering. New York: Marcel Dekker, (1999) pp. 13-57.

Edwards J.S. et al, *In silico* predictions of *Escherichia coli* Metabolic Capabilities are Consistent with Experimental data. Nat Biotechnol, (2001), vol. 19, No. 2, pp. 125-130.

Eikmanns B. et al., Unusual Pathway of Isoleucine Biosynthesis in *Methanobacterium thermoautotrophicum*. Arch Microbiol, (1983), vol. 136, No. 2, pp. 111-113.

Famili I., k-Cone Analysis: Determining All Candidate Values for Kinetic Parameters on a Network Scale. Biophys J, (2005), vol. 88, No. 3, pp. 1616-1625.

Feist A.M. et al., Modeling Methanogenesis with a Genome-scale Metabolic Reconstruction of *Methanosarcina barkeri*. Molecular Systems Biology (2006), vol. 2, No. (2006) 0004.

Flythe M.D. et al., Fermentation acids inhibit amino acid deamination by *Clostridium sporogenes* MD1 via a mechanism involving a decline in intracellular glutamate rather than protonmotive force. Microbiology, (2006), vol. 152, pp. 2619-2624.

Foerster J. et al., Genome-scale Reconstruction of the *Saccharomyces cerevisiae* Metabolic network. Genome Res, (2003), vol. 13, No. 2, pp. 244-253.

Foerster J et al., Large-scale Evaluation of in Silico Gene Deletions in *Saccharomyces cerevisiae*. Omics, (2003), vol. 7, No. 2, pp. 193-202.

Francke C. et al. Reconstructing the Metabolic network of a Bacterium from its Genome, Trends Microbiol, (2005), vol. 13, No. 11, pp. 550-558.

Friedrich B. et al., N2-acetylornithine 5-Aminotransferase of *Klebsiella aerogenes*—Control of Synthesis by Induction, Catabolite Repression, and Activation by Glutamine Synthetase, J Bacteriol, (1978), vol. 133, No. 2, pp. 686-691.
Gaasterland T. et al., Reconstruction of Metabolic networks Using Incomplete Information. Proceeding from International Conference, Intelligent Systems for Molecular Biologyl, (1995), vol. 3, pp. 127-135.
Gianchandani E.P. et al., Systems Analyses Characterize Integrated Functions of Biochemical networks, Trends Biochem Sci, (2006), vol. 31, No. 5, pp. 284-291.
Gianchandani E.P. et al., Matrix Formalism to Describe Functional States of Transcriptional Regulatory Systems, PLoS Comput Biol, (2006), vol. 2, No. 8, pp. 0902-0917.
Gille C. et al., Metannogen: Compiling Features of Biochemical Reactions Need for the Reconstruction of Metabolic networks. BMC System Biology, (2007), vol. 1, No. 5.
Girbal L. et al., Regulation of Clostridium acetobutylicum Metabolism as Revealed by Mixed-Substrate Steady-State Continuous Cultures: Role of NADH/NAD ratio and ATP pool, J Bacteriol, (1994), vol. 176, No. 21, pp. 6433-6438.
Goelzer A. et al., Reconstruction and analysis of the Genetic and Metabolic Regulatory Networks of the Central Metabolism of *Bacillus subtilis*, BMC Syst Biol, (2008), Vo. 2, No. 20.
Gonzalez O. et al., Reconstruction, Modeling & Analysis of Halobacterium salinarum R-1 Metabolism, Mol Biosyst, (2008), vol. 4, No. 2,: pp. 148-159.
Green E. M. et al., Genetic manipulation of Acid and Solvent formation in *Clostridium acetobutylicum* ATCC 824, Biotechnol Bioeng, 1998, vol. 58 No. 2-3, pp. 215-221.
Gros J.B. et al., Estimation of $O_2$ and $CO_2$ Solubility in Microbial Culture Media. Biotechnol Prog, (1999), vol. 15, No. 5, pp. 923-927.
Grupe H. et al., Physiological Events in *Clostridium acetobutylicum* during the Shift from Acidogenesis to Solventogenesis in Continuous Culture and Presentation of a Model for Shift Induction, Appl Environ Microbiol, (1992), vol. 58, 12, pp. 3896-3902.
Harris L.M. et al., Northern, Morphological, and Fermentation Analysis of spo0A Inactivation and Overexpression in Clostridium acetobutylicum ATCC 824, J Bacteriol, (2002), vol. 184, No. (13), pp. 3586-3597.
Harris L.M et al., Characterization of Recombinant Strains of the *Clostridium acetobutylicum* butyrate Kinase Inactivation Mutant: Need for New Phenomenological Models for Solventogenesis and Butanol inhibition? Biotechnol Bioeng, (2000), vol. 67, No. 1.
Heinemann M. et al., In Silico Genome-Scale Reconstruction and Validation of the *Staphylococcus aureus* Metabolic Network, Biotechnol Bioeng, (2005), vol. 92, No. 7, pp. 850-864.
Henry C.S. et al., Thermodynamics-Based Metabolic Flux Analysis, Biophys J, (2007), vol. 92, No. 5, pp. 1792-1805.
Henry C.S. et al., Genome-Scale Thermodynamic Analysis of *Escherichia coli* metabolism, Biophys J, (2006), vol. 90, No. 4, pp. 1453-1461.
Holland I.B. et al., ABC-ATPases, Adaptable Energy Generators Fuelling Transmembrane Movement of a Variety of Molecules in Organisms from Bacteria to Humans, J Mol Biol, (1999), vol. 293, No. 2, pp. 381-399.
Huesemann M.H.W., et al., Solventogenesis in *Clostridium acetobutylicum* Fermentations Related to Carboxylic acid and Proton Concentrations, Biotechnol Bioeng, 1988, vol. 32, No. 7, pp. 843-852.
Hyland C. et al., metaSHARK: a WWW Platform for Interactive Exploration of Metabolic Networks. Nucleic Acids Res 34 (Web Server issue), (2006), vol. 34, pp. W725-W728.
Ishii K. et al., Comparison of Metabolite Production Capability Indices Generated by Network Analysis Methods, Biosystems, (2008), vol. 91, No. 1, pp. 166-170.
Jamshidi N. et al., Investigating the Metabolic Capabilities of Mycobacterium Tuberculosis H37Rv Using the in Silico Strain iNJ661 and Proposing Alternative Drug Targets. BMC Syst Biol, (2007), vol. 1, No. 26.
Jhee K.H. et al., Thermostable ornithine aminotransferase from *Bacillus* sp YM-2—purification and characterization, J Biochem, (1995), 118(1):101-108.
Johnston N.C. et al., Replacement of the Aliphatic Chains of *Clostridium acetobutylicum* by Exogenous fatty acids: Regulation of Phospholipid and Glycolipid Composition, J Bacteriol, 1992, vol. 174, No. 6, pp. 1848-1853.
Jones D.T. ,et al., Acetone-Butanol Fermentation Revisited, Microbiol, Rev., 1986, vol., No. 50, pp. 484-524.
Joyce A.R. et al., Predicting Gene Essentiality Using Genome-Scale in Silico Models. Methods Mol Biol, (2007), vol. 416, pp. 433-458.
Kanehisa M. et al., KEGG: Kyoto Encyclopedia of Genes and Genomes, Nucleic Acids Res. (2000), vol. 28, No. 1, pp. 27-30.
Kanehisa M. et al., The KEGG Databases at GenomeNet. Nucleic Acids Res, (2002), vol. 30, No. 1, pp. 42-46.
Kharchenko P. et al., Identifying metabolic enzymes with multiple types of association evidence, BMC Bioinformatics (2006), vol. 7, No. 177.
Kim T.Y. et al., Genome-Scale Analysis of Mannheimia Succiniciproducens Metabolism. Biotechnol Bioeng, vol. 97, No. 4,pp. 657-671, 2007.
Kiriukhin M.Y. et al., D-Alanylation of Lipoteichoic Acid: Role of the D-Alanyl Carrier Protein in Acylation, J Bacteriol, (2001), vol. 183, No. 6, pp. 2051-2058.
Knorr Al et al., Bayesian-Based Selection of Metabolic Objective Functions. Bioinformatics, (2007), vol. 23, No. 3, pp. 351-357.
Konings W.N. et al., the Generation of Metabolic energy by Solute Transport, Arch Microbiol, (1995), vol. 164, No. 4, pp. 235-242.
Kuemmel A. et al., Systematic Assignment of Thermodynamic Constraints in Metabolic network Models, BMC Bioinformatics, (2006),vol. 7, No. 512.
Kuemmel A. et al..Putative Regulatory Sites Unraveled by Network-Embedded Thermodynamic Analysis of Metabolome data, Mol Syst Biol., (2006), vol. 2, No. 0034.
Kunst F. et al., The Complete Genome Sequence of the Gram-Positive Bacterium *Bacillus Subtilis*. Nature, 1997, vol. 390, No. 6657, pp. 249-256.
Kumar V.S. et al., Optimization Based Automated Curation of Metabolic Reconstructions, (2007) vol. 8, No. 212.
Kuroda M. et al., Whole Genome Sequencing of Meticillin-Resistant *Staphylococcus aureus*, Lancet, (2001), vol. 357, No. 9264, No. 1 pp. 1225-1240.
Lee N.H. et al., Genomic Approaches for Reconstructing Gene Networks, Pharmacogenomics, (2005), vol. 6, 3, pp. 245-258.
J. Lee et al., Genome-scale Reconstruction and in *Si lico* Analysis of the *Clostridium Acetobutylicum* ATCC 824 Metabolic Network Appl. Microbiol, Biotechnol, (2008), 80 (5) 849-862.
Lepage C. et al., Changes in Membrane Lipid Composition of *Clostridium acetobutylicum* During Acetone-butanol Fermentation: Effects of Solvents, Growth Temperature and pH. J Gen Microbiol, (1987), vol. 133, 1, pp. 103-110.
Lin H. et al., Genetic Reconstruction of the Aerobic Central Metabolism in *Escherichia Coli* for the Absolute Aerobic Production of Succinate. Biotechnol Bioeng, (2005), vol. 89, No. 2, pp. 148-156.
Ma H. et al., The Edinburgh Human Metabolic Network Reconstruction and its Functional Analysis, Mol Syst Biol, (2007), vol. 3, No. 135.
Ma H. et al., Reconstruction of Metabolic networks From Genome Data and Analysis of their Global Structure for Various Organisms, Bioinformatics (2003), vol. 19, No. 2, pp. 270-277.
MaCarthy T. et al., Using Large-Scale Perturbations in Gene Network Reconstruction, BMC Bioinformatics, (2005), vol. 6, No. 11.
MacDonald D. L. et al., Effects of Solvents and Alcohols on the Polar Lipid Composition of *Clostridium butyricum* Under Conditions of Controlled Lipid Chain Composition. Appl Environ Microbiol, (1991), vol. 57, No. 12, pp. 3517-3521.
Makino S. et al., Hydrolysis of Cortex Peptidoglycan During Bacterial Spore Germination. Med Sci Monit, (2002), vol. 8, No. 6, pp. RA119-RA127.
Maltsev N. et al., PUMA2—Grid-Based hHgh-Throughput Analysis of Genomes and Metabolic Pathways, Nucleic Acids Res (Database issue), (2006), vol. 34, pp. D369-D372.
Maskow T. et al., How Reliable are Thermodynamic Feasibility Statements of Biochemical Pathways, Biotechnol Bioeng, (2005), vol. 92, No. 2, pp. 223-230.

Mavrovouniotis M.L., Group Contributions for Estimating Standard Gibbs Energies of Formation of Biochemical-Compounds in Aqueous-Solution, Biotechnol Bioeng, (1990), vol. 36, No. 10, pp. 1070-1082.

Messner K.R. et al., Mechanism of Superoxide and Hydrogen Peroxide Formation by Fumarate Reductase, Succinate Dehydrogenase, and Aspartate Oxidase, J Biol Chem, (2002), vol. 77, No. 45, pp. 42563-42571.

Meyer C.L. et al., Increased Levels of ATP and NADH are Associated with Increased Solvent Production in Continuous Cultures of *Clostridium acetobutylicum*, Appl Environ Microbiol, (1989), vol. 30, No. 5, pp. 450-459.

Monot F., et al., Acetone and Butanol Production by *Clostridium acetobutylicum* in a Synthetic Medium. Appl Environ Microbiol, (1982), vol. 44, No. 6, pp. 1318-1324.

Montoya .D. et al., New Solvent-Producing *Clostridium* sp. Strains, Hydrolyzing a Wide Range of Polysaccharides, are Closely Related to *Clostridium butyricum*, J Ind Microbiol Biotechnol, (2001), vol. 27, No. 5, pp. 329-335.

Mueller T. et al., Mutation-Induced Metabolite Pool Alterations in *Corynebacterium glutamicum*: Towards the Identification of Nitrogen Control Signals, J Biotechnol, (2006), vol. 126, No. 4, pp. 440-453.

Muro-Pastor M.I. et al., Cyanobacteria Perceive Nitroen Status by Sensing Intracellular 2-Oxoglutarate Levels, J Biol Chem, (2001), vol. 276, No. 41, pp. 38320-38328.

Neuhaus F.C. et al., Continuum of Anionic Charge: Structures and Functions of D-Alanyl-Teichoic Acids in Gram-Positive Bacteria, Microbiol Mol Biol Rev, (2003), vol. 67, 4, pp. 686-723.

Nielsen J. et al., The Next Wave in Metabolome Analysis, Trends Biotechnol, (2005), vol. 23, No. 11, pp. 544-546.

Nikiforova V. J. et al., Network Visualization and Network Analysis, Plant Systems Biology (2007), vol. 97, pp. 245-275.

Nikolaev E.V. et al., Elucidation and structural analysis of conserved pools for genome-scale metabolic reconstructions, Biophys J, (2005), vol. 88, No. 1, pp. 37-49.

Noelling J. et al., Genome Sequence and Comparative Analysis of the Solvent-Producing Bacterium *Clostridium acetobutylicum*, J Bacteriol, (2001), vol. 183, No. 16, pp. 4823-4838.

Notebaart R.A. et al., Accelerating the Reconstruction of Genome-Scale Metabolic networks, BMC Bioinformatics, (2006), vol. 7, No. 296.

Oberhardt M.A. et al., Genome-Scale Metabolic network Analysis of the Opportunistic Pathogen Pseudomonas Aeruginosa PAO1, J Bacteriol, (2008), vol. 190, No. 8, pp. 2790-2803.

Oh S.J. et al., Construction of Phylogenetic Trees by Kernel-Based Comparative Analysis of Metabolic Networks, BMC Bioinformatics, (2006), vol. 7, No. 284.

Oh Y.K. et al., Genome-Scale Reconstruction of Metabolic network in *Bacillus subtilis* Based on High-Throughput Phenotyping and Gene Essentiality Data, J Biol Chem, (2007), vol. 282, No. 39, pp. 28791-28799.

Oliveira A.P. et al., Modeling Lactococcus Lactis Using a Genome-Scale Flux Model, BMC Microbiol,(2005), vol. 5, No. 39.

Osterman A. et al., Missing genes in Metabolic Pathways: A Comparative Genomics Approach, Curr Opin Chem Biol, (2003), vol. 7, No. 2, pp. 238-251.

Papin J.A. et al., Metabolic pathways in the Post-Genome Era, Trends Biochem Sci, (2003), vol. 28, No. 5, pp. 250-258.

Papoutsakis E.T., Equations and Calculations for Fermentations of Butyric-Acid Bacteria. Biotechnology and Bioengineering, (1984), vol. 26, No. 2, pp. 174-187.

Papoutsakis E.T. et al., Equations and Calculations of Product Yields and Preferred Pathways for Butanediol and Mixed-Acid Fermentations, Biotechnol Bioeng, (1985), vol. 27, No. 1, pp. 50-66.

Papoutsakis E.T. et al, Fermentation Equations for Propionic Acid Bacteria and Production of Assorted Oxychemicals from Various Sugars, Biotechnol Bioeng, (1985b), vol. 27, No. 1, pp. 67-80.

Paredes C.J. et al., A Comparative Genomic View of Clostridial Sporulation and Physiology, Nature Reviews, Microbiol, (2005), vol. 3, No. 12, pp. 969-978.

Parker G.F. et al., Timing and Genetic Regulation of Commitment to Sporulation in *Bacillus subtilis*, Microbiology, (1996), vol. 142, pp. 3445-3452.

Patil K.R. et al., Use of Genome-Scale Microbial Models for Metabolic Engineering. Curr Opin Biotechnol, (2004), vol. 15, No. 1, pp. 64-69.

Patil K.R. et al. Uncovering Transcriptional Regulation of Metabolism by Using Metabolic Network Topology, Proc Natl Acad Sci U S A, (2005), vol. 102. No. 8, pp. 2685-2689.

Pearson W.R., Effective Protein Sequence Comparison, Methods Enzymol, (1996), vol. 266, pp. 227-258.

Perego M. et al., Incorporation of D-Alanine int Lipoteichoic Acid and Wall Teichoic acid in *Bacillus subtilis*. Identification of Genes and Regulation. J Biol Chem, (1995), vol. 270, No. 26, pp. 15598-15606.

Peterson J.D. et al., The Comprehensive Microbial Resource. Nucleic Acids Res, (2001), vol. 29, No. 1, pp. 123-125.

Pinney J.W. et al., Metabolic Reconstruction and Analysis for Parasite Genomes, Trends Parasitol, (2007), vol. 23, No. 11, pp. 548-554.

Pinney J.W. et al., MetaSHARK: Software for Automated Metabolic network Prediction from DNA Sequence and its Application to the Genomes of Plasmodium Falciparum and Eimeria Tenella, Nucleic Acids Res, (2005), vol. 33, No. 4, pp. 1399-1409.

Pollack J.H. et al., Changes in Wall Teichoic Acid During the Rod-Sphere Transition of *Bacillus subtilis* 168, J Bacteriol, (1994), vol. 176, No. 23, pp. 7252-7259.

Poolman B. et al. Regulation of Arginine-ornithine Exchange and the Arginine Deiminase Pathway in *Streptococcus lactis*, J Bacteriol, (1987), vol. 169, No. 12, pp. 5597-5604.

Poolman M.G. et al., Challenges to be Faced in the Reconstruction of Metabolic networks from Public Databases, Syst Biol (Stevenage), (2006), vol. 153, No. 5, pp. 379-384.

Poolman M.G. et al., Modular Decomposition of Metabolic Systems via Null-Space Analysis, J Theor Biol, (2007), vol. 249. No. 4, pp. 691-705.

Price N.D. et al., Candidate states of Helicobacter pylori's Genome-Scale Metabolic network Upon Application of "Loop Law" Thermodynamic Constraints, Biophys J, (2006), vol. 90, No. 11, pp. 3919-3928.

Price N.D. et al, Genome-Scale Microbial in Silico Models: The Constraints-Based Approach, Trends Biotechnol, (2003), vol. 21, No. 4, pp. 162-169.

Price N.D. et al., Genome-scale Models of Microbial Cells: Evaluating the Consequences of Constraints, Nat Rev Microbiol, (2004), vol. 2, No. 11, pp. 886-897.

Reed J.L. et al., Systems Approach to Refining Genome Annotation, Proc Natl Acad Sci U S A, (2006), vol. 103, No. 46, pp. 17480-17484.

Reed J.L. et al., An Expanded Genome-Scale Model of *Escherichia coli* K-12 (iJR904 GSM/GPR), Genome Biol, (2003), vol. 4, No. 9, pp. R54-R54.12.

Reed J.L. et al., Genome-Scale in Silico Models of *E. Coli* have Multiple Equivalent Phenotypic States: Assessment of Correlated Reaction Subsets that Comprise Network States, Genome Res, (2004), vol. 14, No. 9, pp. 1797-1805.

Ren Q. et al., TransportDB: A Comprehensive Database Resource for Cytoplasmic Membrane Transport Systems and Outer Membrane Channels, Nucleic Acids Res (Database issue), (2007), vol. 35, pp. D274-D279.

Resendis-Antonio O. et al., Metabolic Reconstruction and Modeling of Nitrogen fixation in Rhizobium etli, PLoS Comput Biol, (2007), vol. 3, No. 10, pp. 1887-1895.

Riebeling V. et al., Properties and Function of Clostridial Membrane ATPase, Biochim Biophys Acta, (1976), vol. 430, No. 3, pp. 434-444.

Rodionov D.A. et al., Reconstruction of Regulatory and Metabolic Pathways in Metal-Reducing Delta-Proteobacteria, Genome Biol, (2004), vol. 5, No. 11, Article R90, pp. R90-R90.27.

Roe A.J. et al., Perturbation of Anion Balance During Inhibition of Growth of *Escherichia coli* by Weak Acids, J Bacteriol, (1998), vol. 180, No. 4, pp. 767-772.

Roos J.W. et al., The Effect of pH on Nitrogen Supply, Cell-Lysis, and Solvent Production in Fermentations of Clostridium Acetobutylicum, Biotechnol Bioeng, (1985), vol. 27, No. 5, pp. 681-694.

Saier M.H. et al., TCDB: the Transporter Classification Database for Membrane Transport protein Analyses and Information, Nucleic Acids Res 34(Database issue), (2006) vol. 34, pp. D181-D186.

Sakuraba H. et al., L-Aspartate Oxidase is present in the Anaerobic hyperthermophilic archaeon *Pyrococcus horikoshii* OT-3: Characteristics and Role in the *de novo* Biosynthesis of Nicotinamide Adenine Dinucleotide Proposed by Genome Sequencing, Extremophiles, (2002), vol. 6, No. 4, pp. 275-281.

Schilling C.H. et al., Genome-Scale Metabolic Model of Helicobacter Pylori 26695, J. Bacteriol, (2002), vol. 184, No. 16, pp. 4582-4593.

Schleifer K.H. et al., Peptidoglycan Types of Bacterial Cell Walls and Their Taxonomic Implications, Bacteriol Rev, (1972), vol. 36, No. 4, pp. 407-477.

Schomburg I. et al., Brenda, the Enzyme Database: Updates and Major new Developments, Nucleic Acids Res 32(Database issue), (2004), vol. 32, pp. D431-D433.

Schreier H.J., Smith et al., Regulation of Nitrogen Catabolic Enzymes in *Bacillus* spp. J Bacteriol, (1982), vol. 151, No. 2, pp. 971-975.

Schuster S., et al., A General Definition of Metabolic Pathways Useful for Systematic Orrganization and Analysis of Complex Metabolic networks, Nat Biotechnol, (2000), vol. 18, No. 3, pp. 326-332.

Schwarz W.H., The Cellulosome and Cellulose Degradation by Anaerobic bacteria, Appl Microbiol Biotechnol, (2001), vol. 56, pp. 634-649.

Senger R.S. et al., Development of a Culture Sub-Population Induction Model: Signaling Pathways Synergy and Taxanes Production by Taxus Canadensis, Biotechnol Prog, (2006) vol. 22, No. 6, pp. 1671-1682.

Shlomi T. et al., A Genome-Scale Computational Study of the Interplay Between Transcriptional Regulation and Metabolism, Mol Syst Biol, (2007), vol. 3, No. 101.

Shlomi T.et al., Network-Based Prediction of Human Tissue-Specific Metabolism, Nature Biotechnology, (2008), vol. 26, No. 9, pp. 1003-1010.

Soehling B. et al., Molecular Analysis of the Anaerobic Succinate Degradation Pathway in *Clostridium kluyveri*. J Bacteriol, (1996), vol. 178, No. 3, pp. 871-880.

Song H. et al., Development of Chemically Defined Medium for Mannheimia Succiniciproducens Based on its Genome Sequence, Appl Microbiol Biotechnol, (2008), vol. 79, pp. 263-272.

Stephanopoulos G. et al., Metabolic Engineering, Principles and Metholologies. San Diego: Academic Press, (1998), Chapters 3 and 4, pp. 81-146.

Sun J. et al., Metabolic Peculiarities of *Aspergillus Niger* Disclosed by Comparative Metabolic Genomics, Genome Biol, (2007), vol. 8, No. 9, Article R182.

Tedeschi G. et al., L-aspartate Oxidase from *Escherichia coli*. II. Interaction with C4 Dicarboxylic Acids and Identification of a Novel L-Aspartate: Fumarate Oxidoreductase Activity, Eur J Biochem, (1996), vol. 239, No. 2, pp. 427-433.

Tegner J. et al., 2003. Reverse Engineering Gene Networks: Integrating Genetic Perturbations with Dynamical Modeling. Proc Natl Acad Sci U S A, 2003, vol. 100, No. 10, pp. 5944-5949.

Teusink B. et al., Analysis of Growth of *Lactobacillus plantarum* WCFS1 on a complex Medium Using a Genome-Scale Metabolic model, J Biol Chem, (2006), vol. 281, No. 52, pp. 40041-40048.

Thomas R. et al., A model-Based Optimization Framework for the Inference on Gene Regulatory Networks from DNA Array data, Bioinformatics, (2004), vol. 20, No. 17, pp. 3221-3235.

Thomas R. et al., A Model-Based Optimization Framework for the Inference of Regulatory Interactions Using Time-Course DNA Microarray Expression Data, BMC Bioinformatics, (2007), vol. 8, No. 228.

Thormann K. et al., Control of Butanol Formation in *Clostridium acetobutylicum* by Transcriptional Activation, J Bacteriol (2002), vol. 184, vol. 7, No. 7, pp. 1966-1973.

Tomas C.A. et al., DNA array-Based Transcriptional Analysis of Asporogenous, Nonsolventogenic *Clostridium acetobutylicum* strains SKO1 and M5. J Bacteriol, 2003, vol. 185, No. 15, pp. 4539-4547.

Tomas C.A. et al., Transcriptional Analysis of Butanol Stress and Tolerance in Clostridium Acetobutylicum, J Bacteriol, (2004), vol. 186, No. 7, pp. 2006-2018.

Tummala S.B. et al., Transcriptional Analysis of Product-Concentration Driven Changes in Cellular Programs of Recombinant Clostridium Acetobutylicum strains, Biotechnol Bioeng, (2003), vol. 84, No. 7, pp. 842-854.

Urbanczik R., SNA—A Toolbox for the Stoichiometric Analysis of Metabolic networks. BMC Bioinformatics, (2006), vol. 7, No. 129.

Vasconcelos I. et al., Regulation of Carbon and Electron Flow in *Clostridium acetobutylicum* Grown in Chemostat Culture at Neutral pH on Mixtures of Glucose and Glycerol, Journal of Bacteriology, (1994), vol. 176, No. 3, pp. 1443-1450.

Vo Td et al., Reconstruction and Functional Characterization of the Human Mitochondrial Metabolic Network Based on Proteomic and Biochemical data, J Biol Chem, (2004), vol. 279, No. 38, pp. 39532-39540.

Voellmy R. et al., Dual Role for $N^2$-Acetylornithine 5-Aminotransferase from *Pseudomonas aeruginosa* in Arginine Biosynthesis and Arginine Catabolism, Journal of Bacteriology, (1975), vol. 122, No. 3, pp. 799-809.

Vollherbst-Schneck K. et al., Effect of Butanol on Lipid Composition and Fluidity of *Clostridium acetobutylicum* ATCC 824. Appl Environ Microbiol, (1984), vol. 47, No. 1, pp. 193-194.

Wiback Sj et al., Monte Carlo Sampling Can Be Used to Determine the Size and Shape of the Steady-State Flux Space, Journal Theoretical Biology (2004), vol. 228, No. 4, pp. 437-447.

Wilkinson S.R. et al., Molecular Genetics and the Initiation of Solventogenesis in Clostridium beijerinckii (formerly Clostridium acetobutylicum) NCIMB 8052, FEMS Microbiology Reviews, (1995), vol. 17, No. 3, pp. 275-285.

Xie T. et al., Reconstruction of ABC Transporter Pathways of Archaea and Comparison of Their Genomes, Sheng Wu Hua Xue Yu Sheng Wu Wu Li Xue Bao (Shanghai) (2000), vol. 32, No. 2, pp. 169-174.

Yang Y. T. et al., The effects of Feed and Intracellular Pyruvate Levels on the Redistribution of Metabolic Fluxes in *Escherichia coli*. Metababolic Engineering, (2001), vol. 3, No. 2, pp. 115-123.

Zhao J., et al., Modular Co-evolution of Metabolic Networks. BMC Bioinformatics, (2007), vol. 8, No. 311.

Zhao Y. et al., Expression of a Cloned Cyclopropane Fatty Acid Synthase Gene Reduces Solvent Formation in Clostridium Acetobutylicum ATCC 824, Applied Environmental Microbiology, (2003), vol. 69, No. 5, pp. 2831-2841.

Zhao Y et al., Intracellular butyryl phosphate and acetyl Phosphate Concentrations in *Clostridium acetobutylicum* and Their Implications for Solvent Formation, Applied Environmental Microbiology, (2005), vol. 71, No. 1, pp. 530-537.

* cited by examiner

I. Reaction scheme with singularity

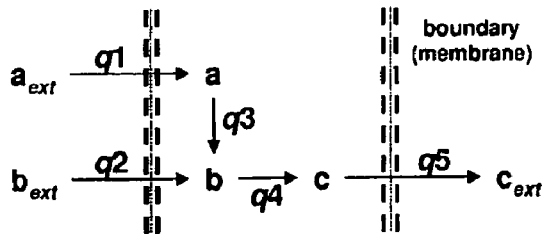

1. Three boundary transport reactions with fluxes, q1, q2, q5.
2. Two intracellular reactions with fluxes q3 and q4. Metabolites a, b and c (internal and external).

II. Corresponding Stoichiometric Matrix $$S' = \begin{bmatrix} 1 & 0 & -1 & 0 & 0 \\ 0 & 1 & 1 & -1 & 0 \\ 0 & 0 & 0 & 1 & -1 \end{bmatrix} \begin{matrix} a \\ b \\ c \end{matrix}$$

with columns $r1\ r2\ r3\ r4\ r5$

1. Rank(S') = 3
2. Number of reactions = 5
3. Null Space Dimensions = 2
4. ∴ No unique solution
5. Singularities to be resolved = 1

III. Identification of a Flux Relationship $$\frac{q1}{q2} = 0.6$$

$$q1 - 0.6(q2) = 0$$

1. Simple hypothetical case shown here: Ratio of fluxes is known
2. Relationships are dependent on thermodynamic parameters.

IV. Incorporation into the Stoichiometric Matrix $$S' = \begin{bmatrix} 1 & 0 & -1 & 0 & 0 \\ 0 & 1 & 1 & -1 & 0 \\ 0 & 0 & 0 & 1 & -1 \\ 1 & -0.6 & 0 & 0 & 0 \end{bmatrix} \begin{matrix} a \\ b \\ c \\ ratio \end{matrix}$$

with columns $r1\ r2\ r3\ r4\ r5$

1. Rank(S') = 4
2. Number of reactions = 5
3. Null Space Dimensions = 1
4. ∴ Unique basis set solution exists

V. Calculation of the Null Space Basis Set (n)   $(S' \cdot v' = 0)$ $$n = \begin{bmatrix} 0.23 \\ 0.38 \\ 0.23 \\ 0.61 \\ 0.61 \end{bmatrix} \qquad v' = \frac{n}{n_i} \cdot \text{scalar}_i$$

1. Scalar derived from enzyme kinetics for reaction i.
2. For genome-scale models, this can be an assumed growth rate or substrate uptake rate.
3. One relation needed to one reaction to numerically-define the model.

Fig. 6

REVERSE ENGINEERING GENOME-SCALE METABOLIC NETWORK RECONSTRUCTIONS FOR ORGANISMS WITH INCOMPLETE GENOME ANNOTATION AND DEVELOPING CONSTRAINTS USING PROTON FLUX STATES AND NUMERICALLY-DETERMINED SUB-SYSTEMS

CROSS REFERENCE TO RELATED APPLICATIONS

This application claims priority to U.S. provisional application Ser. No. 61/123,791, filed Apr. 11, 2008, the entire contents of which are incorporated by reference herein, in their entirety and for all purposes.

STATEMENT OF GOVERNMENT SUPPORT

Research leading to the disclosed inventions was funded, in part, with funds from the National Institute of Health, grant number F32GM078947. Accordingly, the United States government has certain rights in the inventions described herein.

BACKGROUND OF THE INVENTION

Various publications, including patents, published applications, technical articles and scholarly articles are cited throughout the specification. Each of these cited publications is incorporated by reference herein, in its entirety.

Genome-scale models involve the application of flux balance analysis (FBA) to the two-dimensional stoichiometric matrix of a reconstructed metabolic network (Edwards et al. 1999; Stephanopoulos et al. 1998). Maximizing the specific growth rate has become an accepted objective function of FBA (Edwards et al. 1999), but not the only one (Knorr et al. 2007). Thermodynamic (Henry et al. 2007; Kummel et al. 2006) and regulatory (Covert et al. 2001; Gianchandani et al. 2006; Thomas et al. 2004; Thomas et al. 2007) flux constraints along with metabolite conservation relationships (Cakir et al. 2006; Nikolaev et al. 2005) have been developed to decrease the size of the steady-state flux-distribution solution space of FBA.

Solventogenic butyric-acid clostridia are of interest for industrial solvent (particularly bio-butanol) production from diverse substrates, including most hexoses and pentoses, cellulose and xylans (Demain et al. 2005; Montoya et al. 2001; Schwarz 2001). *C. acetobutylicum* ATCC 824 is the first sequenced solventogenic *Clostridium* and can be argued that it serves as a model organism for clostridial metabolism and sporulation in general (Paredes et al. 2005; Thormann et al. 2002). It is an endospore former that displays several defined cascading sigma-factor regulated metabolic programs which impact or are driven by the extracellular environment (Husemann and Papoutsakis 1988; Jones and Woods 1986; Paredes et al. 2005; Zhao et al. 2005). It also has an incomplete TCA cycle that may operate in reverse to synthesize fumarate from oxaloacetate (Nolling et al. 2001). Although a genome-scale model has also been constructed for the endospore-forming *Bacillus subtilis* (Oh et al. 2007), clostridia differ substantially from bacilli in many different ways (Paredes et al. 2005). For example, clostridia are strict anaerobes while bacilli are facultative aerobes. Thus, a genome-scale model of *C. acetobutylicum* will not only serve genetic, biotechnological and physiological research needs of butyric-acid clostridia, but significantly, its genome-scale metabolic model may eventually be extrapolated to similar pathogenic and non-pathogenic clostridia with annotated genomes.

The development of a genome-scale metabolic network reconstruction and associated stoichiometric matrix can require the piece-wise integration of: (i) enzymes with annotated Enzyme Commission (EC) numbers and associated biological reactions; (ii) metabolic pathway blueprints from biochemical reaction, enzymatic, and membrane transport databases; and (iii) physiological knowledge of the organism transcriptome, proteome and metabolome, including high-throughput data when available. The traditional model-building methodology involves iterative organization of these data into a functional flux network (Becker and Palsson 2005; Forster et al. 2003; Heinemann et al. 2005). Automation of a metabolic network reconstruction, based on enzyme homology, can require the use of a generalized metabolic network topology readily available from reaction network databases such as KEGG and MetaCyc (Caspi et al. 2006; Francke et al. 2005; Kanehisa and Goto 2000). Due to incomplete genome annotation, these methods commonly result in a non-functional metabolic network due to missing enzymes and other gaps in the network. Thus, algorithms have been developed to automate the processes needed to rectify these discrepancies in metabolic network drafts.

From initial drafts of the genome-scale metabolic network for *C. acetobutylicum* presented here, two categories of network gaps were identified: (i) gaps resulting from missing enzymes or unknown biological reactions and (ii) gaps resulting from discrepancies in biological reaction databases due to incorrect and mislabeling of compounds and reactions. The first category of network gaps have been addressed by many recently developed algorithms. Techniques used by these algorithms include: genome context analysis (advances of comparative genomics), metabolic pathway homology, enzymatic databases, and high-throughput-omics data (Francke et al. 2005; Kharchenko et al. 2006; Kumar et al. 2007; Notebaart et al. 2006; Osterman and Overbeek 2003). Other useful algorithms make use of growth phenotyping data (Reed et al. 2006) and genetic perturbations (MacCarthy et al. 2005; Tegner et al. 2003), but these data exist only for a very small percentage of organisms with sequenced and annotated genomes. To address both types of network gaps, analysis of the stoichiometric matrix can be used to identify compounds without both an origin of biosynthesis and degradation (or transport in/out of the network) (Kumar et al. 2007; Reed et al. 2003). From our experience, many discrepancies of the reconstructed metabolic network are not evident from direct analysis of the stoichiometric matrix itself. We found that some discrepancies result in internal cycling of isolated pathways within the metabolic network. Common fixes to metabolic network discrepancies allow transport of inadequately synthesized (or degraded) biological macromolecules into (or out of) the network. This methodology may result in a miscalculation of the metabolic flux profile.

*Clostridium acetobutylicum* ATCC 824 is a strict anaerobe that undergoes an acidogenic phase of vegetative growth followed by acid re-uptake, solventogenesis and sporulation in the later stages of the culture (Husemann and Papoutsakis 1988; Jones and Woods 1986; Monot et al. 1982; Papoutsakis and Meyer 1985a; Roos et al. 1985). To generate a regulated genome-scale model of an organism in which differentiation involves a cascading expression of sigma-factors (Paredes et al. 2005), a model describing the metabolic events (including vegetative growth) leading up to the expression of the first sigma-factor of the cascade (Spo0A in *C. acetobutylicum* (Alsaker et al. 2004; Harris et al. 2002; Wilkinson et al. 1995)) is desired. The primary metabolism of *C. acetobutylicum* has been extensively studied and has been further characterized by the first flux balance analysis (Papoutsakis 1984; Papoutsakis and Meyer 1985a; Papoutsakis and Meyer 1985b). Further developments addressed a key singularity of the metabolic network and model through the use of a non-linear constraint (Desai et al. 1999a; Desai et al. 1999b).

SUMMARY OF THE INVENTION

The present invention is embodied in systems and methods for constructing a metabolic network model for a cell using flux balance analysis (FBA) or, similarly, metabolic flux analysis (MFA). Flux models have been described in scientific literature, and their applications to biological systems and metabolic pathways over whole cells have also been described in the literature (Edwards et al., 1999; Stephanopoulos et al., 1998). In some aspects, the methods described in this invention can be used for (i) constructing any metabolic network (including genome-scale and multi-genome); (ii) providing reactions absolutely required of anaerobic genome-scale models; (iii) reducing the number of available solutions by considering environmental interactions; and (iv) addressing network singularities with numerically-determined subsystems. A metabolic network model for a cell may be developed by identifying with a computer one or more errors in metabolic network information of the cell by reverse engineering the metabolic network information, determining at least one solution to at least one of the one or more errors in the metabolic network information, and correcting with a computer the at least one of the one or more errors in the metabolic network information by substituting the at least one solution for the at least one of the one or more errors.

Another aspect of the present invention is embodied in a method for identifying a numerically-determined subsystem. A numerically-determined subsystem of a metabolic network mode may be identified by extracting with a computer one or more metabolic reactions from the metabolic network model corresponding to a singularity of the metabolic network model, generating with a computer a stoichiometric matrix using the one or more metabolic reactions, providing at least one arbitrary ratio of the flux of at least two components across a boundary of the singularity, and calculating with a computer a numeric solution to the stoichiometric matrix based on the ratio of the flux of the at least two components in order to determine the numerically-determined subsystem.

Another aspect of the present invention is embodied in a method for calculating metabolic flux profiles as a function of the number of protons entering/leaving the cell (specific proton flux). In many cell types, including the clostridia, this is determined by the pH of the extracellular environment of a cell. The extracellular pH is calculated using a proton balance that includes all medium components. Thus, the extracellular pH serves as a means of calculating the specific proton flux which is then used as a constraint for obtaining an optimum flux profile by solving the metabolic network flux equation using linear programming.

Yet another aspect of the present invention is embodied in a method for optimizing a metabolic network model for a cell. A metabolic network for a cell may be optimized by obtaining the metabolic network model for the cell, determining the pH of the extracellular environment of the cell and the number of protons the cell can exchange with the extracellular environment, and optimizing with a computer the metabolic network model by limiting the number of possible solutions to a flux balancing equation based on the determined pH of the extracellular environment of the cell and the determined number of protons the cell can exchange with the extracellular environment.

Still another aspect of the present invention is embodied in a computer-readable medium or media. The computer-readable medium or media comprises a data structure relating a plurality of reactants of an anaerobic cell to a plurality of reactions of the anaerobic cell, wherein each of the plurality of reactions comprises a reactant corresponding to the substrate of the reaction, a reactant corresponding to the product of the reaction, and a stoichiometric coefficient relating the substrate to the product. The further computer-readable medium or media comprises a constraint set for the plurality of reactions of the anaerobic cell. The computer-readable medium or media also comprises instructions for configuring a computer to predict a growth of the anaerobic cell when the constraint set is applied to the data structure.

synthesized from 2-oxoglutarate or L-glutamate, (ii) require the 2-oxoglutarate/L-glutamate interconversion during a processing step or (iii) require a succinyltransferase during synthesis. Pathways leading to the biosynthesis of aromatic L-amino acids and L-histidine are shown in region 416. ORFs of *C. acetobutylicum* encoding required enzymes of a particular pathway are given. Gene names separated by commas designate sequential processing steps. A slash (/) separator identifies genes encoding enzymes capable of parallel operation. Pathways involving a large number of genes are labeled in the figure as Lists. The corresponding genes for these pathways are given below.

List 1: CAC3169/CAC3176/CAC3652, CAC0091, CAC3170/CAC3604, CAC1479, CAC2399.
List 2: CAC3169/CAC3176/CAC3652, CAC0091, CAC3170/CAC2604, CAC0273, CAC3172/CAC3173, CAC3171, CAC1479.
List 3: CAC3169/CAC3176/CAC3652, CAC0091, CAC3170/CAC3604, CAC1479, CAC3038.
List 4: CAC0998, CAC2378/CAC3600, CAC2379, CAC2381, CAC2380, CAC2723, CAC2624, CAC0608
List 5: CAC1825, CAC0390, CAC0391, CAC3348/CAC0578
List 6: CAC0737/CAC1001/CAC1819/CAC2832/CAC0764/CAC1673/CAC1674
List 7: (from DAHP) CAC0894, CAC0713/CAC0899, CAC0897, CAC0898, CAC0895, CAC0896
List 8: CAC2680, CAC0944, CAC1348, CAC1730, CAC0726, CAC0819/CAC3221
List 9: CAC0936, CAC0943, CAC0942, CAC0940, CAC0939, CAC0938, CAC1369, CAC2727, CAC0937
List 10: CAC3162/CAC3163, CAC3161, CAC3159, CAC3160, CAC3157/CAC3158
List 11: CAC1234, CAC0893, CAC1369/CAC3031/CAC1001/CAC1819/CAC2832
List 12: CAC1234, CAC0217, CAC1369/CAC3031/CAC1001/CAC1819/CAC2832
List 13: CAC2391/CAC3020, CAC2388, CAC2389, CAC2390

Figure 5:
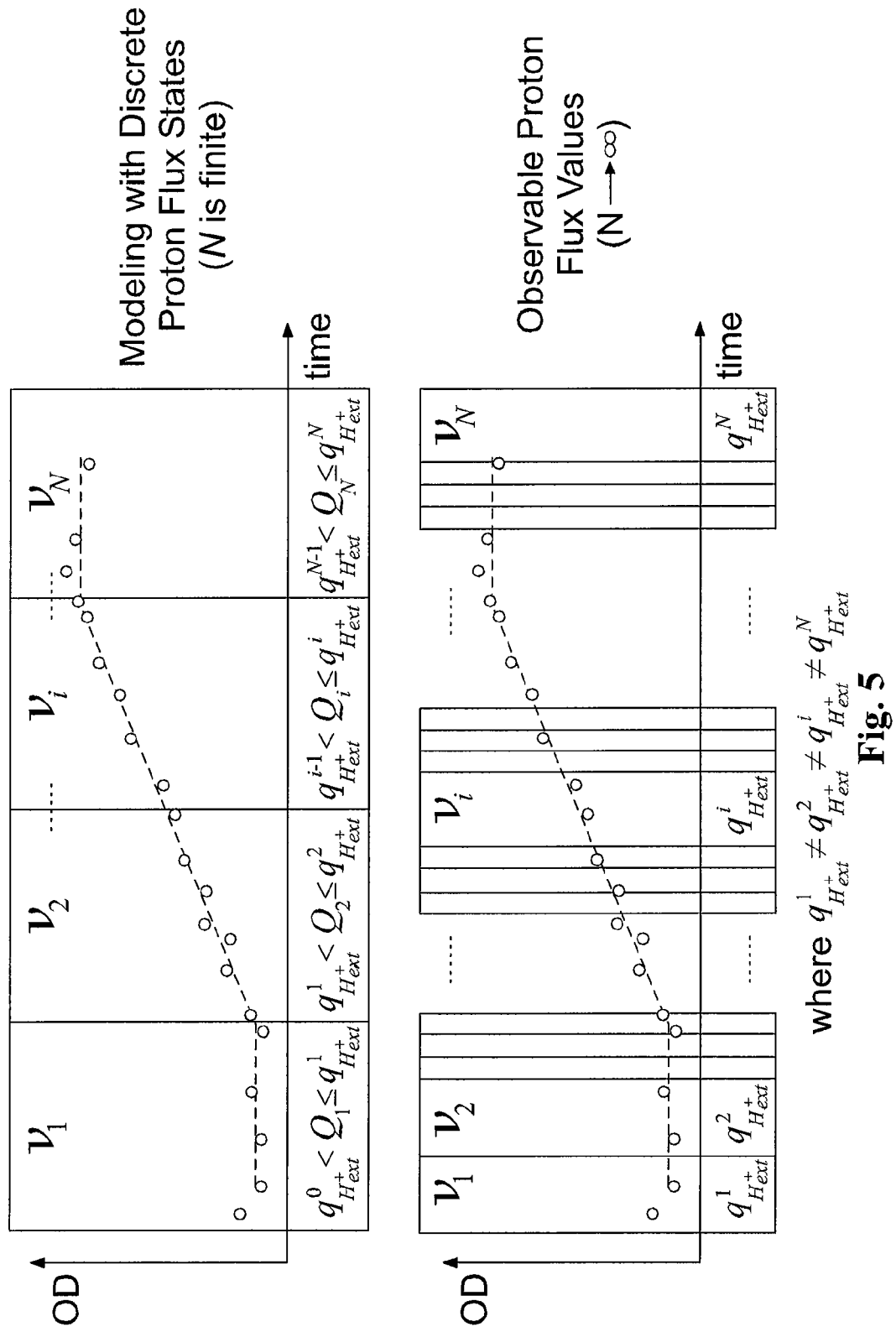

FIG. 5 shows an illustration of discretized and continuous proton flux states using fictitious optical density (OD) data. Specific proton flux values are represented by $q_{H_{ext}^+}{}^i$ and discrete proton flux states are represented by $Q_i$. The number of flux solutions, v, to the flux balance equation, $S \cdot v = 0$, based on proton flux state, is represented by N.

FIG. 6 shows a simple example of numerically defining a sub-system by resolving a singularity with a flux ratio relationship and applying kinetic parameters.

Figure 7:
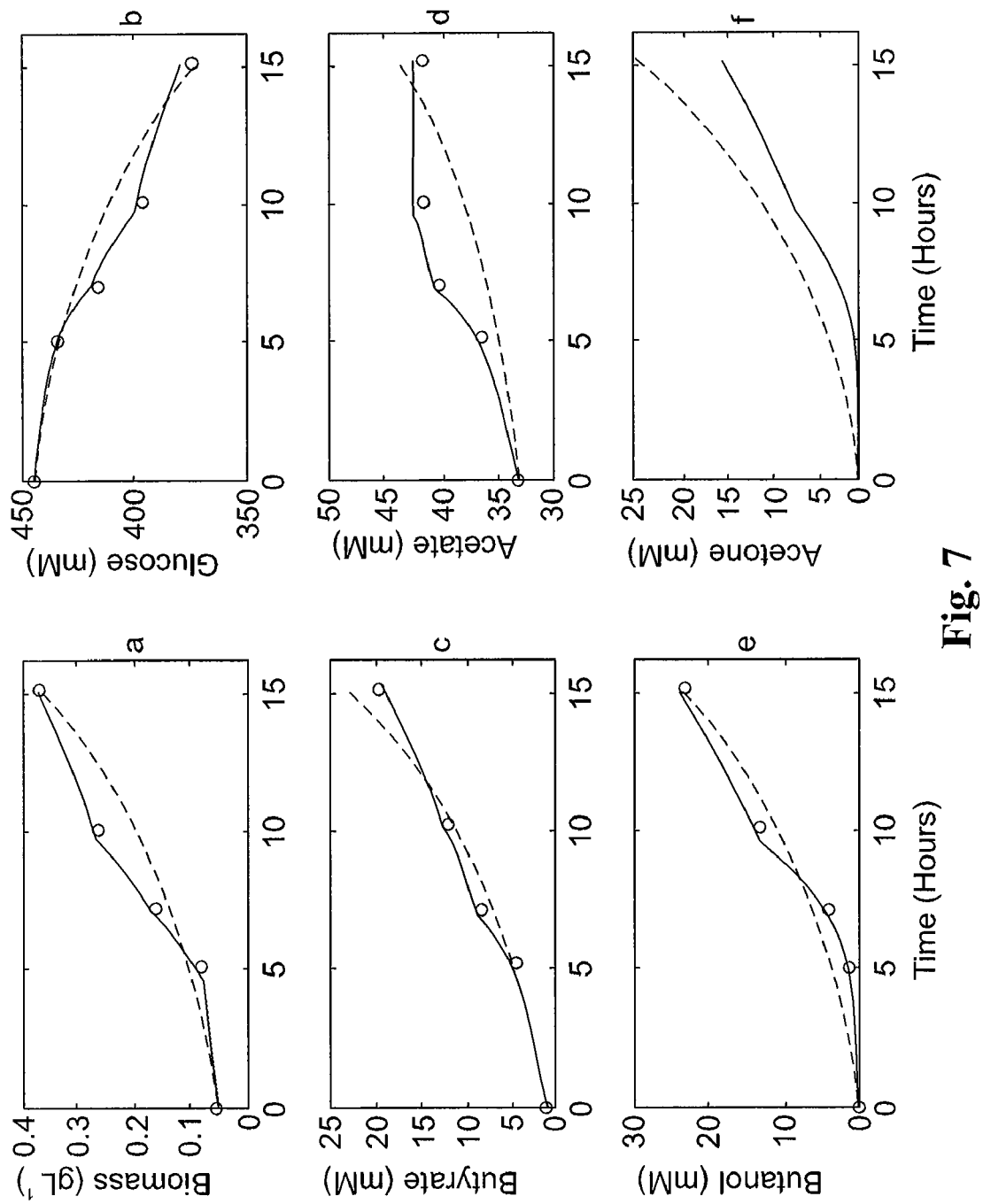

FIG. 7 (*a-f*) shows raw data (circles) and optimized genome-scale model predictions (lines) for biomass production, glucose consumption, acids and solvents production during exponential growth of *C. acetobutylicum* on minimal media (Monot et al. 1982). The following model predictions are shown: (i) six discrete proton flux states (Set 3 of Table 10) (solid lines) and (ii) single proton flux state model (Set 1 of Table 10) (dashed lines). Note: experimental observations with minimal media were not reported for acetone; only model predictions are shown for this case.

Figure 8:
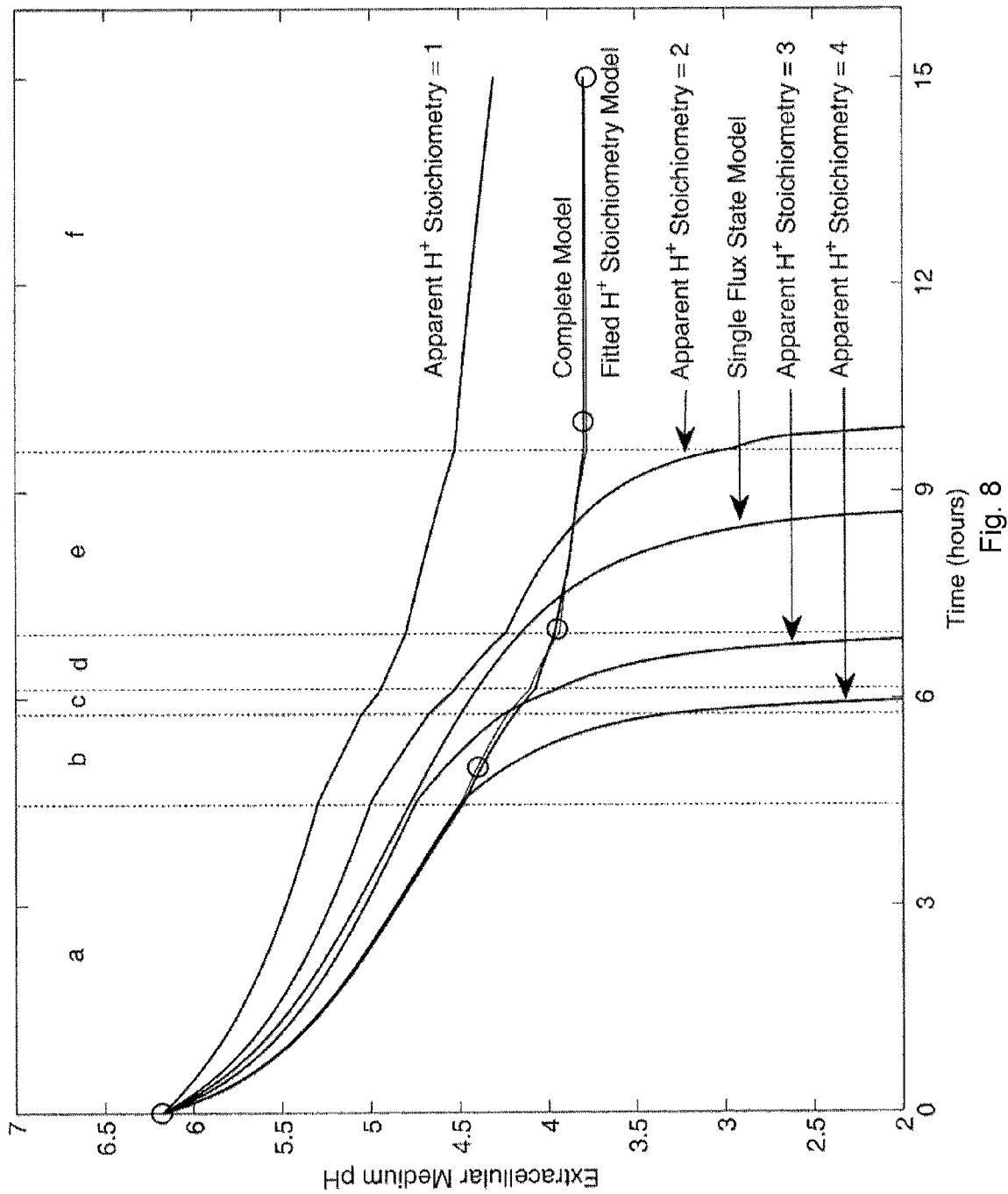

FIG. 8 shows model-derived values (lines) and raw data points (circles) of extracellular media pH for batch growth of *C. acetobutylicum* in minimal media (Monot et al. 1982). Proton flux states are labeled by letters: (a) <55 mmol $H^+h^{-1}g$ biomass$^{-1}$, (b) −55 to −35 mmol $H^+h^{-1}g$ biomass$^{-1}$, (c) −35 to −25 mmol $H^+h^{-1}g$ biomass$^{-1}$, (d) −25 to −15 mmol $H^+h^{-1}g$ biomass$^{-1}$, (e) −15 to −5 mmol $H^+h^{-1}g$ biomass$^{-1}$, and (f) −5 to 5 mmol $H^+h^{-1}g$ biomass$^{-1}$. The Complete Model is composed of six discrete proton flux states with specific fluxes and growth rates shown in Table 11 and growth and metabolite predictions shown in FIG. 7. The Single Flux State Model consists of a single proton flux state with growth and metabolite predictions shown in FIG. 7. The Apparent $H^+$ Stoichiometry curves correspond to specific fluxes in Table 11 with proton flux from cation transport reactions ignored. Stoichiometric coefficient for protons associated with acetate and butyrate efflux was adjusted from 1 to 4 and is listed for each case. The Fitted $H^+$ Stoichiometry Model contains adjusted stoichiometric coefficients for proton efflux with weak acids to fit the observed extracellular medium pH profile.

Figure 9:
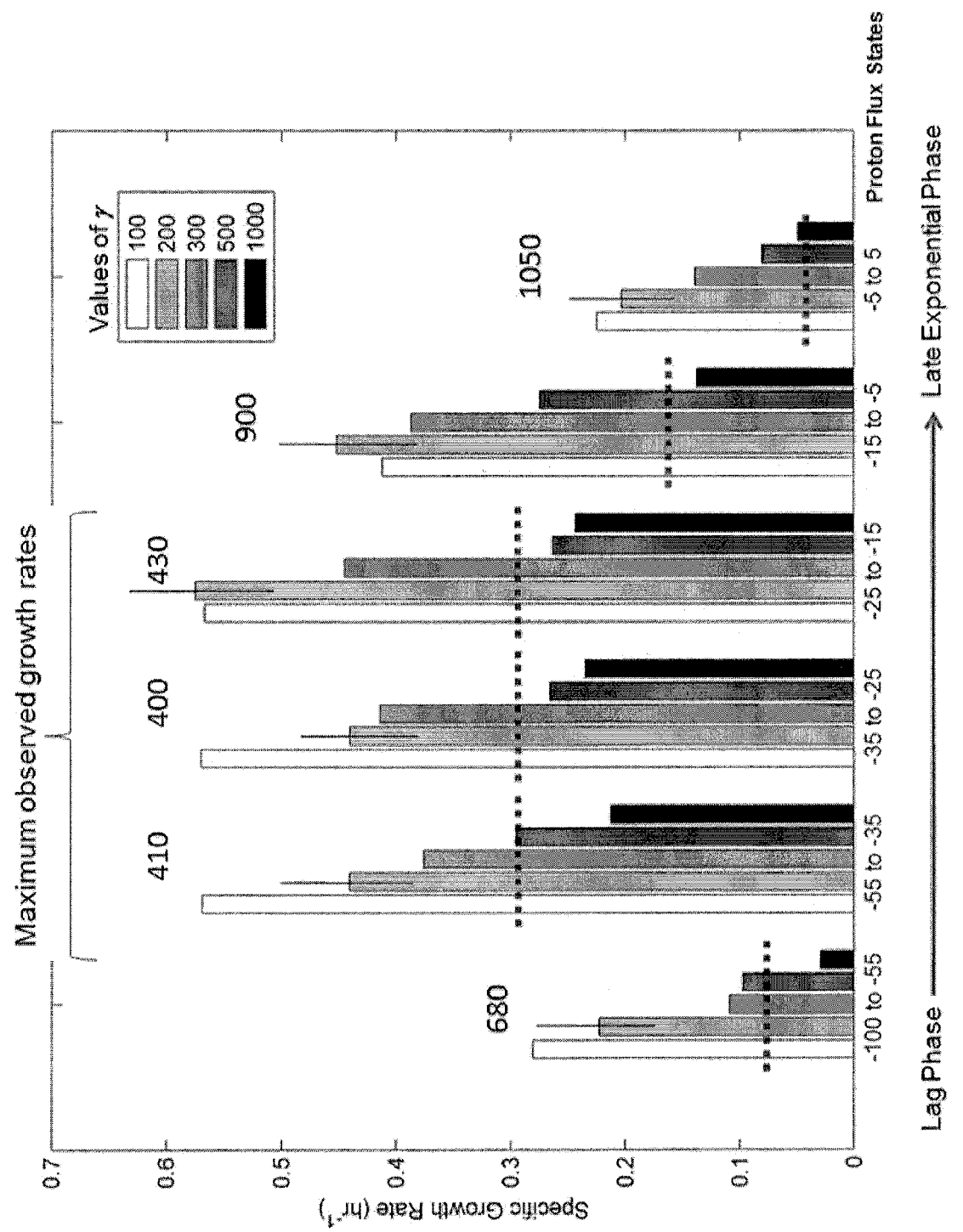

FIG. 9 shows the calculated specific growth rate for specified proton flux states given multiple values of the stoichiometry of ATP (shown by colors) in the biomass constituting equation (Eq. 10). The horizontal dotted lines correspond to the experimentally observed value (Monot et al. 1982). Numerical values printed above the data correspond to the optimized value of the stoichiometric coefficient of ATP (also referred to as γ in Eq. 10) for each proton flux state. Error ranges of one standard deviation are given for the case in which the stoichiometric coefficient of ATP is equal to 60.

Figure 10:
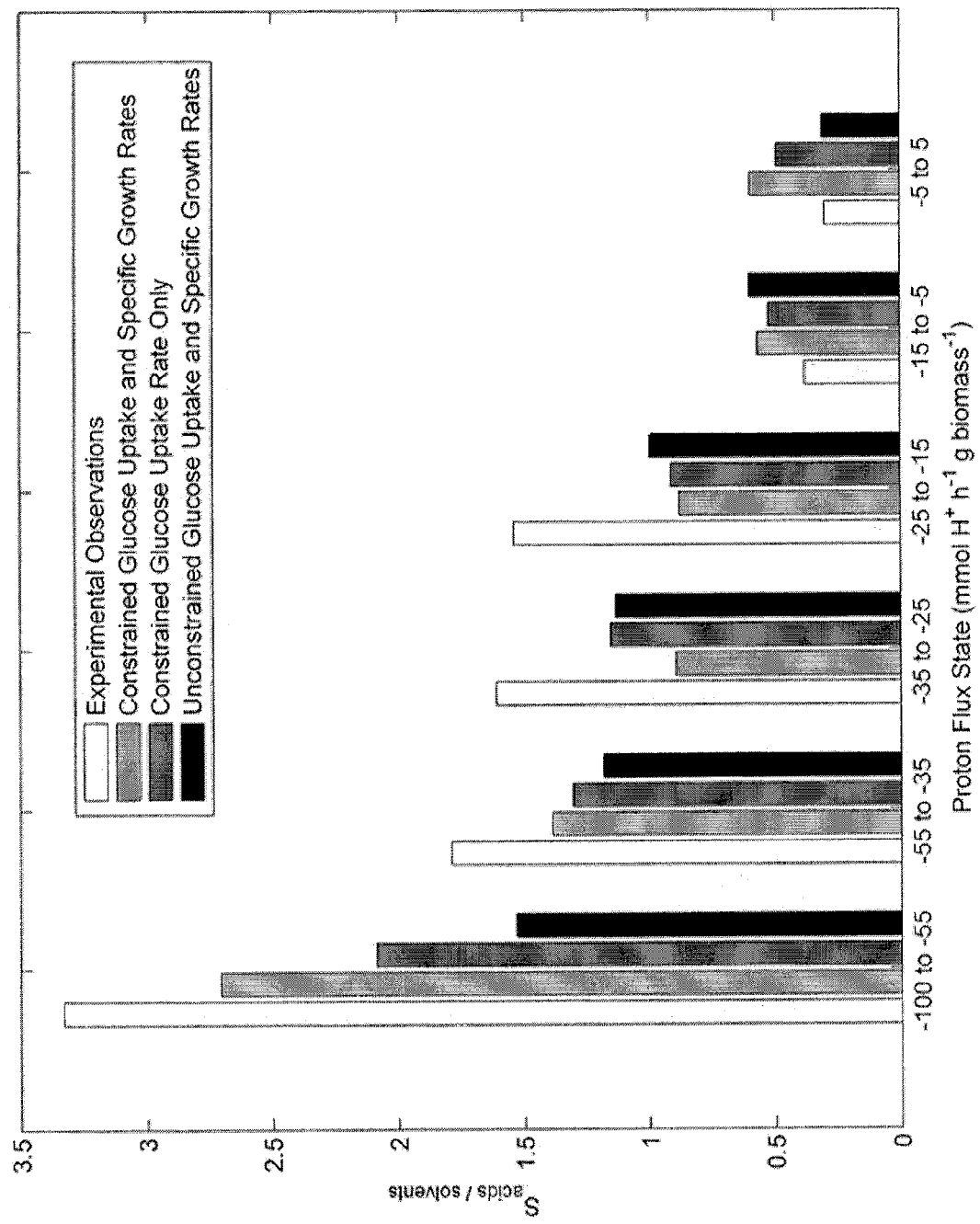

FIG. 10 shows the selectivity of acids to solvents for: (i) experimental observations, (ii) simulation of the genome-scale model in which glucose uptake and specific growth rates were constrained to experimentally observed values (Monot et al. 1982), (iii) simulations in which only the glucose uptake rate was constrained, and (iv) model simulations with no constraints on glucose uptake or specific growth rates. In all cases, reaction fluxes determining the proton flux state (including butyrate, acetate, and lactate effluxes) and solvent (acetone, butanol, and ethanol) effluxes were left unconstrained. The selectivity of acids to solvents is defined as the sum of acetate, butyrate, and lactate effluxes divided by the sum of acetone, butanol, and ethanol effluxes.

Figure 11:
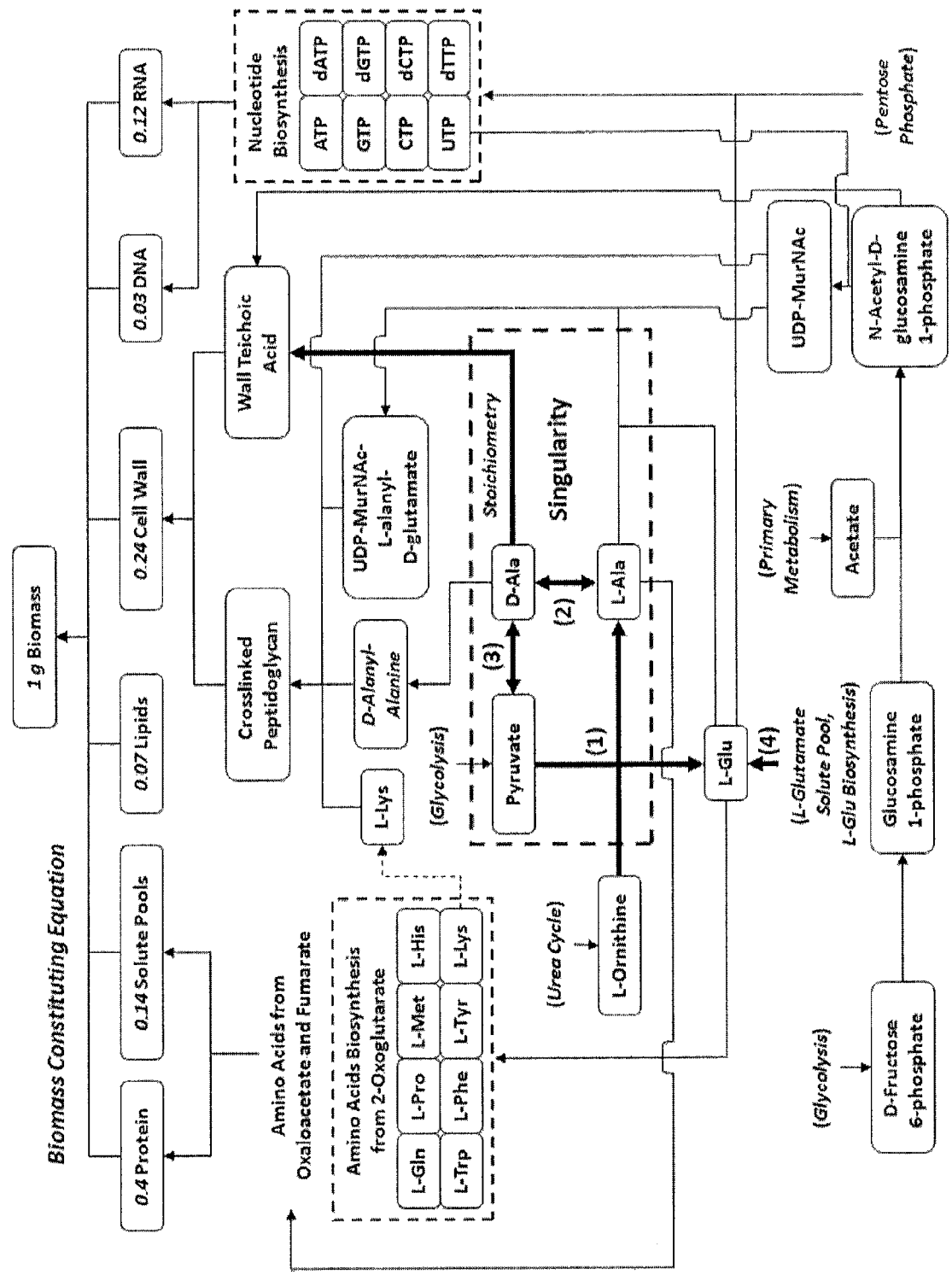

FIG. 11 shows a sub-system of the genome-scale model to investigate flux constraint bounds around D-alanine and probe metabolic capacity based on its incorporation into D-alanylation of wall teichoic acids. The location of the singularity of the sub-system is identified. It was resolved by varying the ratio of Reaction 1 (through acetylornithine transaminase (ArgD, EC 2.6.1.11, CAC2388)) to Reaction 4 (L-glutamate biosynthesis through L-arginine biosynthesis pathway). Reaction 2 is catalyzed by the alanine racemace (EC 5.1.1.1, CAC0492) and D-alanine transaminase (EC 2.6.2.21, CAC0792) drives Reaction 3. Not present in the diagram above, but assumed to be available in excess were: (i) all L-amino acids not derived from L-glutamate, (ii) all required lipids for biomass synthesis, (iii) phosphorylated carbohydrate required by nucleotide biosynthesis, (iv) all intracellular solute pools, (v) sources of all additional molecules required by synthesis reactions, (vi) sinks for all byproducts of synthesis reactions and (vii) all energy requirements.

Figure 12A:
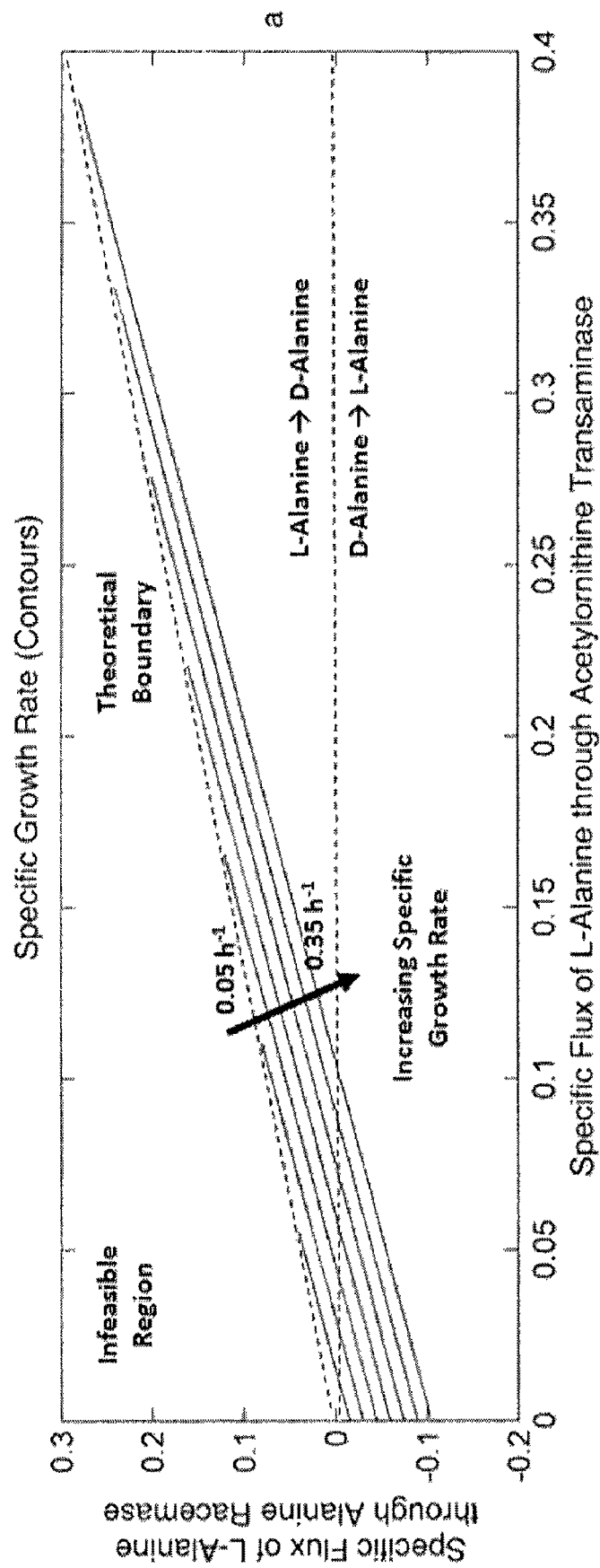
Figure 12B:
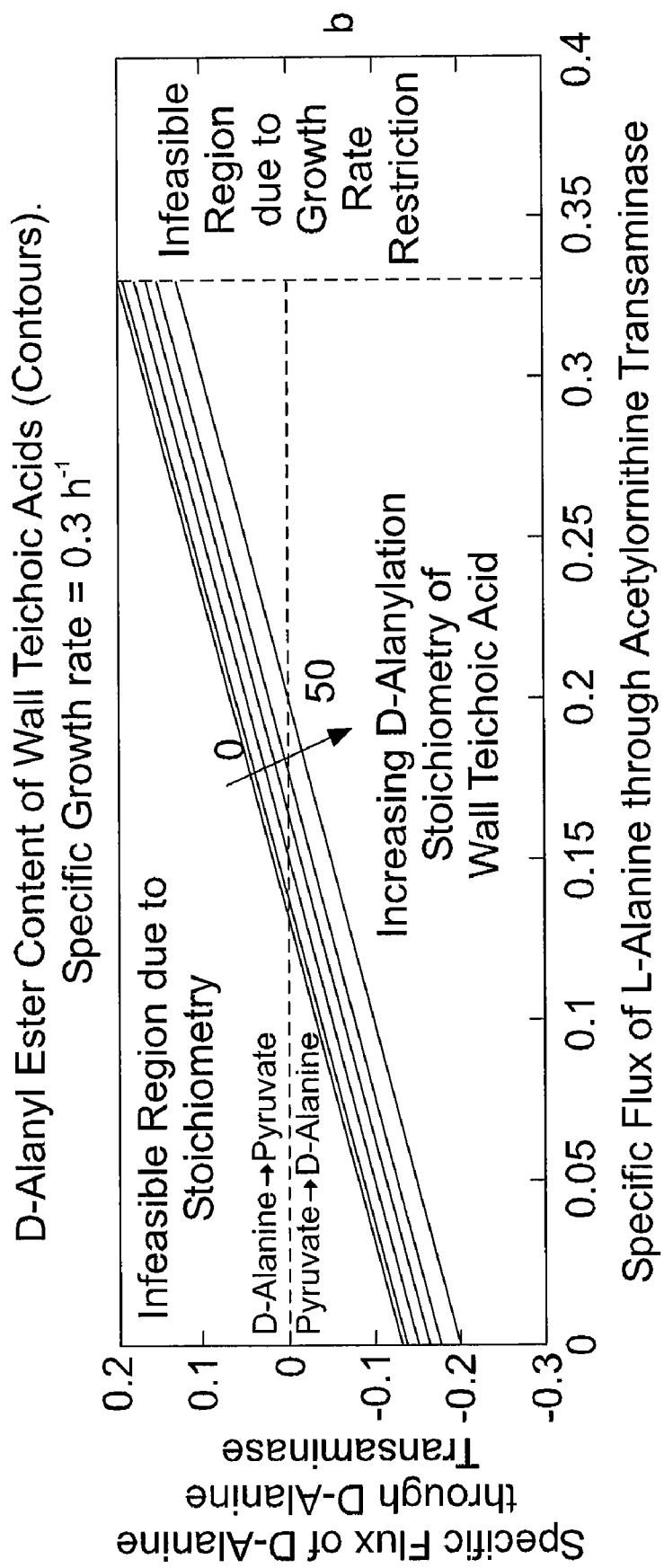

FIGS. 12*a* and 12*b* show results of simulations for the numerically-determined sub-system shown in FIG. 10. (a) The flux ratio for L-glutamate production from ArgD to nitrogen assimilation (Reactions 1 and 4 in FIG. 10), was varied to produce ratios of the specific flux of L-alanine through alanine racemace (Reaction 2 in FIG. 10) against the flux of L-alanine through acetylornithine transaminase (Reaction 1 in FIG. 10). The simulation was performed for multiple assumed specific growth rates between 0.05 h$^{-1}$ and 0.35 h$^{-1}$. (b) The relationship between the specific flux of D-alanine through D-alanine transaminase (Reaction 3 in FIG. 10) and the specific flux of L-alanine through acetylornithine transaminase (Reaction 1 in FIG. 10) was produced by varying the flux ratio for L-glutamate production. This is shown for an increasing number (0 to 50) of D-alanine residues involved in D-alanylation of wall teichoic acids. For these calculations, a specific growth rate of 0.3 h$^{-1}$ was assumed.

Figure 13:
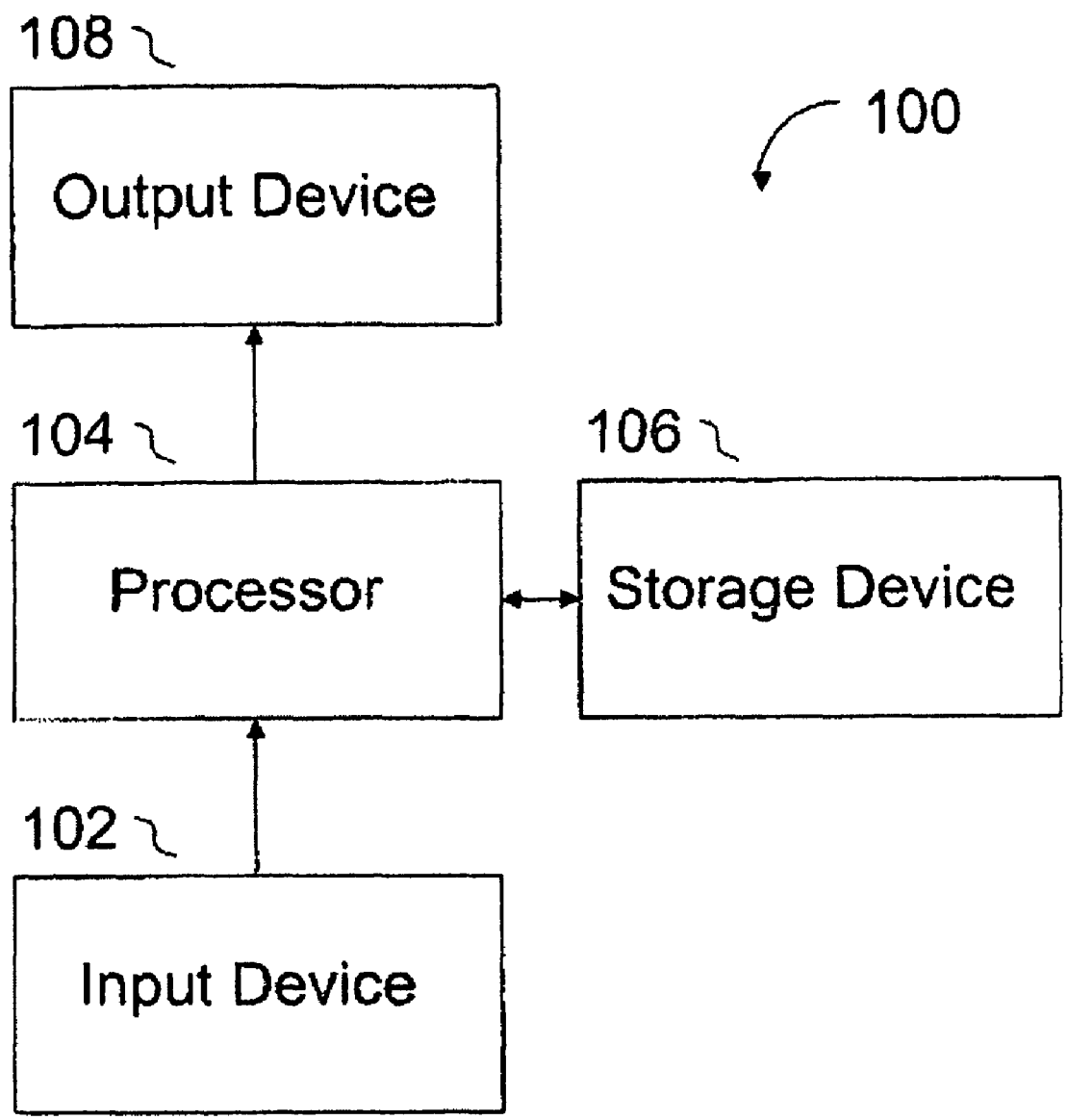

FIG. 13 shows an exemplary system for constructing a metabolic network model in accordance with an aspect of the present invention.

Figure 14:
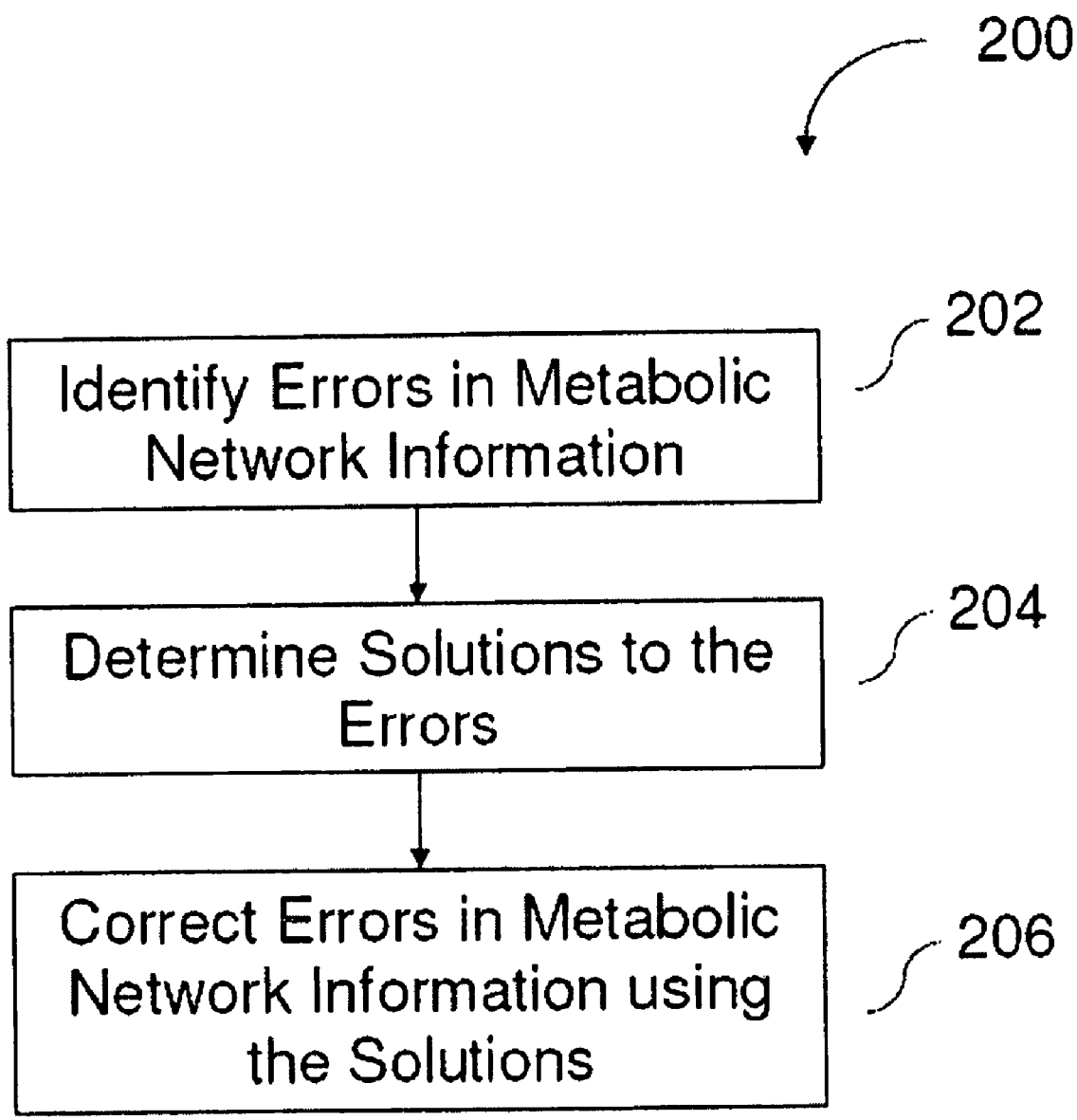

FIG. 14 shows a flow chart of exemplary steps for constructing a metabolic network model in accordance with an aspect of the present invention.

Figure 15:
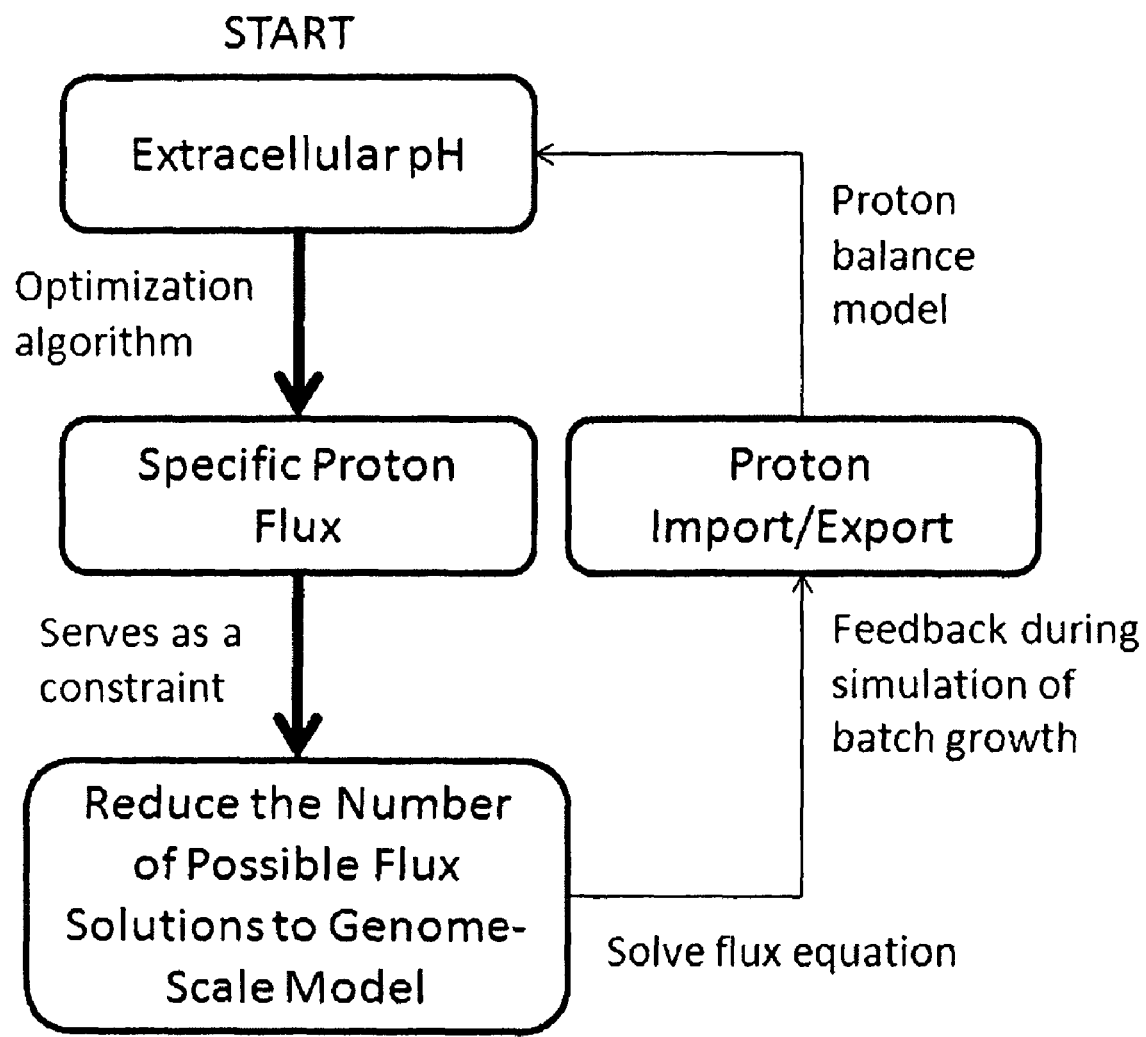

FIG. 15 shows a flow-diagram for integrating a determination of extracellular pH with development of a genome scale metabolic network.

DETAILED DESCRIPTION

Various terms relating to the methods and other aspects of the present invention are used throughout the specification and claims. Such terms are to be given their ordinary meaning in the art to which the invention pertains, unless otherwise indicated. Other specifically defined terms are to be construed in a manner consistent with the definition provided herein.

The following definitions of variables and units are used throughout the specification where appropriate.

Acids all acids in minimal medium: acetate, butyrate, lactate, carbonate, phosphate ion, mono- and di-basic potassium phosphate
Bases all bases in minimal medium: ammonia
Counterions all species with counterions in minimal medium: mono- and di-basic potassium phosphate
$C_A$ total acids concentration of the extracellular medium [mM]
$C_B$ total base concentration of the extracellular medium [mM]
$C_C$ total concentration of species with counterions in the extracellular medium [mM]
d number of acidic dissociation sites
D total number of acidic and basic dissociation sites
γ stoichiometric coefficient of ATP in the biomass constituting equation
$H_{ext}^+$ total extracellular hydrogen ion concentration (contains those of protonated weak acids) [mM]
$H_{free}^+$ extracellular free proton concentration (pH=−log($H_{free}^+$)) [mM]
$H_{butyrate}^+$ extracellular protonated butyrate (butyric acid) concentration [mM]
$H_{acetate}^+$ extracellular acetic acid concentration [mM]
$H_{lactate}^+$ extracellular lactic acid concentration [mM]
$H_{carbonate}^+$ extracellular carbonic acid concentration [mM]
$H_{phosphates}^+$ extracellular mono- and dibasic potassium phosphates concentration [mM]
$H_{ammonium}^+$ extracellular ammonium concentration [mM]
$h_r$ stoichiometric coefficient of H$^+$ in membrane transport equation r
$K_{aj}$ acid dissociation constant of species j
$K_w$ water ionization constant (=10$^{-14}$)
M number of membrane transport equations
N number of specific proton flux states needed to model fermentation data
n null space basis set vector
$n_c$ number of counterions
$q_{H_{ext}^+}$ specific proton flux [mmol h$^{-1}$ g biomass$^{-1}$]
$q_r$ specific flux of reaction r [mmol h$^{-1}$ g biomass$^{-1}$]
$Q_i$ Discrete specific proton flux state i with bounds $q_{H_{ext}^+}^{i-1}$ and $q_{H_{ext}^+}^i$
S stoichiometric matrix of the genome scale model
S' stoichiometric matrix of the sub-system
t time [hours]
v vector of specific flux values for the genome scale model
v' vector of specific flux values for the sub-system
X biomass concentration [g L$^{-1}$]
$z_k$ signed charge of the k$^{th}$ counterion Methods of metabolic network reconstruction have been published and have been a budding niche of computational biology research over the last 5-10 years. However, many types of fully-automated approaches have emerged in the literature regarding network reconstruction. Our approach is different in that our algorithm is semi-automated, requiring a user input and interactive development of the genome-scale model. It is believed that fully-automated systems infer many characteristics of a metabolic network, through reaction pathway homology, that do not actually exist in all organisms. For example, methods of reaction pathway homology resulted in a completed TCA cycle for *C. acetobutylicum*. Using our semi-automated algorithm, we were able to preserve this unique clostridial pathway and locate other areas of the metabolic network where further discovery was needed. These capabilities are not available with the established fully-automated algorithms.

In some aspects, the inventive methods use a reverse engineering approach for resolving metabolic pathways, which include various embodiments and steps that are described and exemplified herein. Reverse engineering refers to, for example, these embodiments and steps for identifying errors in and/or resolving metabolic pathways and developing metabolic networks, as well as all modifications and variations of these embodiments and steps.

Metabolic networks exist for many well-studied cell-types such as: *Escherichia coli* K-12, human red blood cell, yeast, *Staphylococcus aureus, Bacillus subtilis, Mycobacterium tuberculosis, Rhizobium etli, Helicobacer pylori*, and *Methanosarcina barkeri* (among others). However, the metabolic networks of these organisms differ considerably. The current invention highlights multiple metabolic reactions and pathways that were found unique to the clostridia and obligate anaerobic metabolism. One specific example of this is the use of the incomplete TCA cycle by the metabolic network for *C. acetobutylicum*. This is unique to all previously reconstructed metabolic networks. The metabolic network for *C. acetobutylicum* is also the only network reconstructed for an obligate anaerobe. In addition, for metabolic networks published in the scientific literature, this is not reported in a format that includes coordinates of reactions and compounds so the stoichiometric matrix can be easily reconstructed. The company Genomatica has a method for doing this with their software package SimPheny, but their method remains unknown to us at this time. However, the invention includes a platform that allows the addition/deletion of metabolic reactions with minimal effort on the part of the user.

Aspects of the invention provide the advantage of allowing user-input into a genome-scale metabolic network reconstruction in order to preserve unique metabolic pathways of the particular cell-type. The disadvantage of this approach is that many times the request for user input may occur at a point in the metabolic network unfamiliar to the user. Thus, approximations may be required by the user in certain cases, making the performance of the invention uniquely tied to the knowledge and experience of the user. The benefits of practicing this approach are that the areas of metabolism needing further identification are revealed to the user instead of being approximated by pathways with somewhat close homology. The use of homologous pathways in metabolic network reconstruction may result in genome-scale models not representative of a cell-type's actual metabolic capacity. Our invention assures this despite the fact that additional data may need to be gathered from other sources or in the laboratory to complete the genome-scale model.

Other aspects of the invention include the only model in existence that can effectively describe the metabolism of solventogenic clostridia, and possibly pathogenic clostridia, on the genome-scale. The benefits of this invention for solventogenic clostridia include that it provides a metabolic network for which the user can study the metabolic impact of adding/deleting reaction-catalyzing enzymes. This computational study is commonly supplementary to experimental metabolic engineering practiced in the laboratory. By comparing computational and experimental results, iterative methodology can be developed where model results influence which experimental trials should proceed, and these results are fed back into the computational algorithm to improve future predictions.

Other available technology does not allow for unique metabolic pathways to remain intact in the reconstructed metabolic network. Most likely, these are replaced by well-characterized homologous pathways known in other cell types. Our invention preserves these characteristics of the reconstructed metabolic network. This is particularly useful as genome-scale models are built for the hundreds of under-studied organisms with incomplete genome annotation. In addition, no other model-building algorithm, to our knowledge, has been able to specifically address discrepancies in biochemical reaction network databases, such as KEGG.

The metabolic effects of adding/disrupting reaction-catalyzing enzymes on the genome-scale cannot be fully comprehended by the human brain. Genome-scale models are necessary to generate holistic understandings of cellular metabolism. However, the metabolic profiles generated by genome-scale models are meaningless if the computational model of metabolism does not match that within the cell. Using other established metabolic networks to model clostridial metabolism on the genome-scale results in a misrepresentation of the metabolic capabilities of solventogenic clostridia and leads to ineffective metabolic engineering. Thus, a clostridial model of metabolism is absolutely required to predict the change in metabolic capabilities through genetic manipulations. Similarly, only a clostridial model of metabolism can be used to identify gene targets in pathogenic clostridia for future antimicrobial development.

The detailed metabolism of *C. acetobutylicum* was unknown on the genome-scale before its elucidation by the present invention. However, the primary metabolic network involving weak acids and solvents production has been well-known for over 25 years, and the knowledge of an incomplete TCA cycle was published with the genome sequencing results in 2001. The importance of the urea cycle was well-documented in the literature, but the biosynthesis of L-glutamate and anaerobic biosyntheses of NAD and L-isoleucine remained unaddressed in the literature and unknown until the metabolic network was resolved by our invention. Thus, the level of detail of the metabolic network returned by our invention is too vast and complicated to be predicted completely by experts in clostridial metabolism. This will hold true for other under-studied cell-types and may be true for well-studied organisms such as *Escherichia coli* K-12 W3110.

The metabolic network for *C. acetobutylicum* is believed to contain 552 reactions. To perceive a holistic understanding of metabolism, one must know the fate of each reaction flux in response to a stimulus or change, such as adding/disrupting one or more reaction-catalyzing enzymes. Only a genome-scale model can realize the changes in all reaction fluxes, which makes it a valuable tool to computational biologists and metabolic engineers. Even those with access to other metabolic networks, such as the *E. coli* metabolic network, could not extrapolate that model to produce predictions for *C. acetobutylicum* and other clostridia because of the differences in the metabolic networks.

A new semi-automated algorithm, based on reverse engineering, has been developed in accordance with the present invention to quickly identify both categories of discrepancies in the stoichiometric matrix and illustrate a few examples encountered in metabolic network reconstruction for *C. acetobutylicum*. The method allows for the conservation of pathways unique to each bacterial genome. The usefulness of thermodynamic analysis of proposed pathways is also demonstrated here.

A genome-scale metabolic network reconstruction for *Clostridium acetobutylicum* (ATCC 824) was created using a new semi-automated reverse engineering algorithm. The reconstructed metabolic network consists of 422 intracellular metabolites involved in 552 reactions and includes 80 membrane transport reactions. This strict anaerobic bacterium is the model organism for the solventogenic clostridia. Its metabolic network supports the conversion of many complex substrates (most hexoses, pentoses, xylans, and cellulose) to weak acids (acetate, butyrate, and lactate) as well as solvents (acetone, butanol, and ethanol) of interest to the biofuels and chemical industries. Through a series of redox reactions involving ferredoxins, *C. acetobutylicum* is also an excellent producer of hydrogen gas. The metabolic network illustrates the reliance of clostridia on the urea cycle, intracellular L-glutamate solute pools, and the acetylornithine transaminase for amino acid biosynthesis from the 2-oxoglutarate precursor. Thermodynamic analyses were performed to assess the feasibility of pathways used to complete the metabolic network (e.g., a partial reverse TCA cycle and reverse arginine biosynthesis pathway) and calculate the intracellular metabolite concentrations required of these reactions. Results were consistent with published intracellular metabolite concentrations. Flux constraints have also been applied to all reactions of the metabolic network using methods developed in other research.

The semi-automated reverse engineering algorithm not only identified incomplete metabolic pathways quickly, it identified discrepancies in reaction network databases that are major obstacles for fully-automated network-building algorithms. The semi-automated approach allowed for the conservation of unique clostridial metabolic pathways, such as an incomplete TCA cycle. This aspect of the invention includes software that can reconstruct genome-scale metabolic networks for cell-types available through the Kyoto Encyclopedia of Genes and Genomes. The software may use a semi-automated approach which uses a priori knowledge of the cell-type from the user. This approach assures that unique metabolic pathways of a microorganism are not compromised by a program that infers pathway homology between cell-types. This approach allows a user to input cell-type-specific data to fill identified metabolic network discrepancies, while providing the user with a list of known alternatives from other organisms. This approach allowed for the completion of the genome-scale metabolic network of *C. acetobutylicum* containing a partial TCA cycle. Upon completion, the program output is a genome-scale stoichiometric matrix capable of cell growth in silico.

Aspects of the invention include the complete metabolic network of *C. acetobutylicum* in a form that was designed to easily accommodate metabolic engineering through the addition and deletion of metabolic reactions. The compounds, reactions, and stoichiometric coefficients of the metabolic network are represented by a coordinate system that greatly simplifies the construction of the stoichiometric matrix from the metabolic network to solve the flux balance equation, S·v=0, where S is the stoichiometric matrix and v is the vector of reaction flux values.

Aspects of the invention feature software encoding a reverse-engineering algorithm that makes use of genome annotation and freely-available information from the Kyoto Encyclopedia of Genes and Genomes (KEGG) (among other sources, see Item 3) to create a functional genome-scale metabolic model of a particular cell type. This particular software excels at creating genome-scale models for relatively under-studied organisms with incomplete genome annotation. Of the hundreds of organisms with sequenced and annotated genomes, a very small number (fewer than 10) are well-studied enough to have nearly-complete genome annotation.

Aspects of the invention also include a platform for the reconstructed metabolic network, including an automated procedure for stoichiometric matrix self-assembly from a list of chemical reactions. The fully-reconstructed metabolic network of the model organism for solventogenic clostridia (*C. acetobutylicum*) is provided with this platform. The platform can be amended for the metabolic network of any cell-type using the reverse engineering software. Its intended use is for computational biology with metabolic engineering endeavors. The invention provides a platform for the metabolic model that is easily amendable to allow the insertion of new metabolic reactions or entire pathways into the network. In addition, reactions or pathways can easily be eliminated from the metabolic network. Using the provided set of reaction constraints, the metabolic network can be evaluated by solving the flux balance equation, S·v=0, using linear programming methods that have been thoroughly discussed in the literature and are available through other commercial products. Solutions to the flux balance equation give the user a calculation of the metabolic capabilities of the organism. Thus, using this metabolic network, metabolic engineers can quickly determine the metabolic impact of adding/disrupting enzymes that catalyze biochemical reactions before dedicating the time and laboratory resources to physically construct and evaluate mutant strains of solventogenic clostridia. This amendable platform also allows the user to add additional proprietary information to the model to create customized versions of the metabolic network that are unavailable to competitors.

Aspects of the invention feature methods for metabolic network building in silico by adding/deleting membrane transport equations to identify incomplete connections in the network. The methods can be applied to one or more of a genome-scale model of a single cell, any metabolic network less than genome-scale, systems of multiple cells, cell-cell interactions, cell signaling networks, and to other regulatory networks at the DNA, RNA, protein, or metabolite level.

The methods can use information from multiple sources. In some aspects, the methods are automated methods of compiling reactions, compounds, and stoichiometric coefficients into a stoichiometric matrix.

In some aspects, the methods feature genome-scale metabolic networks resulting from the genome annotation of *Clostridium acetobutylicum* ATCC 824. Including, any metabolic network using the following metabolic connections derived for this invention: The urea cycle to complete the TCA cycle; anaerobic NAD biosynthesis involving the conversion of L-aspartate to iminoaspartate by an L-aspartate oxidase; anaerobic L-isoleucine biosynthesis involving the biosynthesis route from L-aspartate to homoserine to 2-oxobutanoate.

Also included are sets of enzymes resulting in arrested growth of *C. acetobutylicum* when disrupted by any method. This applies to all solventogenic and pathogenic clostridia containing these and homologous genes.

The inventions described and exemplified herein have utility for one or more of the following applications: to resolve metabolic networks for any organism or cell-type; to resolve metabolic networks for cases of well-established genome annotation; to incorporate new discoveries into existing genome-scale metabolic networks; and to resolve errors in biochemical reaction network databases, such as the Kyoto Encyclopedia of Genes and Genomes (KEGG). The algorithm, itself, is not only limited to metabolic networks. It can be used to elucidate any type of network involving linear or non-linear connections. The metabolic network is representative of all solventogenic clostridia. The metabolic network may be representative of all pathogenic clostridia and may be used to identify enzyme targets of next-generation antimicrobial agents. The model exists as a platform upon which regulatory rules and reactions may be applied to describe changes in cellular metabolism and differentiation through sporulation. Reactions may be added and deleted from this base-set of clostridial metabolic reactions upon discoveries in *C. acetobutylicum* or other clostridial metabolic reaction networks.

II. Specific Proton Flux States and Numerically-Determined Sub-Systems to Determine Constraints for Genome-Scale Models.

In accordance with aspects of the present invention, the model of primary metabolism was combined with other resolved metabolic pathways of macromolecular biosynthesis and cell proliferation to develop a genome-scale model for the vegetative growth phase of *C. acetobutylicum*.

Using the metabolic network of *C. acetobutylicum*, we present a genome-scale model and a constraint that originates at the endo- exo-metabolome interface and becomes further identified at the fluxome-level of regulation (Nielsen and Oliver 2005). To do this, we introduce the concept of specific proton flux states into constraints-based optimization in metabolic flux analysis. The specific proton flux state is defined by a range of allowable specific proton flux values across the cell membrane. Flux solutions located in the phenotypic solution space that conform to a specific proton flux state contain intracellular and membrane transport specific flux values that are uniquely defined. Also, using the genome-scale reconstructed metabolic network of *C. acetobutylicum*, we present a study of metabolic flux capacity using a sub-network we call a numerically-determined sub-system. We defined a sub-network in the underdetermined genome-scale stoichiometric matrix that contains a one-dimensional null space basis set. Through the assumption of various growth rates, we (i) demonstrate how numerically-determined sub-systems can further identify the phenotypic solution space around matrix singularities and (ii) determine the metabolic impact of experimentally uncharacterized physiological processes.

A pH-sensitive genome-scale model for *Clostridium acetobutylicum* ATCC 824 was developed based on its metabolic network reconstruction. To aid model convergence and limit the number of flux-vector possible solutions (the size of the phenotypic solution space), this invention consists of software encoding modeling strategies that impose a new type of constraint at the endo-exo-metabolome interface. This constraint is termed the specific proton flux state, and its use enabled accurate prediction of the extracellular medium pH during vegetative growth of batch cultures. The specific proton flux refers to the influx or efflux of free protons (per unit biomass) across the cell membrane, and a specific proton flux state encompasses a defined range of specific proton fluxes and includes all metabolic flux distributions resulting in a specific proton flux within this range. Simulation of time-course batch fermentation involved application of independent flux balance solutions based on specified ranges of discrete specific proton flux states. Using a real-coded genetic algorithm to optimize temporal bounds of specific proton flux states, we show that six separate specific proton flux states are required to model vegetative-growth metabolism of *C. acetobutylicum* and accurately predict the extracellular medium pH. Given a user-input of a reconstructed metabolic network model and experimental observations of extracellular metabolite concentrations and pH, the invention determines the number of specific proton flux states required to model the data. The invention also returns a set of constraints that can be used with the model in genome-scale modeling. This invention may interface with a method or program to perform linear programming to solve the flux balance equation.

As part of this invention, we have also developed the concept of numerically-determined sub-systems of genome-scale metabolic networks here as a sub-network with a one-dimensional null space basis set. As an example, a numerically-determined sub-system was constructed in the genome-scale metabolic network of *C. acetobutylicum* to study the flux magnitudes and directions of acetylornithine transaminase, alanine racemase, and D-alanine transaminase. These results were then used to establish additional constraints for the genome-scale model. This invention includes software to identify numerically-determined sub-systems within any metabolic network defined by the user and return a reduced set of constraints for use with the genome-scale model. The use of numerically-determined sub-systems does not require the access to a method/program for linear programming.

One aspect of the genome-scale model tools presented in this invention is to provide constraints that limit the phenotypic solution space when solving the flux balance equation, $S \cdot v = 0$, where S is the stoichiometric matrix and v is the optimized vector of specific flux values. In genome-scale models, the number of reactions commonly exceeds the number of intracellular metabolites; thus, S is not a square matrix, resulting in many possible solutions to the flux balance equation. Flux constraints are useful to limit the number of possible solutions to the flux balance equation (all possible flux vectors comprise the phenotypic solution space). The genome-scale model tool of specific proton fluxes enables constraints to be derived based on the quantity of protons exchanged with the extracellular environment, which can be calculated with the included pH model. Constraints derived from specific proton flux states were vital in modeling exponential growth of *Clostridium acetobutylicum*, in our research. Likewise, the number of specific proton flux states required to model batch exponential growth is a required parameter to use the concept of specific proton flux states. This invention uses a real-coded genetic algorithm, with user-defined data sets, to determine this number. In short, specific proton flux states are required for modeling exponential growth using a genome-scale model.

The development of numerically-determined sub-systems is an invention that will revolutionize the way many constraints are derived for a genome-scale model. Although numerically-determined sub-systems have the same objective as specific proton flux states of deriving constraints, numerically-determined subsystems perform this job by calculating metabolic capacity, which are then translated into flux constraints. Numerically-determined subsystems are also of particular use since they do not require linear programming and can determine the change in the cellular metabolic capacity given addition/subtraction of cellular reactions, metabolic pathways, or entire cellular processes.

In some aspects, the invention features methods of using the specific proton flux to limit the number of available solutions to the flux balance equation or determine parameters of a kinetic model of cellular biochemistry. The flux balance equation can also be $S \cdot v = b$, where b is the exchange fluxes of intracellular metabolites with the extracellular environment or cytoplasm or another cell. The specific proton flux can be a continuous function or a discrete function. The specific proton flux can be applied to all phases of growth. The specific proton flux can be used for batch, fed batch, and perfusion cultures. The specific proton flux can be used with homogenous or heterogeneous cultures.

In some aspects, the invention provides methods to discretize the specific proton flux state given extracellular metabolite and pH data. The algorithm can use any type of optimization scheme.

The invention further provides methods and numerically-determined sub-systems within a metabolic model to determine flux constraints or kinetic parameters of a biochemical model. For example, the methods can comprise calculating the impact on metabolism from adding or deleting any biochemical reactions, entire pathways, or cellular processes. The methods can be applied to one or more of a genome-scale model or any metabolic network, a system of one or multiple cells or metabolic networks, to cell metabolism, cell signaling and all other regulatory events, to metabolic networks, as well as networks of all other types.

Also featured are methods for identifying any and all numerically-determined sub-systems in a metabolic network, and methods for determining solutions to a numerically-determined sub-system given one or more singularities resolved by one or multiple numerically-determined sub-systems.

The inventions described and exemplified herein have utility for one or more of the following applications: The genome-scale model tools of this invention may be applied broadly for any genome-scale model of any cell-type or system. Discrete states can be formed and optimized based on any type of metabolite exchange occurring between the cell and the environment or a cell and another cell or a cell organelle and the cytoplasm or an organelle and another organelle. Specific proton flux states can be used to model growth or non-growth events in batch, fed-batch or perfusion cultures. The batch, fed-batch, or perfusion system may also exist within the cell or between multiple cells. One or multiple numerically-determined sub-systems can co-exist for any given system. The system for which numerically-determined sub-systems can be applied does not need to be metabolic or biochemical. Numerically-determined sub-systems can be used to establish relationships between fluxes within a metabolic network, which may then be used to establish regulatory relationships and those possible mechanisms.

The concept of constraining the proton flux in a genome-scale model has been published (most notably, Reed J L et al., (2003) Genome Biol., vol. 4(9): R54). However, these researchers determined the effect of proton flux across the membrane boundary on the predicted growth rate and dedicated significant effort to balancing protons within the cell. The method of Reed et al. (2003) differs significantly from this invention as this invention contains a model to predict the extracellular pH, which is used to determine the correct exchange of protons across the cell membrane. The method introduced by Reed et al. (2003) lacks this vital connection. Thus, the method of Reed et al. (2003) cannot be used to constrain reaction fluxes and develop discrete states to model exponential growth; whereas, this invention excelled at the task.

The concept of numerically-determined sub-systems is unique; although, it appears closely related to the concept of "artificial metabolites" (see Choi H S et al., (2007) J. Biotechnol. 129:696-705). The method of numerically-determined sub-systems differs from the method of artificial metabolites in that by using our method of a numerically-determined sub-system a stoichiometric matrix with only one unique null space flux vector results. This means, that numerically-determined sub-systems have a unique answer that does not require the use of linear programming. The artificial metabolites method developed by Choi et al. (2007) still required the use of linear programming, and this method produced a stoichiometric matrix that had multiple possible solutions. In addition, the method of numerically-determined sub-systems does not require the presence of a conceptual metabolite; it requires the definition of a ratio of pathway fluxes.

The benefits of the invention are that it provides two very useful tools for constraining a genome-scale model. Discrete proton flux states offer the best method (in our experience) to effectively model exponential growth of a cell-type using a genome-scale model. This is because the pH model of the invention enables the resolution of interactions between the cell and the extracellular environment. Of all the possible solutions to the flux balance equation, few were found to accurately describe these cell-to-environment interactions. Thus, this method drastically reduced the phenotypic solution space, leading to better optimum solutions upon linear programming optimization of the flux vector. No other method offers this method for reducing the phenotypic solution space, and the method of discrete proton flux states can be combined with any other methods for reducing the phenotypic solution space. Thus, this method can be applied to genome-scale models universally.

Similarly, the method of numerically-determined sub-spaces can also be applied universally to any genome-scale model. In addition, this tool also serves to dramatically reduce the size of the phenotypic solution space. This method is particularly useful as it does not require experimental data in order to develop constraints. In addition, this method can also be used to evaluate the metabolic demands of adding/subtracting pathways or metabolic processes from a cell. This is an incredibly useful feature to metabolic engineers who look to alter the capabilities of the cell. Now, they will be able to answer the question, what is the metabolic expense of adding/subtracting certain metabolic pathways.

No other genome-scale model has successfully predicted the extracellular pH. Using discrete proton flux states, this invention correctly predicted the extracellular pH while effectively predicting production of biomass, weak acids, and solvents as well as glucose utilization. In addition, this type of interface between the intracellular and extracellular environments has never before been described quantitatively using a model such as the pH model of this invention.

The method of numerically-determined sub-systems provides a method for constraining metabolic fluxes based on the capabilities of the cell. This is a new concept that is designed to eliminate the common problem of "flux cycling" within a metabolic network. This problem exists in metabolic networks where a series of reactions occur in a cycle or loop that result in the net production of ATP (for example) even though this is known not to occur in vivo. The in vivo system generally has systems like these governed by regulatory mechanisms and irreversibility that is not known to systems in silico. Numerically-determined sub-systems, on the other hand, make this distinction by separating regions of the metabolic network into energy and precursor biosynthesis and macromolecular biosynthesis. Numerically-determined sub-systems also have the capability to generate constraints based on the relationship of other fluxes in the metabolic network to one another. This is a unique concept that will eventually generate a list flux relationships important to governing cellular metabolism.

The genome-scale model tools of this invention both produce results that could not be predicted by experts in the fields of quantitative biochemistry and physiology or by experts in the field of genome-scale modeling. Determining the effects of metabolic engineering approaches on the genome-scale metabolic network cannot be conceived by the human brain, as hundreds (thousands in some cases) of reactions are impacted by altering the flux of a single reaction. The optimization of discrete states to accommodate the specific proton flux is conceivable, but the temporal limits of the discrete states to model exponential growth of a cell-type is not predictable without a simulating a genome-scale model of metabolism. Likewise, the results of numerically-determined sub-systems are not predictable without fully constructing the sub-network required of the sub-system.

The invention will now be described with reference to one or more exemplary embodiments, the accompanying Figures, and one or more Examples provided herein. FIG. 13 depicts an exemplary system 100 for constructing a metabolic network for a cell in accordance with one aspect of the present invention. The metabolic network may be a group of interrelated metabolic pathways and membrane transfer reactions for the cell. The metabolic pathways may consist of reactions for the cell. Reactions may include, for example, metabolic reactions for the cell, reactions specific to organelles or compartments of the cell, reactions occurring outside or on the surface of the cell, and reactions occurring as signaling between the cell and another cell or the cell's environment. The reactions may have components such as enzymes for controlling the reactions and reactants. As used herein, the term reactant may refer to a component of the reaction including a substrate or product of the reaction such as, for example, a metabolite. Exemplary metabolic reactants will be known to one of ordinary skill in the art from the description herein. Exemplary cells may include any anaerobic cell. In an exemplary embodiment, the cell is any suitable obligate anaerobic bacterial cell such as, for example, *Clostridium acetobutylicum*.

As a general overview, system 100 includes input device 102, processor 104, storage device 106, and output device 108. Additional details of system 100 are provided below.

Input device 102 receives input from the user and provides electronic data to processor 104. The electronic data may include, for example, metabolic network information about the cell. The metabolic network information may include information about metabolic pathways and membrane transfer reactions of the cell. The metabolic network information may be, for example, an incomplete or inaccurate metabolic network model for the cell. The electronic data may further include instructions for locating errors in the metabolic network information. The electronic data may also include experimental information for the cell for correcting errors in the metabolic network information. In an exemplary embodiment, input device 102 may be a keyboard, mouse, or other computer peripheral device capable of receiving input from an external source. A suitable input device 102 for use with the present invention will be understood by one of ordinary skill in the art from the description herein.

Processor 104 receives electronic data from input device 102. In an exemplary embodiment, processor 104 may receive electronic data from input device 102 including metabolic network information for the cell. Processor 104 may then locate errors in the metabolic data using a process of reverse engineering. Processor 104 may, for example, deconstruct the metabolic network information in order to locate errors. Processor 104 may further receive electronic data from input device 102 including experimental information for the cell. Processor 104 may use the experimental information to correct the errors in the metabolic network information. By correcting errors in the metabolic network information, processor 104 may construct a metabolic network model for the cell. Processor 104 may store electronic data received from input device 102 in storage device 106 (described below). Processor 104 may further transmit electronic data to output device 108 (described below). The electronic data stored or outputted by processor 104 may include a constructed metabolic network model. A suitable processor for use with the present invention will be understood by one of ordinary skill in the art from the description herein.

Storage device 106 stores electronic data received from processor 104. The electronic data may include, for example, metabolic network information for the cell, experimental information for the cell, or a constructed metabolic network model of the cell. A suitable storage device for use with the present invention will be understood by one of ordinary skill in the art from the description herein.

Output device 108 receives electronic data from processor 104 and outputs the data. The electronic data may include, for example, a metabolic network model of a cell. In an exemplary embodiment, output device 108 may be a display, printer, or other computer peripheral device for generating output from received electronic data. Output device 108 may further be a device for generating computer-readable media containing the electronic information received from processor 104. A suitable output device 108 for use with the present invention will be understood by one of ordinary skill in the art from the description herein.

FIG. 14 is a flow chart 200 depicting exemplary steps for constructing a metabolic network model of a cell in accordance with one aspect of the present invention. To facilitate description, the steps of FIG. 14 are described with reference to the system components of FIG. 13. It will be understood by one of ordinary skill in the art from the description herein that one or more steps may be omitted and/or different components may be utilized without departing from the spirit and scope of the present invention.

In step 202, errors in metabolic network information are identified. In an exemplary embodiment, metabolic network information is received by input device 102, and input device 102 transmits electronic data relating to the metabolic network information to processor 104. Processor 104 may then store the metabolic network information in storage device 106. The metabolic network information may include a number of metabolic pathways and membrane transfer reactions for the cell. Additionally, the metabolic network information may contain errors. In a further exemplary embodiment, the metabolic network information may be an incomplete or inaccurate metabolic network model of the cell. Errors in the metabolic network information may include gaps or inaccuracies in the metabolic network information. Metabolic network information may be incomplete by lacking, for example, metabolic pathways, membrane transfer reactions, enzymes, reactants, or metabolites for one or more metabolic reactions. A metabolic network model may be inaccurate by including, for example, incorrect metabolic pathways, incorrect membrane transfer reactions, incorrect enzymes, incorrect reactants, or incorrect metabolites for one or more metabolic reactions. Errors in the metabolic network information may additionally include multiple identity markers for the same compound, one or more compounds lacking an origin or synthesis or an origin of degradation within a database, incorrect stoichiometry of one or more metabolic reactions, or misappropriated enzymes to a particular cell type. Suitable metabolic network information will be understood by one of skill in the art from the description herein.

Processor 104 may identify errors in the metabolic network information by reverse engineering the metabolic network information. Reverse engineering, as used herein, refers to, for example, steps for deconstructing the metabolic network information into component elements in order to locate errors in the metabolic network information. The component elements of the metabolic network information may be metabolic pathways and membrane transfer reactions. The process of reverse engineering will be later described in detail with respect to FIGS. 2 and 3 and Examples 1 and 3-5. An exemplary process of reverse engineering is discussed below. However, it will be understood to one of ordinary skill in the art from the description herein that modifications and variations of these embodiments and steps that can be carried out In an exemplary embodiment, processor 104 may simulate a growth of the cell based on the metabolic network information. Processor 104 may simulate growth of the cell using a biomass constituting equation. If there is simulated growth, or growth in silico, the metabolic network information may contain no errors, in which case the metabolic network information may be a complete metabolic network model of the cell. If there is no simulated growth, then the metabolic network information may contain errors.

Processor 104 may then activate a plurality of biomass transfer equations. The plurality of biomass transfer equations may simulate a flux of biomass building-blocks into the cell including, for example, protein, DNA, RNA, lipids, cell walls, and solute pools. Processor 104 may then iteratively inactivate each of the plurality of biomass transfer equations, and check for growth in silico following the inactivation of each biomass transfer equation. If there is growth, then the corresponding biomass building-block may not be associated with any errors. If there is no simulated growth, then the metabolic network information may contain errors relating to the corresponding biomass building-block.

Processor 104 may then activate a plurality of component transfer equations, corresponding to components of the inactivated biomass transfer equation. The plurality of component transfer equations may simulate a flux of biomass building-block components into the cell. Suitable components for each of the biomass building-blocks will be known to one or ordinary skill in the art. Processor 104 may then iteratively inactivate each of the plurality of component transfer equations, each time checking for growth in silico. If there is growth, then the corresponding component may not be associated with any errors. If there is no simulated growth, then the metabolic network information may contain errors relating to the corresponding component. Processor 104 may then transmit electronic data relating to the errors in the metabolic network information to output device 108.

In step 204, a solution to the errors in the metabolic network information is determined. In an exemplary embodiment, output device 108 receives electronic data from processor 104 relating to errors identified in the metabolic network information. Output device 108 may then present the errors to a user. A user may then supply at least one solution for correcting the errors to input device 102. Input device 102 may receive at least one solution from the user and transmit the solution to processor 104. In an alternative exemplary embodiment, processor 104 may access information containing possible solutions stored on storage device 106. Processor 104 may be configured to select a solution from the information stored on storage device 106 that corresponds to the errors in the metabolic network information. Solutions for the errors in the metabolic network information may include, for example, metabolic pathways of the cell or similar cells, membrane transfer equations of the cell or similar cells, enzymes of the cell or similar cells, reactants of the cell or similar cells, or metabolites of the cell or similar cells.

In step 206, errors in the metabolic network information are corrected using the at least one solution. In an exemplary embodiment, processor 104 receives electronic data relating to a solution to an error in the metabolic network information for the cell. Processor 104 may then correct an error using the solution by, for example, substituting the solution for either the missing or incorrect metabolic network information.

In an exemplary embodiment, when processor 104 has corrected the errors in the metabolic network information, processor 104 may store the newly constructed metabolic network model in storage device 106, or may output the metabolic network model to output device 108.

Another aspect of the present invention is embodied in a computer-readable medium or media for predicting a growth of an anaerobic cell. The anaerobic cell may be any obligate anaerobic bacterial cell such as, for example, *Clostridium acetobutylicum*. As a general overview, the computer-readable medium includes a data structure, a constraint set, and a set of instructions. Features of the computer-readable medium will later be described in detail with reference to Example 13. Additional details of the computer-readable medium are provided below.

The computer-readable medium includes a data structure relating a plurality of reactants of the cell to a plurality of reactions. In an exemplary embodiment, the data structure comprises a plurality of reactions having a plurality of reaction components. The plurality of reactions may include, for example, metabolic reactions for the cell, reactions specific to organelles or compartments of the cell, reactions occurring outside or on the surface of the cell, and reactions occurring as signaling between the cell and another cell or the cell's environment. Exemplary reactants may include reaction components such as enzymes, substrates, or products of the reaction such as, for example, metabolites. The data structure may further include a stoichiometric matrix including coefficients for the plurality of reactions. The coefficients may relate the substrates of the reactions to the products of the reactions. An exemplary stoichiometric coefficient may, for example, define a rate or flux balance of the reaction. The creation of a data structure on a computer-readable medium including the above-described features will be understood by one of ordinary skill in the art from the description herein.

The computer-readable medium also includes a constraint set for the plurality of the reactions. In an exemplary embodiment, the constraint set comprises a metabolic network model for the anaerobic cell. The constraint set may define metabolic pathways and membrane transfer reactions for the cell. The metabolic pathways may further include reactions for the cell. The metabolic network model defined by the constraint set may include a set of relationships and connections between the plurality of reactants and reactions included in the data structure. For example, the constraint set may indicate how the products of one or more reactions of the cell relate to or become the substrates of one or more other reactions of the cell. The constraint set may be determined using the above-disclosed method for constructing a metabolic network for an anaerobic cell. The creation of a constraint set configured for application to a data structure will be understood by one of ordinary skill in the art by the description herein.

The computer-readable medium further includes instructions for configuring a computer to predict a growth of the anaerobic cell. In an exemplary embodiment, the computer-readable medium includes an instruction to apply the constraint set to the reactions and reactants described in the data structure. The computer-readable medium may further include instructions to simulate the growth of the cell based on the application of the constraint set to the data structure. One exemplary instruction may include activating a biomass constituting equation. A biomass constituting equation may simulate the function of the plurality of reactions of the cell according to the constraint set applied to the reactions and the reactants included in the data structure. The biomass constituting equation may then determine whether biomass is added to the cell based on the occurrence of the plurality of reactions according to the constraint set. This simulation may thereby allow for the prediction of growth of the cell based on the application of the constraint set to the data structure of the computer-readable medium. The programming of instructions on a suitable computer-readable medium will be understood by one of skill in the art.

A method of identifying a numerically-determined subsystem of a metabolic network model will now be described in accordance with another aspect of the present invention. To facilitate description, the steps of this method are described with reference to the system components of FIG. 13. This method will later be described in detail with reference to FIGS. 6, 7, 11, 12a and 12b and Examples 2, 21, and 26. It will be understood by one of ordinary skill in the art from the description herein that one or more steps may be omitted and/or different components may be utilized without departing from the spirit and scope of the present invention.

First, metabolic reactions are extracted from a metabolic network model. In an exemplary embodiment, processor 104 receives electronic data from input device 102 or storage device 103. The electronic data contains a metabolic network model for a cell. The metabolic network model may include a first stoichiometric matrix. This first stoichiometric matrix may define a set of constraints for all of the metabolic pathways of the cell. The first matrix may further define a set of relations between substrates and the products for all of the reactions of the cell. The first stoichiometric matrix of the metabolic network model may include one or more singularities arising from the reactions defined by the matrix. Processor 104 may extract from the matrix one or more reactions corresponding to a singularity of the matrix.

A second stoichiometric matrix is then generated. In an exemplary embodiment, processor 104 generates a second stoichiometric matrix using the extracted reactions. The second stoichiometric matrix may define a set of relations for the reactions relating to the one or more singularities. Generation of a suitable stoichiometric matrix using the one or more reactions will be understood by one of ordinary skill in the art.

At least one arbitrary flux ratio is then provided. In an exemplary embodiment, a flux ratio across a boundary of the singularity is assumed. The flux ratio may relate at least two components of the extracted reactions to each other. The arbitrary flux ratio may correspond to a flux of components to or from a metabolic reaction or pathway of the cell. The assumed flux may alternately correspond to a specific growth rate of the cell for genome-scale metabolic network models.

Processor 104 then uses the arbitrary flux ratio to supplement the generated second stoichiometric matrix.

A numeric solution to the second stoichiometric matrix is then calculated. In an exemplary embodiment, processor 104 solves the second stoichiometric matrix. Processor 104 may use the arbitrary flux ratio provided in order to obtain a numeric solution to the second stoichiometric matrix. The numeric solution of the second stoichiometric matrix may define a subsystem of the metabolic network model for the cell.

Another method of optimizing a metabolic network model for a cell will now be described in accordance with yet another aspect of the present invention. To facilitate description, the steps of this method are described with reference to the system components of FIG. 13. Exemplary steps of this method will later be described in detail with reference to FIGS. 5-9 and Examples 14-17 and 22-23. It will be understood by one of ordinary skill in the art from the description herein that one or more steps may be omitted and/or different components may be utilized without departing from the spirit and scope of the present invention.

First, a metabolic network model for a cell is obtained. In an exemplary embodiment, the model may be obtained using system 100 pursuant to the steps described above with respect to FIGS. 13 and 14.

The pH of the extracellular environment and the number of protons the cell can exchange with the extracellular environment is then determined. FIG. 15 depicts an exemplary flow chart of steps for integrating the determination of the extracellular pH with the optimization of a genome-scale metabolic network model. In an exemplary embodiment, processor 104 may determine the extracellular pH of the cell. Processor 104 may calculate an extracellular pH directly, as will be understood by one of skill in the art. As shown in FIG. 15, processor 104 may then calculate the number of protons the cell can exchange with the extracellular environment. This proton flux may be calculated based on the extracellular pH of the cell and one or more membrane transport reactions contained in the metabolic network information. Appropriate membrane transport reactions for determining the proton flux may have reactants or products including protons which are taken from or provided to the extracellular environment.

The metabolic network model is then optimized. In an exemplary embodiment, processor 104 optimizes the metabolic network model based on the pH of the extracellular environment and the number of protons the cell can exchange with the extracellular environment. As shown in FIG. 15, processor 104 may optimize the metabolic network model by limiting a number of solutions to the flux balancing equation, as will later be described in detail. The limitation of a number of solutions to the flux balancing equation may increase the ability of the metabolic network model to predict the activity within the cell.

One or more of the steps of the methods described above may be embodied in computer-executable instructions stored on a computer-readable storage medium. The computer-readable storage medium may be essentially any tangible storage medium capable of storing instructions for performance by a general or specific purpose computer such as an optical disc, magnetic disk, or solid state device, for example.

The following Examples are provided to describe the invention in greater detail. They are intended to illustrate, not to limit, the invention.

EXAMPLE 1

Genome-Scale Metabolic Network Reconstruction for *C. acetobutylicum*

The genome-scale metabolic model for *C. acetobutylicum* was derived from mass balances given all known or predicted intracellular metabolic and membrane transport reactions as well as empirical relations for biomass composition. The pseudo-steady state assumption was assumed for all mass balances, resulting in a system of linear equations (Edwards et al. 1999; Papoutsakis 1984). Prediction of metabolic reactions or transport processes were based on the annotated genome (Nolling et al. 2001) in conjunction with accumulated physiological data. The reconstruction of the metabolic network and integration of these pathways to simulate cell growth in silico was divided into the following separate processes: (i) building metabolic pathways and membrane transport reactions based on genomic annotation, enzyme homology and experimental observations; (ii) developing biomass constituting equations based on physiological data; and (iii) identifying incomplete metabolic pathways and missing metabolite membrane transport reactions through semi-automated reverse engineering of the metabolic network. These three model-building processes are discussed in detail below and were used iteratively to generate a genome-scale model of *C. acetobutylicum* capable of cell growth in silico.

Figure 1:
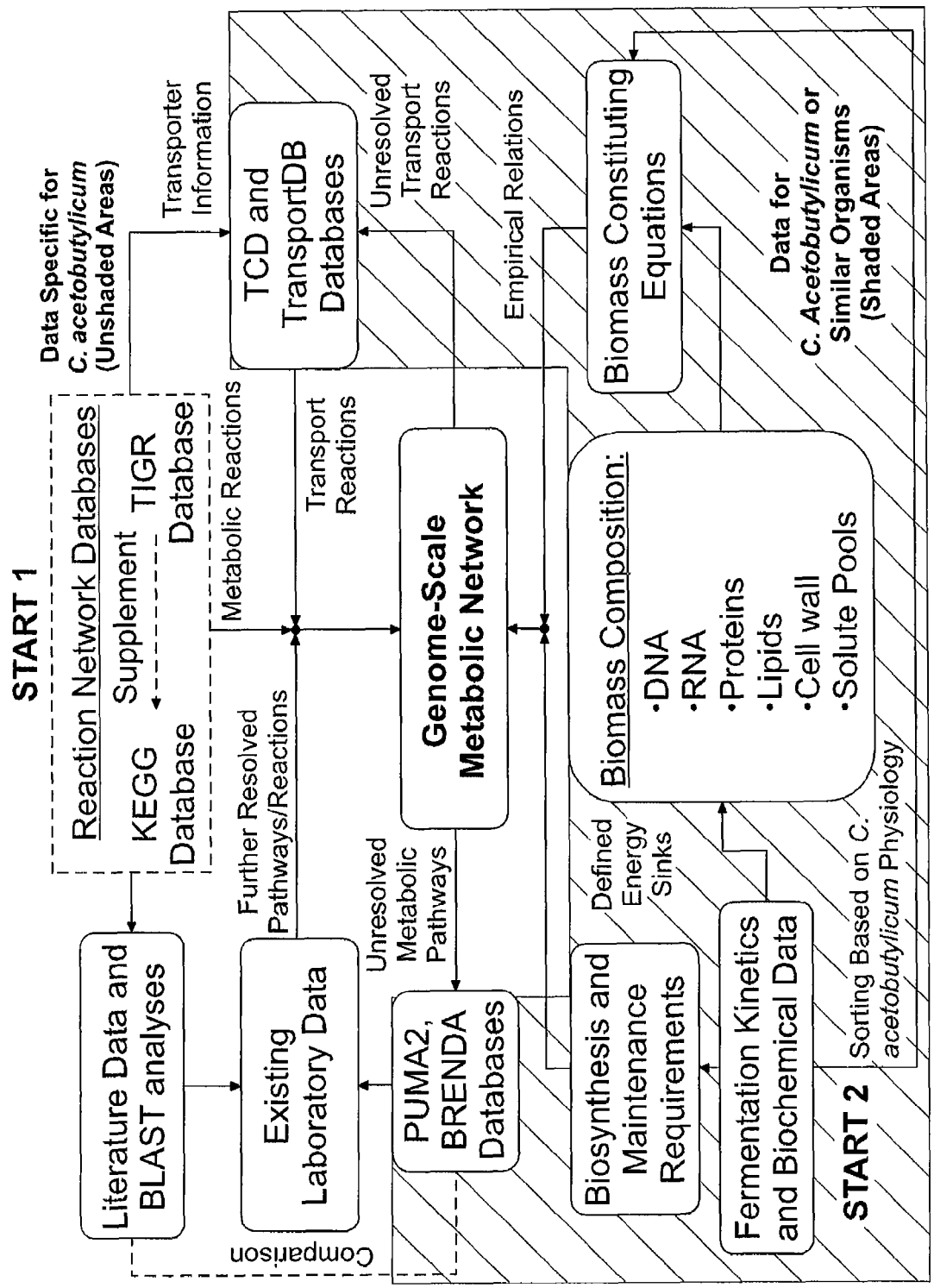
FIG. 1 shows a flow diagram of iterative construction of the genome-scale metabolic network. The un-shaded (white) background corresponds to data obtained from resources specific to *C. acetobutylicum*. Elements of the flow diagram located in shaded (dark grey) background regions represent data compiled from resources specific to *C. acetobutylicum* and supplemented with information obtained from organisms similar to *C. acetobutylicum*, namely: other clostridia, *B. subtilis*, *S. aureus* and *E. coli*.
Figure 2:
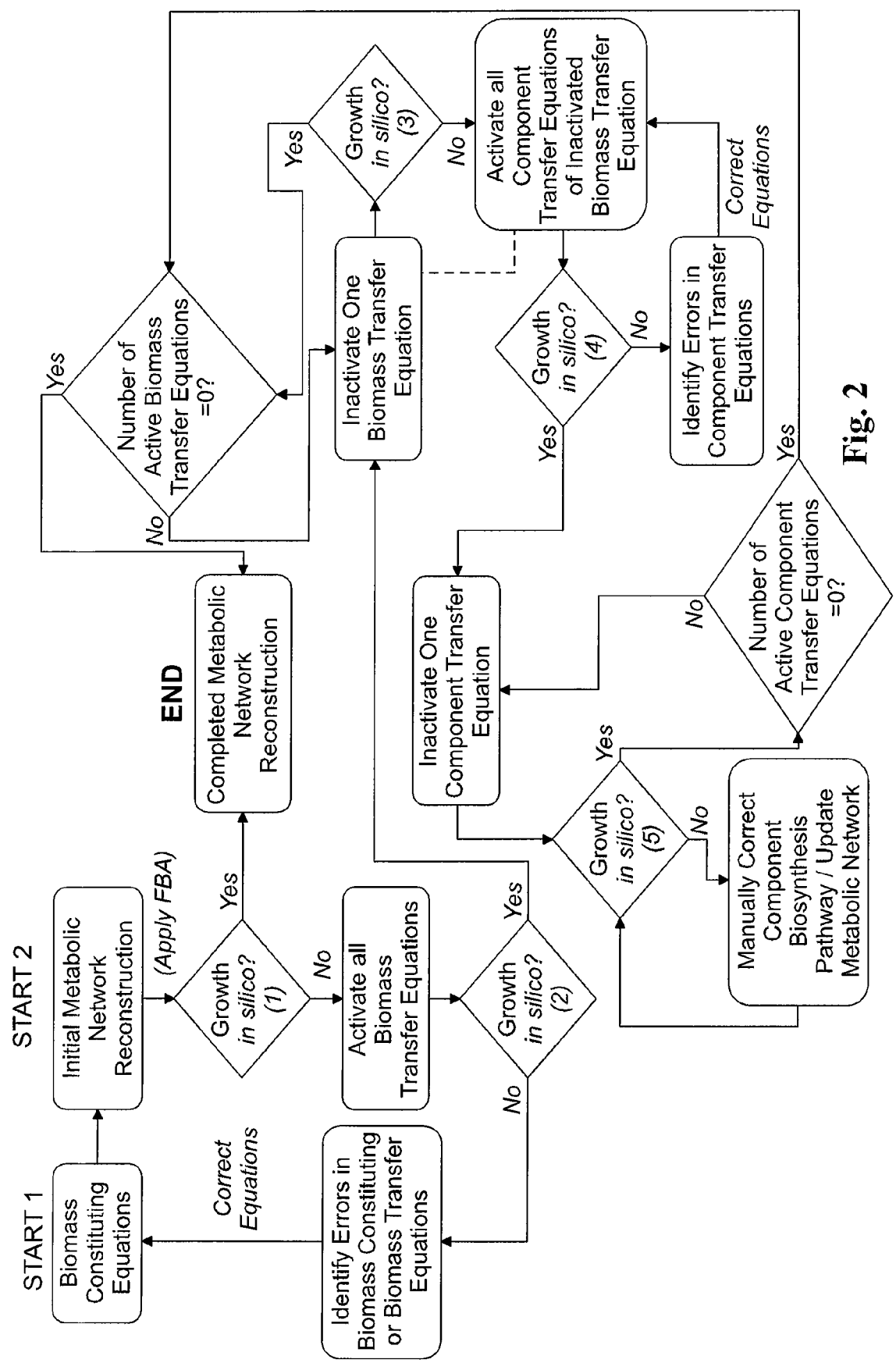
FIG. 2 shows a flow-diagram for reverse engineering of a metabolic network reconstruction. Complete lists of biomass transfer equations and component transfer equations are presented in Table 5.

The genome-scale metabolic network for *C. acetobutylicum* was constructed using the iterative methods of pathway construction shown in FIG. 1 and the reverse engineering algorithm of FIG. 2. Based on information currently available, it is believed that the network comprises at least 422 metabolites involved in at least 552 reactions, including at least 80 metabolite transport reactions across the cell membrane. The number of metabolites, reactions, and metabolite transport reactions may increase as resolution of the network progresses.

Simulation of the genome-scale model produced a positive specific growth rate for the wild-type genome with the complete set of transporter reactions. The buk gene knock-out mutant (Green and Bennett 1998; Harris et al. 2000) was simulated by restricting flux through the butyrate kinase enzyme (Buk, EC 2.7.2.7, CAC3075) to zero using constraints. In addition, the pSOL1 mega-plasmid degenerate M5 strain (Tomas et al. 2003) was simulated by restricting flux through enzymes encoded by mega-plasmid genes. These reactions are specifically labeled in Table 3. The qualitative results of these simulations are given in Table 1. Resulting specific growth rates of these simulation studies did not match experimental observations due to the lack of regulatory mechanisms and large number of reversible reactions in this initial version of the genome-scale model. We further investigated the capabilities of the genome-scale model to simulate growth on the published minimal medium formulation for *C. acetobutylicum* (Monot et al. 1982) and a glycerol-containing synthetic medium (Vasconcelos et al. 1994). These results are also summarized in Table 1. In all cases, growth in silico was successful without adding further additional transport equations to provide metabolites or macromolecules not adequately synthesized or effectively degraded by the metabolic network. In addition, observed phenotypes of knock-out strains were obtained in silico, suggesting that the network is complete and represents *C. acetobutylicum* metabolism, The number of reactions in the reconstructed metabolic network used to represent specified metabolic functions is shown in Table 2. This table also provides statistics that relate the completed metabolic network to the genomic annotation used to reconstruct it.

Figure 3:
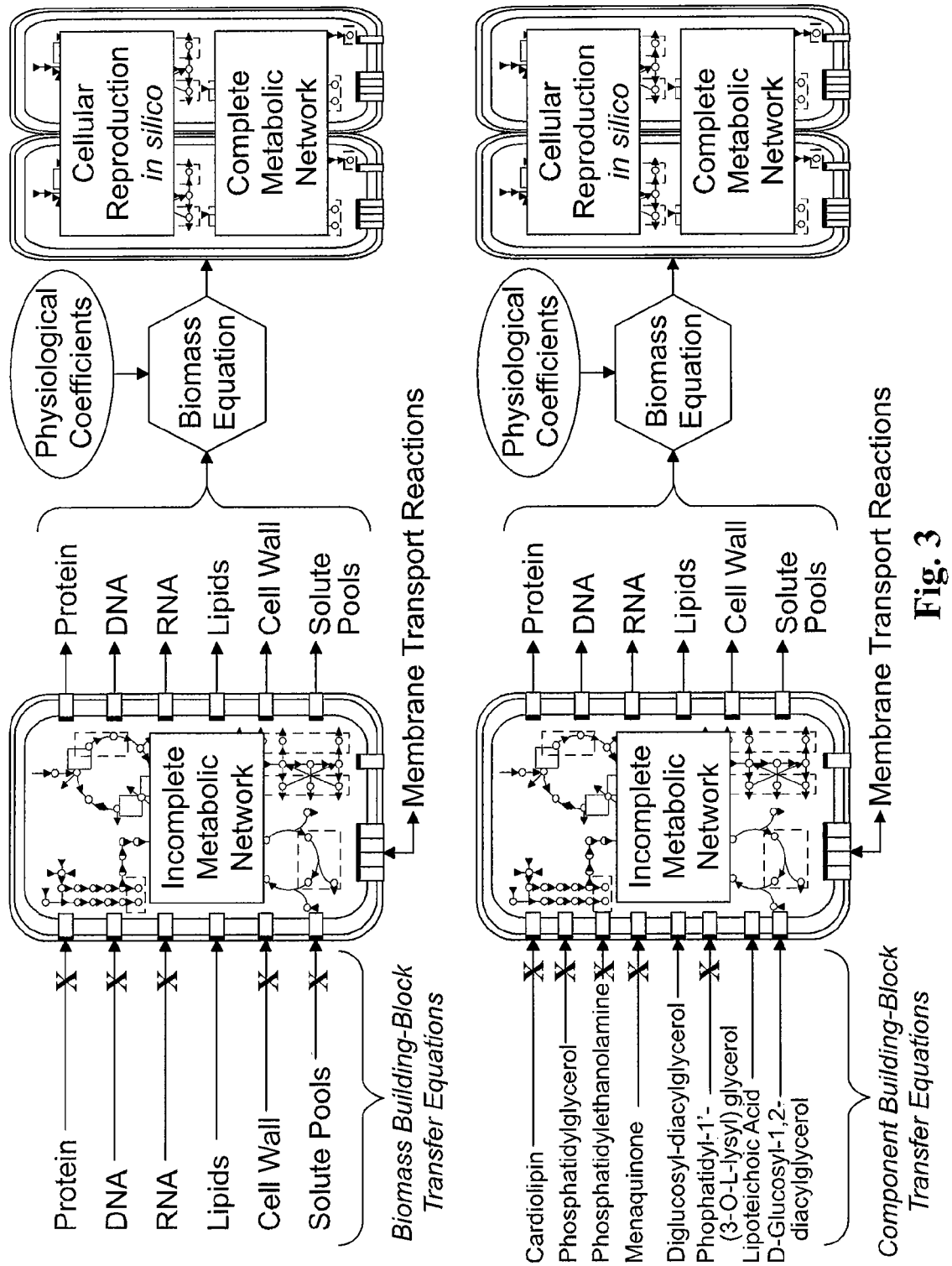
FIG. 3 shows reverse engineering of metabolic network completion through the inclusion of additional biomass building-block transfer reactions. The procedure initiated with an incomplete metabolic network (incapable of producing biomass). All components of the biomass constituting equation were imported (called building-block transfer equations). One-by-one, building-block transfer equations were eliminated until those required for in silico biomass growth were located. Then, transfer equations of generalized biomass building-blocks were evaluated in order to identify specific regions of the metabolic network impeding biomass growth. The following example is shown for a case in which deficiencies in lipoteichoic acid, diglucosyl-diacylglycerol and D-glucosyl-1,2-diacylglycerol biosynthesis pathways in the metabolic network impeded biosynthesis of the lipids block of the biomass constituting equation, resulting in impeded growth. This procedure was developed to quickly locate incomplete metabolic pathways (e.g., from missing or unidentified enzymes) in the metabolic network.

An example of one iteration of the semi-automated reverse engineering process for completing the genome-scale metabolic network is shown in FIG. 3, whereby deficient lipid biosynthesis of lipoteichoic acid, diglucosyl diacylglycerol and D-glucosyl-1,2-diacylglycerol were found responsible for arresting cell growth when the metabolic flux profile was optimized. The metabolic pathways for these precursors were investigated and manually rectified. Employing the reverse engineering procedure iteratively was necessary for identifying and correcting these growth-preventing errors in the metabolic network. Application of the reverse engineering algorithm of FIG. 2 to an initial draft of the *C. acetobutylicum* metabolic network largely created from the KEGG database, revealed reaction network discrepancies beyond simply missing enzymes. These discrepancies are shown as Table 4 and include a list of aerobic reactions annotated in KEGG to belong to *C. acetobutylicum*, a strict anaerobe.

TABLE 1

In silico growth results of *C. acetobutylicum* genome-scale model given genetic and environmental manipulations.

| in silico Strain | Medium | Additional Transport Reactions Required | Comment | Growth in silico? |
|---|---|---|---|---|
| Wild-type[1] | Complex[4] | None | Acidogenic and solventogenic | Yes |
| Wild-type[1] | Minimal[5] | None | Acidogenic and solventogenic | Yes |
| Wild-type[1] | Synthetic[6] | None | Acidogenic and solventogenic | Yes |
| buk knock-out[2] | Minimal[5] | None | No production of butyrate | Yes |
| M5[3] | Minimal[5] | None | No production of acetone or butanol; decreased ethanol production | Yes |

[1]The wild-type in silico strain contains all reactions and constraints as listed in the metabolic network in Table 3.
[2]The buk knock-out in silico strain was created by constraining the reaction catalyzed by the butyrate kinase (Buk, EC 2.7.2.7, CAC3075) to zero.
[3]The M5 in silico strain was created by constraining reactions only catalyzed by megaplasmid genes to zero. Megaplasmid genes contain locus number beginning with the CAP prefix.
[4]We simulated a complex medium by leaving all membrane transport reactions unconstrained.
[5]A minimal medium (Monot et al. 1982) was simulated by constraining all membrane transport reactions of Table 3 to zero except those given the label Minimal.
[6]The synthetic medium (Vasconcelos et al. 1994) is similar to the minimal medium except that it contains glycerol and ammonium chloride replaced ammonium acetate. The membrane transport reactions needed in addition to the Minimal transport reactions to support this medium are labeled Synthetic in Table 3.

TABLE 2

Summary of the metabolic network reconstructed for *C. acetobutylicum*.

| | |
|---|---|
| Total number of protein-encoding genes in *C. acetobutylicum* genome (including pSOL1 megaplasmid) | 3748 (including 176 from pSOL1) |
| Number of protein-encoding genes with role in reconstructed metabolic network | 474 (12.6% of protein-encoding genes) |
| Number of enzyme-encoding genes excluded from the metabolic network | 366 (9.77% of protein-encoding genes) |
| DNA polymerases | 31 |
| tRNA ligases | 46 |
| Number of genes associated with uncharacterized membrane transporters | 242 (6.46% of protein-encoding genes) |
| Number of intracellular metabolites | 422 |
| Number of reactions (non-redundant)[1] | 552 |
| Carbohydrate metabolism | 125 (28) |
| Energy metabolism | 11 (3) |
| Lipid metabolism | 46 (22) |
| Nucleotide metabolism | 82 (14) |
| Amino acids metabolism | 125 (13) |
| Metabolism of cofactors and vitamins | 76 (24) |
| Membrane transport | 80 (20) |
| Biomass and maintenance | 20 (20) |
| Number of irreversible metabolic reactions (excluding biomass equations and membrane transporters) | 26 |

[1]Some reactions are included in more than one classification and some classifications are not included in this table. Numbers in parentheses represent the number of reactions in the pathway not currently assigned to a specific gene. These reactions were constructed from pathway completion methods given physiological data of *C. acetobutylicum*.

TABLE 3

The complete genome-scale metabolic network with gene identification where available. The stoichiometric coefficients of the biomass constituting equation are represented as variables since these values have been observed to change with growth stage-related cellular physiology.

| Locus Number | Reaction |
|---|---|
| CAC3169/ CAC3176/ CAC3652 | 2-Acetolactate + CO2 <=> 2 Pyruvate |
| N/A | 2 Glyoxylate <=> 2-Hydroxy-3-oxopropanoate + CO2 |
| CAC3169/ CAC3176/ CAC3652/ CAP0025 | 2-(alpha-Hydroxyethyl)thiamine diphosphate + CO2 <=> Thiamin diphosphate + Pyruvate |
| N/A | Maltose + H2O <=> 2 alpha-D-Glucose |
| CAC0591/ CAC0593 | 2 6,7-Dimethyl-8-(1-D-ribityl)lumazine <=> Riboflavin + 4-(1-D-Ribitylamino)-5-amino-2,6-dihydroxypyrimidine |
| N/A | NAD+ + H2O <=> AMP + Nicotinamide D-ribonueleotide |
| CAC2075 | ATP + NAD+ <=> ADP + NADP+ |
| CAC0764/ CAC1673/ CAC1674 | 2 L-Glutamate + NADP+ <=> L-Glutamine + 2-Oxoglutarate + NADPH + H+ |
| N/A | NADP+ + H2O <=> Orthophosphate + NAD+ |
| CAC3112 | ATP + AMP <=> 2 ADP |
| CAC1099 | ATP + Dephospho-CoA <=> ADP + CoA |
| N/A | Urea + H2O <=> CO2 + 2 NH3 |
| CAC1262 | ATP + Nicotinamide D-ribonueleotide <=> Pyrophosphate + NAD+ |
| N/A | ATP + NH3 + CO2 <=> ADP + Carbamoyl phosphate |

TABLE 3-continued

The complete genome-scale metabolic network with gene identification where available. The stoichiometric coefficients of the biomass constituting equation are represented as variables since these values have been observed to change with growth stage-related cellular physiology.

| Locus Number | Reaction |
|---|---|
| N/A | ATP + UDP <=> ADP + UTP |
| CAC1848 | ATP + UMP <=> ADP + UDP |
| CAC1806 | ATP + FMN <=> Pyrophosphate + FAD |
| CAC2856 | Orthophosphate + Pyrophosphate + S-Adenosyl-L-Methionine <=> ATP + $H_2O$ + L-Methionine |
| N/A | Adenosine 3',5'-bisphosphate + $H_2O$ <=> AMP + Orthophosphate |
| CAC2275/ CAC3203 | AMP + Pyrophosphate <=> Adenine + 5-Phospho-alpha-D-ribose 1-diphosphate |
| N/A | S-Adenosyl-L-Homocysteine + $H_2O$ <=> Adenosine + L-Homocyseine |
| CAC2117 | S-Adenosyl-L-Homocysteine + $H_2O$ <=> S-Ribosyl-L-Homocysteine + Adenine |
| CAC0534 | ATP + Pyruvate + $H_2O$ <=> AMP + Phosphoenolpyruvate + Orthophosphate |
| CAC0518/ CAC1036 | ATP + Pyruvate <=> ADP + Phosphoenolpyruvate |
| CAC1589/ CAC1596 | (S)-Malate + NAD+ <=> Pyruvate + $CO_2$ + NADH |
| CAC1589/ CAC1596 | (S)-Malate + NADP+ <=> Pyruvate + $CO_2$ + NADPH |
| CAC0673/ CAC0674 | L-Serine <=> Pyruvate + $NH_3$ |
| CAP0035/ CAP0162 | Acetaldehyde + CoA + NAD+ <=> Acetyl-CoA + NADH |
| CAC1742 | Acetyl-CoA + Orthophosphate <=> CoA + Acetyl phosphate |
| N/A | Oxaloacetate + Acetyl CoA + ADP + Orthophoshpate <=> Citrate + ATP + CoA |
| CAC2873/ CAP0078 | 2 Acetyl-CoA <=> CoA + Acetoacetyl-CoA |
| CAC3253 | ATP + L-Glutamate <=> ADP + L-Glutamyl 5-phosphate |
| CAC0737 | L-Glutamate + NADP+ + $H_2O$ <=> 2-Oxoglutarate + $NH_3$ + NADPH + H+ |
| CAC2658 | ATP + L-Glutamate + $NH_3$ <=> ADP + Orthophosphate + L-Glutamine |
| CAC1050/ CAC1782 | ATP + Deamino-NAD+ + L-Glutamine + $H_2O$ <=> AMP + Pyrophosphate + NAD+ + L-Glutamate |
| CAC2391/ CAC3020 | Acetyl-CoA + L-Glutamate <=> CoA + N-Acetyl-L-glutamate |
| CAC3250 | L-Glutamate <=> D-Glutamate |
| CAC2250/ CAC2335 | UTP + D-Glucose 1-phosphate <=> Pyrophosphate + UDPglucose |
| CAC0794/ CAC1429/ CAC2334/ CAC2960 | UDP-D-galactose <=> UDPglucose |
| CAC1743 | ATP + Acetate <=> ADP + Acetyl phosphate |
| CAC2830 | Acetyl phosphate + $H_2O$ <=> Acetate + Orthophosphate |
| CAC1718 | ATP + GMP <=> ADP + GDP |
| CAC0566 | (S)-Malate + NAD+ <=> Oxaloacetate + NADH + H+ |
| CAC2660 | ATP + Pyruvate + $HCO_3-$ <=> ADP + Orthophosphate + Oxaloacetate |
| CAC1001/ CAC1819/ CAC2832 | L-Aspartate + 2-Oxoglutarate <=> Oxaloacetate + L-Glutamate |
| CAC0492/ CAC3331 | L-Alanine <=> D-Alanine |
| N/A | Succinate + ATP + CoA <=> Succinyl CoA + ADP + Orthophosphate |
| CAC3222 | UTP + N-Acetyl-D-glucosamine 1-phosphate <=> Pyrophosphate + UDP-N-acetyl-D-glucosamine |
| CAC0592 | GTP + 3 $H_2O$ <=> Formate + 2,5-Diamino-6-hydroxy-4-(5'-phosphoribosylamino)-pyrimidine + Pyrophosphate |
| CAC3626 | GTP + $H_2O$ <=> Formamidopyrimidine nucleoside triphosphate |
| CAC0518/ CAC1036 | GTP + Pyruvate <=> GDP + Phosphoenolpyruvate |
| CAC0608 | meso-2,6-Diaminoheptanedioate <=> L-Lysine + $CO_2$ |
| N/A | (S)-Malate + CoA <=> Acetyl-CoA + $H_2O$ + Glycoxylate |
| CAC0278/ CAC1810 | ATP + L-Aspartate <=> ADP + 4-Phospho-L-aspartate |
| N/A | ATP + L-Aspartate + $NH_3$ <=> AMP + Pyrophosphate + L-Asparagine |
| CAC1714 | L-Asparagine + $H_2O$ <=> L-Aspartate + $NH_3$ |
| CAC2916 | L-Aspartate <=> beta-Alanine + $CO_2$ |
| CAC0274/ CAC1652 | Fumarate + $NH_3$ <=> L-Aspartate |
| CAC2844/ CAC2961 | UTP + alpha-D-Galactose 1-phosphate <=> Pyrophosphate + UDP-D-galactose |

TABLE 3-continued

The complete genome-scale metabolic network with gene identification where available. The stoichiometric coefficients of the biomass constituting equation are represented as variables since these values have been observed to change with growth stage-related cellular physiology.

| Locus Number | Reaction |
|---|---|
| CAC0103/ CAC0110 | ATP + Adenylylsulfate <=> ADP + 3'-Phosphoadenylyl sulfate |
| CAC1848 | ATP + CMP <=> ADP + CDP |
| CAC0672 | ATP + Cytidine <=> ADP + CMP |
| CAC0672 | UTP + Cytidine <=> UDP + CMP |
| CAC0672 | GTP + Cytidine <=> GDP + CMP |
| N/A | Formate + NAD+ <=> H+ + CO2 + NADH |
| N/A | Formamide + H2O <=> Formate + NH3 |
| CAC0109/ CAC0110 | ATP + Sulfate <=> Pyrophosphate + Adenylylsulfate |
| CAC1806 | ATP + Riboflavin <=> ADP + FMN |
| CAC1054 | L-Arginine + H2O <=> L-Ornithine + Urea |
| CAC0025 | CTP + H2O <=> UTP + NH3 |
| N/A | ATP + CDP <=> ADP + CTP |
| CAC2892 | ATP + UTP + L-Glutamine + H2O <=> ADP + Orthophosphate + CTP + L-Glutamate |
| CAC2644/ CAC2645 | 2 ATP + L-Glutamine + HCO3− + H2O <=> 2 ADP + Orthophosphate + L-Glutamate + Carbamoyl phosphate |
| CAC2243 | ATP + L-Aspartate + L-Glutamine + H2O <=> AMP + Pyrophosphate + L-Asparagine + L-Glutamate |
| N/A | O-Phospho-L-serine + H2O <=> L-Serine + Orthophosphate |
| CAC0687 | L-Serine + Acetyl-CoA <=> O-Acetyl-L-serine + CoA |
| N/A | ATP + Thiamin monophosphate <=> ADP + Thiamin diphosphate |
| N/A | ATP + Thiamin <=> AMP + Thiamin diphosphate |
| CAC3348 | S-Adenosyl-L-Methionine + L-Homocysteine <=> S-Adenosyl-L-Homocyseine + L-Methionine |
| CAC0713 | 2-Phospho-D-glycerate <=> Phosphoenolpyruvate + H2O |
| CAC2862/ CAC3539 | Phosphoenolpyruvate + UDP-N-acetyl-D-glucosamine <=> UDP-N-acetyl-3-(1-carboxyvinyl)-D-glucosamine + Orthophosphate |
| N/A | L-Ornithine + 2-Oxoglutarate <=> L-Glutamate 5-semialdehyde + L-Glutamate |
| CAC3157/ CAC3158 | L-Serine + Indole <=> L-Tryptophan + H2O |
| CAC1001/ CAC1819/ CAC2832/ CAC1369/ CAC3031 | Phenylpyruvate + L-Glutamate <=> L-Phenylalanine + 2-Oxoglutarate |
| CAC0267/ CAC3552 | (S)-Lactate + NAD+ <=> Pyruvate + NADH + H+ |
| CAC1543/ CAC2691 | (R)-Lactate + NAD+ <=> Pyruvate + NADH + H+ |
| CAC0972 | Isocitrate + NAD+ <=> 2-Oxoglutarate + CO2 + NADH + H+ |
| CAC2945 | Glycolate + NAD+ <=> Glyoxylate + NADH + H+ |
| CAC1001/ CAC1819/ CAC2832/ CAC1369/ CAC3031 | 3-(4-Hydroxyphenyl)pyruvate + L-Glutamate <=> L-Tyrosine + 2-Oxoglutarate |
| CAC3568/ CAC3569/ CAC3570 | ADP + Orthophosphate + Malonyl-CoA <=> ATP + Acetyl-CoA + HCO3− |
| CAC3420 | L-Threonine <=> Glycine + Acetaldehyde |
| CAC3375/ CAP0035/ CAP0162 | Ethanol + NAD+ <=> Acetaldehyde + NADH + H+ |
| CAP0025 | Acetaldehyde + Thiamin diphosphate <=> 2-(alpha-Hydroxyethyl)thiamine diphosphate |
| CAC1088/ CAC1572 | D-Fructose 1,6-bisphosphate + H2O <=> D-Fructose 6-phosphate + Orthophosphate |
| CAC0187 | D-Glucosamine 6-phosphate + H2O <=> D-Fructose 6-phosphate + NH3 |
| CAC0158 | L-Glutamine + D-Fructose 6-phosphate <=> L-Glutamate + D-Glucosamine 6-phosphate |
| CAC0391 | L-Cysteine + H2O <=> Hydrogen sulfide + Pyruvate + NH3 |
| CAC0094 | NH3 + 2 H2O + 6 Oxidized ferredoxin <=> Nitrite + 6 Reduced ferredoxin + 7 H+ |
| N/A | Nitrite + H20 + 2 Oxidized ferredoxin <=> Nitrate + 2 Reduced ferredoxin |
| CAC0425 | Sucrose + H2O <=> beta-D-Fructose + alpha-D-Glucose |
| N/A | Sucrose 6-phosphate + H2O <=> Sucrose + Orthophosphate |
| CAC0533 | H2O + alpha,alpha'-Trehalose 6-phosphate <=> D-Glucose + alpha-D-Glucose 6-phosphate |

TABLE 3-continued

The complete genome-scale metabolic network with gene identification where available. The stoichiometric coefficients of the biomass constituting equation are represented as variables since these values have been observed to change with growth stage-related cellular physiology.

| Locus Number | Reaction |
| --- | --- |
| CAC0533 | H2O + Maltose 6'-phosphate <=> D-Glucose + alpha-D-Glucose 6-phosphate |
| CAC1712 | sn-Glycerol 3-phosphate + NAD+ <=> Glycerone phosphate + NADH + H+ |
| CAC1712 | sn-Glycerol 3-phosphate + NADP+ <=> Glycerone phosphate + NADPH + H+ |
| CAC1321 | ATP + Glycerol <=> ADP + sn-Glycerol 3-phosphate |
| CAC1322 | sn-Glycerol 3-phosphate + FAD <=> Glycerone phosphate + FADH2 |
| N/A | sn-Glycerol 3-phosphate + Acyl-CoA <=> 1-Acyl-sn-glycerol 3-phosphate + CoA |
| N/A | CDP-Glycerol + H2O <=> CMP + sn-Glycerol 3-phosphate |
| N/A | CTP + sn-Glycerol 3-phosphate <=> Pyrophosphate + CDP-Glycerol |
| N/A | Hydrogen sulfide + 3 NADP+ + 3 H2O <=> Sulfite + 3 NADPH |
| CAC2968/ CAC3058/ CAC3072 | Orthophosphate + GDPmannose <=> GDP + D-Mannose 1-phosphate |
| CAC2981/ CAC3056 | GTP + D-Mannose 1-phosphate <=> Pyrophosphate + GDPmannose |
| CAC0931/ CAC2235 | O-Acetyl-L-serine + Hydrogen sulfide <=> L-Cysteine + Acetate |
| CAC0368/ CAC1427 | beta-Alanine + 2-Oxoglutarate <=> 3-Oxopropanoate + L-Glutamate |
| CAC3004 | Tetrahydrofolate + NAD+ <=> Dihydrofolate + NADH + H+ |
| CAC3004 | Tetrahydrofolate + NAD+ <=> Folate + NADH |
| CAC3004 | Tetrahydrofolate + NADP+ <=> Dihydrofolate + NADPH + H+ |
| CAC3004 | Tetrahydrofolate + NADP+ <=> Folate + NADPH |
| CAC2083/ CAC3201 | Tetrahydrofolate + Formate + ATP <=> ADP + Orthophosphate + 10-Formyltetrahydrofolate |
| CAC2264 | 5,10-Methylenetetrahydrofolate + Glycine + H2O <=> Tetrahydrofolate + L-Serine |
| CAC0578 | 5-Methyltetrahydrofolate + L-Homocysteine <=> Tetrahydrofolate + L-Methionine |
| CAC2237/ CAC2238 | D-Glucose 1-phosphate + ATP <=> ADPglucose + Pyrophosphate |
| CAC0484 | D-Glucose 1-phosphate <=> alpha-D-Glucose 6-phosphate |
| CAC0672 | ATP + Uridine <=> ADP + UMP |
| CAC2652 | Orotidine 5'-phosphate <=> UMP + CO2 |
| CAC2113/ CAC2879 | Uracil + 5-Phospho-alpha-D-ribose 1-diphosphate <=> UMP + Pyrophosphate |
| CAC0672 | UTP + Uridine <=> UDP + UMP |
| CAC0672 | GTP + Uridine <=> GDP + UMP |
| N/A | Cytosine + H2O <=> Uracil + NH3 |
| CAC3162/ CAC3163 | Chorismate + NH3 <=> Anthranilate + Pyruvate + H2O |
| CAC3162/ CAC3163 | Chorismate + L-Glutamine <=> Anthranilate + Pyruvate + L-Glutamate |
| CAC0390/ CAC0930 | O-Succinyl-L-homoserine + H2O <=> 2-Oxobutanoate + Succinate + NH3 |
| CAC0711 | (2R)-2-Hydroxy-3-(phosphonooxy)-propanal <=> Glycerone phosphate |
| CAC1604 | Glycerone phosphate <=> Methylglyoxal + Orthophosphate |
| CAC3375/ CAP0035/ CAP0162 | Glycerol + NAD+ <=> D-Glyceraldehyde + NADH + H+ |
| CAC3375/ CAP0035/ CAP0162 | Glycerol + NADP+ <=> D-Glyceraldehyde + NADPH + H+ |
| CAC0819/ CAC3221 | ATP + D-Ribose 5-phosphate <=> AMP + 5-Phospho-alpha-D-ribose 1-diphosphate |
| N/A | ATP + D-Ribose <=> ADP + D-Ribose 5-phosphate |
| CAC0726/ CAC1431/ CAC2880 | D-Ribose 5-phosphate <=> D-Ribulose 5-phosphate |
| CAC0709 | (2R)-2-Hydroxy-3-(phosphonooxy)-propanal + Orthophosphate + NAD+ <=> 3-Phospho-D-glyceroyl phosphate + NADH + H+ |
| CAC1545 | 2-Deoxy-D-ribose 5-phosphate <=> (2R)-2-Hydroxy-3-(phosphonooxy)-propanal + Acetaldehyde |
| CAC0944/ CAC1348 | D-Fructose 6-phosphate + (2R)-2-Hydroxy-3-(phosphonooxy)-propanal <=> D-Erythrose 4-phosphate + D-Xylulose 5-phosphate |
| N/A | D-Tagatose 1,6-bisphosphate <=> Glycerone phosphate + (2R)-2-Hydroxy-3-(phosphonooxy)-propanal |
| CAC0827/ CAP0064 | beta-D-Fructose 1,6-bisphosphate <=> Glycerone phosphate + (2R)-2-Hydroxy-3-(phosphonooxy)-propanal |

TABLE 3-continued

The complete genome-scale metabolic network with gene identification where available. The stoichiometric coefficients of the biomass constituting equation are represented as variables since these values have been observed to change with growth stage-related cellular physiology.

| Locus Number | Reaction |
|---|---|
| CAC0936 | Phosphoribosyl-ATP + Pyrophosphate <=> ATP + 5-Phospho-alpha-D-ribose 1-diphosphate |
| CAC1392 | 5-Phosphoribosylamine + Pyrophosphate + L-Glutamate <=> L-Glutamine + 5-Phospho-alpha-D-ribose 1-diphosphate + H2O |
| CAC3161 | Anthranilate + 5-Phospho-alpha-D-ribose 1-diphosphate <=> N-(5-Phospho-D-ribosyl)anthranilate + Pyrophosphate |
| N/A | ATP + Biotin <=> Pyrophosphate + Biotinyl-5'-AMP |
| CAC3090/ CAC3091 | (S)-Malate <=> Fumarate + H2O |
| CAC1821 | N6-(1,2-Dicarboxyethyl)-AMP <=> Fumarate + AMP |
| CAC0974 | N-(L-Arginino)succinate <=> Fumarate + L-Arginine |
| CAC1479 | 4-Methyl-2-oxopentanoate + L-Glutamate <=> L-Leucine + 2-Oxoglutarate |
| CAC2959 | ATP + D-Galactose <=> ADP + alpha-D-Galactose 1-phosphate |
| N/A | Isopentenyl diphosphate <=> Dimethylallyl diphosphate |
| CAC1395 | 1-(5'-Phosphoribosyl)-5-formamido-4-imidazolecarboxamide <=> IMP + H2O |
| CAC2701 | IMP + NAD+ + H2O <=> Xanthosine 5'-phosphate + NADH + H+ |
| CAC3203 | IMP + Pyrophosphate <=> Hypoxanthine + 5-Phospho-alpha-D-ribose 1-diphosphate |
| CAC3471 | IMP + NH3 + NADP+ <=> GMP + NADPH + H+ |
| CAC3593 | GTP + IMP + L-Aspartate <=> GDP + Orthophosphate + N6-(1,2-Dicarboxyethyl)-AMP |
| CAC0518/ CAC1036 | dADP + Phosphoenolpyruvate <=> dATP + Pyruvate |
| CAC0792 | D-Alanine + 2-Oxoglutarate <=> Pyruvate + D-Glutamate |
| CAC2895 | ATP + 2 D-Alanine <=> ADP + Orthophosphate + D-Alanyl-D-alanine |
| CAC0937 | L-Histidinal + H2O + 2 NAD+ <=> L-Histidine + 2 NADH + H+ |
| N/A | L-Histidine <=> Urocanate + NH3 |
| CAC2711 | Butanoyl-CoA + NAD+ <=> Crotonoyl-CoA + NADH + H+ |
| CAP0035/ CAP0162 | Butanal + CoA + NAD+ <=> Butanoyl-CoA + NADH |
| CAC3076 | Butanoyl-CoA + Orthophosphate <=> CoA + Butanoylphosphate |
| N/A | Reduced ferredoxin + NADP+ <=> Oxidized ferredoxin + NADPH + H+ |
| N/A | Reduced ferredoxin + Acetyl-CoA + CO2 <=> Oxidized ferredoxin + Pyruvate + CoA |
| CAC2458/ CAC2459 | Oxidized ferredoxin + 2-Oxoglutarate + CoA <=> Reduced ferredoxin + Succinyl-CoA + CO2 |
| CAC3170/ CAC3604 | 2,3-Dihydroxy-3-methylbutanoate <=> 3-Methyl-2-oxobutanoic acid + H2O |
| CAC0273/ CAC3174 | (2S)-2-Isopropylmalate + CoA <=> Acetyl-CoA + 3-Methyl-2-oxobutanoic acid + H2O |
| CAC1479 | L-Valine + 2-Oxoglutarate <=> 3-Methyl-2-oxobutanoic acid + L-Glutamate |
| N/A | 5,10-Methylenetetrahydrofolate + Reduced Ferredoxin <=> 5-Methyltetrahydrofolate + Oxidized Ferredoxin |
| CAC2083 | 5,10-Methenyltetrahydrofolate + NADPH <=> 5,10-Methylenetetrahydrofolate + NADP+ |
| CAC2914 | 5,10-Methylenetetrahydrofolate + 3-Methyl-2-oxobutanoic acid + H2O <=> Tetrahydrofolate + 2-Dehydropantoate |
| CAC2275/ CAC3203 | GMP + Pyrophosphate <=> Guanine + 5-Phospho-alpha-D-ribose 1-diphosphate |
| CAC2700 | ATP + Xanthosine 5'-phosphate + L-Glutamine + H2O <=> AMP + Pyrophosphate + GMP + L-Glutamate |
| CAC0887 | Adenine + H2O <=> Hypoxanthine + NH3 |
| CAC3252 | L-Proline + NAD+ <=> (S)-1-Pyrroline-5-carboxylate + NADH + H+ |
| CAC3252 | L-Proline + NADP+ <= (S)-1-Pyrroline-5-carboxylate + NADPH + H+ |
| N/A | ATP + Hexadecanoic acid + CoA <=> AMP + Palmitoyl-CoA + Pyrophosphate |
| CAC0391 | Cystathionine + H2O <=> L-Homocysteine + NH3 + Pyruvate |
| CAC0391 | L-Cystathionine + H2O <=> L-Homocysteine + NH3 + Pyruvate |
| CAC2942 | S-Ribosyl-L-Homocysteine + H2O <=> D-Ribose + L-Homocysteine |
| CAC0971 | Citrate <=> Isocitrate |
| CAC0971 | cis-Aconitate + H2O <=> Citrate |
| N/A | Glycolaldehyde + NAD+ + H2O <=> Glycolate + NADH |
| N/A | Acetoacetyl-CoA + Acetate <=> Acetoacetate + Acetyl-CoA |
| CAP0163/ CAP0164 | Butanoic Acid + Acetoacetyl-CoA <=> Butanoyl-CoA + Acetoacetate |
| CAP0165 | Acetoacetate <=> Acetone + CO2 |
| CAC0217 | Prephenate <=> Phenylpyruvate + H2O + CO2 |
| CAC2945 | D-Glycerate + NAD+ <=> Hydroxypyruvate + NADH + H+ |
| N/A | Hydroxypyruvate <=> Glycolaldehyde + CO2 |
| CAC2653/ | Carbamoyl phosphate + L-Aspartate <=> Orthophosphate + N- |

TABLE 3-continued

The complete genome-scale metabolic network with gene identification where available. The stoichiometric coefficients of the biomass constituting equation are represented as variables since these values have been observed to change with growth stage-related cellular physiology.

| Locus Number | Reaction |
|---|---|
| CAC2654 | Carbamoyl-L-aspartate |
| CAC0316 | Carbamoyl phosphate + L-Ornithine <=> Orthophosphate + L-Citrulline |
| N/A | D-Xylose <=> D-Xylulose |
| N/A | (S)-Lactate <=> (R)-Lactate |
| CAC0999 | O-Phospho-L-homoserine + H2O <=> L-Threonine + Orthophosphate |
| CAC0710 | ATP + 3-Phospho-D-glycerate <=> ADP + 3-Phospho-D-glyceroyl phosphate |
| CAC0015/ CAC0089 | 3-Phospho-D-glycerate + NAD+ <=> 3-Phosphonooxypyruvate + NADH + H+ |
| CAC2834 | ATP + D-Glycerate <=> ADP + 3-Phospho-D-glycerate |
| CAC2830 | 3-Phospho-D-glyceroyl phosphate + H2O <=> 3-Phospho-D-glycerate + Orthophosphate |
| CAC0167/ CAC0712/ CAC2741/ CAC3021 | 2-Phospho-D-glycerate <=> 3-Phospho-D-glycerate |
| N/A | D-Ribitol 5-phosphate + NAD+ <=> D-Ribulose 5-phophate + NADH + H+ |
| N/A | D-Ribitol 5-phosphate + NADP+ <=> D-Ribulose 5-phosphate + NADPH + H+ |
| N/A | 6-phopho-D-gluconate + NADP+ <=> D-ribulose 5-phosphate + CO2 + NADPH + H+ |
| CAC1730 | D-Ribulose 5-phosphate <=> D-Xylulose 5-phosphate |
| N/A | D-Gluconic acid <=> 2-Dehydro-3-Deoxy-D-Gluconate |
| CAC0395/ CAC2684 | ATP + 2-Dehydro-3-deoxy-D-gluconate <=> ADP + 2-Dehydro-3-deoxy-6-phospho-D-gluconate |
| CAC3112 | ATP + dAMP <=> ADP + dADP |
| CAC0672 | dATP + Cytidine <=> dADP + CMP |
| CAC0672 | dATP + Uridine <=> dADP + UMP |
| CAC2685 | Maltose + Orthophosphate <=> D-Glucose + beta-D-Glucose 1-phosphate |
| CAC3005 | Adenosine + H2O <=> Inosine + NH3 |
| CAC2064 | Adenine + alpha-D-Ribose 1-phosphate <=> Adenosine + Orthophosphate |
| CAC2887 | ADP + dTMP <=> Thymidine + ATP |
| N/A | Thymidine + Orthophosphate <=> Thymine + 2-Deoxy-D-ribose 1-phosphate |
| CAC2613 | ATP + beta-D-Glucose <=> ADP + beta-D-Glucose 6-phosphate |
| CAC1349 | alpha-D-Glucose <=> beta-D-Glucose |
| CAC0604/ CAC3421 | Acyl-carrier protein + H2O <=> Pantetheine 4'-phosphate + Apo-[acyl-carrier protein] |
| CAC0814/ CAC2008/ CAC3573/ CAC3578/ CAP0088 | Acetyl-CoA + Acyl-carrier protein <=> CoA + Acetyl-[acyl-carrier protein] |
| CAC0489 | CoA + Apo-[acyl-carrier protein] <=> Adenosine 3',5'-bisphosphate + Acyl-carrier protein |
| CAC3575 | Malonyl-CoA + Acyl-carrier protein <=> CoA + Malonyl-[acyl-carrier protein] |
| CAC2612 | ATP + D-Xylulose <=> ADP + D-Xylulose 5-phosphate |
| CAC0944/ CAC1348 | D-Ribose 5-phosphate + D-Xylulose 5-phosphate <=> D-Sedoheptulose 7-phosphate + (2R)-2-Hydroxy-3-(phosphonooxy)-propanal |
| N/A | (2S)-2-Isopropyl-3-oxosuccinate <=> 4-Methyl-2-oxopentanoate + CO2 |
| CAC2083/ CAC3201 | 5,10-Methenyltetrahydrofolate + H2O <=> 10-Formyltetrahydrofolate + H+ |
| CAC2080 | Dimethylallyl diphosphate + Isopentenyl diphosphate <=> Pyrophosphate + Geranyl diphosphate |
| CAC2876 | dCMP + H2O <=> dUMP + NH3 |
| N/A | dCMP + H2O <=> Deoxycytidine + Orthophosphate |
| CAC1848 | ATP + dCMP <=> ADP + dCDP |
| CAC0282 | Guanine + H2O <=> Xanthine + NH3 |
| CAC3075 | ATP + Butanoic acid <=> ADP + Butanoylphosphate |
| N/A | Hexadecanoyl-[acp] + H2O <=> Acyl-carrier protein + Hexadecanoic acid |
| CAC0896 | 5-O-(1-Carboxyvinyl)-3-phosphoshikimate <=> Chorismate + Orthophosphate |
| CAC1234 | Chorismate <=> Prephenate |
| N/A | Chorismate <=> Isochorismate |
| CAC0893 | Prephenate + NAD+ <=> 3-(4-Hydroxyphenyl)pyruvate + CO2 + NADH + H+ |
| N/A | ATP + D-Gluconic acid <=> ADP + 6-phospho-D-Gluconate |
| N/A | D-Glycerate + NAD+ <=> 2-Hydroxy-3-oxopropanoate + NADH + H+ |
| N/A | D-Glycerate + NADP+ <=> 2-Hydroxy-3-oxopropanoate + NADPH + H+ |

TABLE 3-continued

The complete genome-scale metabolic network with gene identification where available. The stoichiometric coefficients of the biomass constituting equation are represented as variables since these values have been observed to change with growth stage-related cellular physiology.

| Locus Number | Reaction |
|---|---|
| N/A | D-Glyceraldehyde + NAD+ + H2O <=> D-Glycerate + NADH + H+ |
| CAC1342/ CAC1346 | L-Arabinose <=> L-Ribulose |
| CAC1235 | ATP + L-Homoserine <=> ADP + O-Phospho-L-homoserine |
| CAC0998 | L-Homoserine + NAD+ <=> L-Aspartate 4-semialdehyde + NADH + H+ |
| CAC0998 | L-Homoserine + NADP+ <=> L-Aspartate 4-semialdehyde + NADPH + H+ |
| CAC1825 | Succinyl-CoA + L-Homoserine <=> CoA + O-Succinyl-L-homoserine |
| CAC2708 | (S)-3-Hydroxybutanoyl-CoA + NAD+ <=> Acetoacetyl-CoA + NADH |
| CAC2613 | ATP + alpha-D-Glucose <=> ADP + alpha-D-Glucose 6-phosphate |
| CAC1792 | CTP + Phosphatidate <=> Pyrophosphate + CDPdiacylglycerol |
| CAC1814/ CAC3596 | CDPdiacylglycerol + sn-Glycerol 3-phosphate <=> CMP + Phosphatidylglycerophosphate |
| CAC2337/ CAC2981 | D-Mannose 6-phosphate <=> D-Mannose 1-phosphate |
| CAC2918 | D-Mannose 6-phosphate <=> beta-D-Fructose 6-phosphate |
| CAC0892 | Phosphoenolpyruvate + D-Erythrose 4-phosphate + H2O <=> 2-Dehydro-3-deoxy-D-arabino-heptonate 7-phosphate + Orthophosphate |
| CAC1347 | D-Sedoheptulose 7-phosphate + (2R)-2-Hydroxy-3-(phosphonooxy)-propanal <=> D-Erythrose 4-phosphate + D-Fructose 6-phosphate |
| CAC0944/ CAC1348 | beta-D-Fructose 6-phosphate + (2R)-2-Hydroxy-3-(phosphonooxy)-propanal <=> D-Erythrose 4-phosphate + D-Xylulose 5-phosphate |
| CAC0518/ CAC1036 | dGTP + Pyruvate <=> dGDP + Phosphoenolpyruvate |
| CAC2064 | Inosine + Orthophosphate <=> Hypoxanthine + alpha-D-Ribose 1-phosphate |
| N/A | (S)-Dihydroorotate + NAD+ <=> Orotate + H+ + NADH |
| CAC0027 | Orotidine 5'-phosphate + Pyrophosphate <=> Orotate + 5-Phospho-alpha-D-ribose 1-diphosphate |
| CAC1544/ CAC2609 | Cytidine + H2O <=> Uridine + NH3 |
| CAC0672 | dGTP + Uridine <=> dGDP + UMP |
| CAC0971 | Isocitrate <=> cis-Aconitate + H2O |
| CAC0973 | ATP + L-Citrulline + L-Aspartate <=> AMP + Pyrophosphate + N-(L-Arginino)succinate |
| N/A | ATP + Deoxyguanosine <=> ADP + dGMP |
| N/A | dGMP + H2O <=> Deoxyguanosine + Orthophosphate |
| CAC2064 | Deoxyguanosine + Orthophosphate <=> Guanine + 2-Deoxy-D-ribose 1-phosphate |
| N/A | (S)-3-Hydroxybutanoyl-CoA + NAD+ <=> Acetoacetyl-CoA + NADH |
| CAC0519 | (S)-Dihydroorotate + H2O <=> N-Carbamoyl-L-aspartate |
| CAC2080 | Geranyl diphosphate + Isopentenyl diphosphate <=> Pyrophosphate + trans, trans-Farnesyl diphosphate |
| CAC0480/ CAC1209 | ATP + Thioredoxin <=> dATP + Oxidized thioredoxin + H2O |
| CAC0869 | Thioredoxin + NADP+ <=> Oxidized thioredoxin + NADPH + H+ |
| CAC1047/ CAC3276/ CAC3277 | dADP + Oxidized thioredoxin + H2O <=> Thioredoxin + ADP |
| CAC1047/ CAC3276/ CAC3277 | dGDP + Oxidized thioredoxin + H2O <=> GDP + Thioredoxin |
| CAC0480/ CAC1209 | dGTP + Oxidized thioredoxin + H2O <=> GTP + Thioredoxin |
| N/A | Thioredoxin + 3'-Phosphoadenylyl sulfate <=> Oxidized thioredoxin + Sulfite + Adenosine 3',5'-bisphosphate + H+ |
| CAC0480/ CAC1209 | dCTP + Oxidized thioredoxin + H2O <=> CTP + Thioredoxin |
| CAC0480/ CAC1209 | dUTP + Oxidized thioredoxin + H2O <=> UTP + Thioredoxin |
| N/A | Phosphatidylglycerol + H2O <=> 1,2-Diacyl-sn-glycerol + sn-Glycerol 3-phosphate |
| N/A | Phosphatidylglycerophosphate + H2O <=> Phosphatidylglycerol + Orthophosphate |
| CAC2875/ CAC3316 | Phosphatidylglycerol + CDPdiacylglycerol <=> Cardiolipin + CMP |
| N/A | D-Glucono-1,5-Lactone 6-phosphate + H2O <=> 6-phopho-D-Gluconate |
| CAC0188 | N-Acetyl-D-glucosamine 6-phosphate + H2O <=> D-Glucosamine 6-phosphate + Acetate |
| N/A | D-Glucosamine 1-phosphate <=> D-Glucosamine 6-phosphate |
| N/A | trans, trans-Farnesyl diphosphate + Isopentenyl diphosphate <=> Pyrophosphate + Geranylgeranyl diphosphate |

TABLE 3-continued

The complete genome-scale metabolic network with gene identification where available. The stoichiometric coefficients of the biomass constituting equation are represented as variables since these values have been observed to change with growth stage-related cellular physiology.

| Locus Number | Reaction |
|---|---|
| CAC0232 | ATP + D-Fructose 1-phosphate <=> ADP + beta-D-Fructose 1,6-bisphosphate |
| N/A | N-Acetyl-D-glucosamine 6-phosphate <=> N-Acetyl-D-glucosamine 1-phosphate |
| N/A | dAMP + H2O <=> Deoxyadenosine + Orthophosphate |
| N/A | ATP + Deoxyadenosine <=> ADP + dAMP |
| CAC1718 | ATP + dGMP <=> ADP + dGDP |
| CAC0672 | dGTP + Cytidine <=> dGDP + CMP |
| N/A | ATP + dTDP <=> ADP + dTTP |
| N/A | ATP + dTMP <=> ADP + dTDP |
| CAC0672 | dTTP + Cytidine <=> dTDP + CMP |
| CAC0672 | dTTP + Uridine <=> dTDP + UMP |
| CAC2887 | ATP + Deoxyuridine <=> ADP + dUMP |
| CAC1210/ CAC1425 | dUTP + H2O <=> dUMP + Pyrophosphate |
| CAC3003 | dUMP + 5,10-Methylenetetrahydrofolate <=> Dihydrofolate + dTMP |
| CAC3203 | Xanthosine 5'-phosphate + Pyrophosphate <=> Xanthine + 5-Phospho-alpha-D-ribose 1-diphosphate |
| CAC1479 | L-Isoleucine + 2-Oxoglutarate <=> (S)-3-Methyl-2-oxopentanoic acid + L-Glutamate |
| CAC3004 | Dihydrofolate + NAD+ <=> Folate + NADH + H+ |
| CAC3004 | Dihydrofolate + NADP+ <=> Folate + NADPH + H+ |
| CAC2398 | ATP + Dihydropteroate + L-Glutamate <=> ADP + Orthophosphate + Dihydrofolate |
| CAC1294 | ATP + 1,2-Diacyl-sn-glycerol <=> ADP + Phosphatidate |
| CAC0965 | Phosphatidate + CoA <=> 1-Acyl-sn-glycerol 3-phosphate + Acyl-CoA |
| CAC2391/ CAC3020 | N-Acetylornithine + L-Glutamate <=> L-Ornithine + N-Acetyl-L-glutamate |
| CAC2388 | N-Acetylornithine + 2-Oxoglutarate <=> N-Acetyl-L-glutamate 5-semialdehyde + L-Glutamate |
| N/A | N-Formimino-L-Glutamate + H2O <=> L-Glutamate + Formamide |
| N/A | 4-Imidazalone-5-Propanoate + H2O <=> N-Formidino-L-Glutamate + H+ |
| CAC0022/ CAC0568 | L-Aspartate 4-semialdehyde + Orthophosphate + NADP+ <=> 4-Phospho-L-aspartate + NADPH + H+ |
| CAC2378/ CAC3600 | L-Aspartate 4-semialdehyde + Pyruvate <=> L-2,3-Dihydrodipicolinate + 2 H2O |
| CAC2064 | Nicotinamide + alpha-D-Ribose 1-phosphate <=> N-Ribosylnicotinamide + Orthophosphate |
| CAC1546 | Cytidine + Orthophosphate <=> Cytosine + alpha-D-Ribose 1-phosphate |
| N/A | 5-Formyltetrahydrofolate <=> 5,10 Methenyltetrahydrofolate + H2O |
| CAC1090 | ATP + 5-Formyltetrahydrofolate <=> ADP + Orthophosphate + 5,10-Methenyltetrahydrofolate |
| N/A | Nicotinamide D-ribonucleotide + H2O <=> Nicotinate D-ribonucleotide + NH3 |
| N/A | N-Ribosylnicotinamide + Orthophosphate <=> Nicotinamide D-ribonucleotide + H2O |
| CAC0025 | dCTP + H2O <=> dUTP + NH3 |
| N/A | ATP + dCDP <=> ADP + dCTP |
| CAC0672 | dCTP + Uridine <=> dCDP + UMP |
| CAC0672 | dUTP + Uridine <=> dUDP + UMP |
| CAC3157/ CAC3158 | Indole + (2R)-2-Hydroxy-3-(phosphonooxy)-propanal <=> Indoleglycerol phosphate |
| CAC0672 | dCTP + Cytidine <=> dCDP + CMP |
| CAC0672 | dUTP + Cytidine <=> dUDP + CMP |
| CAC0898 | ATP + Shikimate <=> ADP + Shikimate 3-phosphate |
| CAC0897 | Shikimate + NADP+ <=> 3-Dehydroshikimate + NADPH + H+ |
| N/A | ATP + L-Ribulose <=> ADP + L-Ribulose 5-phosphate |
| CAC2937 | (R)-Pantoate + NADP+ <=> 2-Dehydropantoate + NADPH |
| CAC2915 | ATP + (R)-Pantoate + beta-Alanine <=> AMP + Pyrophosphate + Pantothenate |
| N/A | Deoxyuridine + Orthophosphate <=> Uracil + 2-Deoxy-D-ribose 1-phosphate |
| CAC1544/ CAC2609 | Deoxycytidine + H2O <=> Deoxyuridine + NH3 |
| CAC0390/ CAC0930 | Cystathionine + Succinate <=> O-Succinyl-L-homoserine + L-Cysteine |
| CAC3298/ CAC3299 | Methylglyoxal + NADPH <=> Hydroxyacetone + NADP+ |
| CAC3005 | Deoxyadenosine + H2O <=> Deoxyinosine + NH3 |
| CAC2064 | Deoxyadenosine + Orthophosphate <=> Adenine + 2-Deoxy-D-ribose 1-phosphate |
| CAC0827/ CAP0064 | D-Fructose 1-phosphate <=> Glycerone phosphate + D-Glyceraldehyde |

TABLE 3-continued

The complete genome-scale metabolic network with gene identification where available. The stoichiometric coefficients of the biomass constituting equation are represented as variables since these values have been observed to change with growth stage-related cellular physiology.

| Locus Number | Reaction |
|---|---|
| CAC2389 | ATP + N-Acetyl-L-glutamate <=> ADP + N-Acetyl-L-glutamate 5-phosphate |
| N/A | UDPglucose + 1,2-Diacyl-sn-glycerol <=> UDP + 3-D-Glucosyl-1,2-diacylglycerol |
| CAC0157 | D-Mannitol 1-phosphate + NAD+ <=> beta-D-Fructose 6-phosphate + NADH |
| N/A | alpha,alpha-Trehalose + Orthophosphate <=> D-Glucose + beta-D-Glucose 1-phosphate |
| CAC2614 | beta-D-Glucose 1-phosphate <=> beta-D-Glucose 6-phosphate |
| CAC2723 | N-Succinyl-LL-2,6-diaminoheptanedioate + H2O <=> Succinate + LL-2,6-Diaminoheptanedioate |
| CAC2624 | LL-2,6-Diaminoheptanedioate <=> meso-2,6-Diaminoheptanedioate |
| N/A | beta-D-Glucose 6-phosphate + NADP+ <=> D-Glucono-1,5-Lactone 6-phosphate + NADPH + H+ |
| CAC2680 | alpha-D-Glucose 6-phosphate <=> beta-D-Glucose 6-phosphate |
| CAC2680 | alpha-D-Glucose 6-phosphate <=> beta-D-Fructose 6-phosphate |
| CAC2064 | Deoxyinosine + Orthophosphate <=> Hypoxanthine + 2-Deoxy-D-ribose 1-phosphate |
| CAC2065 | 2-Deoxy-D-ribose 1-phosphate <=> 2-Deoxy-D-ribose 5-phosphate |
| N/A | D-Glucarate <=> 5-Dehydro-4-deoxy-D-glucarate + H2O |
| N/A | 5-Dehydro-4-deoxy-D-glucarate <=> Pyruvate + 2-Hydroxy-3-oxopropanoate |
| N/A | alpha,alpha'-Trehalose 6-phosphate + H2O <=> alpha,alpha-Trehalose + Orthophosphate |
| CAC3194 | ATP + UDP-N-acetylmuramoyl-L-alanine + D-Glutamate <=> ADP + Orthophosphate + UDP-N-acetylmuramoyl-L-alanyl-D-glutamate |
| N/A | 4-Imidazolone-5-Propanoate <=> Urocanate + H2O |
| N/A | CTP + D-Ribitol 5-phosphate <=> Pyrophosphate + CDPribitol |
| CAC2697 | Acetolactate <=> Acetoin + CO2 |
| N/A | Deamino-NAD+ + H2O <=> AMP + Nicotinate D-ribonucleotide |
| CAC1262 | ATP + Nicotinate D-ribonucleotide <=> Pyrophosphate + Deamino-NAD+ |
| CAC0937 | L-Histidinol + NAD+ <=> L-Histidinal + NADH + H+ |
| CAC2727 | L-Histidinol phosphate + H2O <=> L-Histidinol + Orthophosphate |
| N/A | ATP + Pantothenate <=> ADP + D-4'-Phosphopantothenate |
| N/A | (S)-3-Hydroxybutanoyl-CoA <=> Crotonoyl-CoA + H2O |
| CAC2712 | (R)-3-Hydroxybutanoyl-CoA <=> Crotonoyl-CoA + H2O |
| CAC1738 | ATP + Pantetheine 4'-phosphate <=> Pyrophosphate + Dephospho-CoA |
| CAC0091 | 2-Acetolactate + NADPH + H+ <=> 2,3-Dihydroxy-3-methylbutanoate + NADP+ |
| CAC2926 | 2-Amino-7,8-dihydro-4-hydroxy-6-(diphosphooxymethyl)pteridine + 4-Aminobenzoate <=> Pyrophosphate + Dihydropteroate |
| CAC0894 | 2-Dehydro-3-deoxy-D-arabino-heptonate 7-phosphate <=> 3-Dehydroquinate + Orthophosphate |
| CAC0899 | 3-Dehydroquinate <=> 3-Dehydroshikimate + H2O |
| CAC0510 | UDP-N-acetylmuramate + NAD+ <=> UDP-N-acetyl-3-(1-carboxyvinyl)-D-glucosamine + NADH |
| CAC0510 | UDP-N-acetylmuramate + NADP+ <=> UDP-N-acetyl-3-(1-carboxyvinyl)-D-glucosamine + NADPH + H+ |
| CAC3225 | ATP + UDP-N-acetylmuramate + L-Alanine <=> ADP + Orthophosphate + UDP-N-acetylmuramoyl-L-alanine |
| CAC0495/ CAC2920 | 2-Methyl-4-amino-5-hydroxymethylpyrimidine diphosphate + 4-Methyl-5-(2-phosphoethyl)-thiazole <=> Pyrophosphate + Thiamin monophosphate |
| CAC0517/ CAC0232/ CAC2951 | D-Tagatose 6-phosphate + ATP <=> D-Tagatose 1,6-bisphosphate + ADP |
| CAC0517 | CTP + D-Tagatose 6-phosphate <=> CDP + D-Tagatose 1,6-bisphosphate |
| CAC0517 | UTP + D-Tagatose 6-phosphate <=> UDP + D-Tagatose 1,6-bisphosphate |
| CAC2953/ CAC2954 | D-Galactose 6-phosphate <=> D-Tagatose 6-phosphate |
| CAC1369/ CAC3031 | L-Histidinol phosphate + 2-Oxoglutarate <=> 3-(Imidazol-4-yl)-2-oxopropyl phosphate + L-Glutamate |
| CAC2963 | Lactose 6-phosphate + H2O <=> beta-D-Glucose + D-Galactose 6-phosphate |
| CAC0390/ CAC0930 | O-Succinyl-L-homoserine + L-Cysteine <=> L-Cystathionine + Succinate |
| CAC1720 | (R)-4'-Phosphopantothenoyl-L-cysteine <=> Pantetheine 4'-phosphate + CO2 |
| N/A | (S)-3-Hydroxybutanoyl-CoA <=> (R)-3-Hydroxybutanoyl-CoA |
| N/A | 2-Hydroxy-3-oxopropanoate + Pyruvate <=> 2-Dehydro-3-deoxy-D-glucarate |

TABLE 3-continued

The complete genome-scale metabolic network with gene identification where available. The stoichiometric coefficients of the biomass constituting equation are represented as variables since these values have been observed to change with growth stage-related cellular physiology.

| Locus Number | Reaction |
| --- | --- |
| CAC3254 | L-Glutamate 5-semialdehyde + Orthophosphate + NADP+ <=> L-Glutamyl 5-phosphate + NADPH + H+ |
| CAC2680 | beta-D-Glucose 6-phosphate <=> beta-D-Fructose 6-phosphate |
| CAC1023 | Nicotinate D-ribonucleotide + Pyrophosphate + CO2 <=> Pyridine-2,3-Dicarboxylate + 5-phopho-alpha-D-Ribose 1-diphosphate |
| CAC2390 | N-Acetyl-L-glutamate 5-semialdehyde + Orthophosphate + NADP+ <=> N-Acetyl-L-glutamate 5-phosphate + NADPH + H+ |
| CAC0938 | D-erythro-1-(Imidazol-4-yl)glycerol 3-phosphate <=> 3-(Imidazol-4-yl)-2-oxopropyl phosphate + H2O |
| CAC0590 | 5-Amino-6-(5'-phosphoribitylamino)uracil + NADP+ <=> 5-Amino-6-(5'-phosphoribosylamino)uracil + NADPH |
| CAC0590 | 2,5-Diamino-6-hydroxy-4-(5'-phosphoribosylamino)-pyrimidine + H2O <=> 5-Amino-6-(5'-phosphoribosylamino)uracil + NH3 |
| CAC0895 | Phosphoenolpyruvate + Shikimate 3-phosphate <=> Orthophosphate + 5-O-(1-Carboxyvinyl)-3-phosphoshikimate |
| CAC3095 | ATP + 4-Amino-5-hydroxymethyl-2-methylpyrimidine <=> ADP + 4-Amino-2-methyl-5-phosphomethylpyrimidine |
| N/A | 4-Amino-5-hydroxymethyl-2-methylpyrimidine <=> Aminoimidazole ribotide |
| CAC2927 | ATP + 2-Amino-4-hydroxy-6-hydroxymethyl-7,8-dihydropteridine <=> AMP + 2-Amino-7,8-dihydro-4-hydroxy-6-(diphosphooxymethyl)pteridine |
| CAC2927 | 2-Amino-4-hydroxy-6-(D-erythro-1,2,3-trihydroxypropyl)-7,8- <=> Glycolaldehyde + 2-Amino-4-hydroxy-6-hydroxymethyl-7,8-dihydropteridine |
| CAC3160 | 1-(2-Carboxyphenylamino)-1'-deoxy-D-ribulose 5'-phosphate <=> Indoleglycerol phosphate + CO2 + H2O |
| CAC3159 | N-(5-Phospho-D-ribosyl)anthranilate <=> 1-(2-Carboxyphenylamino)-1'-deoxy-D-ribulose 5'-phosphate |
| CAC3298/ CAC3299 | Butanal + NADH <=> 1-Butanol + NAD+ |
| CAC3298/ CAC3299 | Butanal + NADPH + H+ <=> 1-Butanol + NADP+ |
| CAC0424/ CAC1523 | ATP + beta-D-Fructose <=> ADP + beta-D-Fructose 6-phosphate |
| CAC0425 | Sucrose 6-phosphate + H2O <=> beta-D-Fructose + alpha-D-Glucose 6-phosphate |
| CAC3172/ CAC3173 | (2S)-2-Isopropylmalate <=> 2-Isopropylmaleate + H2O |
| CAC3172/ CAC3173 | (2R,3S)-3-Isopropylmalate <=> 2-Isopropylmaleate + H2O |
| N/A | ATP + 2-Succinylbenzoate + CoA <=> AMP + Pyrophosphate + 2-Succinylbenzoyl-CoA |
| CAC3571 | 2-Succinylbenzoate + H2O <=> 2-Succinyl-6-hydroxy-2,4-cyclohexadiene-1-carboxylate |
| CAC0943 | Phosphoribosyl-ATP + H2O <=> Phosphoribosyl-AMP + Pyrophosphate |
| CAC0942 | Phosphoribosyl-AMP + H2O <=> 5-(5-Phospho-D-ribosylaminoformimino)-1-(5-phosphoribosyl)-imidazole-4-carboxamide |
| CAC1396 | ATP + 5-Phosphoribosylamine + Glycine <=> ADP + Orthophosphate + 5'-Phosphoribosylglycinamide |
| N/A | 2-Succinylbenzoyl-CoA <=> 1,4-Dihydroxy-2-naphthoate + CoA |
| N/A | O-Phospho-L-serine + 2-Oxoglutarate <=> 3-Phosphonooxypyruvate + L-Glutamate |
| CAC2379 | 2,3,4,5-Tetrahydrodipicolinate + NAD+ <=> L-2,3-Dihydrodipicolinate + NADH + H+ |
| CAC2379 | 2,3,4,5-Tetrahydrodipicolinate + NADP+ <=> L-2,3-Dihydrodipicolinate + NADPH + H+ |
| CAC1393 | ATP + 2-(Formamido)-N1-(5'-phosphoribosyl)acetamidine <=> ADP + Orthophosphate + Aminoimidazole ribotide |
| CAC1390 | 1-(5-Phospho-D-ribosyl)-5-amino-4-imidazolecarboxylate <=> Aminoimidazole ribotide + CO2 |
| CAC1720 | CTP + D-4'-Phosphopantothenate + L-Cysteine <=> CDP + Orthophosphate + (R)-4'-Phosphopantothenoyl-L-cysteine |
| N/A | Pyridine-2,3-dicarboxylate + 2 H2O + Orthophosphate <=> Iminoaspartate + Glycerone Phosphate |
| CAC1394 | 10-Formyltetrahydrofolate + 5'-Phosphoribosylglycinamide <=> Tetrahydrofolate + 5'-Phosphoribosyl-N-formylglycinamide |
| CAC1394 | 5'-Phosphoribosylglycinamide + 5,10-Methenyltetrahydrofolate + H2O <=> 5'-Phosphoribosyl-N-formylglycinamide + Tetrahydrofolate |
| CAC2381 | Succinyl-CoA + 2,3,4,5-Tetrahydrodipicolinate + H2O <=> CoA + N-Succinyl-2-L-amino-6-oxoheptanedioate |
| N/A | 3-D-Glucosyl-1,2-diacylglycerol + UDPglucose <=> Diglucosyl-diacylglycerol + UDP |

TABLE 3-continued

The complete genome-scale metabolic network with gene identification where available. The stoichiometric coefficients of the biomass constituting equation are represented as variables since these values have been observed to change with growth stage-related cellular physiology.

| Locus Number | Reaction |
|---|---|
| CAC3570 | ATP + Holo-[carboxylase] + HCO3– <=> ADP + Orthophosphate + Carboxybiotin-carboxyl-carrier protein |
| CAC3568/ CAC3569/ CAC3570 | Acetyl-CoA + Carboxybiotin-carboxyl-carrier protein <=> Malonyl-CoA + Holo-[carboxylase] |
| CAC3171 | (2R,3S)-3-Isopropylmalate + NAD+ <=> (2S)-2-Isopropyl-3-oxosuccinate + NADH + H+ |
| CAC0091 | (R)-2,3-Dihydroxy-3-methylbutanoate + NADP+ <=> 3-Hydroxy-3-methyl-2-oxobutanoic acid + NADPH |
| CAC3170/ CAC3604 | (R)-2,3-Dihydroxy-3-methylbutanoate <=> 3-Methyl-2-oxobutanoic acid + H2O |
| N/A | 6,7-Dimethyl-8-(1-D-ribityl)lumazine + Orthophosphate <=> D-Ribose 5-phosphate + 5-Amino-6-(5'-phosphoribitylamino)uracil |
| CAC1655 | ATP + 5'-Phosphoribosyl-N-formylglycinamide + L-Glutamine + H2O <=> ADP + Orthophosphate + 2-(Formamido)-N1-(5'-phosphoribosyl)acetamidine + L-Glutamate |
| CAC2380 | N-Succinyl-LL-2,6-diaminoheptanedioate + 2-Oxoglutarate <=> N-Succinyl-2-L-amino-6-oxoheptanedioate + L-Glutamate |
| CAC3095 | ATP + 4-Amino-2-methyl-5-phosphomethylpyrimidine <=> ADP + 2-Methyl-4-amino-5-hydroxymethylpyrimidine diphosphate |
| N/A | 1-(5'-Phosphoribosyl)-5-amino-4-imidazolecarboxamide + L-Glutamate + D-erythro-1-(Imidazol-4-yl)glycerol 3-phosphate <=> N-(5'-Phospho-D-1'-ribulosylformimino)-5-amino-1-(5''-phospho-D-ribosyl)-4-imidazolecarboxamide + L-Glutamine |
| CAC1821 | 1-(5'-Phosphoribosyl)-5-amino-4-(N-succinocarboxamide)-imidazole <=> Fumarate + 1-(5'-Phosphoribosyl)-5-amino-4-imidazolecarboxamide |
| CAC1395 | 10-Formyltetrahydrofolate + 1-(5'-Phosphoribosyl)-5-amino-4-imidazolecarboxamide <=> Tetrahydrofolate + 1-(5'-Phosphoribosyl)-5-formamido-4-imidazolecarboxamide |
| CAC1391 | ATP + 1-(5-Phospho-D-ribosyl)-5-amino-4-imidazolecarboxylate + L-Aspartate <=> ADP + Orthophosphate + 1-(5'-Phosphoribosyl)-5-amino-4-(N-succinocarboxamide)-imidazole |
| CAC1003/ CAC1729/ CAC1736/ CAC2137/ CAC2674/ CAC2687/ CAC2828/ CAC3396/ CAC3715 | 2-Amino-4-hydroxy-6-(D-erythro-1,2,3-trihydroxypropyl)-7,8- + Orthophosphate <=> Dihydroneopterin phosphate + H2O |
| CAC1003/ CAC1729/ CAC1736/ CAC2137/ CAC2674/ CAC2687/ CAC2828/ CAC3396/ CAC3715 | 2-Amino-4-hydroxy-6-(erythro-1,2,3-trihydroxypropyl)dihydropteridine + H2O <=> Dihydroneopterin phosphate + Pyrophosphate |
| CAC3626 | 2-Amino-4-hydroxy-6-(erythro-1,2,3-trihydroxypropyl)dihydropteridine + H2O <=> 2,5-Diamino-6-(5'-triphosphoryl-3',4'-trihydroxy-2'-oxopentyl)- |
| CAC0940 | 5-(5-Phospho-D-ribosylaminoformimino)-1-(5-phosphoribosyl)-imidazole-4-carboxamide <=> N-(5'-Phospho-D-1'-ribulosylformimino)-5-amino-1-(5''-phospho-D-ribosyl)-4-imidazolecarboxamide |
| CAC3169/ CAC3176/ CAC3652 | (S)-2-Acetolactate + Thiamin diphosphate <=> 2-(alpha-Hydroxyethyl)thiamine diphosphate + Pyruvate |
| CAC3169/ CAC3176/ CAC3652 | 2-Oxobutanoate + 2-(alpha-Hydroxyethyl)thiamine diphosphate <=> (S)-2-Aceto-2-hydroxybutanoate + Thiamin diphosphate |
| CAC0517 | ATP + beta-D-Fructose 6-phosphate <=> ADP + beta-D-Fructose 1,6-bisphosphate |
| CAC1088/ CAC1572 | beta-D-Fructose 1,6-bisphosphate + H2O <=> beta-D-Fructose 6-phosphate + Orthophosphate |
| CAC0523/ CAC0700/ CAC1284/ CAC1435/ CAC2132/ CAC2784/ CAC2885/ CAC2986/ | 2-Demethylmenaquinone + S-Adenosyl-L-methionine <=> Menaquinone + S-Adenosyl-L-homocysteine |

TABLE 3-continued

The complete genome-scale metabolic network with gene identification where available. The stoichiometric coefficients of the biomass constituting equation are represented as variables since these values have been observed to change with growth stage-related cellular physiology.

| Locus Number | Reaction |
|---|---|
| CAC3154 | |
| CAC3626 | Formamidopyrimidine nucleoside triphosphate + H2O <=> 2,5-Diaminopyrimidine nucleoside triphosphate + Formate |
| CAC3626 | 2,5-Diaminopyrimidine nucleoside triphosphate <=> 2,5-Diamino-6-(5'-triphosphoryl-3',4'-trihydroxy-2'-oxopentyl)- |
| CAC0091 | (R)-2,3-Dihydroxy-3-methylpentanoate + NADP+ <=> (R)-3-Hydroxy-3-methyl-2-oxopentanoate + NADPH + H+ |
| CAC0091 | (S)-2-Aceto-2-hydroxybutanoate <=> (R)-3-Hydroxy-3-methyl-2-oxopentanoate |
| CAC3170/ CAC3604 | (R)-2,3-Dihydroxy-3-methylpentanoate <=> (S)-3-Methyl-2-oxopentanoic acid + H2O |
| CAC0091 | (S)-2-Acetolactate <=> 3-Hydroxy-3-methyl-2-oxobutanoic acid |
| N/A | Phosphatidylglycerol + Diglucosyl-diacylglycerol <=> 1,2-Diacyl-sn-glycerol + Glycerophosphoglycoglycerolipid |
| CAC0253/ CAC0256/ CAC0257 | 16 ATP + Nitrogen + 8 Reduced ferredoxin + 8 H+ + 16 H2O <=> 16 Orthophosphate + 16 ADP + 8 Oxidized ferredoxin + 2 NH3 + H2 |
| CAC3222 | Acetyl-CoA + D-Glucosamine 1-phosphate <=> CoA + N-Acetyl-D-glucosamine 1-phosphate |
| CAC0394/ CAC2973 | 2-Dehydro-3-deoxy-6-phospho-D-gluconate <=> (2R)-2-Hydroxy-3-(phosphonooxy)-propanal + Pyruvate |
| N/A | all-trans-Hexaprenyl diphosphate + Isopentenyl diphosphate <=> all-trans-Heptaprenyl diphosphate + Pyrophosphate |
| N/A | all-trans-Pentaprenyl diphosphate + Isopentenyl diphosphate <=> all-trans-Hexaprenyl diphosphate + Pyrophosphate |
| N/A | 1,4-Dihydroxy-2-naphthoate + all-trans-Octaprenyl diphosphate <=> 2-Demethylmenaquinone + Pyrophosphate + CO2 |
| CAC3184 | 2-C-Methyl-D-erythritol 4-phosphate + CTP <=> 4-(Cytidine 5'-diphospho)-2-C-methyl-D-erythritol + Pyrophosphate |
| CAC2902 | 4-(Cytidine 5'-diphospho)-2-C-methyl-D-erythritol + ATP <=> 2-Phospho-4-(cytidine 5'-diphospho)-2-C-methyl-D-erythritol + ADP |
| CAC2077/ CAP0106 | Pyruvate + (2R)-2-Hydroxy-3-(phosphonooxy)-propanal <=> 1-Deoxy-D-xylulose 5-phosphate + CO2 |
| CAC0434 | 2-Phospho-4-(cytidine 5'-diphospho)-2-C-methyl-D-erythritol <=> 2-C-Methyl-D-erythritol 2,4-cyclodiphosphate + CMP |
| CAC1795 | 2-C-Methyl-D-erythritol 4-phosphate + NADP+ <=> 1-Deoxy-D-xylulose 5-phosphate + NADPH + H+ |
| CAC1341 | L-Ribulose 5-phosphate <=> D-Xylulose 5-phosphate |
| N/A | Reduced ferredoxin + NAD+ <=> Oxidized ferredoxin + NADH + H+ |
| N/A | 1-Hydroxy-2-methyl-2-butenyl 4-diphosphate + NADPH + H+ <=> Isopentenyl diphosphate + NADP+ + H2O |
| N/A | 2-Oxoglutarate + Isochorismate <=> 2-Succinyl-6-hydroxy-2,4-cyclohexadiene-1-carboxylate + Pyruvate + CO2 |
| N/A | 2-Dehydro-3-deoxy-D-glucarate + H2O <=> D-Glucarate |
| N/A | Acetyl-[acyl-carrier protein] + 7 Malonyl-[acyl-carrier protein] + 7 NADPH + 7 NADH + 14 H+ <=> Hexadecanoyl-[acp] + 7 Acyl-carrier protein + 7 NADP+ + 7 NAD+ + 7 CO2 |
| N/A | Palmitoyl-CoA + 6 CoA + 7 FAD + 6 NAD+ + 6 H2O <=> Crotonoyl-CoA + 6 Acetyl-CoA + 7 FADH2 + 6 NADH + 6 H+ |
| N/A | Palmitoyl-CoA + 6 CoA + 7 FAD + 6 NADP+ + 6 H2O <=> Crotonoyl-CoA + 6 Acetyl-CoA + 7 FADH2 + 6 NADPH + 6 H+ |
| N/A | Lactate (extracellular) + H+ (extracellular) <=> Lactate-H |
| N/A | CO2 (extracellular) <=> CO2 |
| N/A | Ethanol (extracellular) <=> Ethanol |
| N/A | H2O (extracellular) <=> H2O |
| N/A | K+ (extracellular) + H+ (extracellular) <=> Potassium + H+ |
| CAC0444 | Na+ (extracellular) + H+ <=> Sodium + H+ (extracellular) |
| N/A | NH3 (extracellular) <=> NH3 |
| CAC0618/ CAC0619/ CAC0620/ CAC1399/ CAC1400/ CAC1401 | Nitrate (extracellular) + ATP + H2O => Nitrate + ADP + Orthophosphate |
| CAC1706 | Orthophosphate (extracellular) + ATP + H2O => 2 Orthophosphate + ADP |
| CAC3093 | Orthophosphate (extracellular) + H+ (extracellular) <=> Orthophosphate + H+ |
| N/A | Phosphoenolpyruvate + D-Glucose (extracellular) <=> Pyruvate + alpha-D-Glucose 6-phosphate |
| N/A | Sulfate (extracellular) + ATP + H2O <=> Sulfate + H+ + ADP + Orthophosphate |
| N/A | Butanol (extracellular) <=> 1-Butanol |

TABLE 3-continued

The complete genome-scale metabolic network with gene identification where available. The stoichiometric coefficients of the biomass constituting equation are represented as variables since these values have been observed to change with growth stage-related cellular physiology.

| Locus Number | Reaction |
| --- | --- |
| N/A | Acetone (extracellular) <=> Acetone |
| N/A | .0635 L-Alanine + .0345 L-Arginine + .0559 L-Asparagine + .0575 L-Aspartate + .00619 L-Cysteine + .0641 L-Glutamine + .0410 L-Glutamate + .0596 Glycine + .0229 L-Histidine + .0849 L-Isoleucine + .0902 L-Leucine + .0743 L-Lysine + .0260 L-Methionine + .0442 L-Phenylalanine + .0317 L-Proline + .0605 L-Serine + .0571 L-Threonine + .00735 Thymine + .0129 L-Tryptophan + .0384 L-Tyrosine + .0663 L-Valine <=> Protein |
| N/A | 0.336 dATP + 0.164 dCTP + 0.336 dGTP + 0.164 dTTP <=> DNA |
| N/A | 0.25 ATP + 0.25 CTP + 0.25 GTP + 0.25 UTP <=> RNA |
| N/A | 0.000201 ATP + 0.0292 L-Alanine + 0.00724 L-Arginine + 0.15 L-Aspartate + 0.132 L-Glutamate + 0.00216 L-Glutamine + 0.01 Glycine + 0.00425 L-Histidine + 0.0121 L-Isoleucine + 0.00558 L-Leucine + 0.0102 L-Lysine + 0.0325 L-Methionine + 0.00108 L-Phenylalanine + 0.0325 L-Proline + 0.19 L-Serine + 0.00392 L-Threonine + 0.000427 Thymine + 0.00407 L-Valine + 0.25 Orthophosphate + 0.119 D-Glucose + 0.0000829 Acetyl-CoA + 0.000101 CoA + 0.000168 FAD + 0.0036 NAD+ + 0.000083 NADH + 0.00029 NADP+ + 0.000671 NADPH + 0.251 L-Citrulline <=> Solute Pools |
| N/A | 0.497 Phosphatidylglycerol + 0.0622 Cardiolipin + 0.0623 3-Phosphatidyl-1'-(3'-O-L-lysyl)glycerol + 0.0125 3-D-Glucosyl-1,2-diacylglycerol + 0.0747 Diglucosyl-diacylglycerol + 0.0830 Menaquinone + 0.207 1,2-Diacyl-sn-glycerol <=> Lipid |
| N/A | 0.950 Crosslinked peptidoglycan + 0.05 Wall Teichoic Acid <=> Cell Wall |
| N/A | $\alpha$ Protein + $\beta$ RNA + $\chi$ DNA + $\delta$ Lipid + $\epsilon$ Cell Wall + $\Phi$ Solute Pools + $\eta$ Lipoteichoic acid + $\phi$ Fatty acids + $\kappa$ Granulose + $\gamma$ ATP + $\gamma$ H2O <=> Biomass + $\gamma$ ADP + $\gamma$ Orthophosphate |
| N/A | H2 (extracellular) <=> H2 |
| N/A | Phosphatidylglycerol + L-Lysine <=> 3-Phosphatidyl-1'-(3'-O-L-lysyl)glycerol + H2O |
| N/A | Nitrogen (extracellular) <=> Nitrogen |
| N/A | 5-Formyltetrahydrofolate <=> 10-Formyltetrahydrofolate |
| N/A | Geranylgeranyl diphosphate + Isopentenyl diphosphate <=> all-trans-Pentaprenyl diphosphate + Pyrophosphate |
| N/A | all-trans-Heptaprenyl diphosphate + Isopentenyl diphosphate <=> all-trans-Octaprenyl diphosphate + Pyrophosphate |
| N/A | Pyruvate + Glyceraldehyde 3-phosphate <=> 1-Deoxy-D-xylulose 5-phosphate + CO2 |
| N/A | 1-Deoxy-D-xylulose 5-phosphate + Glycine + L-Cysteine <=> 4-Methyl-5-(2-phosphoethyl)-thiazole + L-Alanine + 3 H2O + CO2 |
| N/A | 4-(1-D-ribitylamino)-5-amino-2,6-dihydroxypyrimidine + ATP <=> 5-amino-6-(5'-phosphoribitylamino)uracil + ADP + H2O |
| N/A | 3-Oxopropanoate <=> Acetaldehyde + CO2 |
| N/A | 2-C-Methyl-D-erythritol 2,4-cyclodiphosphate + 2 H+ <=> 1-Hydroxy-2-methyl-2-butenyl 4-diphosphate + H2O |
| N/A | Butyrate (extracellular) + H+ (extracellular) <=> Butanoic acid |
| N/A | Acetate (extracellular) + H+ (extracellular) <=> Acetic acid |
| N/A | ADP + H2O <=> AMP + Orthophosphate |
| N/A | Biotinyl-5'-AMP <=> AMP + holo[carboxylase] |
| N/A | Pyrophosphate + H20 <=> 2 Orthophosphate |
| N/A | Biotin (extracellular) + H+ (extracellular) <=> Biotin + H+ |
| N/A | 4-aminobenzoate (extracellular) + H+ (extracellular) <=> 4-aminobenzoate + H+ |
| N/A | Hexadecanoate + CoA <=> Acyl-CoA + H2O |
| N/A | L-Aspartate + Fumarate <=> Iminoaspartate + Succinate |
| N/A | D-Fructose 1,6-bisphosphate <=> beta-D-Fructose 1,6-bisphophate |
| N/A | UDP-N-Acetylmuramoyl-L-Alanyl-D-Glutamate + 3 ATP + H2O + NH3 + L-Lysine + 5 Glycine + D-Alanyl-D-Alanine + UDP-N-Acetyl-D-Glucosamine <=> Peptidoglycan (Cross-Linked) |
| N/A | UDP-N-Acetylglucosamine + CDPribitol <=> Wall Teichoic Acid |
| N/A | Phophatidyl Glycerol + Glycerophophoglycoglycerolipid + D-Alanine <=> Lipoteichoic Acid |
| N/A | alpha-D-Glucose <=> D-Glucose |
| N/A | Reduced ferredoxin (extracellular) <=> Reduced ferredoxin |
| N/A | Reduced ferredoxin + 2 H+ <=> 2 H2 + Oxidized ferredoxin |
| N/A | Thioredoxin (extracellular) <=> Thioredoxin |
| N/A | Glucose (extracellular) + H+ (extracellular) <=> D-Glucose + H+ |
| N/A | Glucose (extracellular) + H2O + ATP <=> D-Glucose + H+ + ADP + Orthophosphate |
| CAC3680/ CAC2681/ CAC3682 | 3 Na+ + 2 K+ (extracellular) + ATP + H2O <=> 3 Na+ (extracellular) + 2 K+ + ADP + Orthophosphate |

TABLE 3-continued

The complete genome-scale metabolic network with gene identification where available. The stoichiometric coefficients of the biomass constituting equation are represented as variables since these values have been observed to change with growth stage-related cellular physiology.

| Locus Number | Reaction |
|---|---|
| N/A | $H_2O + CO_2 <=> HCO_3^- + H^+$ |
| N/A | L-Ornithine + Pyruvate <=> L-Glutamate 5-semialdehyde + L-Alanine |
| CAC2229 | Succinate + CoA + 2 Oxidized ferredoxin <=> Succinyl-CoA + 2 Reduced ferredoxin + 2 H+ |
| CAC0744/ CAP0140 | 2 Na+ + 3 H+ (extracellular) <=> 2 Na+ (extracellular) + 3 H+ |
| CAC2864/ CAC2865/ CAC2866/ CAC2867/ CAC2868/ CAC2869/ CAC2870/ CAC2871 | 3 H+ (extracellular) + ADP + Orthophosphate <=> 3 H+ + ATP + H2O |
| CAC3550/ CAC3551 | Na+ (extracellular) + ADP + Orthophosphate <= Na+ + ATP + H2O |
| N/A | (S)-1-Pyrroline-5-carboxylate + H2O <=> L-Glutamate 5-Semialdehyde |
| N/A | Acetoin (extracellular) + ADP + Orthophosphate <= Acetoin + ATP + H2O |
| N/A | Citrulline (extracellular) <=> Citrulline |
| N/A | D-fructose 6-phosphate <=> Beta-D-fructose 6-phosphate |
| N/A | Acetoacetyl-CoA + Acetate (extracellular) <=> Acetoacetate + Acetyl-CoA |
| CAP0163/ CAP0164 | Butyrate (extracelluar) + Acetoacetyl-CoA <=> Butanoyl-CoA + Acetoacetate |
| N/A | Hexadecanoate <=> Fatty acids |
| N/A | 1000 ADP glucose <=> Granulose + 1000 ADP |

TABLE 4

Examples of reaction network database error and inconsistencies identified by the reverse engineering algorithm.

| Noted Database Discrepancy | Correction |
|---|---|
| "Extracellular" compounds are not given "compound" identification numbers in the KEGG database | These were manually assigned. |
| Membrane transport reactions are not given "reaction" identification numbers in the KEGG database | These were manually assigned. |
| "Fatty acid" is a general compound name used in "Glycerolipid Metabolism." This compound has no origin of biosynthesis. | Hexadecanoate was used to replace the generalized "fatty acid" term in this pathway of biosynthesis. Hexadecanoate was chosen as the fatty acid representative based on clostridial physiology. |
| The fate or function of urea is undefined. | Allowed the degradation of urea to ammonia and $CO_2$. |
| Ferricytochrome C and ferrocytochrome C have no origin of biosynthesis in the metabolic network. | These compounds were imported into the metabolic network and were available in excess. |
| The following crucial metabolic reaction: Butyrate + Acetoacetyl-CoA ↔ Butyryl-CoA + Acetoacetate was not assigned to C. acetobutylicum | This reaction was added to the Primary Metabolism pathway. |
| $H_2$ biosynthesis is not representative of literature pathway. | Reconstructed from literature data and known pathways |
| "Diacylglycerol" of Glycerolipid Metabolism has no degradation reactions. | Replaced this compound with 1,2-Diacyl-sn-glycerol. |
| Valine, Leucine, Isoleucine, Histidine, Cysteine and aromatic amino acids degradation pathways are largely incomplete. | Made the assumption that amino acids are not degraded for energy and that amino acids were only incorporated into protein or used as building-blocks for other macromolecules. |
| Conversion of Riboflavin to Dimethyl benzimidazole is undefined. | This reaction pathway was eliminated. The pathway was redirected to terminate with FAD biosynthesis. |

TABLE 4-continued

Examples of reaction network database error and inconsistencies identified by the reverse engineering algorithm.

| Noted Database Discrepancy | Correction |
| --- | --- |
| Octaprenyl-diphosphate has no defined origin of biosynthesis. | Geranyl-diphosphate was synthesized through the non-mevalonate pathway of steroids biosynthesis and processed to a farnesyl-diphosphate intermediate, then directly to octaprenyl-diphosphate. |
| The reaction mechanism and associated enzymes for the conversion of Glyceraldehyde-3-phosphate and Pyruvate to 5-(2-Hydroxyethyl)-4-methylthiazole in the Thiamine biosynthesis pathway is required but undefined. | The following composite reaction was composed, based on published data (Begley et al. 1999). Pyruvate + Glyceraldehyde-3-phosphate + Glycine + L-Cysteine → 5-(2-Hydroxyethyl)-4-methylthiazole + L-Alanine + 3 $H_2O$ + $CO_2$ |
| The cytosine-specific DNA methyltransferase (e.c. 2.1.1.37, CAC1222, CAC1501) has associated reaction mechanism: S-Adenosyl-L-methionine + DNA cytosine ↔ S-Adenosyl-L-homocysteine + DNA 5-methylcytosine. Both DNA cytosine and DNA 5-methylcytosine have no origins of biosynthesis or degradation. | The reaction in question was eliminated. S-Adenosyl-L-homocysteine is a byproduct of one path of L-Methionine production and Menaquinone biosynthesis. It is converted to L-Homocysteine through an S-D-Ribosyl-L-homosysteine intermediate with D-Ribose and Adenine byproducts. |
| The compounds "Iron," "$Fe^{2+}$," and "$Fe^{3+}$" all have separate identifiers. | "Iron" and "$Fe^{2+}$" were grouped under the same identifier. "$Fe^{3+}$" was given a separate identifier. |
| No degradation pathway exists for 3-oxopropanoate. | Conversion to Acetaldehyde and $CO_2$ was added based on the similar organism C. tetani E88. |
| The Biotin-carboxyl-carrier protein required of fatty acid biosynthesis is synthesized from Biotin and requires an "Apo-[carboxylase]." This compound has no root-origin of biosynthesis or defined chemical composition. | The Biotin-carboxyl-carrier protein is involved in a cycle that results in the conversion of Acetyl-CoA to Malonyl-CoA at the expense of ATP. Due to the unknown (R-group) structure of this protein in clostridia and its cycling nature as a carrier compound (rather than a macromolecule precursor), a simplification was made for its biosynthesis: Biotinyl-5'-AMP ↔ AMP + Biotin-carboxyl-carrier protein (Holo-[carboxylase]). |
| In Glycerolipid biosynthesis, there is a requirement of "Acyl-CoA," but this compound does not have an origin of biosynthesis. | For the "acyl" group, hexadecanoate was used, based on clostridial physiology. The following reaction was created to define "Acyl-CoA" in the original KEGG pathways: Hexadecanoate + CoA ↔ Acyl-CoA + $H_2O$ |
| The compounds "β-D-fructose 1,6-biphosphate" and "D-fructose 1,6-biphosphate" are given separate identifiers in KEGG. | The following reaction was added to the metabolic network to allow the unconstrained exchange between these two identical compounds: β-D-fructose 1,6-biophosphate ↔ D-fructose 1,6-biphosphate |
| The compounds "β-D-fructose 6-phosphate" and "D-fructose 6-phosphate" are given separate identifiers in KEGG. | The following reaction was added to the metabolic network to allow the unconstrained exchange between these two identical compounds: β-D-fructose 6-phosphate ↔ D-fructose 6-phosphate |
| Peptidoglycan biosynthesis is missing certain key enzymes that are not recognized in clostridia through homology. | A broad approximation was formulated: UDP-N-acetylmuramoyl-L-alanyl-D-glutamate + 3 ATP + $H_2O$ + $NH_3$ + L-Lysine + 5 Glycine + D-Aanyl-D-alanine + UDP__N-Acetyl__D-glucosamine ↔ Peptidoglycan |
| KEGG does not support the biosynthesis of Wall Teichoic acid, an essential macromolecular component of the bacterial cell wall. | A composite reaction was formulated from an earlier publication (Heinemann et al. 2005): 41 UDP-N-Acetylglucosamine + 3 CDP glycerol + 40 CDP ribitol + 2 D-Alanine + 2 ATP ↔ Wall Teichoic acid + 40 UDP + 43 CMP + 2 AMP + 2 Pyrophosphate |
| KEGG does not support the biosynthesis of Lipoteichoic acid, an essential macromolecular component of the bacterial cell wall. | A composite reaction was formulated from an earlier publication (Heinemann et al. 2005): 48 Phosphatidylglycerol + Glycerophosphoglycoglycerolipid + 33 D-Alanine + 7 N-Acetyl-D-glucosamine-c55 |

TABLE 4-continued

Examples of reaction network database error and inconsistencies identified by the reverse engineering algorithm.

| Noted Database Discrepancy | Correction |
|---|---|
| | ↔ Lipoteichoic acid + 48 1,2-Diacylglycerol + 33 AMP + 33 Orthophosphate |
| The compounds "D-Glucose," "α-D-Glucose" and "β-D-Glucose" are given separate identifiers in KEGG. | A clostridial enzyme exists for the reversible conversion of α-D-Glucose to β-D-Glucose. The following reaction was added so "D-Glucose" could be utilized in glycolysis:<br>α-D-Glucose ↔ D-Glucose |
| Ferredoxin has no origin of biosynthesis or degradation. | Ferredoxin has reduced and oxidized states that stay in balance given an electrochemical potential. To provide origins of biosynthesis/degradation, reduced ferredoxin was imported into the metabolic network and retained as part of the pooled solutes. |
| Thioredoxin has no origin of biosynthesis or degradation | To provide origins of biosynthesis/degradation, reduced thioredoxin was imported into the metabolic network and retained as part of the pooled solutes. |
| Folate biosynthesis involves the production of species (e.g., Molybdopterin) that do not contain defined synthesis or degradation pathways. | A lumped reaction was generated for folate biosynthesis and was based on a simplified version of the biosynthesis pathway:<br>$GTP + H_2O + 4$-Aminobenzoate + L-Glutamate + $NAD^+$ + ATP ↔ Folate + Formate + Glycoaldehyde + ADP + NADH + $H^+$ + 2 Orthophosphate + 2 Pyrophosphate |
| The previously presented equations for Lipoteichoic acid and Wall Teichoic acid are possibly creating a large burden of macromolecular biosynthesis and inhibiting growth rate in silico. | It is possible that the un-cross-linked forms of these species are represented in the biomass equation. Comparisons were made to *B. subtilis* (Atrih et al. 1999; Perego et al. 1995).<br>1. UDP-N-Acetoglucosamine + CDP-Ribitol ↔ Wall Teichoic acid<br>2. Phosphatidylglycerol + Glycerophosphoglycerolipid + D-alanine ↔ Lipoteichoic acid |
| The following important reaction is contained in KEGG that involves two generalized terms ("2-Oxo acid" and "L-Amino acid"). Neither of the generalized terms contains an origin of biosynthesis/degradation.<br>L-Ornithine + 2-Oxo acid ↔ L-Glutamate 5-semialdehyde + L-Amino acid | Through the combination of BLAST and enzymatic database searches (BRENDA), Pyruvate was found a suitable "2-Oxo acid" and L-Alanine was the corresponding "L-Amino acid." |
| The compounds "Starch," "Dextrin," "Amylose," and "Cellulose" are broadly defined as polymer chains of length n. | Since a clostridial minimal medium was used, these compounds were not included in the current metabolic network reconstruction. However, these compounds and their degradation reactions must be specifically defined before their inclusion in a metabolic network is feasible. |

EXAMPLE 2

The Stoichiometric Matrix and Constraints

The resulting composite equation, $S \cdot v = 0$, consisted of a two-dimensional stoichiometric matrix, S, and a vector, v, of all intracellular and membrane transport fluxes. Integration of transport reaction fluxes into the stoichiometric matrix of a metabolic model was published (Edwards et al. 2001). Constraints, in the form $\alpha_i \leq v_i \leq \beta_i$, were applied to all components of the flux vector. A constraint for irreversibility consisted of setting $\alpha_i$ or $\beta_i$ to zero (depending on the reaction-flux direction) while setting the opposite constraint near infinity. The flux vector was optimized through linear programming, a technique commonly referred to as flux balance analysis (FBA) (Edwards et al. 1999; Papoutsakis 1984). The objective function used in the optimization algorithm was to maximize the specific growth rate. The stoichiometric matrix was constructed in MATLAB (The Mathworks, Inc.; Natick, Mass.). Constrained optimization by linear programming was performed with LINDO API (Lindo Systems; Chicago, Ill.), within the MATLAB environment. A list of all chemical reactions, biomass constituting equations, exchange reactions, and associated ranges of applied constraints for FBA is given as Table 3.

EXAMPLE 3

Identification of Metabolic Pathways and Transporters

The iterative metabolic pathway construction procedure is summarized in FIG. 1. The procedure was initiated with data mining of metabolic pathways specific to *C. acetobutylicum* contained in the Kyoto Encyclopedia of Genes and Genomes (KEGG) (Kanehisa and Goto 2000), the GenomeNet (Kanehisa et al. 2002), MetaCyc (Caspi et al. 2006) and the Comprehensive Microbial Resource (CMR) (Peterson et al. 2001) at The Institute for Genomic Research (TIGR) (http://www.tigr.org/). This set of metabolic reactions was further supplemented with metabolite transport reactions obtained from the Transport Classification Database (TCD) (Busch and Saier 2002; Saier et al. 2006) and TransportDB (Ren et al. 2007). Unresolved metabolic pathways were identified through reverse engineering of metabolic network reconstruction (discussed below). Additional metabolic and transport reactions were identified through the PUMA2 database (Maltsev et al. 2006) and literature specific to the *C. acetobutylicum* physiology. Furthermore, BLASTP analyses of *C. acetobutylicum* proteins of unknown function to other annotated clostridial genomes were used to identify additional enzymes contained in KEGG and CMR that were required by the metabolic network. In the absence of clostridial data, genomes of the well-studied bacteria (in order) *Bacillus subtilis* (Kunst et al. 1997), *Staphylococcus aureus* N315 (Kuroda et al. 2001), and *Escherichia coli* K-12 MG1655 (Blattner et al. 1997) were used. The BRENDA enzymatic database (Schomburg et al. 2004) and ExPASy ENZYME database (Bairoch 2000) were used to further identify substrates/products and stoichiometry of reactions catalyzed by individual enzymes and characterize unresolved pathways. The BRENDA database was also parsed to obtain a list of all enzymes catalyzing irreversible reactions under physiological conditions, and this list was used to identify enzymes in the *C. acetobutylicum* metabolic network catalyzing irreversible reactions.

EXAMPLE 4

Overview of Biomass Constituting Equations

The contribution of the metabolic network to the production of biomass was calculated based on genomic and physiological data available for *C. acetobutylicum*. The components of the biomass constituting equation were adapted from a platform initially created for *S. aureus* N315 (Heinemann et al. 2005) and recently used for Methanosarcina barkeri (Feist et al. 2006). Specifically, biomass was defined as a sum of: RNA, DNA, protein, lipids, cell wall, and solute pools of the cytoplasm. The specific definition of each of these broad terms was constructed according to genomic information obtained from NCBI and from literature data. The total list of biomass constituting equations and energetic requirements are shown in Table 3. The average DNA composition was based on the nucleotide content of the entire genome and the pSOL1 megaplasmid. The average protein and RNA compositions were calculated from an analysis of known ORFs. The calculation of the average RNA sequence included ribosomal and tRNA sequences in addition to ORFs. Previously published data, specific to *C. acetobutylicum* and *B. subtilis*, enabled specifically-tailored constituting equations for lipids, teichoic acids, and peptidoglycan biosyntheses. These equations are also shown in Table 3. Due to the unavailability of specific data, the composition of the intracellular solute pool (shown in Table 3) was assumed similar to those published for *S. aureus* N315 (Heinemann et al. 2005) with some notable exceptions (discussed later). Also consistent with the model for *S. aureus* (Heinemann et al. 2005), a growth maintenance value of 40 mmol ATP/(g cell dry weight per hour) was assumed (Stephanopoulos et al. 1998).

EXAMPLE 5

Pathway Resolution Through Reverse Engineering of the Metabolic Network

Data mining of biochemical pathway databases (KEGG, in particular) were used in compiling initial drafts of the metabolic network for *C. acetobutylicum*. However, as is currently the case for most genomes, incomplete gene annotation leads to several incomplete metabolic pathways within such biochemical pathway databases. In addition, other inconsistencies were observed in data obtained directly from these biochemical pathway databases. These included: (i) multiple identity markers for the same compound; (ii) compounds that lacked an origin of synthesis/degradation within the biochemical database; (iii) incorrect stoichiometry of metabolic reactions; and (iv) misappropriated enzymes to a particular cell type. Identification of the source of a broken metabolic pathway (gaps) of the network is a laborious task, especially in the case where multiple sources of inconsistencies may exist (Kumar et al. 2007; Reed et al. 2003). Thus, a reverse engineering approach was developed to identify such inconsistencies within the metabolic network. The approach was designed to be used in conjunction with or after the identification of dead-ends through stoichiometric matrix analysis (Reed et al. 2003). The proposed reverse engineering approach includes optimizing the reaction flux network with an objective function of maximizing the specific growth rate. In general, a metabolic network with one or multiple incomplete biochemical pathways (from substrate to biomass building blocks) was found to result in a maximized specific growth rate of zero (no growth in silico). This approach is illustrated by a flow diagram of FIG. 2. Our reverse engineering algorithm uses a set of biomass constituting equations (see Table 3) and a metabolic network (complete or incomplete). The set of membrane transporters required for minimal medium (Monot et al. 1982) (see Table 3) were used here as well. If the application of FBA to the existing metabolic network does not yield the production of biomass in silico, biomass transfer equations are added to the metabolic network. These equations are listed in Table 5 and consist of the individual components comprising biomass (e.g., RNA, DNA, protein, lipids, cell wall, and pooled solutes) and which are separately transported into an incomplete metabolic network. The addition of biomass transfer equations results in a positive specific growth rate in silico when FBA is applied. It is noted that biomass transfer equations and component transfer equations (discussed later) are arbitrary membrane transport equations used to identify metabolic network discrepancies only. These equations are not present in the final version of the metabolic network reconstruction. Following their addition, one-by-one the biomass transfer equations are eliminated. Once the elimination of a biomass transfer equation results in a specific growth rate of zero (arrested growth in silico), that broadly-defined component of biomass is broken down into its constituents. For example, the biomass component RNA is composed of genome-specific stoichiometric amounts of ATP, CTP, GTP and UTP. In this case, the RNA biomass transfer equation would be removed and ATP, CTP, GTP and UTP would be added to the metabolic network by separate equations termed component transfer equations. The full list of component transfer equations used in the model-building process is given in Table 5. In a similar procedure, the component transfer equations are systematically eliminated until a specific growth rate of zero is realized. The component responsible for arresting growth in silico is recognized as being inadequately synthesized/degraded in the existing metabolic network. Upon identification of this type of discrepancy in the metabolic network, iterative measures, as shown in FIG. 1, are implemented to resolve the network connectivity.

Figure 4:
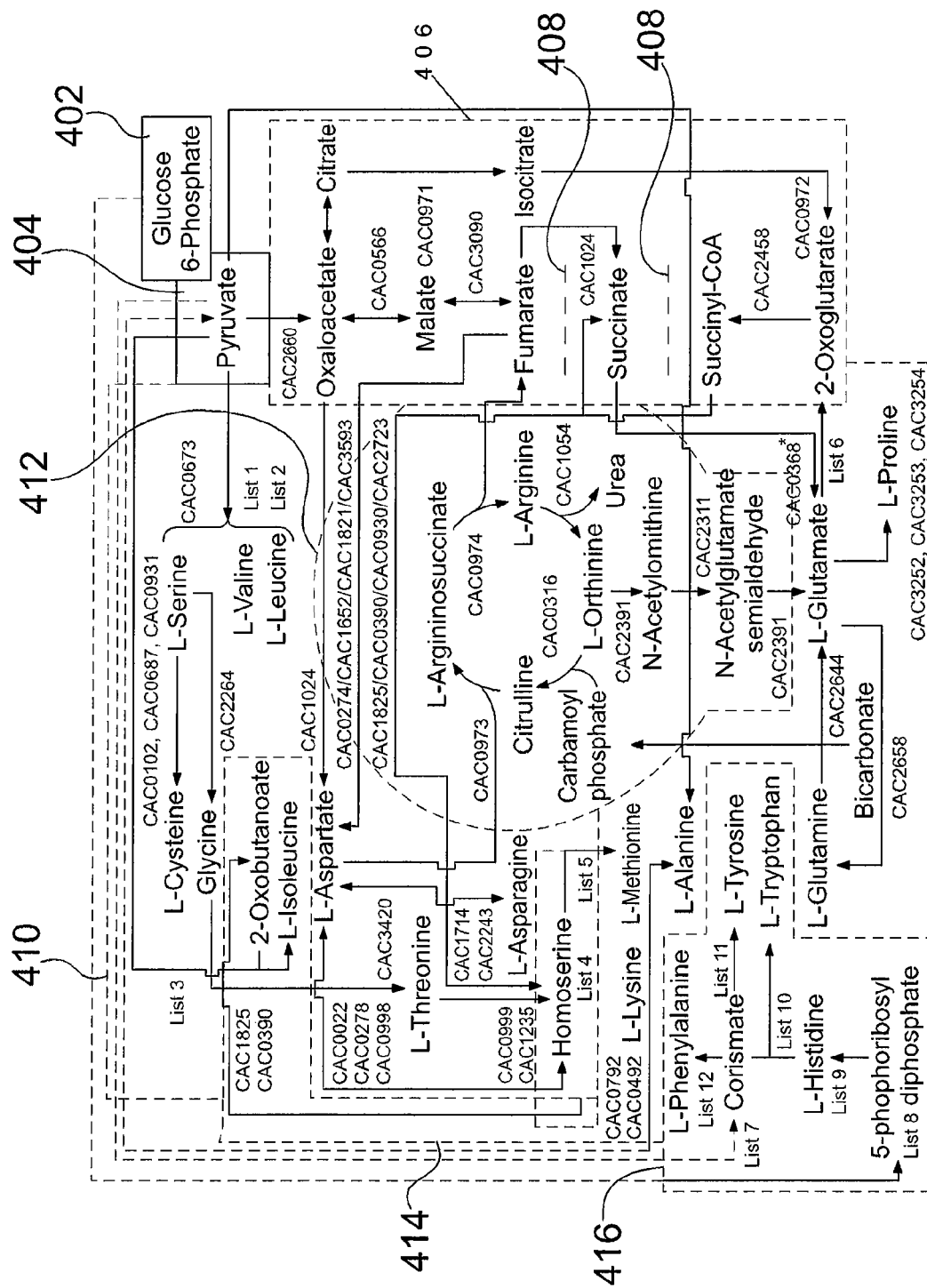
FIG. 4 shows reconstructed pathways of L-amino acids biosynthesis in *C. acetobutylicum* in view of the incomplete TCA cycle. The following pathways and sub-categories are highlighted within the broadly-defined pathway of amino acids biosynthesis. The links to carbohydrate metabolism, pyruvate and glucose-6-phosphate (which are linked through glycolysis) are shown in regions 402 and 404, respectively. The incomplete TCA cycle (region 406) contains separators (dashed lines 408) to show locations of missing conventional TCA cycle enzymes. L-amino acids synthesized directly from pyruvate, oxaloacetate or malate precursors are shown in region 410. Other TCA cycle L-amino acid precursors (2-oxoglutarate, succinyl-CoA and succinate) are connected to oxaloacetate, malate and fumarate through the urea cycle (region 412). Region 414 shows L-amino acids, which are (i)

An important example of the applied model-building methodology described here is illustrated in FIG. 4. Using this method, we resolved the entire network of amino acids biosynthesis. To our knowledge this is the first representation of this completed set of metabolic pathways for any of the clostridia. FIG. 4 demonstrates clearly the involvement of the urea cycle in this process. This is extraordinary as *C. acetobutylicum* contains an incomplete TCA cycle

TABLE 5

List of Biomass building-block transfer equations and Component building-block transfer equations.

Biomass Building-Block Transfer Equations

Protein (extracellular) ↔ Protein
RNA (extracellular) ↔ RNA
DNA (extracellular) ↔ DNA
Lipid (extracellular) ↔ Lipid
Cell Wall (extracellular) ↔ Cell Wall
Solute Pools (extracellular) ↔ Solute Pools
Component Building-Block Transfer Equations:
Protein Building-Block Transfer Equations L-Alanine (extracellular) ↔ L-Alanine
L-Arginine (extracellular) ↔ L-Arginine
L-Asparagine (extracellular) ↔ L-Asparagine
L-Aspartate (extracellular) ↔ L-Aspartate
L-Cysteine (extracellular) ↔ L-Cysteine
L-Glutamate (extracellular) ↔ L-Glutamate
L-Glutamine (extracellular) ↔ L-Glutamine
Glycine (extracellular) ↔ Glycine
L-Histidine (extracellular) ↔ L-Histidine
L-Isoleucine (extracellular) ↔ L-Isoleucine
L-Leucine (extracellular) ↔ L-Leucine
L-Lysine (extracellular) ↔ L-Lysine
L-Methionine (extracellular) ↔ L-Methionine
L-Phenylalanine (extracellular) ↔ L-Phenylalanine
L-Proline (extracellular) ↔ L-Proline
L-Serine (extracellular) ↔ L-Serine
L-Threonine (extracellular) ↔ L-Threonine
Thymine (extracellular) ↔ Thymine
L-Tryptophan (extracellular) ↔ L-Tryptophan
L-Tyrosine (extracellular) ↔ L-Tyrosine
RNA Building-Block Transfer Equations ATP (extracellular) ↔ ATP
CTP (extracellular) ↔ CTP
GTP (extracellular) ↔ GTP
UTP (extracellular) ↔ UTP
DNA Building-Block Transfer Equations dATP (extracellular) ↔ dATP
dCTP (extracellular) ↔ dCTP
dGTP (extracellular) ↔ dGTP
dTTP (extracellular) ↔ dTTP
Lipid Building-Block Transfer Equations Phosphatidylglycerol (extracellular) ↔ Phosphatidylglycerol
Cariolipin (extracellular) ↔ Cardiolipin
3-Phosphatidyl-1'-(3'-O-L-lysyl)glycerol (extracellular) ↔ 3-Phosphatidyl-1'-(3'-O-L-lysyl)glycerol
D-Glucosyl-1,2-diacylglycerol (extracellular) ↔ D-Glucosyl-1,2-diacylglycerol

TABLE 5-continued

List of Biomass building-block transfer equations and Component building-block transfer equations.

Diglucosyl-diacylglycerol (extracellular) ↔ Diglucosyl-diacylglycerol
Lipoeichoic acid (extracellular) ↔ Lipoteichoic acid
Menaquinone (extracellular) ↔ Menaquinone
1,2-Diacyl-sn-glycerol (extracellular) ↔ 1,2-Diacyl-sn-glycerol
Phosphatidylglycerol (extracellular) ↔ Phosphatidylglycerol
Cell Wall Building-Block Transfer Equations Crosslinked Peptidoglycan (extracellular) ↔ Crosslinked Peptidoglycan
Wall Teichoic acid (extracellular) ↔ Wall Teichoic acid
Solute Pools Building-Block Transfer Equations (only unique equations listed)

Orthophosphate (extracellular) ↔ Orthophosphate
D-Glucose (extracellular) ↔ D-Glucose
Acetyl-CoA (extracellular) ↔ Acetyl-CoA
CoA (extracellular) ↔ CoA
FAD (extracellular) ↔ FAD
FADH$_2$ (extracellular) ↔ FADH$_2$
NAD$^+$ (extracellular) ↔ NAD$^+$
NADH (extracellular) ↔ NADH
NADP$^+$ (extracellular) ↔ NADP$^+$
NADPH (extracellular) ↔ NADPH

EXAMPLE 6

Thermodynamic Analysis of Proposed Pathways

We also assessed the thermodynamic feasibility of proposed metabolic pathways (e.g., the reverse TCA cycle) for *C. acetobutylicum* that are not common to reaction network database. This was done by calculating the Gibbs free energy of all reactions of the pathway using previously published methods and estimated values for the standard Gibbs free energy of formation, $\Delta_f G'_{est}{}^o$, and estimated standard Gibbs free energy of reaction, $\Delta_r G'_{est}{}^o$ (Henry et al. 2007; Henry et al. 2006).

$$\Delta_r G'^o_{est} = \sum_{i=1}^{m} n_i \Delta_f G'^o_{est} \qquad (1)$$

A negative Gibbs free energy of reaction, $$\Delta_r G' = \Delta_r G'^o_{est} + RT \ln\left( \prod_{i=1}^{m} (c_i \gamma_i)^{n_i} \right) \qquad (2)$$

is required for a metabolic reaction to occur and was calculated given m compounds of a chemical reaction with stoichiometric coefficients n, where R is the ideal gas constant, and an assumed temperature, T, of 298K. Millimolar concentrations, ci, of reaction components (Henry et al. 2006) and dimensionless activity coefficients, γi were used to calculate the concentration-dependent term of the Gibbs free energy of reaction equation (Eq. 2). As shown previously (Henry et al. 2007), the standard error in $\Delta_f G'_{est}{}^o$ and $\Delta_r G'_{est}{}^o$ terms calculated from group contribution theory (Mavrovouniotis 1990) outweighed the influence of ionic strength, despite the illustration of its strong influence on $\Delta_r G'$ (Maskow and von Stockar 2005). Given these results, activity coefficients were set to 1 for our calculations. For proposed pathways in *C. acetobutylicum* not native to reaction network databases (e.g., KEGG), combinations of metabolite concentrations yielding negative $\Delta_r G'$ values for every reaction in the pathway were calculated. Pathways incapable of producing negative $\Delta_r G'$ values for every reaction are thermodynamically infeasible. Resulting metabolite concentrations were compared to measured physiological metabolite concentrations of *C. acetobutylicum* (when available) to assess the practicality of the proposed reaction, similar to that done for glycolysis (Maskow and von Stockar 2005). For cases in which not all metabolite data were available, ranges of metabolite concentrations at which a proposed pathway is feasible were calculated. It is noted that a wide range of short-comings currently exist for the thermodynamic analysis of metabolic pathways (Maskow and von Stockar 2005). Aside from the obvious pitfalls of accurate $\Delta_f G'_{est}{}^{10}$ and cytoplasm ionic strength calculations, the influence of intracellular pH on $\Delta_r G'_{est}{}^{10}$ remains ambiguous in the literature and is unaccounted for in our calculations.

EXAMPLE 7

Representation of Lipid Biosynthesis

Total lipids in *C. acetobutylicum* have been found to account for 5-6% of the dry cell weight (Lepage et al. 1987). It has been also reported that solvent exposure leads to an increase in the ratio of saturated and cyclopropane fatty acids to unsaturated membrane fatty acids (Baer et al. 1987; Vollherbst-Schneck et al. 1984; Zhao et al. 2003), changes in the mean fatty acid acyl chain length (Lepage et al. 1987; Vollherbst-Schneck et al. 1984; Zhao et al. 2003) and changes in the membrane phospholipid composition (Johnston and Goldfine 1992; Lepage et al. 1987; MacDonald and Goldfine 1991). Nevertheless, due to the absence of specific compositional information about these changes, a single lipid biosynthesis equation (see Table 3) was used in the calculation of biomass composition over the entire course of exponential growth. The relative amounts of lipids and phospholipids of the lipids biosynthesis equation was derived based on a consensus of the cited literature data corresponding to exponential growth. The fatty acid composition in all cases was also held constant at 16:0 (carbon chain-length:number of double-bonds), which is a dominant experimental observation (Lepage et al. 1987; Vollherbst-Schneck et al. 1984). For the lipid-equation component of lipoteichoic acid (LTA), literature data specific to *B. subtilis* (Neuhaus and Baddiley 2003; Perego et al. 1995) were used, due to insufficient data available for *C. acetobutylicum*. The average LTA composition of 29 glycerophosphate units per chain was used. Also, an average of 13 glycerophosphate units per chain were substituted with D-alanine esters (D-alanylation) in *B. subtilis* (Neuhaus and Baddiley 2003; Perego et al. 1995). The process of D-alanylation was ignored in the *C. acetobutylicum* model due to the absence of a dlt operon (Kiriukhin and Neuhaus 2001; Perego et al. 1995).

EXAMPLE 8

Cell-Wall Composition

Cell wall is made up of crosslinked peptidoglycan and wall teichoic acid (WTA). Due to the lack of information specific to *C. acetobutylicum*, in the cell-wall equation (see Table 3), the stoichiometric coefficients of these components were kept identical to those found for *S. aureus* N315 (Heinemann et al. 2005). At the time of model construction, the genome-scale model of *B. subtilis* (Oh et al. 2007) had not yet been published, and thus information from *B. subtilis* was not employed in our model. Modifications of peptidoglycan structures and amino acids of the interpeptide bridge have been observed as a result of environmental changes (Schleifer and Kandler 1972), and large differences exist between the peptidoglycan structures of vegetative cells and spores (Atrih and Foster 2001; Makino and Moriyama 2002). However, a single description of crosslinked peptidoglycan (Cummins and Johnson 1971; Schleifer and Kandler 1972) (see Table 3) was used for model development of *C. acetobutylicum* vegetative growth. In addition, a model of wall teichoic acid from *B. subtilis* (Neuhaus and Baddiley 2003; Perego et al. 1995) was used, in absence of specific literature data for *C. acetobutylicum*. As with LTA, the cellular process of D-alanylation of WTA was ignored for the *C. acetobutylicum* model.

EXAMPLE 9

Other Resolved Pathways of Anaerobic Metabolism

Development of a genome-scale model for a strict anaerobe, such as *C. acetobutylicum*, from reaction network databases and enzyme homology yielded multiple aerobic reactions that were further resolved using the BRENDA database to locate anaerobic reactions catalyzed by available enzymes. The list of aerobic reactions assigned to the *C. acetobutylicum* genome in the KEGG database (as of August, 2007) is presented in Table 4. It is possible that many of the enzymes identified through homology searches that catalyze aerobic reactions also catalyze anaerobic reactions that remain uncharacterized. Two examples are: (i) the NAD biosynthesis pathway; and (ii) anaerobic biosynthesis of L-isoleucine.

Anaerobic NAD biosynthesis. The quinolinate precursor of NAD is commonly synthesized in vivo from L-aspartate through an iminoaspartate intermediate by L-aspartate oxidase (NadB, EC 1.4.3.16, CAC1024) and quinolinate synthase (NadA, EC 3.2.2.5, CAC1025). Alternatively, quinolinate is synthesized from the metabolism of L-tryptophan. However, with current genome annotation of *C. acetobutylicum*, the pathway of possible L-tryptophan utilization, yielding quinolinate, is largely uncharacterized. This biochemical process requires, at minimum, five enzymes, and none have been identified in *C. acetobutylicum* through gene homology. Since a minimal medium (Monot et al. 1982), that contained no amino acids or peptides was used, the assumption was made that amino acids were synthesized in vivo for incorporation into protein and as precursors of other biological macromolecules. Thus, quinolinate biosynthesis from L-tryptophan was not considered a feasible pathway of biosynthesis in a minimal medium. Thus, a feasible pathway of NAD biosynthesis requires the conversion of L-aspartate to iminoaspartate by L-aspartate oxidase (NadB, EC 1.4.3.16, CAC1024) under anaerobic conditions. Incidentally, L-aspartate oxidase is also one of multiple catalysts for the conversion between L-aspartate and oxaloacetate. However, reaction mechanisms catalyzed by L-aspartate oxidase currently available in the KEGG database are aerobic. Through the BRENDA database and a further literature investigation, fumarate was identified as a possible electron acceptor for the conversion of L-aspartate to oxaloacetate catalyzed by L-aspartate oxidase under anaerobic conditions (Messner and Imlay 2002; Tedeschi et al. 1996). Further, an L-asparate oxidase has been identified in an anaerobic hyperthermophilic bacterium and has been found to catalyze anaerobic L-aspartate dehydrogenation (Sakuraba et al. 2002). Thus, we propose the conversion of L-aspartate to iminoasparate by L-asparate oxidase (NadB, EC 1.4.3.16, CAC1024) in the *C. acetobutylicum* metabolic network through the use of fumarate as a terminal electron acceptor, resulting in the production of succinate as well as iminoaspartate, as shown by Eq. 5.

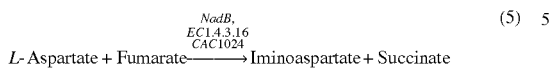

$$\text{L-Aspartate + Fumarate} \xrightarrow[\substack{EC 1.4.3.16 \\ CAC1024}]{NadB,} \text{Iminoaspartate + Succinate} \quad (5)$$

Anaerobic L-isoleucine biosynthesis. The biosynthesis pathway of L-isoleucine in *C. acetobutylicum* was found not to include L-threonine (Nolling et al. 2001). Homology analysis of the threonine dehydratase from *B. subtilis* (IlvA, EC 4.3.1.19, BG10673), which catalyzes the reaction of L-threonine to 2-oxobutanoate, yielded a low bit-score (Pearson 1996) when compared to ORFs of *C. acetobutylicum*. The biosynthesis of 2-oxobutanoate through a 2-methylmaleate intermediate was investigated since this pathway was suggested for M. thermaautotrophicum (Eikmanns et al. 1983). However, a homology search of the *B. subtilis* L-serine dehydratase (SdaAA, SdaAB; EC 4.3.1.17; BG13397, BG13398) against proteins of the *C. acetobutylicum* genome using BLASTP returned low bit-scores as well. Finally, biosynthesis was traced from L-aspartate to homoserine to 2-oxobutanoate through homoserine-O-succinyl-transferase (MetB, EC 2.3.1.46 CAC1825) and cystathione-γ-synthase (EC 2.5.1.48, CAC0390). This metabolic route of L-isoleucine biosynthesis is inefficient as MetB requires succinyl-CoA as a substrate.

EXAMPLE 10

Utilization of Succinate

In the current model, succinate is produced from succinyl-CoA in the biosynthesis of homoserine and from the anaerobic biosynthesis of NAD. However, a clear path for its degradation remains elusive. Utilization of succinate through the reverse reaction of Eq. 5 is infeasible since iminoaspartate is consumed by NAD biosynthesis. Other possibilities for succinate assimilation exist: (i) it is transported out of the cell, (ii) it is converted back to succinyl-CoA by an enzyme not commonly associated with the TCA cycle (iii) it is processed to butyrate through a crotonyl-CoA intermediate by a pathway similar to that observed for *C. kluyveri* (Sohling and Gottschalk 1996). The conversion of succinate to succinyl-CoA was chosen for the genome-scale model for the following reasons: (i) the primary metabolism of *C. acetobutylicum* is well-established and does not support butyrate production from succinate, (ii) succinate is not a byproduct commonly found in *C. acetobutylicum* fermentation broths, and (iii) the genome annotation surrounding succinate utilization remains underdeveloped at this time. Therefore, we realize that the proposed pathway of succinate assimilation to succinyl-CoA is an approximation based on the best available data at this time. We parsed the ExPASy ENZYME database (Bairoch 2000) for enzymes catalyzing reactions containing coenzyme A and cross-referenced this list with known enzymes of *C. acetobutylicum*. Enzyme annotation was then used to eliminate additional candidates, and those (26 enzymes in total) that could possibly catalyze succinate to succinyl-CoA in *C. acetobutylicum* are given as an additional list in Table 3. Of the notable candidates, a ferredoxin oxidoreductase (EC 1.2.7.-, CAC229) remains uncharacterized and may catalyze the conversion of succinate to succinyl-CoA. Due to the uncertainty of this reaction pathway in *C. acetobutylicum* and the tight control over the oxidative state of ferredoxins, the conversion of succinate to succinyl-CoA at the expense of ATP was also included in the genome-scale model.

EXAMPLE 11

Identification of Growth-Arresting Knock-Outs in Silico

The reconstructed metabolic network for *C. acetobutylicum* was used with FBA and systematic gene knock-outs to identify those enzymes (and their encoding genes) that will prevent growth when knocked-out in silico. One goal of this computational study is to identify gene knock-outs that arrest growth but do not disrupt the primary metabolism of *C. acetobutylicum*. Cells were grown in silico on three different media in this study, given the developed genome-scale model for *C. acetobutylicum*: (i) the minimal medium extracellular environment (Monot et al. 1982), (ii) minimal medium supplemented with L-glutamine, L-asparagine, L-histidine and L-cysteine (called partially-supplemented medium), and (iii) minimal medium supplemented with all L-amino acids as well as D-ribose and glycerol 3-phosphate (called supplemented medium). It is noted that the energetics and metabolic capacities of these in silico knock-out strains were not probed in depth. Only the ability of the altered metabolic network to produce biomass in silico was investigated, so the underlying membrane transport mechanisms of supplemented media nutrients and details of resulting metabolic capacity were ignored for these simulations. Reactions resulting in arrested growth in silico of *C. acetobutylicum* for each medium are included in Table 3. Table 11 contains a summary of the number of reactions arresting growth in silico, broken-down into broadly-defined metabolic pathways. In particular, in the absence of an extracellular source of amino acids (minimal medium), the pathways of amino acids biosynthesis (e.g., aromatic amino acids biosynthesis) contained a large number of reactions that arrested growth in silico when knocked-out. In the presence of supplemented media, predictably, these pathways did not arrest growth in silico when knocked-out. However, four reactions in amino acids metabolism did arrest growth in this medium following in silico knock-outs. These particular enzymes are responsible for processing amino acids into precursors of other pathways. One member of this group is the D-alanine-D-alanine ligase (ddlA, EC 6.3.2.4, CAC2895) that produces D-alanyl-D-alanine, which is vital to peptidoglycan biosynthesis. Conversely, in the presence of supplemented media, the large numbers of related reactions leading to arrested growth in silico were in the biosynthesis of steroids, riboflavin, purine and glycerolipids.

TABLE 11

Number of reactions preventing growth when knocked-out of reconstructed metabolic network. Results are reported in groups of biosynthetic pathways or programs.

| Pathway | Minimal Medium[1] | Partially-Supplemented Medium[2] | Supplemented Medium[3] |
|---|---|---|---|
| Carbohydrate metabolism | 25 | 10 | 3 |
| Energy metabolism | 7 | 0 | 0 |
| Lipid metabolism | 29 | 27 | 27 |
| Nucleotide metabolism | 22 | 15 | 9 |
| Amino acids metabolism | 71 | 42 | 4 |

TABLE 11-continued

Number of reactions preventing growth when knocked-out of reconstructed metabolic network. Results are reported in groups of biosynthetic pathways or programs.

| Pathway | Minimal Medium[1] | Partially-Supplemented Medium[2] | Supplemented Medium[3] |
|---|---|---|---|
| Metabolism of cofactors and vitamins | 41 | 36 | 32 |
| Biomass and maintenance | 12 | 10 | 10 |
| Total Number of Reactions | 207 | 140 | 85 |

[1]Minimal medium for *C. acetobutylicum* has been published (Monot et al. 1982).
[2]Partially-supplemented medium consists of minimal medium plus L-glutamine, L-asparagine, L-histidine and L-cysteine.
[3]Supplemented medium consists of minimal medium plus all L-amino acids, D-ribose and glycerol 3-phosphate.

EXAMPLE 12

Conclusions from Examples 1-11

Semi-automated reverse engineering of a genome-scale reaction network using building-block transfer equations was developed and coupled with iterative measures of network-building through database and literature mining resulting in the first genome-scale reaction network for *C. acetobutylicum*. This is the first genome-scale model for any of the clostridia. Thus, several examples of the use of reaction and enzyme databases to characterize anaerobic reactions catalyzed by pathways for several well-known enzymes were presented. In addition, the function of the incomplete TCA cycle, through incorporation of the urea cycle, was resolved in detail based on homology searches and metabolic demands of the genome-scale reaction network. Our model successfully predicted acidogenesis and solventogenesis of the wild-type strain, the loss of butyrate production in the buk knock-out, and the loss of butanol and acetone production by the M5 strain.

EXAMPLE 13

Genome-Scale Model of *C. acetobutylicum*

The metabolic network reconstruction for *C. acetobutylicum* ATCC 824 was described in previous research (Senger and Papoutsakis 2008). The reconciled metabolic network for *C. acetobutylicum* includes 422 intracellular metabolites involved in 552 reactions, including 80 membrane transport reactions. The full list of reactions of the metabolic network reconstruction was given previously (Senger and Papoutsakis 2008). The genome-scale model and an updated set of reaction constraints are listed in Table 7. The model contains many more constrained and irreversible reactions than did the previous version. Constraints were applied based on the irreversibility (or known direction) of metabolic reactions as well as applying order-of-magnitude approximations to constraints. For example dGTP is produced by the metabolic network because of its inclusion in the DNA biosynthesis equation, which is a component of the biomass constituting equation (see Table 7). If a maximum growth rate of $0.5\,h^{-1}$ is assumed, the maximum production rate of dGTP is equal to the growth rate multiplied by the stoichiometric coefficient of DNA in the biomass constituting equation (0.03) multiplied by the stoichiometric coefficient of dGTP in the DNA equation (0.33) to yield a required dGTP biosynthesis flux of $5\times10^{-3}$ mmol $h^{-1}g$ biomass$^{-1}$. The corresponding stoichiometric matrix was constructed using MATLAB® (The Mathworks, Inc.; Natick, Mass.) and the flux balance equation, $S \cdot v = 0$, was solved using LINDO API (Lindo Systems, Inc.; Chicago, Ill.). We explored the objective function of maximizing the specific growth rate, but we found that maximizing the rate of reduced ferredoxins production yielded superior results (comparison not shown). In *C. acetobutylicum*, NADPH regeneration is achieved through oxidation of the ferredoxins instead of through the pentose phosphate pathway.

TABLE 7

Constraints used with specific proton flux calculations.

| Membrane Transport Reaction | <−55 lower | upper | −55 to −35 lower | upper | −35 to −25 lower | upper |
|---|---|---|---|---|---|---|
| *Varied and Tight Constraints for Table 3* | | | | | | |
| Orthophosphate (extracellular) + H+ (extracellular) <=> Orthophosphate + H+ | 0 | 5 | 0 | 5 | 0 | 5 |
| Biotin (extracellular) + H+ (extracellular) <=> Biotin + H+ | 0 | 1 | 0 | 1 | 0 | 1 |
| 4-aminobenzoate (extracellular) + H+ (extracellular) <=> 4-aminobenzoate + H+ | 0 | 1 | 0 | 1 | 0 | 1 |
| 3 Na+ + 2 K+ (extracellular) + ATP + H2O <=> 3 Na+ (extracellular) + 2 K+ + ADP + Orthophosphate | 1 | 1 | 1 | 1 | 1 | 1 |
| Na+ (extracellular) + H+ <=> Sodium + H+ (extracellular) | 0 | 250 | 0 | 250 | 0 | 250 |
| K+ (extracellular) + H+ (extracellular) <=> Potassium + H+ | −250 | 0 | −250 | 0 | −250 | 0 |
| 3 H+ (extracellular) + ADP + Orthophosphate <=> 3 H+ + ATP + H2O | −250 | 250 | −250 | 250 | −250 | 250 |
| Lactate (extracellular) + H+ (extracellular) <=> Lactic Acid | −4 | 2 | −4 | 2 | −1 | 0 |
| Ethanol (extracellular) <=> Ethanol | −0.5 | −0.1 | −0.5 | −0.1 | −0.5 | −0.1 |
| Phosphoenolpyruvate + D-Glucose (extracellular) <=> Pyruvate + alpha-D-Glucose 6-phosphate | 29 | 31 | 79 | 81 | 89 | 91 |
| Butanol (extracellular) <=> 1-Butanol | −5 | −3 | −11 | −9 | −11 | −9 |
| Acetone (extracellular) <=> Acetone | −3 | −1 | −8 | −6 | −8 | −6 |

TABLE 7-continued

Constraints used with specific proton flux calculations.

| | | | | | | |
|---|---|---|---|---|---|---|
| Butyrate (extracellular) + H+ (extracellular) <=> Butyric Acid | −10 | −8 | −15 | −13 | −15 | −13 |
| Acetate (extracellular) + H+ (extracellular) <=> Acetic Acid | −10 | −8 | −15 | −13 | −15 | −13 |
| Biomass Constituting Equation | 0.07 | 0.07 | 0.3 | 0.3 | 0.3 | 0.3 |
| Varied and Tight Constraints for FIG. 5 | | | | | | |
| Orthophosphate (extracellular) + H+ (extracellular) <=> Orthophosphate + H+ | 0 | 5 | 0 | 5 | 0 | 5 |
| Biotin (extracellular) + H+ (extracellular) <=> Biotin + H+ | 0 | 1 | 0 | 1 | 0 | 1 |
| 4-aminobenzoate (extracellular) + H+ (extracellular) <=> 4-aminobenzoate + H+ | 0 | 1 | 0 | 1 | 0 | 1 |
| 3 Na+ + 2 K+ (extracellular) + ATP + H2O <=> 3 Na+ (extracellular) + 2 K+ + ADP + Orthophosphate | 1 | 1 | 1 | 1 | 1 | 1 |
| Na+ (extracellular) + H+ <=> Sodium + H+ (extracellular) | 0 | 250 | 0 | 250 | 0 | 250 |
| K+ (extracellular) + H+ (extracellular) <=> Potassium + H+ | −250 | 0 | −250 | 0 | −250 | 0 |
| 3 H+ (extracellular) + ADP + Orthophosphate <=> 3 H+ + ATP + H2O | −250 | 250 | −250 | 250 | −250 | 250 |
| Lactate (extracellular) + H+ (extracellular) <=> Lactic Acid | −4 | 2 | −4 | 2 | −1 | 0 |
| Ethanol (extracellular) <=> Ethanol | −0.5 | −0.1 | −0.5 | −0.1 | −0.5 | −0.1 |
| Phosphoenolpyruvate + D-Glucose (extracellular) <=> Pyruvate + alpha-D-Glucose 6-phosphate | 29 | 31 | 79 | 81 | 89 | 91 |
| Butanol (extracellular) <=> 1-Butanol | −5 | −3 | −11 | −9 | −11 | −9 |
| Acetone (extracellular) <=> Acetone | −3 | −1 | −8 | −6 | −8 | −6 |
| Butyrate (extracellular) + H+ (extracellular) <=> Butyric Acid | −10 | −8 | −15 | −13 | −15 | −13 |
| Acetate (extracellular) + H+ (extracellular) <=> Acetic Acid | −10 | −8 | −15 | −13 | −15 | −13 |
| Biomass Constituting Equation | 0.01 | 1 | 0.01 | 1 | 0.01 | 1 |
| Varied and Tight Constraints for FIG. 6 "Constrained Glucose Uptake and Growth Rate" | | | | | | |
| Orthophosphate (extracellular) + H+ (extracellular) <=> Orthophosphate + H+ | 0 | 5 | 0 | 5 | 0 | 5 |
| Biotin (extracellular) + H+ (extracellular) <=> Biotin + H+ | 0 | 1 | 0 | 1 | 0 | 1 |
| 4-aminobenzoate (extracellular) + H+ (extracellular) <=> 4-aminobenzoate + H+ | 0 | 1 | 0 | 1 | 0 | 1 |
| 3 Na+ + 2 K+ (extracellular) + ATP + H2O <=> 3 Na+ (extracellular) + 2 K+ + ADP + Orthophosphate | 1 | 1 | 1 | 1 | 1 | 1 |
| Na+ (extracellular) + H+ <=> Sodium + H+ (extracellular) | 0 | 250 | 0 | 250 | 0 | 250 |
| K+ (extracellular) + H+ (extracellular) <=> Potassium + H+ | −250 | 0 | −250 | 0 | −250 | 0 |
| 3 H+ (extracellular) + ADP + Orthophosphate <=> 3 H+ + ATP + H2O | −250 | 250 | −250 | 250 | −250 | 250 |
| Lactate (extracellular) + H+ (extracellular) <=> Lactic Acid | −100 | 0 | −100 | 0 | −100 | 0 |
| Ethanol (extracellular) <=> Ethanol | −100 | 0 | −100 | 0 | −100 | 0 |
| Phosphoenolpyruvate + D-Glucose (extracellular) <=> Pyruvate + alpha-D-Glucose 6-phosphate | 29 | 31 | 79 | 81 | 89 | 91 |
| Butanol (extracellular) <=> 1-Butanol | −100 | 0 | −100 | 0 | −100 | 0 |
| Acetone (extracellular) <=> Acetone | −100 | 0 | −100 | 0 | −100 | 0 |
| Butyrate (extracellular) + H+ (extracellular) <=> Butyric Acid | −100 | 0 | −100 | 0 | −100 | 0 |
| Acetate (extracellular) + H+ (extracellular) <=> Acetic Acid | −100 | 0 | −100 | 0 | −100 | 0 |
| Biomass Constituting Equation | 0.07 | 0.07 | 0.3 | 0.3 | 0.3 | 0.3 |
| Varied and Tight Constraints for FIG. 6 "Constrained Glucose Uptake Only" | | | | | | |
| Orthophosphate (extracellular) + H+ (extracellular) <=> Orthophosphate + H+ | 0 | 5 | 0 | 5 | 0 | 5 |
| Biotin (extracellular) + H+ (extracellular) <=> Biotin + H+ | 0 | 1 | 0 | 1 | 0 | 1 |
| 4-aminobenzoate (extracellular) + H+ (extracellular) <=> 4-aminobenzoate + H+ | 0 | 1 | 0 | 1 | 0 | 1 |
| 3 Na+ + 2 K+ (extracellular) + ATP + H2O <=> 3 Na+ (extracellular) + 2 K+ + ADP + Orthophosphate | 1 | 1 | 1 | 1 | 1 | 1 |

TABLE 7-continued

Constraints used with specific proton flux calculations.

| Reaction | | | | | | |
|---|---|---|---|---|---|---|
| Na+ (extracellular) + H+ <=> Sodium + H+ (extracellular) | 0 | 250 | 0 | 250 | 0 | 250 |
| K+ (extracellular) + H+ (extracellular) <=> Potassium + H+ | −250 | 0 | −250 | 0 | −250 | 0 |
| 3 H+ (extracellular) + ADP + Orthophosphate <=> 3 H+ + ATP + H2O | −250 | 250 | −250 | 250 | −250 | 250 |
| Lactate (extracellular) + H+ (extracellular) <=> Lactic Acid | −100 | 0 | −100 | 0 | −100 | 0 |
| Ethanol (extracellular) <=> Ethanol | −100 | 0 | −100 | 0 | −100 | 0 |
| Phosphoenolpyruvate + D-Glucose (extracellular) <=> Pyruvate + alpha-D-Glucose 6-phosphate | 29 | 31 | 79 | 81 | 89 | 91 |
| Butanol (extracellular) <=> 1-Butanol | −100 | 0 | −100 | 0 | −100 | 0 |
| Acetone (extracellular) <=> Acetone | −100 | 0 | −100 | 0 | −100 | 0 |
| Butyrate (extracellular) + H+ (extracellular) <=> Butyric Acid | −100 | 0 | −100 | 0 | −100 | 0 |
| Acetate (extracellular) + H+ (extracellular) <=> Acetic Acid | −100 | 0 | −100 | 0 | −100 | 0 |
| Biomass Constituting Equation | 0.01 | 1 | 0.01 | 1 | 0.01 | 1 |
| Varied and Tight Constraints for FIG. 6 "Unconstrained" | | | | | | |
| Orthophosphate (extracellular) + H+ (extracellular) <=> Orthophosphate + H+ | 0 | 5 | 0 | 5 | 0 | 5 |
| Biotin (extracellular) + H+ (extracellular) <=> Biotin + H+ | 0 | 1 | 0 | 1 | 0 | 1 |
| 4-aminobenzoate (extracellular) + H+ (extracellular) <=> 4-aminobenzoate + H+ | 0 | 1 | 0 | 1 | 0 | 1 |
| 3 Na+ + 2 K+ (extracellular) + ATP + H2O <=> 3 Na+ (extracellular) + 2 K+ + ADP + Orthophosphate | 1 | 1 | 1 | 1 | 1 | 1 |
| Na+ (extracellular) + H+ <=> Sodium + H+ (extracellular) | 0 | 250 | 0 | 250 | 0 | 250 |
| K+ (extracellular) + H+ (extracellular) <=> Potassium + H+ | −250 | 0 | −250 | 0 | −250 | 0 |
| 3 H+ (extracellular) + ADP + Orthophosphate <=> 3 H+ + ATP + H2O | −250 | 250 | −250 | 250 | −250 | 250 |
| Lactate (extracellular) + H+ (extracellular) <=> Lactic Acid | −100 | 0 | −100 | 0 | −100 | 0 |
| Ethanol (extracellular) <=> Ethanol | −100 | 0 | −100 | 0 | −100 | 0 |
| Phosphoenolpyruvate + D-Glucose (extracellular) <=> Pyruvate + alpha-D-Glucose 6-phosphate | 0 | 150 | 0 | 150 | 0 | 150 |
| Butanol (extracellular) <=> 1-Butanol | −100 | 0 | −100 | 0 | −100 | 0 |
| Acetone (extracellular) <=> Acetone | −100 | 0 | −100 | 0 | −100 | 0 |
| Butyrate (extracellular) + H+ (extracellular) <=> Butyric Acid | −100 | 0 | −100 | 0 | −100 | 0 |
| Acetate (extracellular) + H+ (extracellular) <=> Acetic Acid | −100 | 0 | −100 | 0 | −100 | 0 |
| Biomass Constituting Equation | 0.01 | 1 | 0.01 | 1 | 0.01 | 1 |

| Membrane Transport Reaction | −25 to −15 | | −15 to −5 | | −5 to 5 | |
|---|---|---|---|---|---|---|
| | lower | upper | lower | upper | lower | upper |
| Varied and Tight Constraints for Table 3 | | | | | | |
| Orthophosphate (extracellular) + H+ (extracellular) <=> Orthophosphate + H+ | 0 | 5 | 0 | 5 | 0 | 5 |
| Biotin (extracellular) + H+ (extracellular) <=> Biotin + H+ | 0 | 1 | 0 | 1 | 0 | 1 |
| 4-aminobenzoate (extracellular) + H+ (extracellular) <=> 4-aminobenzoate + H+ | 0 | 1 | 0 | 1 | 0 | 1 |
| 3 Na+ + 2 K+ (extracellular) + ATP + H2O <=> 3 Na+ (extracellular) + 2 K+ + ADP + Orthophosphate | 1 | 1 | 1 | 1 | 1 | 1 |
| Na+ (extracellular) + H+ <=> Sodium + H+ (extracellular) | 0 | 250 | 0 | 250 | 0 | 250 |
| K+ (extracellular) + H+ (extracellular) <=> Potassium + H+ | −250 | 0 | −250 | 0 | −250 | 0 |
| 3 H+ (extracellular) + ADP + Orthophosphate <=> 3 H+ + ATP + H2O | −250 | 250 | −250 | 250 | −250 | 250 |
| Lactate (extracellular) + H+ (extracellular) <=> Lactic Acid | 0 | 0 | 0 | 0 | 0 | 0 |
| Ethanol (extracellular) <=> Ethanol | −0.5 | −0.1 | −0.5 | −0.1 | −0.5 | −0.1 |
| Phosphoenolpyruvate + D-Glucose (extracellular) <=> Pyruvate + alpha-D-Glucose 6-phosphate | 89 | 91 | 39 | 41 | 12 | 14 |

TABLE 7-continued

Constraints used with specific proton flux calculations.

| Reaction | | | | | | |
|---|---|---|---|---|---|---|
| Butanol (extracellular) <=> 1-Butanol | −11 | −9 | −16 | −14 | −7 | −5 |
| Acetone (extracellular) <=> Acetone | −8 | −7 | −9 | −8 | −4 | 5 |
| Butyrate (extracellular) + H+ (extracellular) <=> Butyric Acid | −15 | −13 | −6 | −4 | −5 | −3 |
| Acetate (extracellular) + H+ (extracellular) <=> Acetic Acid | −15 | −13 | −4 | −2 | 0 | 0 |
| Biomass Constituting Equation | 0.3 | 0.3 | 0.17 | 0.17 | 0.06 | 0.06 |
| Varied and Tight Constraints for FIG. 5 | | | | | | |
| Orthophosphate (extracellular) + H+ (extracellular) <=> Orthophosphate + H+ | 0 | 5 | 0 | 5 | 0 | 5 |
| Biotin (extracellular) + H+ (extracellular) <=> Biotin + H+ | 0 | 1 | 0 | 1 | 0 | 1 |
| 4-aminobenzoate (extracellular) + H+ (extracellular) <=> 4-aminobenzoate + H+ | 0 | 1 | 0 | 1 | 0 | 1 |
| 3 Na+ + 2 K+ (extracellular) + ATP + H2O <=> 3 Na+ (extracellular) + 2 K+ + ADP + Orthophosphate | 1 | 1 | 1 | 1 | 1 | 1 |
| Na+ (extracellular) + H+ <=> Sodium + H+ (extracellular) | 0 | 250 | 0 | 250 | 0 | 250 |
| K+ (extracellular) + H+ (extracellular) <=> Potassium + H+ | −250 | 0 | −250 | 0 | −250 | 0 |
| 3 H+ (extracellular) + ADP + Orthophosphate <=> 3 H+ + ATP + H2O | −250 | 250 | −250 | 250 | −250 | 250 |
| Lactate (extracellular) + H+ (extracellular) <=> Lactic Acid | 0 | 0 | 0 | 0 | 0 | 0 |
| Ethanol (extracellular) <=> Ethanol | −0.5 | −0.1 | −0.5 | −0.1 | −0.5 | −0.1 |
| Phosphoenolpyruvate + D-Glucose (extracellular) <=> Pyruvate + alpha-D-Glucose 6-phosphate | 89 | 91 | 39 | 41 | 12 | 14 |
| Butanol (extracellular) <=> 1-Butanol | −11 | −9 | −16 | −14 | −7 | −5 |
| Acetone (extracellular) <=> Acetone | −8 | −7 | −9 | −8 | −4 | 5 |
| Butyrate (extracellular) + H+ (extracellular) <=> Butyric Acid | −15 | −13 | −6 | −4 | −5 | −3 |
| Acetate (extracellular) + H+ (extracellular) <=> Acetic Acid | −15 | −13 | −4 | −2 | 0 | 0 |
| Biomass Constituting Equation | 0.01 | 1 | 0.01 | 1 | 0.01 | 1 |
| Varied and Tight Constraints for FIG. 6 "Constrained Glucose Uptake and Growth Rate" | | | | | | |
| Orthophosphate (extracellular) + H+ (extracellular) <=> Orthophosphate + H+ | 0 | 5 | 0 | 5 | 0 | 5 |
| Biotin (extracellular) + H+ (extracellular) <=> Biotin + H+ | 0 | 1 | 0 | 1 | 0 | 1 |
| 4-aminobenzoate (extracellular) + H+ (extracellular) <=> 4-aminobenzoate + H+ | 0 | 1 | 0 | 1 | 0 | 1 |
| 3 Na+ + 2 K+ (extracellular) + ATP + H2O <=> 3 Na+ (extracellular) + 2 K+ + ADP + Orthophosphate | 1 | 1 | 1 | 1 | 1 | 1 |
| Na+ (extracellular) + H+ <=> Sodium + H+ (extracellular) | 0 | 250 | 0 | 250 | 0 | 250 |
| K+ (extracellular) + H+ (extracellular) <=> Potassium + H+ | −250 | 0 | −250 | 0 | −250 | 0 |
| 3 H+ (extracellular) + ADP + Orthophosphate <=> 3 H+ + ATP + H2O | −250 | 250 | −250 | 250 | −250 | 250 |
| Lactate (extracellular) + H+ (extracellular) <=> Lactic Acid | −100 | 0 | −100 | 0 | −100 | 0 |
| Ethanol (extracellular) <=> Ethanol | −100 | 0 | −100 | 0 | −100 | 0 |
| Phosphoenolpyruvate + D-Glucose (extracellular) <=> Pyruvate + alpha-D-Glucose 6-phosphate | 89 | 91 | 39 | 41 | 12 | 14 |
| Butanol (extracellular) <=> 1-Butanol | −100 | 0 | −100 | 0 | −100 | 0 |
| Acetone (extracellular) <=> Acetone | −100 | 0 | −100 | 0 | −100 | 0 |
| Butyrate (extracellular) + H+ (extracellular) <=> Butyric Acid | −100 | 0 | −100 | 0 | −100 | 0 |
| Acetate (extracellular) + H+ (extracellular) <=> Acetic Acid | −100 | 0 | −100 | 0 | −100 | 0 |
| Biomass Constituting Equation | 0.3 | 0.3 | 0.17 | 0.17 | 0.06 | 0.06 |
| Varied and Tight Constraints for FIG. 6 "Constrained Glucose Uptake Only" | | | | | | |
| Orthophosphate (extracellular) + H+ (extracellular) <=> Orthophosphate + H+ | 0 | 5 | 0 | 5 | 0 | 5 |
| Biotin (extracellular) + H+ (extracellular) <=> Biotin + H+ | 0 | 1 | 0 | 1 | 0 | 1 |
| 4-aminobenzoate (extracellular) + H+ (extracellular) <=> 4-aminobenzoate + H+ | 0 | 1 | 0 | 1 | 0 | 1 |

TABLE 7-continued

Constraints used with specific proton flux calculations.

| Reaction | | | | | | |
|---|---|---|---|---|---|---|
| 3 Na+ + 2 K+ (extracellular) + ATP + H2O <=> 3 Na+ (extracellular) + 2 K+ + ADP + Orthophosphate | 1 | 1 | 1 | 1 | 1 | 1 |
| Na+ (extracellular) + H+ <=> Sodium + H+ (extracellular) | 0 | 250 | 0 | 250 | 0 | 250 |
| K+ (extracellular) + H+ (extracellular) <=> Potassium + H+ | −250 | 0 | −250 | 0 | −250 | 0 |
| 3 H+ (extracellular) + ADP + Orthophosphate <=> 3 H+ + ATP + H2O | −250 | 250 | −250 | 250 | −250 | 250 |
| Lactate (extracellular) + H+ (extracellular) <=> Lactic Acid | −100 | 0 | −100 | 0 | −100 | 0 |
| Ethanol (extracellular) <=> Ethanol | −100 | 0 | −100 | 0 | −100 | 0 |
| Phosphoenolpyruvate + D-Glucose (extracellular) <=> Pyruvate + alpha-D-Glucose 6-phosphate | 89 | 91 | 39 | 41 | 12 | 14 |
| Butanol (extracellular) <=> 1-Butanol | −100 | 0 | −100 | 0 | −100 | 0 |
| Acetone (extracellular) <=> Acetone | −100 | 0 | −100 | 0 | −100 | 0 |
| Butyrate (extracellular) + H+ (extracellular) <=> Butyric Acid | −100 | 0 | −100 | 0 | −100 | 0 |
| Acetate (extracellular) + H+ (extracellular) <=> Acetic Acid | −100 | 0 | −100 | 0 | −100 | 0 |
| Biomass Constituting Equation | 0.01 | 1 | 0.01 | 1 | 0.01 | 1 |
| Varied and Tight Constraints for FIG. 6 "Unconstrained" | | | | | | |
| Orthophosphate (extracellular) + H+ (extracellular) <=> Orthophosphate + H+ | 0 | 5 | 0 | 5 | 0 | 5 |
| Biotin (extracellular) + H+ (extracellular) <=> Biotin + H+ | 0 | 1 | 0 | 1 | 0 | 1 |
| 4-aminobenzoate (extracellular) + H+ (extracellular) <=> 4-aminobenzoate + H+ | 0 | 1 | 0 | 1 | 0 | 1 |
| 3 Na+ + 2 K+ (extracellular) + ATP + H2O <=> 3 Na+ (extracellular) + 2 K+ + ADP + Orthophosphate | 1 | 1 | 1 | 1 | 1 | 1 |
| Na+ (extracellular) + H+ <=> Sodium + H+ (extracellular) | 0 | 250 | 0 | 250 | 0 | 250 |
| K+ (extracellular) + H+ (extracellular) <=> Potassium + H+ | −250 | 0 | −250 | 0 | −250 | 0 |
| 3 H+ (extracellular) + ADP + Orthophosphate <=> 3 H+ + ATP + H2O | −250 | 250 | −250 | 250 | −250 | 250 |
| Lactate (extracellular) + H+ (extracellular) <=> Lactic Acid | −100 | 0 | −100 | 0 | −100 | 0 |
| Ethanol (extracellular) <=> Ethanol | −100 | 0 | −100 | 0 | −100 | 0 |
| Phosphoenolpyruvate + D-Glucose (extracellular) <=> Pyruvate + alpha-D-Glucose 6-phosphate | 0 | 150 | 0 | 150 | 0 | 150 |
| Butanol (extracellular) <=> 1-Butanol | −100 | 0 | −100 | 0 | −100 | 0 |
| Acetone (extracellular) <=> Acetone | −100 | 0 | −100 | 0 | −100 | 0 |
| Butyrate (extracellular) + H+ (extracellular) <=> Butyric Acid | −100 | 0 | −100 | 0 | −100 | 0 |
| Acetate (extracellular) + H+ (extracellular) <=> Acetic Acid | −100 | 0 | −100 | 0 | −100 | 0 |
| Biomass Constituting Equation | 0.01 | 1 | 0.01 | 1 | 0.01 | 1 |

EXAMPLE 14

Sampling and Reduction of the Phenotypic Solution Space

Optimization of the flux vector, v, of the flux balance equation is an underdetermined problem for a genome-scale metabolic network with more reactions than metabolites. Thus, multiple solutions of flux distributions to the flux balance equation exist upon constrained optimization by linear programming. The solution or family of flux vector solutions, v, corresponding to an observable phenotype resides within the multidimensional convex polytope that is the phenotypic solution space. Methods of constraining and sampling of the phenotypic solution space to yield computational phenotypes consistent with experimental observations has been of interest to recent computational research (Choi et al. 2007; Covert et al. 2003; Famili et al. 2005; Price et al. 2004; Wiback et al. 2004). In the following sections, we present novel algorithms for developing additional constraints to the phenotypic solution space to reduce the set of possible flux distributions. To obtain a representative flux distribution from the constrained phenotypic solution space, a stochastic sampling algorithm was applied (Wiback et al. 2004), and multiple results for individual fluxes were averaged. The constrained solution space was sampled $10^2$ times to obtain a representative set of fluxes, v. The set of membrane transport equation with their upper and lower constraints that were varied stochastically to probe the phenotypic solution space are provided in Table 8. These particular transport reactions were chosen because they directly determine the specific proton flux across the cell membrane. Their constraints were chosen so that specific proton flux ranges from −200 mmol $H^+h^{-1}g$ biomass$^{-1}$ (efflux) to 5 mmol $H^+h^{-1}g$ biomass$^{-1}$ (influx) could be explored.

TABLE 8

Full stoichiometric matrix of the given numerically-determined subsystem. The values X and Y denote stoichiometric coefficients that were varied in simulations to elucidate the singularity

| Compounds | Reaction Numbers | | | | | | | |
|---|---|---|---|---|---|---|---|---|
| | 1 | 2 | 3 | 4 | 5 | 6 | 7 | 8 |
| Biomass | 1 | 0 | 0 | 0 | 0 | 0 | 0 | 0 |
| Protein | −0.4 | 1 | 0 | 0 | 0 | 0 | 0 | 0 |
| Solute Pools | −0.14 | 0 | 1 | 0 | 0 | 0 | 0 | 0 |
| Lipids | −0.7 | 0 | 0 | 0 | 0 | 0 | 0 | 0 |
| Cell Wall | −0.24 | 0 | 0 | 1 | 0 | 0 | 0 | 0 |
| DNA | −0.03 | 0 | 0 | 0 | 1 | 0 | 0 | 0 |
| RNA | −0.12 | 0 | 0 | 0 | 0 | 1 | 0 | 0 |
| Crosslinked Peptidoglycan | 0 | 0 | 0 | −0.363 | 0 | 0 | 1 | 0 |
| Wall Teichoic Acid | 0 | 0 | 0 | −0.019 | 0 | 0 | 0 | 1 |
| D-Alanyl-Alanine | 0 | 0 | 0 | 0 | 0 | 0 | −1 | 0 |
| UDP-MurNAcL-alanyl-D-glutamate | 0 | 0 | 0 | 0 | 0 | 0 | −1 | 0 |
| ATP | 0 | 0 | 0 | 0 | 0 | −0.496 | 0 | 0 |
| dATP | 0 | 0 | 0 | 0 | −0.676 | 0 | 0 | 0 |
| GTP | 0 | 0 | 0 | 0 | 0 | −0.496 | 0 | 0 |
| dGTP | 0 | 0 | 0 | 0 | −0.33 | 0 | 0 | 0 |
| CTP | 0 | 0 | 0 | 0 | 0 | −0.496 | 0 | 0 |
| dCTP | 0 | 0 | 0 | 0 | −0.33 | 0 | 0 | 0 |
| UTP | 0 | 0 | 0 | 0 | 0 | −0.496 | 0 | 0 |
| dTTP | 0 | 0 | 0 | 0 | −0.676 | 0 | 0 | 0 |
| L-Gln | 0 | −0.318 | −0.0086 | 0 | 0 | 0 | 0 | 0 |
| L-Pro | 0 | −0.246 | −0.1293 | 0 | 0 | 0 | 0 | 0 |
| L-Met | 0 | −0.202 | −0.0222 | 0 | 0 | 0 | 0 | 0 |
| L-His | 0 | −0.178 | −0.0169 | 0 | 0 | 0 | 0 | 0 |
| L-Trp | 0 | −0.1 | 0 | 0 | 0 | 0 | 0 | 0 |
| L-Phe | 0 | −0.343 | −0.0043 | 0 | 0 | 0 | 0 | 0 |
| L-Tyr | 0 | −0.298 | 0 | 0 | 0 | 0 | 0 | 0 |
| L-Lys | 0 | −0.576 | −0.0405 | 0 | 0 | 0 | −1 | 0 |
| Pyruvate | 0 | 0 | 0 | 0 | 0 | 0 | 0 | 0 |
| D-Ala | 0 | 0 | 0 | 0 | 0 | 0 | 0 | −1 |
| L-Ornithine | 0 | 0 | 0 | 0 | 0 | 0 | 0 | 0 |
| L-Ala | 0 | −0.492 | −0.1161 | 0 | 0 | 0 | 0 | 0 |
| L-Glu | 0 | −0.497 | −0.5256 | 0 | 0 | 0 | 0 | 0 |
| UDP-MurNAc | 0 | 0 | 0 | 0 | 0 | 0 | −1 | 0 |
| N-Acetyl-D-glucosamine 1-phosphate | 0 | 0 | 0 | 0 | 0 | 0 | 0 | −1 |
| Acetate | 0 | 0 | 0 | 0 | 0 | 0 | 0 | 0 |
| Glucosamine 1-phosphate | 0 | 0 | 0 | 0 | 0 | 0 | 0 | 0 |
| D-Fructose 6-phosphate | 0 | 0 | 0 | 0 | 0 | 0 | 0 | 0 |
| Tymine | 0 | −0.057 | −0.0017 | 0 | 0 | 0 | 0 | 0 |
| CDPribitol | 0 | 0 | 0 | 0 | 0 | 0 | 0 | −1 |
| Ratio | 0 | 0 | 0 | 0 | 0 | 0 | 0 | 0 |

| Compounds | Reaction Numbers | | | | | | | |
|---|---|---|---|---|---|---|---|---|
| | 9 | 10 | 11 | 12 | 13 | 14 | 15 | 16 |
| Biomass | 0 | 0 | 0 | 0 | 0 | 0 | 0 | 0 |
| Protein | 0 | 0 | 0 | 0 | 0 | 0 | 0 | 0 |
| Solute Pools | 0 | 0 | 0 | 0 | 0 | 0 | 0 | 0 |
| Lipids | 0 | 0 | 0 | 0 | 0 | 0 | 0 | 0 |
| Cell Wall | 0 | 0 | 0 | 0 | 0 | 0 | 0 | 0 |
| DNA | 0 | 0 | 0 | 0 | 0 | 0 | 0 | 0 |
| RNA | 0 | 0 | 0 | 0 | 0 | 0 | 0 | 0 |
| Crosslinked Peptidoglycan | 0 | 0 | 0 | 0 | 0 | 0 | 0 | 0 |
| Wall Teichoic Acid | 0 | 0 | 0 | 0 | 0 | 0 | 0 | 0 |
| D-Alanyl-Alanine | 1 | 0 | 0 | 0 | 0 | 0 | 0 | 0 |
| UDP-MurNAcL-alanyl-D-glutamate | 0 | 1 | 0 | 0 | 0 | 0 | 0 | 0 |
| ATP | 0 | 0 | 0 | 0 | 0 | 0 | 0 | 0 |
| dATP | 0 | 0 | 0 | 0 | 0 | 0 | 0 | 0 |
| GTP | 0 | 0 | 0 | 0 | 0 | 0 | 0 | 0 |
| dGTP | 0 | 0 | 0 | 0 | 0 | 0 | 0 | 0 |
| CTP | 0 | 0 | 0 | 0 | 0 | 0 | 0 | 0 |
| dCTP | 0 | 0 | 0 | 0 | 0 | 0 | 0 | 0 |
| UTP | 0 | 0 | 0 | 0 | 0 | 0 | 0 | 0 |
| dTTP | 0 | 0 | 0 | 0 | 0 | 0 | 0 | 0 |
| L-Gln | 0 | 0 | 0 | 0 | 0 | 0 | 0 | 0 |
| L-Pro | 0 | 0 | 0 | 0 | 0 | 0 | 0 | 0 |
| L-Met | 0 | 0 | 0 | 0 | 0 | 0 | 0 | 0 |
| L-His | 0 | 0 | 0 | 0 | 0 | 0 | 0 | 0 |
| L-Trp | 0 | 0 | 0 | 0 | 0 | 0 | 0 | 0 |
| L-Phe | 0 | 0 | 0 | 0 | 0 | 0 | 0 | 0 |
| L-Tyr | 0 | 0 | 0 | 0 | 0 | 0 | 0 | 0 |
| L-Lys | 0 | 0 | 0 | 0 | 0 | 0 | 0 | 0 |

TABLE 8-continued

Full stoichiometric matrix of the given numerically-determined subsystem.
The values X and Y denote stoichiometric coefficients that were varied in simulations
to elucidate the singularity

| Compounds | | | | | | | | |
|---|---|---|---|---|---|---|---|---|
| Pyruvate | 0 | 0 | 1 | 1 | 0 | 0 | −1 | 0 |
| D-Ala | −2 | 0 | 0 | −1 | 1 | 0 | 0 | 0 |
| L-Ornithine | 0 | 0 | 0 | 0 | 0 | 1 | −1 | 0 |
| L-Ala | 0 | −1 | 0 | 0 | −1 | 0 | 1 | 0 |
| L-Glu | 0 | −1 | 0 | 0 | 0 | 0 | 1 | 1 |
| UDP-MurNAc | 0 | −1 | 0 | 0 | 0 | 0 | 0 | 0 |
| N-Acetyl-D-glucosamine 1-phosphate | 0 | 0 | 0 | 0 | 0 | 0 | 0 | 0 |
| Acetate | 0 | 0 | 0 | 0 | 0 | 0 | 0 | 0 |
| Glucosamine 1-phosphate | 0 | 0 | 0 | 0 | 0 | 0 | 0 | 0 |
| D-Fructose 6-phosphate | 0 | 0 | 0 | 0 | 0 | 0 | 0 | 0 |
| Tymine | 0 | 0 | 0 | 0 | 0 | 0 | 0 | 0 |
| CDPribitol | 0 | 0 | 0 | 0 | 0 | 0 | 0 | 0 |
| Ratio | 0 | 0 | 0 | 0 | 0 | 0 | X | Y |

| | Reaction Numbers | | | | | | | |
|---|---|---|---|---|---|---|---|---|
| Compounds | 17 | 18 | 19 | 20 | 21 | 22 | 23 | 24 |
| Biomass | 0 | 0 | 0 | 0 | 0 | 0 | 0 | 0 |
| Protein | 0 | 0 | 0 | 0 | 0 | 0 | 0 | 0 |
| Solute Pools | 0 | 0 | 0 | 0 | 0 | 0 | 0 | 0 |
| Lipids | 0 | 0 | 0 | 0 | 0 | 0 | 0 | 0 |
| Cell Wall | 0 | 0 | 0 | 0 | 0 | 0 | 0 | 0 |
| DNA | 0 | 0 | 0 | 0 | 0 | 0 | 0 | 0 |
| RNA | 0 | 0 | 0 | 0 | 0 | 0 | 0 | 0 |
| Crosslinked Peptidoglycan | 0 | 0 | 0 | 0 | 0 | 0 | 0 | 0 |
| Wall Teichoic Acid | 0 | 0 | 0 | 0 | 0 | 0 | 0 | 0 |
| D-Alanyl-Alanine | 0 | 0 | 0 | 0 | 0 | 0 | 0 | 0 |
| UDP-MurNAcL-alanyl-D-glutamate | 0 | 0 | 0 | 0 | 0 | 0 | 0 | 0 |
| ATP | 0 | 0 | 0 | 0 | 0 | 0 | 0 | 0 |
| dATP | 0 | 0 | 0 | 0 | 0 | 0 | 0 | 0 |
| GTP | 0 | 0 | 0 | 0 | 0 | 0 | 0 | 0 |
| dGTP | 0 | 0 | 0 | 0 | 0 | 0 | 0 | 0 |
| CTP | 0 | 0 | 0 | 0 | 0 | 0 | 0 | 0 |
| dCTP | 0 | 0 | 0 | 0 | 0 | 0 | 0 | 0 |
| UTP | 0 | 0 | 0 | 0 | 0 | 0 | 0 | 0 |
| dTTP | 0 | 0 | 0 | 0 | 0 | 0 | 0 | 0 |
| L-Gln | 1 | 0 | 0 | 0 | 0 | 0 | 0 | 0 |
| L-Pro | 0 | 1 | 0 | 0 | 0 | 0 | 0 | 0 |
| L-Met | 0 | 0 | 1 | 0 | 0 | 0 | 0 | 0 |
| L-His | 0 | 0 | 0 | 1 | 0 | 0 | 0 | 0 |
| L-Trp | 0 | 0 | 0 | 0 | 1 | 0 | 0 | 0 |
| L-Phe | 0 | 0 | 0 | 0 | 0 | 1 | 0 | 0 |
| L-Tyr | 0 | 0 | 0 | 0 | 0 | 0 | 1 | 0 |
| L-Lys | 0 | 0 | 0 | 0 | 0 | 0 | 0 | 1 |
| Pyruvate | 0 | 0 | 0 | 0 | 0 | 0 | 0 | 0 |
| D-Ala | 0 | 0 | 0 | 0 | 0 | 0 | 0 | 0 |
| L-Ornithine | 0 | 0 | 0 | 0 | 0 | 0 | 0 | 0 |
| L-Ala | 0 | 0 | 0 | 0 | 0 | 0 | 0 | 0 |
| L-Glu | −1 | −1 | 0 | 0 | 0 | 0 | 0 | 0 |
| UDP-MurNAc | 0 | 0 | 0 | 0 | 0 | 0 | 0 | 0 |
| N-Acetyl-D-glucosamine 1-phosphate | 0 | 0 | 0 | 0 | 0 | 0 | 0 | 0 |
| Acetate | 0 | 0 | 0 | 0 | 0 | 0 | 0 | 0 |
| Glucosamine 1-phosphate | 0 | 0 | 0 | 0 | 0 | 0 | 0 | 0 |
| D-Fructose 6-phosphate | 0 | 0 | 0 | 0 | 0 | 0 | 0 | 0 |
| Tymine | 0 | 0 | 0 | 0 | 0 | 0 | 0 | 0 |
| CDPribitol | 0 | 0 | 0 | 0 | 0 | 0 | 0 | 0 |
| Ratio | 0 | 0 | 0 | 0 | 0 | 0 | 0 | 0 |

| | Reaction Numbers | | | | | | | |
|---|---|---|---|---|---|---|---|---|
| Compounds | 25 | 26 | 27 | 28 | 29 | 30 | 31 | 32 |
| Biomass | 0 | 0 | 0 | 0 | 0 | 0 | 0 | 0 |
| Protein | 0 | 0 | 0 | 0 | 0 | 0 | 0 | 0 |
| Solute Pools | 0 | 0 | 0 | 0 | 0 | 0 | 0 | 0 |
| Lipids | 0 | 0 | 0 | 0 | 0 | 0 | 0 | 0 |
| Cell Wall | 0 | 0 | 0 | 0 | 0 | 0 | 0 | 0 |
| DNA | 0 | 0 | 0 | 0 | 0 | 0 | 0 | 0 |
| RNA | 0 | 0 | 0 | 0 | 0 | 0 | 0 | 0 |
| Crosslinked Peptidoglycan | 0 | 0 | 0 | 0 | 0 | 0 | 0 | 0 |
| Wall Teichoic Acid | 0 | 0 | 0 | 0 | 0 | 0 | 0 | 0 |
| D-Alanyl-Alanine | 0 | 0 | 0 | 0 | 0 | 0 | 0 | 0 |
| UDP-MurNAcL-alanyl-D-glutamate | 0 | 0 | 0 | 0 | 0 | 0 | 0 | 0 |
| ATP | 1 | 0 | 0 | 0 | 0 | 0 | 0 | 0 |
| dATP | 0 | 1 | 0 | 0 | 0 | 0 | 0 | 0 |

TABLE 8-continued

Full stoichiometric matrix of the given numerically-determined subsystem.
The values X and Y denote stoichiometric coefficients that were varied in simulations
to elucidate the singularity

| | | | | | | | | |
|---|---|---|---|---|---|---|---|---|
| GTP | 0 | 0 | 1 | 0 | 0 | 0 | 0 | 0 |
| dGTP | 0 | 0 | 0 | 1 | 0 | 0 | 0 | 0 |
| CTP | 0 | 0 | 0 | 0 | 1 | 0 | 0 | 0 |
| dCTP | 0 | 0 | 0 | 0 | 0 | 1 | 0 | 0 |
| UTP | 0 | 0 | 0 | 0 | 0 | 0 | 1 | 0 |
| dTTP | 0 | 0 | 0 | 0 | 0 | 0 | 0 | 1 |
| L-Gln | 0 | 0 | 0 | 0 | 0 | 0 | 0 | 0 |
| L-Pro | 0 | 0 | 0 | 0 | 0 | 0 | 0 | 0 |
| L-Met | 0 | 0 | 0 | 0 | 0 | 0 | 0 | 0 |
| L-His | 0 | 0 | 0 | 0 | 0 | 0 | 0 | 0 |
| L-Trp | 0 | 0 | 0 | 0 | 0 | 0 | 0 | 0 |
| L-Phe | 0 | 0 | 0 | 0 | 0 | 0 | 0 | 0 |
| L-Tyr | 0 | 0 | 0 | 0 | 0 | 0 | 0 | 0 |
| L-Lys | 0 | 0 | 0 | 0 | 0 | 0 | 0 | 0 |
| Pyruvate | 0 | 0 | 0 | 0 | 0 | 0 | 0 | 0 |
| D-Ala | 0 | 0 | 0 | 0 | 0 | 0 | 0 | 0 |
| L-Ornithine | 0 | 0 | 0 | 0 | 0 | 0 | 0 | 0 |
| L-Ala | 0 | 0 | 0 | 0 | 0 | 0 | 0 | 0 |
| L-Glu | −1 | −1 | −1 | −1 | −1 | −1 | −1 | −1 |
| UDP-MurNAc | 0 | 0 | 0 | 0 | 0 | 0 | 0 | 0 |
| N-Acetyl-D-glucosamine 1-phosphate | 0 | 0 | 0 | 0 | 0 | 0 | 0 | 0 |
| Acetate | 0 | 0 | 0 | 0 | 0 | 0 | 0 | 0 |
| Glucosamine 1-phosphate | 0 | 0 | 0 | 0 | 0 | 0 | 0 | 0 |
| D-Fructose 6-phosphate | 0 | 0 | 0 | 0 | 0 | 0 | 0 | 0 |
| Tymine | 0 | 0 | 0 | 0 | 0 | 0 | 0 | 0 |
| CDPribitol | 0 | 0 | 0 | 0 | 0 | 0 | 0 | 0 |
| Ratio | 0 | 0 | 0 | 0 | 0 | 0 | 0 | 0 |

| | Reaction Numbers | | | | | | | | |
|---|---|---|---|---|---|---|---|---|---|
| Compounds | 33 | 34 | 35 | 36 | 37 | 38 | 39 | 40 | 41 |
| Biomass | 0 | 0 | 0 | 0 | 0 | 0 | 0 | 0 | −1 |
| Protein | 0 | 0 | 0 | 0 | 0 | 0 | 0 | 0 | 0 |
| Solute Pools | 0 | 0 | 0 | 0 | 0 | 0 | 0 | 0 | 0 |
| Lipids | 0 | 0 | 0 | 0 | 0 | 0 | | 0 | 0 |
| Cell Wall | 0 | 0 | 0 | 0 | 0 | 0 | 0 | 0 | 0 |
| DNA | 0 | 0 | 0 | 0 | 0 | 0 | 0 | 0 | 0 |
| RNA | 0 | 0 | 0 | 0 | 0 | 0 | 0 | 0 | 0 |
| Crosslinked Peptidoglycan | 0 | 0 | 0 | 0 | 0 | 0 | 0 | 0 | 0 |
| Wall Teichoic Acid | 0 | 0 | 0 | 0 | 0 | 0 | 0 | 0 | 0 |
| D-Alanyl-Alanine | 0 | 0 | 0 | 0 | 0 | 0 | 0 | 0 | 0 |
| UDP-MurNAcL-alanyl-D-glutamate | 0 | 0 | 0 | 0 | 0 | 0 | 0 | 0 | 0 |
| ATP | 0 | 0 | 0 | 0 | 0 | 0 | 0 | 0 | 0 |
| dATP | 0 | 0 | 0 | 0 | 0 | 0 | 0 | 0 | 0 |
| GTP | 0 | 0 | 0 | 0 | 0 | 0 | 0 | 0 | 0 |
| dGTP | 0 | 0 | 0 | 0 | 0 | 0 | 0 | 0 | 0 |
| CTP | 0 | 0 | 0 | 0 | 0 | 0 | 0 | −1 | 0 |
| dCTP | 0 | 0 | 0 | 0 | 0 | 0 | 0 | 0 | 0 |
| UTP | −1 | 0 | 0 | 0 | 0 | −1 | 0 | 0 | 0 |
| dTTP | 0 | 0 | 0 | 0 | 0 | 0 | 0 | 0 | 0 |
| L-Gln | 0 | 0 | 0 | 0 | 0 | 0 | 0 | 0 | 0 |
| L-Pro | 0 | 0 | 0 | 0 | 0 | 0 | 0 | 0 | 0 |
| L-Met | 0 | 0 | 0 | 0 | 0 | 0 | 0 | 0 | 0 |
| L-His | 0 | 0 | 0 | 0 | 0 | 0 | 0 | 0 | 0 |
| L-Trp | 0 | 0 | 0 | 0 | 0 | 0 | 0 | 0 | 0 |
| L-Phe | 0 | 0 | 0 | 0 | 0 | 0 | 0 | 0 | 0 |
| L-Tyr | 0 | 0 | 0 | 0 | 0 | 0 | 0 | 0 | 1 |
| L-Lys | 0 | 0 | 0 | 0 | 0 | 0 | 0 | 0 | 0 |
| Pyruvate | 0 | 0 | 0 | 0 | 0 | 0 | 0 | 0 | 0 |
| D-Ala | 0 | 0 | 0 | 0 | 0 | 0 | 0 | 0 | 0 |
| L-Ornithine | 0 | 0 | 0 | 0 | 0 | 0 | 0 | 0 | 0 |
| L-Ala | 0 | 0 | 0 | 0 | 0 | 0 | 0 | 0 | 0 |
| L-Glu | 0 | 0 | 0 | 0 | 0 | 0 | 0 | 0 | 0 |
| UDP-MurNAc | 1 | 0 | 0 | 0 | 0 | 0 | 0 | 0 | 0 |
| N-Acetyl-D-glucosamine 1-phosphate | −1 | 0 | 1 | 0 | 0 | 0 | 0 | 0 | 0 |
| Acetate | 0 | 1 | −1 | 0 | 0 | 0 | 0 | 0 | 0 |
| Glucosamine 1-phosphate | 0 | 0 | −1 | 1 | 0 | 0 | 0 | 0 | 0 |
| D-Fructose 6-phosphate | 0 | 0 | 0 | −1 | 1 | 0 | 0 | 0 | 0 |
| Tymine | 0 | 0 | 0 | 0 | 0 | 1 | 0 | 0 | 0 |
| CDPribitol | 0 | 0 | 0 | 0 | 0 | 0 | 0 | 1 | 0 |
| Ratio | 0 | 0 | 0 | 0 | 0 | 0 | 0 | 0 | 0 |

The development of tools to further reduce the size of the phenotypic solution space (and number of possible solutions) is the subject of much on-going research. Here, we propose two additional methods for constraining the resulting phenotypic solution space of flux balance analysis (FBA) solutions: (i) defining a specific proton flux state and examining its relationship with extracellular medium pH changes and (ii) generating sub-networks with a one-dimensional null space vector (we call these numerically-determined sub-systems) through the addition of reaction flux relationships. It is believed that the two proposed methods are particularly useful when dealing with organisms (such as the clostridia) that lack the wealth of literature data and well-developed experimental tools for constructing genetic perturbations (MacCarthy et al. 2005; Reed et al. 2006; Tegner et al. 2003) to determine flux constraints and probe metabolic capacity.

EXAMPLE 15

Calculation of the Specific Proton Flux

Several studies of C. acetobutylicum fermentation kinetics (Husemann and Papoutsakis 1988; Roos et al. 1985), transcriptional data (Alsaker and Papoutsakis 2005; Alsaker et al. 2004; Tummala et al. 2003) and fluxes of the primary metabolic pathways (Desai et al. 1999a; Desai et al. 1999b; Papoutsakis 1984; Papoutsakis and Meyer 1985a; Papoutsakis and Meyer 1985b) have shown that the rates of butyric and acetic acids production and consumption (re-uptake) vary widely over the course of a batch fermentation. Here, we propose that the rates at which free protons are excreted by the cell can be used as an identifier of dominant metabolic programs and can be used to reduce the phenotypic solution space. To do this, we consider the specific proton flux ($q_{H_{ext}^+}$), which is defined as the flux of free protons exchanged between the cell and the extracellular environment (a negative flux corresponds to the excretion of protons). The proton exchange reaction across the cellular membrane is represented as, $$\frac{dH_{ext}^+}{dt} = q_{H_{ext}^+} X \qquad (6)$$

where $H_{ext}^+$ is the total (not necessarily free) extracellular hydrogen ion concentration and X is the biomass concentration. We define the extracellular hydrogen ion concentration as the sum of (i) the extracellular free proton concentration, $H_{free}^+$ (calculated from medium pH, $pH_{extracellular} = -\log(H_{free}^+)$), and (ii) those hydrogen ions associated with weak acids given specific medium pH and $pK_a$ values. For example, the total extracellular hydrogen ion concentration ($H_{ext}^+$) is defined in Eq. 7, for the minimal medium (Monot et al. 1982), as the summation of the extracellular molar concentrations of: (i) free protons ($H_{free}^+$) (ii) protonated butyrate (butyric acid) ($H_{butyrate}$), (iii) acetic acid ($H_{acetate}$), (iv) lactic acid ($H_{lactate}$), (v) carbonic acid ($H_{carbonate}$), (vi) ammonium ion ($H_{ammonium}$), and (vii) monobasic and dibasic potassium phosphates ($H_{phosphates}$).

$$H_{ext}^+ = H_{free}^+ + H_{butyrate} + H_{acetate} + H_{lactate} + H_{carbonate} + H_{phosphates} + H_{ammonium} \qquad (7)$$

We recognize this approximation of the extracellular proton concentration excludes other minor proton sources/sinks. However, these species were chosen to calculate the specific proton flux as they are (i) abundant in the minimal medium and (ii) contain $pK_a$ values within the operating pH range of batch fermentation. Thus, consideration of these species is particularly useful in approximating the extracellular hydrogen ion concentration from minimal media fermentation data. Given a pH value and the $pK_a$ of a weak acid, the fraction of protonated and unprotonated species can be directly calculated using the Henderson-Hasselbalch equation.

The specific proton flux ($q_{H_{ext}^+}$) was calculated directly for the genome-scale model. This was done through the summation of specific fluxes over all membrane transport exchange reactions protons (M in total), where $q_r$ is the flux of a reaction exchanging proton(s) with the extracellular environment and $h_r$ is the stoichiometric coefficient of $H^+$ in the membrane transport reaction.

$$q_{H_{ext}^+} = \sum_{r=1}^{M} h_r q_r \qquad (8)$$

The list of membrane transport equations and related stoichiometry in the genome-scale model considered in the calculation of the specific proton flux is shown as Table 9. The Transport Classification (T.C.) numbers of each reaction were obtained from the Transport Classification Database (TCDB) (Busch and Saier 2002) and are listed in Table 9.

TABLE 9

Transport reactions with contribution to the proton flux state of the culture for growth in minimal media.

| $TC^1$ | Transport Reaction$^{2,3}$ | Constrained? |
|---|---|---|
| 2.A.1 | Butyrate + $H^+$ → Butyrate (ext.) + $H^+$ (ext.) | Yes |
| 2.A.1 | Acetate + $H^+$ → Acetate (ext.) + $H^+$ (ext.) | Yes |
| 2.A.14 | (R,S)-Lactate + $H^+$ → Lactate (ext.) + $H^+$ (ext.) | Yes |
| 2.A.88 | Biotin (ext.) + $H^+$ (ext.) → Biotin + $H^+$ | Yes |
| 2.A.46 | 4-aminobenzoate (ext.) + $H^+$ (ext.) → 4-aminobenzoate + $H^+$ | Yes |
| 2.A.20 | Orthophosphate (ext.) + $H^+$ (ext.) → Orthophosphate + $H^+$ | Yes |
| 3.A.2 | ADP + Orthophosphate + $H^+$ (ext.) ↔ ATP + $H_2O$ + $H^+$ | No |
| 2.A.35 | $K^+$ (ext.) + $H^+$ (ext.) ↔ $K^+$ + $H^+$ | No |
| 2.A.37 | $Na^+$ (ext.) + $H^+$ ↔ $Na^+$ + $H^+$ (ext.) | No |
| 3.A.3 | 3 $Na^+$ + 2 $K^+$ (ext.) + ATP + $H_2O$ ↔ 3 $Na^+$ (ext.) + 2 $K^+$ + ADP + Orthophosphate | No |

[1] Transporter classification (TC) families from the Transport Classification Database (Busch and Saier 2002) are given for each exchange reaction.
[2] All metabolites are located within the cell well unless specifically labeled as "extracellular" ("ext.").
[3] Transport reactions were either constrained to the forward direction (→) or were left unconstrained with respect to direction (↔).

EXAMPLE 16

Calculation of Extracellular Medium pH

To effectively study the significance of specific proton flux states of the genome-scale metabolic model, calculation of the extracellular medium pH was required. A semi-mechanistic, partial buffering model (Dougherty et al. 2006) was derived from a charge balance and adapted for a minimal medium (Monot et al. 1982) supporting C. acetobutylicum growth. It is shown as Eq. 9, and model parameters are defined in Table 7.

$$\sum_{Acids} C_A \frac{\sum_{i=1}^{D}\left[(d+1-i)[H_{free}^+]^{i-1}\prod_{j=1}^{D+1-i}K_{aj}\right]}{\sum_{i=1}^{D+1}\left[[H_{free}^+]^{(i-1)}\prod_{j=1}^{D+1-i}K_{aj}\right]} + \frac{K_w}{H_{free}^+} - \quad (9)$$

$$H_{free}^+ \cdots -\sum_{Bases} C_B \frac{\sum_{i=1}^{D}\left[(d+1-i)[H_{free}^+]^{i-1}\prod_{j=1}^{D+1-i}K_{aj}\right]}{\sum_{i=1}^{D+1}\left[[H_{free}^+]^{(i-1)}\prod_{j=1}^{D+1-i}K_{aj}\right]} -$$

$$\sum_{Counterions} C_C \sum_{k=1}^{n_c} z_k = 0$$

The weak acids ($C_A$) included in the model consisted of those of the initial media formulation and those produced/consumed during fermentation: acetic acid ($pK_a$=4.76), butyric acid ($pK_a$=4.83), lactic acid ($pK_a$=3.08), carbonic acid ($pK_{a,1}$=6.35, $pK_{a,2}$=10.33), monobasic and dibasic potassium phosphate ($pK_{a,1}$=2.15, $pK_{a,2}$=7.20, $pK_{a,3}$=12.35). The weak base ($C_B$) considered by the pH model was ammonium ion ($pK_a$=9.25). Monobasic and dibasic potassium phosphates were treated as electrolyte-associated buffers; thus, the charge balance pH model included a term to account for potassium counterions ($C_C$) as fully described by the authors in development of the pH model (Dougherty et al. 2006). The concentration of carbonic acid was held constant and was based on $CO_2$ solubility in fermentation broth (Gros et al. 1999). The pH model (Eq. 9) was solved for $H_{free}^+$ ($pH_{extracellular}$=$-\log(H_{free}^+)$) using a numerical root-finding algorithm.

EXAMPLE 17

Consideration of a Specific Proton Flux State in Modeling Metabolism

From direct calculations of intracellular fluxes in the primary metabolism of *C. acetobutylicum*, it has long been known that these fluxes do not remain constant during the vegetative stage of growth for batch cultures (Desai et al. 1999a; Desai et al. 1999b; Papoutsakis 1984). In addition, calculation of the specific proton flux from fermentation data (using Eqs. 6 and 7) yields a continuous function over the time-course of vegetative growth due to the pH dependence associated with end-product efflux of weak acids. However, the solution of the flux balance equation, $S \cdot v = 0$, yields a single set of intracellular and membrane transport fluxes. To address this problem, much research has been dedicated to the development of constraint-based regulatory networks (Covert et al. 2003; Gianchandani et al. 2006). With time-dependent flux profiles, a large (if not infinite) number of genome-scale flux profiles is required to model the vegetative growth stage of *C. acetobutylicum*. It is believed that the specific proton flux can be used to discretize this continuous time-dependent set of fluxes into a manageable number useful for time-course growth predictions by the genome-scale model. To do this, we define multiple specific proton flux states over the course of a batch fermentation in order to limit the available phenotypic space. This is further illustrated in FIG. 5. Only a limited set of possible intracellular and membrane transport fluxes (a sub-space of the phenotypic solution space) result in a specific proton flux ($q_{H_{ext}^+}$) within a specified range. Thus, the specific proton flux is an additional parameter capable of limiting the number of possible flux solutions to the flux balance equation. Such an approach is illustrated in FIG. 15.

It is believed that this systematic method for reducing the phenotypic space is effective for organisms without highly developed transcriptional regulatory networks and may lead to further insights in better studied organisms. We have not incorporated the thermodynamics of transmembrane ion transport (Henry et al. 2007; Henry et al. 2006) into our approach; although, we anticipate these calculations may be useful in transitioning between specific proton flux states. This requires an accurate representation of the transmembrane ΔpH parameter, and more recent genome-scale models of *Escherichia coli* K-12 (Reed et al. 2003) and *Saccharomyces cerevisiae* (Duarte et al. 2004) have been constructed paying particular attention to the protonation state of biological compounds at physiological pH. Effective use of the specific proton flux parameter to simulate vegetative growth and metabolism requires separating the function into discrete specific proton flux states to limit the number of flux vector solutions. Prediction of the extracellular pH was used as the benchmark for determining whether flux solutions conditioned to fit growth and metabolite data captured the cell-to-environment interactions that determine extracellular medium pH.

EXAMPLE 18

Batch Culture Simulations

Batch culture growth and metabolism were simulated using intracellular and membrane transport reaction flux values (the optimized flux vector, v) obtained from the flux balance equation, $S \cdot v = 0$. The simulation was performed over a time-course of 15 hours of batch growth using the $4^{th}$-order Runge-Kutta numerical method with a step-size of 0.01 hours. The length of the time-course simulation was chosen to correspond with typical vegetative growth of the culture. The pH of the extracellular medium was calculated at each time step using the described pH model (Dougherty et al. 2006) and $pH_{extracellular} = -\log(H_{free}^+)$. The set of intracellular and membrane transport fluxes used at each time-point were unique to the specific proton flux state of the culture. The choice of specific proton flux states and their optimized temporal bounds for *C. acetobutylicum* batch growth are discussed in the following section.

EXAMPLE 19

Optimization of the Biomass Constituting Equation

The biomass constituting equation used in the genome-scale model of *C. acetobutylicum* was adapted from one previously published for *Staphylococcus aureus* N315 (Heinemann et al. 2005). It was anticipated that the biomass composition of the relatively under-studied *C. acetobutylicum* differs (possibly significantly) from that of *S. aureus* and would be apparent when comparing calculations of the specific growth rate of *C. acetobutylicum* by the genome-scale model to experimentally measured values. In addition, it is known that *C. acetobutylicum* morphology and physiology change over the course of batch fermentation due to sporulation (Paredes et al. 2005) and by developing acid- and solvent-tolerant phenotypes (Alsaker and Papoutsakis 2005;

Alsaker et al. 2004; Borden and Papoutsakis 2007; Harris et al. 2002; Tomas et al. 2004). We investigated the ATP requirement, γ, designated to cell maintenance in the biomass constituting equation, shown in Eq. 10, for each specific proton flux state investigated.

0.4 Protein+0.12 RNA+0.03 DNA+0.07 Lipids+0.24 Cell Wall+0.14 Solute Pools+γATP→1 g Biomass+γADP+γOrthophosphate      (10)

For each specific proton flux state, the membrane transport fluxes of (i) glucose, (ii) acetate, (iii) butyrate, (iv) lactate, (v) acetone, (vi) butanol, and (vii) ethanol were tightly constrained to experimentally observed values (Monot et al. 1982). The ATP maintenance requirement, γ, of the biomass constituting equation was varied until the calculated specific growth rate matched experimental observations. Optimum values of γ were obtained for each specific proton flux state examined.

EXAMPLE 20

Optimization of Specific Proton Flux States

It is believed that discrete specific proton flux states may be used to reduce the phenotypic solution space. To study the effectiveness of using specific proton flux states to model vegetative growth, a genetic algorithm was implemented to optimize the temporal bounds of different defined specific proton flux states. The different chosen discretizations (called Sets) of the specific proton flux state are given in Table 10. The precise bounds of the specific proton flux states of Table 10 were chosen based on the availability of raw data points and the desire to have different specific proton flux states exist over similar time intervals when characterizing batch growth. Solutions to the flux balance equation (optimized flux vector, v) were obtained for each specific proton flux state. This was done using the following procedure: (i) the phenotypic solution space was generated by optimizing the flux vector, v, given the objective function of maximizing the production of reduced ferredoxins, (ii) the resulting phenotypic space was probed by varying constraints around the membrane transport fluxes of Table 8, (iii) for each flux vector sampled from the phenotypic solution space, the specific proton flux was calculated using Eq. 8 and the membrane transport reactions of Table 9, (iv) if the specific proton flux fell within the range of a designated specific proton flux state, the flux vector was retained, and (v) for each discrete specific proton flux state, $10^2$ flux vectors were identified and averaged to generate a representative flux vector. For each of the four sets of discretized specific proton flux states (Table 10), a real-coded genetic algorithm was used to optimize the time point at which each flux state was implemented in vegetative growth simulations. The objective function of the optimization algorithm was the minimization of the mean square error (MSE) between model predictions and the following minimal medium experimental observations (Monot et al. 1982): (i) biomass concentration, (ii) glucose, (iii) acetate, (iv) butyrate, and (v) butanol. We refer to this procedure of optimizing temporal bounds of specific proton flux states to predict biomass and metabolite concentrations as model training. Thus, the training data set consists of 25 experimental data points (Monot et al. 1982). The trained model was then used to calculate the medium pH. These predictions were compared to the 5 reported experimental data points composing the extracellular pH profile (Monot et al. 1982). We refer to this procedure as testing the trained model. Details of the genetic algorithm parameters applied here have been published (Senger et al. 2006).

TABLE 10

Investigated sets of specific proton flux states[1].

| | Set 1 | Set 2 | Set 3 | Set 4 |
|---|---|---|---|---|
| State 1 | −200 to 5 | −200 to −100 | −200 to −55 | −200 to −100 |
| State 2 | | −100 to −50 | −55 to −35 | −100 to −60 |
| State 3 | | −50 to −20 | −35 to −25 | −60 to −40 |
| State 4 | | −20 to 5 | −25 to −15 | −40 to −30 |
| State 5 | | | −15 to −5 | −30 to −20 |
| State 6 | | | −5 to 5 | −20 to −10 |
| State 7 | | | | −10 to 0 |
| State 8 | | | | 0 to 5 |

[1]Specific proton flux states have units of mmol H⁺ h⁻¹ g biomass⁻¹.

EXAMPLE 21

Identification of Numerically-Determined Sub-Systems

The stoichiometric matrix of the metabolic network reconstruction of *C. acetobutylicum* is underdetermined (422 metabolites involved in 552 reactions) (Senger and Papoutsakis 2008). In turn, the solution of the flux balance equation (S·v=0) is a multi-dimensional polytope due to the presence of singularities in the stoichiometric matrix. Here, we present a novel method to examine the impact of these singularities on metabolic capacity and the intracellular flux distribution. These results are then used to further constrain the stoichiometric matrix. We do this by first extracting, from the stoichiometric matrix, the reactions resulting in one of the multiple singularities of the matrix. Currently, we are focusing on singularities in reactions leading to macromolecular biosynthesis and the production of biomass. The reactions leading to biomass synthesis are extracted from the point of the singularity. These compounds and reactions are used to create a new stoichiometric matrix, S', and flux balance equation (S'·v'=0). Additional relationships (e.g., thermodynamic, regulatory, etc.) may be applied to the reactions resulting in the singularity to study their impact on distribution of intracellular fluxes and metabolic capacity. Since the sub-network, extracted from the stoichiometric matrix, contains one singularity and relations constraining it specifically, we define this system as a numerically-determined sub-system of the metabolic network reconstruction.

Thermodynamics (Henry et al. 2007; Kummel et al. 2006), observed metabolite selection (Desai et al. 1999b), or other investigated regulatory constraints (Choi et al. 2007; Covert et al. 2003; Price et al. 2003; Shlomi et al. 2007) may provide relationships necessary to constrain fluxes about a singularity. We have incorporated a method for including such information within the stoichiometric matrix to generate systems with a unique null space basis set. Our method is similar to the recent development of artificial metabolites (Choi et al. 2007). An elementary example of this concept is presented as FIG. 6. This example consists of extracellular metabolites $a_{ext}$ and $b_{ext}$ crossing a system boundary (cell membrane) through separate transport reactions with fluxes q1 and q2. Intracellular metabolite a is converted to b with reaction flux q3, and b is converted to c (intracellular) with flux q4. Finally, c is transported across the system boundary with reaction flux q5. The steady-state assumption reveals the following relationship between transport fluxes: q5=q1+q2, and the relationship between q4 and q5 is apparent (q4=q5). However, the flux relationships between q1, q2 and q3 cannot be discerned without information regarding the transport of $a_{ext}$ and $b_{ext}$ into the system. This is also apparent by constructing the stoichiometric matrix of the system, as shown in FIG. 6. The resulting matrix has a rank of 3 for 5 reactions (columns), making the null space 2-dimensional. Thus, for the system to be numerically-determined, the null space must be one-dimensional, meaning that resolution of one singularity is required in this system. To resolve the singularity in this example, boundary (membrane) metabolite selectivity was assumed. An arbitrary reaction flux ratio relationship was assumed between q1 and q2 (assuming a flux relationship between q1 or q2 and q5 would also resolve the singularity). This relationship may then be built-in to the stoichiometric matrix as an additional row as shown in FIG. 6. The resulting stoichiometric matrix has a rank of 4 and contains 5 columns (reactions), so a unique null space basis set solution exists. To the unique basis set, an assumed transport flux (or specific growth rate in genome-scale models) can be applied to numerically define the system. This process is further illustrated in FIG. 6.

EXAMPLE 22

Contributors to the Specific Proton Flux State and the Environmental Response The fluxes of membrane transport reactions used for calculating the specific proton flux in minimal medium simulations are shown in Table 9. This approach allowed for not only calculating the contribution of weak organic-acid secretion to the specific proton flux, but it also enabled the incorporation of proton excretion through ion channels, such as the F-type ATPase, as well. Although multiple mechanisms of ion transport through the cell membrane are known to exist (Dills et al. 1980; Holland and Blight 1999; Konings et al. 1995), a simplified reaction model of transmembrane ion exchange with the extracellular environment was included in the metabolic network and is listed in Table 9. TC numbers and membrane transport reaction stoichiometry were obtained from the Transport Classification Database (Saier et al. 2006). In generating and sampling the phenotypic solution space, the fluxes of membrane transport equations of weak acids were constrained to the limits of observable values (Monot et al. 1982). However, the $F_0F_1$ proton-translocating ATP synthase of the atp operon (CAC2864 to CAC2872) and the ion transport equations listed above (TC 2.A.37, 2.A.38, 2.A.20, 3.A.2, 3.A.3) were left unconstrained.

EXAMPLE 23

Optimization of Specific Proton Flux States

The continuous function of specific proton flux was discretized into multiple specific proton flux states, as described previously. These states are given in Table 10. Representative flux vector solutions were obtained for each specific proton flux state through random sampling of the phenotypic solution space and given constraints of measured extracellular metabolites around observed values (Monot et al. 1982). Simulation results of fitted extracellular metabolite and biomass concentrations (the training data set) by real-coded genetic algorithm optimization of the specific proton flux state temporal bounds are shown in FIG. 7. Results are shown for Set 1 and Set 3 of optimized specific proton flux states given in Table 10. The prediction of extracellular pH (the testing data set) by these flux distributions are shown in FIG. 8. Six temporal specific proton flux states (Set 3 of Table 10) were required to accurately predict the experimentally observed (Monot et al. 1982) extracellular pH profile during vegetative growth. Specific fluxes for metabolites exchanged with the extracellular medium and specific growth rates are given for all six specific proton flux states in Table 11. As shown in FIG. 7 and FIG. 8, the model composed of six specific proton flux states is compared with a model considering only a single specific proton flux state (Set 1 of Table 10). Although a single specific proton flux state model can fit vegetative growth metabolite and growth data with reasonable accuracy, as shown in FIG. 7, this model fails in prediction of extracellular medium pH (see FIG. 8). Likewise, a model with four discrete specific proton flux states (Set 2 of Table 10) was effectively fit to metabolite and growth data but failed to predict the extracellular medium pH. Further, the model with eight discrete specific proton flux states (Set 4 or Table 10) fit experimental metabolite and growth data and accurately predicted extracellular medium pH with excellent accuracy. In this case, the model containing six specific proton flux states is preferable given the time requirement to sample the phenotypic solution space for each specific proton flux state. Results for Set 2 and Set 4 of Table 10 are not displayed in FIG. 7 or FIG. 8.

TABLE 11

Optimized specific flux values [mmol $h^{-1}$ g biomass$^{-1}$] for selected membrane transport reactions for the six optimized proton flux states.

| Classification[1] | Membrane Transport Reaction[2,3,4] | Specific Proton Flux State [mmol $H^+$ $h^{-1}$ g biomass$^{-1}$] | | | | | |
|---|---|---|---|---|---|---|---|
| | | <−55 | −55 to −35 | −35 to −25 | −25 to −15 | −15 to −5 | −5 to 5 |
| Biomass Growth Equation | 0.4 Protein + 0.12 RNA + 0.03 DNA + 0.07 Lipid + 0.24 Cell Wall + 0.14 Solute Pools + γATP ↔ 1 g Biomass + γATP + γ Orthophosphate | 0.070 | 0.30 | 0.30 | 0.30 | 0.17 | 0.060 |
| Glucose Uptake | Phosphoenolpyruvate + D-Glucose (ext.) ↔ Pyruvate + D-Glucose 6-phosphate | 30 | 90 | 90 | 90 | 40 | 13 |
| Weak Acid Production | Butyrate + $H^+$ ↔ Butyrate (ext.) + $H^+$ (ext.) | 9.0 | 14 | 14 | 14 | 5.0 | 4.0 |
| | Acetate + $H^+$ ↔ Acetate | 9.0 | 14 | 14 | 14 | 3.0 | 0 |

TABLE 11-continued

Optimized specific flux values [mmol h$^{-1}$ g biomass$^{-1}$] for selected membrane transport reactions for the six optimized proton flux states.

| Classification[1] | Membrane Transport Reaction[2,3,4] | Specific Proton Flux State [mmol H$^+$ h$^{-1}$ g biomass$^{-1}$] | | | | | |
|---|---|---|---|---|---|---|---|
| | | <−55 | −55 to −35 | −35 to −25 | −25 to −15 | −15 to −5 | −5 to 5 |
| | (ext.) + H$^+$ (ext.) (R,S)-Lactate + H$^+$ ↔ Lactate (ext.) + H$^+$ (ext.) | 3.2 | 1.8 | 0.9 | 0 | 0 | 0 |
| Solvent Production | Butanol (ext.) ↔ 1-Butanol | −3.5 | −10 | −10 | −10 | −15 | −6.0 |
| | Acetone (ext.) ↔ Acetone | −1.9 | −7.0 | −7.0 | −7.8 | −8.2 | −4.5 |
| | Ethanol (ext.) ↔ Ethanol | 0 | −0.47 | −0.52 | −0.50 | −0.99 | −0.060 |
| Freely-Exchanged Small Molecules | CO$_2$ (ext.) ↔ CO$_2$ | −58 (±0.9) | −93 (±2) | −190 (±4) | −210 (±6) | −150 (±4) | −56 (±5) |
| | H$_2$O (ext.) ↔ H$_2$O | 1.1 (±0.8) | 7.8 (±4) | 2.2 (±1) | −34 (±0.6) | −19 (±1) | −2 (±2) |
| | NH$_3$ (ext.) ↔ NH$_3$ | 0.39 (±0.08) | 0.26 (±0.3) | 0.48 (±0.2) | 0.40 (±0.1) | 0.21 (±0.1) | (0.03) (±0.03) |
| | H$_2$ (ext.) ↔ H$_2$ | −73 (±2) | −190 (±3) | −280 (±5) | −300 (±6) | −140 (±5) | −57 (±9) |
| Anion Transport | Sulfate (ext.) + ATP + H$_2$O ↔ Sulfate + H+ + ADP + Orthophosphate | 0.12 (±0.03) | 0.080 (±0.02) | 0.14 (±0.04) | 0.20 (±0.01) | 0.20 (±0.05) | 0.030 (±0.03) |
| | Orthophosphate (ext.) + ATP + H$_2$O ↔ H$^+$ + ADP + 2 Orthophosphate | 0.10 (±0.1) | 0.10 (±0.1) | 0.18 (±0.04) | 0.090 (±0.05) | 0.070 (±0.04) | 0.040 (±0.02) |
| | Orthophosphate (ext.) + H$^+$ (ext.) ↔ Orthophosphate + H$^+$ | 0.090 (±0.08) | 0.53 (±0.1) | 0.27 (±0.1) | 0.13 (±0.07) | 0.060 (±0.04) | 0.010 (±0.01) |
| F$_0$F$_1$ ATPase | ADP + Orthophosphate + H$^+$ (ext.) ↔ ATP + H$_2$O + H$^+$ | 28 (±2) | 51 (±8) | 46 (±3) | 36 (±5) | 16 (±2) | 13 (±2) |
| Cation Transport | K$^+$ (ext.) + H$^+$ (ext.) ↔ K$^+$ + H$^+$ | −29 (±1) | −27 (±3) | −20 (±1) | −12 (±2) | −5.4 (±0.7) | −3.4 (±0.5) |
| | Na$^+$ (ext.) + H$^+$ ↔ Na$^+$ + H$^+$ (ext.) | 43 (±1) | 41 (±4) | 30 (±2) | 18 (±2) | 6.6 (±1) | 5.0 (±0.8) |
| | 3 Na$^+$ + 2 K$^+$ (ext.) + ATP + H$_2$O ↔ 3 Na$^+$ (ext.) + 2 K$^+$ + ADP + Orthophosphate | 14 (±0.5) | 14 (±1) | 10 (±0.7) | 6.1 (±0.8) | 1.2 (±0.4) | 1.7 (±0.3) |

[1]Tight constraints were used for the biomass growth equation, glucose uptake, weak acid production, and solvent production fluxes. These are further detailed in Table 8.
[2]Positive flux values correspond to the forward (left to right) direction of the transport reaction as written. Negative values denote the reverse direction of the reaction as written.
[3]All compounds labeled "extracellular" ("ext.") are located outside the cell (in the medium).
[4]Error values are given in parentheses and correspond to 1 standard deviation.

To study the response of the pH model, in a separate set of simulations, the cation membrane transport equations (TC 2.A.37, 2.A.38, 3.A.2, 3.A.3, see Table 11) were inactivated for the model with six specific proton flux states (Set 2 of Table 10), and this modified model was used to predict extracellular medium pH, assuming the specific membrane transport fluxes and specific growth rates listed in Table 11. As shown in Tables 4 and 6, initial simulations assumed a stoichiometry of one mole of protons secreted with every mole of butyrate and acetate secreted by the culture. Previous research has shown that the protonated acetate and butyrate (acetic and butyric acids) diffuse across the cell membrane of C. acetobutylicum as a primary pathway of weak acids secretion (Desai et al. 1999a; Desai et al. 1999b). However, we simulated the pH profile for the weak acid production and growth rates shown in Table 11, and considered proton exchange with the extracellular medium through secretion with weak acids. Also, the apparent stoichiometry of protons per acetate and butyrate was investigated. Thus, the apparent proton flux stoichiometry per weak acids efflux is defined as the specific proton flux per flux of acetate and butyrate. An apparent proton flux stoichiometry of 1 reveals proton exchange with the environment is primarily through weak acid secretion by the cell. An apparent proton flux stoichiometry greater than 1 reveals significant secretion of protons through ion channels (often at the expense of ATP). Finally, an apparent proton flux stoichiometry less than 1, would imply a significant influx of protons into the cell. Results of these pH simulations are also shown in FIG. 8. If one assumes an apparent proton flux stoichiometry of 1 with acetate and butyrate secretion, the predicted pH profile is higher than the observable values when allowing proton transport through ion channels. Similarly, the apparent proton flux stoichiometry was adjusted to values of 2, 3, and 4 for the acetate and butyrate membrane transport equations, and these simulations were performed. Results are shown in FIG. 8. The apparent proton flux stoichiometry of 4 approximated the extracellular medium pH well for the first specific proton flux state (<−55 mmol H$^+$h$^{-1}$g biomass$^{-1}$). However, in all three cases, the extracellular proton concentration eventually exceeded the buffer capacity of the medium, and the medium pH decreased dramatically.

While it is recognized that ion transport in bacterial cells occurs through more intricate mechanisms (Das et al. 1997;

Dills et al. 1980; Holland and Blight 1999; Jones and Woods 1986; Konings et al., 1995; Riebeling and Jungermann 1976) than the simplified model proposed here, the reaction model used in this study is a first attempt to study the cellular requirement of ATP generation by the $F_0F_1$ ATPase. Fluxes through these reactions were also used to generate a better understanding of the stoichiometry of free-protons transferred to the extracellular medium in addition to acetate and butyrate efflux for the six optimized specific proton flux states. For the case with inactivated specific proton flux through cation channels (apparent proton flux stoichiometry=1), a predicted medium pH greater than the observable value (e.g., apparent proton flux stoichiometry of one for acetate and butyrate membrane transport equations), a proton pump (proton efflux) must be operated through cation channels and the $F_0F_1$ ATPase at the expense of ATP. On the other hand, an extracellular medium prediction below the observable values (e.g., high apparent proton flux stoichiometry with acetate and butyrate efflux), the net flux of protons across the cell membrane must be positive (inward), driving the biosynthesis of ATP. Without physiological data for *C. acetobutylicum* detailing the intracellular accumulation of $Na^+$ and $K^+$, these cations were allowed to enter and exit the cell, in our model, according to the metabolic energy demand and the specific proton flux state, not according to the proton motive force. It is noted that the system of cation transport reactions of Table 11 can result in a computational artifact. The transport of $K^+$ by proton symport is negative (outward) in Table 11; whereas, the transport of $K^+$ by the ATPase is positive (inward). This results in a net reduction of ATP. To rectify this problem of artificial cycling of metabolic fluxes (due to lack of regulation mechanisms), the net production of intracellular $H^+$, $K^+$, $Na^+$, and ATP were calculated of all membrane transport reactions for all six specific proton flux states, given specific flux values of Table 11, and are listed in Table 12. For example, the value listed for ATP in Table 12 is the flux of ATP (positive is biosynthesis) required by the cell from membrane-associated reactions (e.g., the $F_0F_1$ ATPase) to support the metabolic fluxes, listed in Table 11, for that particular specific proton flux state. These values reveal relatively low membrane-associated ATP biosynthesis rates at the start of the culture and as butyric and acetic acid production decreases at the end of vegetative growth.

TABLE 12

Net flux of metabolites in cation transport equations of Table 11 with calculated and fitted apparent proton flux stoichiometry with weak acids efflux.

| | Specific Proton Flux State [mmol $H^+$ $h^{-1}$ g biomass$^{-1}$] | | | | | |
|---|---|---|---|---|---|---|
| | <−55 | −55 to −35 | −35 to −25 | −25 to −15 | −15 to −5 | −5 to 5 |
| $H+^1$ | −44 | −17 | −4.3 | 5.8 | 4.4 | 4.1 |
| $Na+^1$ | 0.01 | 0 | 0.01 | 0.01 | 0 | 0 |
| $K+^1$ | 0 | 0 | −0.01 | 0 | 0 | 0 |
| $ATP^2$ | 14 | 38 | 36 | 30 | 14 | 11 |
| Calculated Specific Proton Flux$^3$ | −64 | −47 | −33 | −22 | −5 | 0.50 |
| Proton Flux from Weak Acid Efflux and Cation Channels Only$^4$ | −62 | −45 | −32 | −22 | −5.6 | 0.12 |
| Calculated Apparent Proton Flux Stoichiometry with Weak Acid Efflux$^5$ | 3.57 | 1.67 | 1.16 | 0.77 | 0.50 | −0.13 |
| Curve-Fitted Apparent Proton Flux Stoichiometry with Weak Acid Efflux$^6$ | 4.0 | 1.5 | 1.0 | 1.0 | 0.40 | 0.20 |

[1] Net flux calculated from cation transport flux values of Table 11.
[2] Net flux of ATP biosynthesized from $F_0F_1$ ATPase and $Na^+/K^+$ ATPase in Table 11.
[3] Calculated from the fluxes of reactions listed in Table 9. The value must be within the proton flux state ranges listed above.
[4] Calculated from the weak acids production and cation transport flux values of Table 11.
[5] The calculated Specific Proton Flux value divided by the sum of acetate and butyrate fluxes of Table 11.
[6] Optimized value from curve-fitting the modified model to the observed pH profile The specific proton fluxes associated with these transport equations (Table 11) were also calculated (positive values are influx, negative is efflux) and are shown in Table 12. These values were used to obtain an estimate of the upper-bound of the stoichiometry of protons associated with weak acid efflux for all six specific proton flux states. As shown in Tables 4 and 6, the stoichiometry of protons associated with butyrate and acetate efflux was 1 for all specific proton flux states. To calculate the apparent proton flux stoichiometry (assumed to be the same for both acetate and butyrate), the specific proton flux from weak acid efflux reactions was added to the specific proton flux (efflux or influx) of the cation transport reactions, as shown in Table 12. This value was then divided by the combined acetate and butyrate efflux to calculate the moles of protons secreted per mole of acetate or butyrate. This number was re-calculated by curve-fitting the extracellular medium pH profile using the abbreviated flux model with inactivated cation transfer equations (see above). The apparent proton flux stoichiometry associated with acetate and butyrate efflux was adjusted for each specific proton flux state to fit the experimental pH data (Monot et al. 1982). The calculated results and curve-fit results of apparent proton flux stoichiometry associated with weak acid efflux are in good agreement, as shown in Table 12. The apparent proton flux stoichiometry associated with weak acid efflux is near 4 (or slightly lower) at the start of the culture and is reduced to roughly 1 when weak acid effluxes are maximized. Toward the end of vegetative growth of *C. acetobutylicum*, model predictions conclude that the net flux of protons across the cell membrane is roughly zero.

EXAMPLE 24

Regarding Optimization of the Biomass Equation

The results of optimizing the ATP maintenance coefficient, γ, of Eq. 10 for the six optimized specific proton flux states discussed above are shown in FIG. 9. The calculated specific growth rates are shown for six separate values of γ, ranging between 20 and 160 for each specific proton flux state. Experimentally observed values (Monot et al. 1982) are indicated for each specific proton flux state by a horizontal dotted line marker in FIG. 9. Optimized values of γ are printed above the data for each specific proton flux state in FIG. 9. Here, we show that the ATP maintenance coefficient, γ, is correlated with the specific proton flux state. Further investigation of optimized values revealed that relatively low values of γ occur during the acidogenic growth phase coupled with maximum growth rates. Larger values of γ were calculated for the culture lag phase and for specific proton flux states corresponding to solventogenesis (e.g., −5 to 5 mmol $H^+h^{-1}g$ biomass$^{-1}$). It is believed that the high ATP maintenance requirements for the latter solventogenic specific proton flux states are coupled with the onset of sporulation. Sporulation has been described as an energy-intensive process (Dworkin and Losick 2005; Parker et al. 1996), and the coupling of sporulation to solventogenesis in C. acetobutylicum has been well-characterized in recent literature (Alsaker and Papoutsakis 2005; Harris et al. 2002; Paredes et al. 2005; Tomas et al. 2003). However, we also anticipate metabolic programs responsible for solvent-tolerant phenotypes are responsible for the increased ATP requirement of biomass growth during solventogenesis (Borden and Papoutsakis 2007; Lepage et al. 1987; Tomas et al. 2004). Thus, we recognize that other stoichiometric coefficients (e.g., lipids) of the biomass constituting equation are also functions of the specific proton flux state. Here, we have approximated a dynamic biomass constituting equation by investigating the ATP maintenance coefficient only.

EXAMPLE 25

"Unconstrained" Simulations of the Genome-Scale Model

Simulations of the genome-scale model were performed with unconstrained production of acids (acetate, butyrate, and lactate) and solvents (acetone, butanol, and ethanol). The selectivity coefficient of acids to solvents for each specific proton flux state is shown in FIG. 10. The genome-scale model with applied constraints is given in Table 7. Stochastically varied constraints, including tight constraints, for every simulation are given in Table 8. Results show that with tight constraints around the glucose uptake rate and unconstrained acid and solvent production rates, the specific proton flux state is capable of characterizing the start of the exponential growth phase of C. acetobutylicum as acidogenic and the end of exponential growth as solventogenic. Without a specified glucose uptake rate, the genome-scale model was unsuccessful in making this distinction. This is shown by the unconstrained case of FIG. 10. Further, even though the specific proton flux state is a useful parameter for limiting the phenotypic space for identifying acidogenesis and solventogenesis, when compared to experimental observations (Monot et al. 1982) in FIG. 10, some differences are apparent. For example, the selectivity of acids to solvents at the start of the culture (specific proton flux state<−55 mmol $H^+h^{-1}g$ biomass$^{-1}$) was observed to be slightly less than 4 but predicted by the model to be slightly greater than two. Additionally, the exponential growth phase was observed to be slightly more acidogenic and the latter stages more solventogenic than calculations predicted. It has been well-established in recent literature that solventogenesis in C. acetobutylicum is under control of the Spo0A transcriptional regulator (Alsaker et al. 2004; Harris et al. 2002). However, these regulatory models have not yet been built into the C. acetobutylicum genome-scale model. These data illustrate the effectiveness of specific proton flux states for predicting acidogenic and solventogenic phenotypes while showing where additional regulatory models could improve genome-scale model predictions.

EXAMPLE 26

Analysis of a Singularity Using a Numerically-Determined Sub-System

In earlier work (Senger and Papoutsakis 2008), we described two pathways in the metabolic network for the biosynthesis of L-glutamate. These were: (i) conversion of pyruvate and L-ornithine to L-glutamate and L-alanine by the acetylornithine transaminase (ArgD, EC 2.6.1.11, CAC2388) and (ii) biosynthesis of L-glutamate through the L-arginine biosynthesis pathway in the presence of a large intracellular L-glutamate solute pool. Thus, L-alanine is a product of L-glutamate biosynthesis by ArgD. However, in C. acetobutylicum, L-alanine may also be biosynthesized from pyruvate through D-alanine by D-alanine transaminase (EC2.6.2.21, CAC0792) and alanine racemase (EC 5.1.1.1, CAC0492). This creates a singularity in the metabolic network. To examine fluxes around this singularity, the numerically-determined sub-system, shown in FIG. 11, was extracted from the genome-scale metabolic network and analyzed in detail by varying the ratio of fluxes responsible for L-glutamate biosynthesis. These reactions are shown in FIG. 11 as Reaction 1 (L-glutamate biosynthesis by ArgD) and Reaction 2 (L-glutamate biosynthesis through the L-arginine biosynthesis pathway). The stoichiometric matrix for this sub-system is given in Table 13. All precursors and energetic requirements are assumed readily available for this sub-system. For example, the sub-system requires the stoichiometric amount of D-fructose-6-phosphate, available from glycolysis (see FIG. 11), to support the specified growth rate.

TABLE 13

Identified reactions (with reaction products) for the numerically-determined sub-system.

| Reaction Number | Reaction Product |
|---|---|
| 1 | Biomass |
| 2 | Protein |
| 3 | Solute Pools |
| 4 | Cell Wall |
| 5 | DNA |
| 6 | RNA |
| 7 | Crosslinked Peptidoglycan |
| 8 | Wall Teichoic Acid |
| 9 | D-Alanyl-Alanine |
| 10 | UDP-MurNAc-L-alanyl-D-glutamate |
| 11 | Pyruvate |
| 12 | D-Ala |
| 13 | L-Ala |
| 14 | L-Ornithine |
| 15 | L-Ala, L-Glu |
| 16 | L-Glu |
| 17 | L-Gln |
| 18 | L-Pro |
| 19 | L-Met |

TABLE 13-continued

Identified reactions (with reaction products) for the numerically-determined sub-system.

| Reaction Number | Reaction Product |
|---|---|
| 20 | L-His |
| 21 | L-Trp |
| 22 | L-Phe |
| 23 | L-Tyr |
| 24 | L-Lys |
| 25 | ATP |
| 26 | dATP |
| 27 | GTP |
| 28 | dGTP |
| 29 | CTP |
| 30 | dCTP |
| 31 | UTP |
| 32 | dTTP |
| 33 | UDP-MurNac |
| 34 | Acetate |
| 35 | N-Acetyl-D-glucosamine 1-P |
| 36 | Glucosamine 1-P |
| 37 | D-Fructose 6-P |
| 38 | Thymine |
| 39 | Lipids |
| 40 | CDPribitol |
| 41 | Biomass (ext) |

The sub-system of FIG. 11 was used to directly study the flux size and direction of alanine racemase (EC 5.1.1.1, CAC0492) (shown as Reaction 2 in FIG. 11) as well as D-alanine transaminase (EC 2.6.1.21, CAC0792) (shown as Reaction 3 in FIG. 11). The sub-system was solved by fixing a value of the specific growth rate and by assuming flux ratios for L-glutamate biosynthesis by ArgD (shown as Reaction 1 in FIG. 11) and through the L-arginine biosynthesis pathway (shown as Reaction 4 in FIG. 11). First, the reaction fluxes through alanine racemase (Reaction 2) and are shown in FIG. 12a as a function of the specific flux of L-alanine through ArgD (Reaction 1) for a range of specific growth rates from $0.05\ h^{-1}$ through $0.35\ h^{-1}$. The catalyzing direction of the alanine racemase enzyme was found to vary (forward or reverse) under normal growth conditions and quantitatively illustrates how reaction direction changes with growth rate and available precursors. Every specific growth rate has a maximum calculated flux of L-alananine through ArgD (Reaction 1) and alanine racemase (Reaction 2), as shown in FIG. 12a. Above these maximum flux values, products of these reactions exceed the demand required of cell growth. Thus, these maximum flux values are labeled as a theoretical boundary in FIG. 12a, and the shaded infeasible region of FIG. 12a represents flux values exceeding this maximum metabolic capacity. The theoretical boundary also represents the line at which the flux ration of Reaction 1 to Reaction 4 goes to infinity. The boundary where the flux ratio of Reaction 1 to Reaction 4 approaches zeros is the ordinate axis of FIG. 12a. Thus, the feasible solution space of L-alanine flux through ArgD and alanine racemase is triangular-shaped and is bounded by: (i) the maximum theoretical boundary discussed above, (ii) the ordinate axis, and (iii) the operating line of the maximum growth rate. This solution space provides ranges for constraints of these reactions in optimization of the flux vector of the flux balance equation using linear programming. Of course, through this approach, we assume adequate ATP biosynthesis and cofactor regeneration by other parts of the metabolic network (e.g., glycolysis and weak acid/solvent production) to support specific growth rates that make-up the bounds of FIG. 12a. With substrate limitations, specific growth rates will approach zero.

With this sub-system, we were also able to probe metabolic capacity in the presence of modified teichoic acids in the cell wall, as has been observed for many pathogenic clostridia and *B. subtilis* (Neuhaus and Baddiley 2003; Pollack and Neuhaus 1994). Thus, intracellular fluxes of the sub-system were also found to be dependent upon the possible presence of D-alanylation of teichoic acids in *C. acetobutylicum*. Although, the presence of D-alanylation in *C. acetobutylicum* is unlikely, due to the absence of a complete dlt operon, its consideration provides a perturbation useful for discovering limits of intracellular flux values given altered metabolic demands. D-alanyl content of wall teichoic acids was varied from 0 to 50 residues. The flux ratio of Reactions 1 and 4 in FIG. 9 were varied to produce the flux relationship between acetylornithine transaminase (ArgD) (Reaction 1) and D-alanine transaminase (Reaction 3), as shown in FIG. 12b. With a specific growth rate of $0.3\ h^{-1}$, results show that at a fixed metabolic flux of ArgD, increasing the D-alanyl content of wall teichoic acids from 0 to 50 increases the metabolic flux of pyruvate through D-alanine transaminase to D-alanine by $0.07\ mmol\ h^{-1}g\ biomass^{-1}$. This accounts for approximately 0.08% of the specific influx of glucose observed for this growth rate (Monot et al. 1982), making the inclusion of D-alanylation relatively insignificant in the metabolic network of *C. acetobutylicum*. In summary, this example demonstrates that numerically-determined sub-systems of the metabolic network can be probed to reveal the metabolic impact of including physiological processes that have not yet been identified through experimental means.

EXAMPLE 27

Conclusions from Examples 13-26

Using the reconstructed metabolic network developed previously (Senger and Papoutsakis 2008), a constrained genome-scale model for *C. acetobutylicum* was developed for published minimal medium data (Monot et al. 1982). Novel techniques were developed in this research that may be used to further reduce the potential phenotypic space of genome-scale models while generating further understanding of metabolic capacities and cell-to-environment interactions. The concept of specific proton flux states was coupled to the pH of the extracellular environment in the first such development for genome-scale models. The specific proton flux state is a type of constraint derived from the endo-exo-metabolome interface and may prove useful in supplementing regulatory models derived around the transcriptome or fluxome levels of metabolic regulation. The specific proton flux was found to become less-negative (fewer protons leaving the cell) over the course of exponential growth in minimal media and achieved a plateau value close to zero toward the end of vegetative growth of the culture. Optimized descritization of the continuous function of specific proton flux resulted in six discrete temporal states that allowed accurate prediction of the extracellular medium pH throughout the vegetative growth stage. In addition, further calculations revealed the apparent stoichiometry of protons secreted with weak acids (acetate and butyrate) during vegetative growth. At the start of the culture, given specific proton fluxes less than $-55\ mmol\ h^{-1}g\ biomass^{-1}$ (proton efflux), approximately 3.5 moles of protons are secreted per mole of acetate or butyrate. Following an initial drop in extracellular medium pH, this value reduces to 1 and coincides with the maximum observed specific production of acetate and butyrate. Further, optimization of the biomass constituting equation revealed maintenance ATP demands of the lag and near-stationary phases exceeded those of the exponential growth phase by a factor of ~4. It is speculated this is due to changing morphology due to endospore germination in the lag phase, development of solvent tolerant phenotypes, and sporulation in the latter stages of batch growth. It is likely these calculations will lead to a dynamic biomass constituting equation to describe batch growth.

The concept of numerically-determined sub-spaces of genome-scale networks for limiting the phenotypic solution space was also introduced in this study. A particular sub-system surrounding L-alanine and D-alanine biosyntheses/degradations was presented and was analyzed in detail given a singularity created by including multiple pathways of L-glutamate biosynthesis in the metabolic network. The sub-system described, quantitatively, the ranges and direction of specific fluxes surrounding L- and D-alanine biosynthesis for various physiological demands for D-alanine in the biosynthesis of peptidoglycan and D-alanylation of teichoic acids.

From the sub-system presented here, we propose the following requirements and strategy for extracting and analyzing a numerically-determined sub-system: (i) the genome-scale metabolic network is complete, (ii) the singularity to be studied has been identified, (iii) no other singularities exist in the sub-system, (iv) a specific growth rate or metabolite membrane exchange flux is known, (v) the biosynthetic precursor entering the sub-system leads to cell growth and is not degraded for energy production. In addition, the following steps are given for the general identification of numerically-determined sub-systems in genome-scale metabolic network reconstructions: (i) identify a singularity in the stoichiometric matrix involving one or more reactions; (ii) identify relationships (e.g., thermodynamics, etc.) to describe the relationship of fluxes that cause the singularity; (iii) reconstruct the metabolic network between the reactions of the singularity and the biomass constituting equation; (iv) allow precursors to reactions of the singularity and energetic requirements to be imported into the sub-network as required; (v) construct the sub-system stoichiometric matrix, S', and flux vector, v', based on the compounds and reactions present in the sub-network; (vi) add flux relationships of the singularity to the stoichiometric matrix as shown in FIG. 6; (vii) obtain the unique null space basis set solution and flux vector values as also shown for the simplified system in FIG. 6; (viii) vary the flux relationships about the singularity (if necessary) to obtain new unique solutions; and (ix) correlate intracellular flux distributions to those flux ratios about the singularity. Numerically-determined sub-systems can also be used to probe changes in intracellular fluxes and metabolic capacity in response to (among others): (i) protein glycosylation, (ii) changes in membrane lipids composition, (iii) possible solvent stress responses, and (iv) physiological processes associated with sporulation.

REFERENCES

Alberty R A, 2004. Equilibrium concentrations for pyruvate dehydrogenase and the citric acid cycle at specified concentrations of certain coenzymes. Biophys Chem 109(1): 73-84.

Alsaker K V, Papoutsakis E T. 2005. Transcriptional program of early sporulation and stationary-phase events in *Clostridium acetobutylicum*. J Bacteriol 187(20):7103-18.

Alsaker K V, Spitzer T R, Papoutsakis E T. 2004. Transcriptional analysis of spo0A overexpression in *Clostridium acetobutylicum* and its effect on the cell's response to butanol stress. J Bacteriol 186(7):1959-71.

Atrih A, Foster S J. 2001. Analysis of the role of bacterial endospore cortex structure in resistance properties and demonstration of its conservation amongst species. J Appl Microbiol 91(2):364-72.

Baer S H, Blaschek H P, Smith T L. 1987. Effect of butanol challenge and temperature on lipid composition and membrane fluidity of butanol-tolerant *Clostridium acetobutylicum*. Appl Environ Microbiol 53(12):2854-2861.

Bairoch A. 2000. The ENZYME database in 2000. Nucleic Acids Res 28(1):304-5.

Baitaluk M, Sedova M, Ray A, Gupta A. 2006. BiologicalNetworks: visualization and analysis tool for systems biology. Nucleic Acids Res 34(Web Server issue):W466-71.

Baumbach J, Brinkrolf K, Czaja L F, Rahmann S, Tauch A. 2006. CoryneRegNet: an ontology-based data warehouse of corynebacterial transcription factors and regulatory networks. BMC Genomics 7:24.

Becker S A, Palsson B O. 2005. Genome-scale reconstruction of the metabolic network in *Staphylococcus aureus* N315: an initial draft to the two-dimensional annotation. BMC Microbiol 5(1):8.

Beste D J, Hooper T, Stewart G, Bonde B, Avignone-Rossa C, Bushell M E, Wheeler P, Klamt S, Kierzek A M, McFadden J. 2007. GSMN-TB: a web-based genome-scale network model of *Mycobacterium tuberculosis* metabolism. Genome Biol 8(5):R89.

Billheimer J T, Carnevale H N, Leisinger T, Eckhardt T, Jones E E. 1976. Ornithine delta-transaminase activity in *Escherichia coli*—identity with acetylornithine delta-transaminase. J Bacteriol 127(3):1315-1323.

Blattner F R, Plunkett G, 3rd, Bloch C A, Perna N T, Burland V, Riley M, Collado-Vides J, Glasner J D, Rode C K, Mayhew G F and others. 1997. The complete genome sequence of *Escherichia coli* K-12. Science 277(5331): 1453-74.

Bleakley K, Biau G, Vert J P. 2007. Supervised reconstruction of biological networks with local models. Bioinformatics 23(13):i57-65.

Borden J R, Papoutsakis E T. 2007. Dynamics of genomic-library enrichment and identification of solvent tolerance genes for *Clostridium acetobutylicum*. Appl Environ Microbiol 73(9):3061-8.

Borodina I, Krabben P, Nielsen J. 2005. Genome-scale analysis of *Streptomyces coelicolor* A3(2) metabolism. Genome Res 15(6):820-9.

Borodina I, Nielsen J. 2005. From genomes to in silico cells via metabolic networks. Curr Opin Biotechnol 16(3):350-5.

Boynton Z L, Bennett G N, Rudolph F B. 1994. Intracellular concentrations of Coenzyme A and Its derivatives from *Clostridium acetobutylicum* ATCC 824 and their roles in enzyme regulation. Appl Environ Microbiol 60(1):39-44.

Breitling R, Vitkup D, Barrett M P. 2008. New surveyor tools for charting microbial metabolic maps. Nat Rev Microbiol 6(2):156-61.

Bro C, Regenberg B, Forster J, Nielsen J. 2006. In silico aided metabolic engineering of *Saccharomyces cerevisiae* for improved bioethanol production. Metab Eng 8(2):102-11.

Busch W, Saier M H, Jr. 2002. The transporter classification (TC) system, 2002. Crit Rev Biochem Mol Biol 37(5):287-337.

Cakir T, Patil K R, Onsan Z, Ulgen K O, Kirdar B, Nielsen J. 2006. Integration of metabolome data with metabolic networks reveals reporter reactions. Mol Syst Biol 2:50.

Caspi R, Foerster H, Fulcher C A, Hopkinson R, Ingraham J, Kaipa P, Krummenacker M, Paley S, Pick J, Rhee S Y and others. 2006. MetaCyc: a multiorganism database of metabolic pathways and enzymes. Nucleic Acids Res 34(Database issue):D511-6.

Choi H S, Kim T Y, Lee D Y, Lee S Y. 2007. Incorporating metabolic flux ratios into constraint-based flux analysis by using artificial metabolites and converging ratio determinants. J Biotechnol 129(4):696-705.

Choi H S, Kim T Y, Lee D Y, Lee S Y. 2007. Incorporating metabolic flux ratios into constraint-based flux analysis by using artificial metabolites and converging ratio determinants. J Biotechnol 129(4):696-705.

Covert M W, Schilling C H, Palsson B. 2001. Regulation of gene expression in flux balance models of metabolism. J Theor Biol 213(1):73-88.

Covert M W, Famili I, Palsson B O. 2003. Identifying constraints that govern cell behavior: a key to converting conceptual to computational models in biology? Biotechnol Bioeng 84(7):763-72.

Cummins C S, Johnson J L. 1971. Taxonomy of clostridia—wall composition and DNA homologies in *Clostridium butyricum* and other butyric acid-producing clostridia. J Gen Microbiol 67 (July):33-&.

da Fontoura Costa L, Rodrigues F A, Travieso G. 2007. Analyzing trails in complex networks. Phys Rev E Stat Nonlin Soft Matter Phys 76(4 Pt 2):046106.

Dandekar T, Moldenhauer F, Bulik S, Bertram H, Schuster S. 2003. A method for classifying metabolites in topological pathway analyses based on minimization of pathway number. Biosystems 70(3):255-70.

Das A, Ivey D M, Ljungdahl L G. 1997. Purification and reconstitution into proteoliposomes of the F1F0 ATP synthase from the obligately anaerobic gram-positive bacterium *Clostridium thermoautotrophicum*. Journal of Bacteriology 179(5):1714-1720.

David H, Akesson M, Nielsen J. 2003. Reconstruction of the central carbon metabolism of *Aspergillus niger*. Eur J Biochem 270(21):4243-53.

Demain A L, Newcomb M, Wu J H. 2005. Cellulase, clostridia, and ethanol. Microbiol Mol Biol Rev 69(1):124-54.

Desai R P, Nielsen L K, Papoutsakis E T. 1999. Stoichiometric modeling of *Clostridium acetobutylicum* fermentations with non-linear constraints. J Biotechnol 71(1-3):191-205.

Desai R P, Harris L M, Welker N E, Papoutsakis E T. 1999a. Metabolic flux analysis elucidates the importance of the acid-formation pathways in regulating solvent production by *Clostridium acetobutylicum*. Metab Eng 1(3):206-13.

Dills S S, Apperson A, Schmidt M R, Saier M H. 1980. Carbohydrate transport in bacteria. Microbiol. Rev 44(3):385-418.

Dougherty D P, Da Conceicao Neta E R, McFeeters R F, Lubkin S R, Breidt F, Jr. 2006. Semi-mechanistic partial buffer approach to modeling pH, the buffer properties, and the distribution of ionic species in complex solutions. J Agric Food Chem 54(16):6021-9.

Duarte N C, Becker S A, Jamshidi N, Thiele I, Mo M L, Vo T D, Srivas R, Palsson B O. 2007. Global reconstruction of the human metabolic network based on genomic and bibliomic data. Proc Natl Acad Sci USA 104(6):1777-82.

Duarte N C, Herrgard M J, Palsson B O. 2004. Reconstruction and validation of *Saccharomyces cerevisiae* iND750, a fully compartmentalized genome-scale metabolic model. Genome Res 14(7):1298-309.

Dworkin J, Losick R. 2005. Developmental commitment in a bacterium. Cell 121(3):401-9.

Edwards E S, Ramakrishna R, Schilling C H, Palsson B O. 1999. Metabolic Flux Analysis. In: Lee S Y, Papoutsakis E T, editors. Metabolic Engineering. New York: Marcel Dekker. p 13-57.

Edwards J S, Ibarra R U, Palsson B O. 2001. In silico predictions of *Escherichia coli* metabolic capabilities are consistent with experimental data. Nat Biotechnol 19(2):125-30.

Eikmanns B, Linder D, Thauer R K. 1983. Unusual pathway of isoleucine biosynthesis in *Methanobacterium thermoautotrophicum*. Arch Microbiol 136(2):111-113.

Famili I, Mahadevan R, Palsson B O. 2005. k-Cone analysis: determining all candidate values for kinetic parameters on a network scale. Biophys J 88(3):1616-25.

Feist A M, Scholten J C, Palsson B O, Brockman F J, Ideker T. 2006. Modeling methanogenesis with a genome-scale metabolic reconstruction of *Methanosarcina barkeri*. Mol Syst Biol 2:2006 0004.

Flythe M D, Russell J B. 2006. Fermentation acids inhibit amino acid deamination by *Clostridium sporogenes* MD1 via a mechanism involving a decline in intracellular glutamate rather than protonmotive force. Microbiology 152(Pt 9): 2619-24.

Forster J, Famili I, Fu P, Palsson B O, Nielsen J. 2003. Genome-scale reconstruction of the *Saccharomyces cerevisiae* metabolic network. Genome Res 13(2):244-53.

Forster J, Famili I, Palsson B O, Nielsen J. 2003b. Large-scale evaluation of in silico gene deletions in *Saccharomyces cerevisiae*. Omics 7(2):193-202.

Francke C, Siezen R J, Teusink B. 2005. Reconstructing the metabolic network of a bacterium from its genome. Trends Microbiol 13(11):550-8.

Friedrich B, Friedrich C G, Magasanik B. 1978. Catabolic N2-acetylornithine 5-aminotransferase of *Klebsiella aerogenes*—control of synthesis by induction, catabolite repression, and activation by glutamine synthetase. J Bacteriol 133(2):686-691.

Gaasterland T, Selkov E. 1995. Reconstruction of metabolic networks using incomplete information. Proc Int Conf Intell Syst Mol Biol 3:127-35.

Gianchandani E P, Brautigan D L, Papin J A. 2006. Systems analyses characterize integrated functions of biochemical networks. Trends Biochem Sci 31(5):284-91.

Gianchandani E P, Papin J A, Price N D, Joyce A R, Palsson B O. 2006. Matrix formalism to describe functional states of transcriptional regulatory systems. PLoS Comput Biol 2(8):e101.

Gille C, Hoffmann S, Holzhutter H G. 2007. METANNOGEN: compiling features of biochemical reactions needed for the reconstruction of metabolic networks. BMC Syst Biol 1:5.

Girbal L, Soucaille P. 1994. Regulation of *Clostridium acetobutylicum* metabolism as revealed by mixed-substrate steady-state continuous cultures: Role of NADH/NAD ratio and ATP pool. J Bacteriol 176(21):6433-6438.

Goelzer A, Bekkal Brikci F, Martin-Verstraete I, Noirot P, Bessieres P, Aymerich S, Fromion V. 2008. Reconstruction and analysis of the genetic and metabolic regulatory networks of the central metabolism of *Bacillus subtilis*. BMC Syst Biol 2(1):20.

Gonzalez O, Gronau S, Falb M, Pfeiffer F, Mendoza E, Zimmer R, Oesterhelt D. 2008. Reconstruction, modeling & analysis of Halobacterium salinarum R-1 metabolism. Mol Biosyst 4(2):148-59.

Green E M, Bennett G N. 1998. Genetic manipulation of acid and solvent formation in *Clostridium acetobutylicum* ATCC 824. Biotechnol Bioeng 58(2-3):215-21.

Gros J B, Dussap C G, Catte M. 1999. Estimation of $O_2$ and $CO_2$ solubility in microbial culture media. Biotechnol Prog 15(5):923-927.

Grupe H, Gottschalk G. 1992. Physiological events in *Clostridium acetobutylicum* during the shift from acidogenesis to solventogenesis in continuous culture and presentation of a model for shift induction. Appl Environ Microbiol 58(12):3896-3902.

Harris L M, Welker N E, Papoutsakis E T. 2002. Northern, morphological, and fermentation analysis of spo0A inactivation and overexpression in *Clostridium acetobutylicum* ATCC 824. J Bacteriol 184(13):3586-97.

Harris L M, Desai R P, Welker N E, Papoutsakis E T. 2000. Characterization of recombinant strains of the *Clostridium acetobutylicum* butyrate kinase inactivation mutant: need for new phenomenological models for solventogenesis and butanol inhibition? Biotechnol Bioeng 67(1):1-11.

Heinemann M, Kummel A, Ruinatscha R, Panke S. 2005. In silico genome-scale reconstruction and validation of the *Staphylococcus aureus* metabolic network. Biotechnol Bioeng 92(7):850-64.

Henry C S, Broadbelt L J, Hatzimanikatis V. 2007. Thermodynamics-based metabolic flux analysis. Biophys J 92(5):1792-805.

Henry C S, Jankowski M D, Broadbelt L J, Hatzimanikatis V. 2006. Genome-scale thermodynamic analysis of *Escherichia coli* metabolism. Biophys J 90(4):1453-61.

Holland I B, Blight M A. 1999. ABC-ATPases, adaptable energy generators fuelling transmembrane movement of a variety of molecules in organisms from bacteria to humans. J Mol Biol 293(2):381-99.

Husemann M H W, Papoutsakis E T. 1988. Solventogenesis in *Clostridium acetobutylicum* fermentations related to carboxylic acid and proton concentrations. Biotechnol Bioeng 32(7):843-852.

Hyland C, Pinney J W, McConkey G A, Westhead D R. 2006. metaSHARK: a WWW platform for interactive exploration of metabolic networks. Nucleic Acids Res 34(Web Server issue):W725-8.

Ishii K, Nakamura S, Morohashi M, Sugimoto M, Ohashi Y, Kikuchi S, Tomita M. 2008. Comparison of metabolite production capability indices generated by network analysis methods. Biosystems 91(1):166-70.

Jamshidi N, Palsson B O. 2007. Investigating the metabolic capabilities of *Mycobacterium tuberculosis* H37Rv using the in silico strain iNJ661 and proposing alternative drug targets. BMC Syst Biol 1:26.

Jhee K H, Yoshimura T, Esaki N, Yonaha K, Soda K. 1995. Thermostable ornithine aminotransferase from *Bacillus* sp YM-2—purification and characterization. J Biochem 118(1):101-108.

Johnston N C, Goldfine H. 1992. Replacement of the aliphatic chains of *Clostridium acetobutylicum* by exogenous fatty acids: regulation of phospholipid and glycolipid composition. J Bacteriol 174(6):1848-53.

Jones D T, Woods D R. 1986. Acetone-butanol fermentation revisited. Microbiol. Rev 50(4):484-524.

Joyce A R, Palsson B O. 2007. Predicting gene essentiality using genome-scale in silico models. Methods Mol Biol 416:433-58.

Kanehisa M, Goto S. 2000. KEGG: kyoto encyclopedia of genes and genomes. Nucleic Acids Res 28(1):27-30.

Kanehisa M, Goto S, Kawashima S, Nakaya A. 2002. The KEGG databases at GenomeNet. Nucleic Acids Res 30(1):42-6.

Kharchenko P, Chen L, Freund Y, Vitkup D, Church G M. 2006. Identifying metabolic enzymes with multiple types of association evidence. BMC Bioinformatics 7:177.

Kim T Y, Kim H U, Park J M, Song H, Kim J S, Lee S Y. 2007. Genome-scale analysis of *Mannheimia succiniciproducens* metabolism. Biotechnol Bioeng 97(4):657-71.

Kiriukhin M Y, Neuhaus F C. 2001. D-alanylation of lipoteichoic acid: role of the D-alanyl carrier protein in acylation. J Bacteriol 183(6):2051-8.

Knorr A L, Jain R, Srivastava R. 2007. Bayesian-based selection of metabolic objective functions. Bioinformatics 23(3):351-7.

Konings W N, Lolkema J S, Poolman B. 1995. The generation of metabolic energy by solute transport. Arch Microbiol 164(4):235-242.

Kumar V S, Dasika M S, Maranas C D. 2007. Optimization based automated curation of metabolic reconstructions. BMC Bioinformatics 8(1):212.

Kummel A, Panke S, Heinemann M. 2006. Systematic assignment of thermodynamic constraints in metabolic network models. BMC Bioinformatics 7:512.

Kummel A, Panke S, Heinemann M. 2006. Putative regulatory sites unraveled by network-embedded thermodynamic analysis of metabolome data. Mol Syst Biol 2:2006 0034.

Kunst F, Ogasawara N, Moszer I, Albertini A M, Alloni G, Azevedo V, Bertero M G, Bessieres P, Bolotin A, Borchert S and others. 1997. The complete genome sequence of the gram-positive bacterium *Bacillus subtilis*. Nature 390(6657):249-56.

Kuroda M, Ohta T, Uchiyama I, Baba T, Yuzawa H, Kobayashi I, Cui L, Oguchi A, Aoki K, Nagai Y and others. 2001. Whole genome sequencing of meticillin-resistant *Staphylococcus aureus*. Lancet 357(9264):1225-40.

Lee N H. 2005. Genomic approaches for reconstructing gene networks. Pharmacogenomics 6(3):245-58.

Lepage C, Fayolle F, Hermann M, Vandercasteele J-P. 1987. Changes in membrane lipid composition of *Clostridium acetobutylicum* during acetone-butanol fermentation: effects of solvents, growth temperature and pH. J Gen Microbiol 133(1): 103-110.

Lin H, Bennett G N, San K Y. 2005. Genetic reconstruction of the aerobic central metabolism in *Escherichia coli* for the absolute aerobic production of succinate. Biotechnol Bioeng 89(2):148-56.

Ma H, Sorokin A, Mazein A, Selkov A, Selkov E, Demin O, Goryanin I. 2007. The Edinburgh human metabolic network reconstruction and its functional analysis. Mol Syst Biol 3:135.

Ma H, Zeng A P. 2003. Reconstruction of metabolic networks from genome data and analysis of their global structure for various organisms. Bioinformatics 19(2):270-7.

MacCarthy T, Pomiankowski A, Seymour R. 2005. Using large-scale perturbations in gene network reconstruction. BMC Bioinformatics 6:11.

MacDonald D L, Goldfine H. 1991. Effects of solvents and alcohols on the polar lipid composition of *Clostridium butyricum* under conditions of controlled lipid chain composition. Appl Environ Microbiol 57(12):3517-21.

Makino S, Moriyama R. 2002. Hydrolysis of cortex peptidoglycan during bacterial spore germination. Med Sci Monit 8(6):RA119-27.

Maltsev N, Glass E, Sulakhe D, Rodriguez A, Syed M H, Bompada T, Zhang Y, D'Souza M. 2006. PUMA2—grid-based high-throughput analysis of genomes and metabolic pathways. Nucleic Acids Res 34(Database issue):D369-72.

Maskow T, von Stockar U. 2005. How reliable are thermodynamic feasibility statements of biochemical pathways? Biotechnol Bioeng 92(2):223-30.

Mavrovouniotis M L. 1990. Group contributions for estimating standard Gibbs energies of formation of biochemical-compounds in aqueous-solution. Biotechnol Bioeng 36(10):1070-1082.

Messner K R, Imlay J A. 2002. Mechanism of superoxide and hydrogen peroxide formation by fumarate reductase, succinate dehydrogenase, and aspartate oxidase. J Biol Chem 277(45):42563-71.

Meyer C L, Papoutsakis E T. 1989. Increased levels of ATP and NADH are associated with increased solvent production in continuous cultures of *Clostridium acetobutylicum*. Appl Environ Microbiol 30(5):450-459.

Monot F, Martin J R, Petitdemange H, Gay R. 1982. Acetone and butanol production by *Clostridium acetobutylicum* in a synthetic medium. Appl Environ Microbiol 44(6):1318-1324.

Montoya D, Arevalo C, Gonzales S, Aristizabal F, Schwarz W H. 2001. New solvent-producing *Clostridium* sp. strains, hydrolyzing a wide range of polysaccharides, are closely related to *Clostridium butyricum*. J Ind Microbiol Biotechnol 27(5):329-35.

Muller T, Strosser J, Buchinger S, Nolden L, Wirtz A, Kramer R, Burkovski A. 2006. Mutation-induced metabolite pool alterations in *Corynebacterium glutamicum*: Towards the identification of nitrogen control signals. J Biotechnol 126 (4):440-453.

Muro-Pastor M I, Reyes J C, Florencio F J. 2001. Cyanobacteria perceive nitrogen status by sensing intracellular 2-oxoglutarate levels. J Biol Chem 276(41):38320-38328.

Neuhaus F C, Baddiley J. 2003. A continuum of anionic charge: structures and functions of D-alanyl-teichoic acids in gram-positive bacteria. Microbiol. Mol Biol Rev 67(4): 686-723.

Nielsen J, Oliver S. 2005. The next wave in metabolome analysis. Trends Biotechnol 23(11):544-6.

Nikiforova V J, Willmitzer L. 2007. Network visualization and network analysis. Exs 97:245-75.

Nikolaev E V, Burgard A P, Maranas C D. 2005. Elucidation and structural analysis of conserved pools for genome-scale metabolic reconstructions. Biophys J 88(1):37-49.

Nolling J, Breton G, Omelchenko M V, Makarova K S, Zeng Q, Gibson R, Lee H M, Dubois J, Qiu D, Hitti J and others. 2001. Genome sequence and comparative analysis of the solvent-producing bacterium *Clostridium acetobutylicum*. J Bacteriol 183(16):4823-38.

Notebaart R A, van Enckevort F H, Francke C, Siezen R J, Teusink B. 2006. Accelerating the reconstruction of genome-scale metabolic networks. BMC Bioinformatics 7:296.

Oberhardt M A, Puchalka J, Fryer K E, Dos Santos V A, Papin J A. 2008. Genome-scale metabolic network analysis of the opportunistic pathogen *Pseudomonas aeruginosa* PAO1. J. Bacteriol.

Oh S J, Joung J G, Chang J H, Zhang B T. 2006. Construction of phylogenetic trees by kernel-based comparative analysis of metabolic networks. BMC Bioinformatics 7:284.

Oh Y K, Palsson B O, Park S M, Schilling C H, Mahadevan R. 2007. Genome-scale reconstruction of metabolic network in *Bacillus subtilis* based on high-throughput phenotyping and gene essentiality data. J Biol Chem 282(39):28791-9.

Oliveira A P, Nielsen J, Forster J. 2005. Modeling *Lactococcus lactis* using a genome-scale flux model. BMC Microbiol 5:39.

Osterman A, Overbeek R. 2003. Missing genes in metabolic pathways: a comparative genomics approach. Curr Opin Chem Biol 7(2):238-51.

Papin J A, Price N D, Wiback S J, Fell D A, Palsson B O. 2003. Metabolic pathways in the post-genome era. Trends Biochem Sci 28(5):250-8.

Papoutsakis E T. 1984. Equations and calculations for fermentations of butyric-acid bacteria. Biotechnology and Bioengineering 26(2):174-187.

Papoutsakis E T, Meyer C L. 1985. Equations and calculations of product yields and preferred pathways for butanediol and mixed-acid fermentations. Biotechnol Bioeng 27(1):50-66.

Papoutsakis E T, Meyer C L. 1985b. Fermentation equations for propionic acid bacteria and production of assorted oxychemicals from various sugars. Biotechnol Bioeng 27(1): 67-80.

Paredes C J, Alsaker K V, Papoutsakis E T. 2005. A comparative genomic view of clostridial sporulation and physiology. Nat Rev Microbiol 3(12):969-78.

Parker G F, Daniel R A, Errington J. 1996. Timing and genetic regulation of commitment to sporulation in *Bacillus subtilis*. Microbiology 142 (Pt 12):3445-52.

Patil K R, Akesson M, Nielsen J. 2004. Use of genome-scale microbial models for metabolic engineering. Curr Opin Biotechnol 15(1):64-9.

Patil K R, Nielsen J. 2005. Uncovering transcriptional regulation of metabolism by using metabolic network topology. Proc Natl Acad Sci USA 102(8):2685-9.

Pearson W R. 1996. Effective protein sequence comparison. Methods Enzymol 266:227-58.

Perego M, Glaser P, Minutello A, Strauch M A, Leopold K, Fischer W. 1995. Incorporation of D-alanine into lipoteichoic acid and wall teichoic acid in *Bacillus subtilis*. Identification of genes and regulation. J Biol Chem 270(26): 15598-606.

Peterson J D, Umayam L A, Dickinson T, Hickey E K, White O. 2001. The Comprehensive Microbial Resource. Nucleic Acids Res 29(1):123-5.

Pinney J W, Papp B, Hyland C, Wambua L, Westhead D R, McConkey G A. 2007. Metabolic reconstruction and analysis for parasite genomes. Trends Parasitol 23(11): 548-54.

Pinney J W, Shirley M W, McConkey G A, Westhead D R. 2005. metaSHARK: software for automated metabolic network prediction from DNA sequence and its application to the genomes of *Plasmodium falciparum* and *Eimeria tenella*. Nucleic Acids Res 33(4):1399-409.

Pollack J H, Neuhaus F C. 1994. Changes in wall teichoic acid during the rod-sphere transition of *Bacillus subtilis* 168. J Bacteriol 176(23):7252-9.

Poolman B, Driessen A J, Konings W N. 1987. Regulation of arginine-ornithine exchange and the arginine deiminase pathway in *Streptococcus lactis*. J Bacteriol 169(12):5597-604.

Poolman M G, Bonde B K, Gevorgyan A, Patel H H, Fell D A. 2006. Challenges to be faced in the reconstruction of metabolic networks from public databases. Syst Biol (Stevenage) 153(5):379-84.

Poolman M G, Sebu C, Pidcock M K, Fell D A. 2007. Modular decomposition of metabolic systems via null-space analysis. J Theor Biol 249(4):691-705.

Price N D, Thiele I, Palsson B O. 2006. Candidate states of *Helicobacter pylori's* genome-scale metabolic network upon application of "loop law" thermodynamic constraints. Biophys J 90(11):3919-28.

Price N D, Papin J A, Schilling C H, Palsson B O. 2003. Genome-scale microbial in silico models: the constraints-based approach. Trends Biotechnol 21(4):162-9.

Price N D, Reed J L, Palsson B O. 2004. Genome-scale models of microbial cells: evaluating the consequences of constraints. Nat Rev Microbiol 2(11):886-97.

Reed J L, Patel T R, Chen K H, Joyce A R, Applebee M K, Herring C D, Bui O T, Knight E M, Fong S S, Palsson B O. 2006. Systems approach to refining genome annotation. Proc Natl Acad Sci USA 103(46):17480-4.

Reed J L, Vo T D, Schilling C H, Palsson B O. 2003. An expanded genome-scale model of *Escherichia coli* K-12 (iJR904 GSM/GPR). Genome Biol 4(9):R54.

Reed J L, Palsson B O. 2004. Genome-scale in silico models of *E. coli* have multiple equivalent phenotypic states: assessment of correlated reaction subsets that comprise network states. Genome Res 14(9):1797-805.

Ren Q, Chen K, Paulsen I T. 2007. TransportDB: a comprehensive database resource for cytoplasmic membrane transport systems and outer membrane channels. Nucleic Acids Res 35(Database issue):D274-9.

Resendis-Antonio O, Reed J L, Encarnacion S, Collado-Vides J, Palsson B O. 2007. Metabolic reconstruction and modeling of nitrogen fixation in *Rhizobium* etli. PLoS Comput Biol 3(10):1887-95.

Riebeling V, Jungermann K. 1976. Properties and function of clostridial membrane ATPase. Biochim Biophys Acta 430(3):434-444.

Rodionov D A, Dubchak I, Arkin A, Alm E, Gelfand M S. 2004. Reconstruction of regulatory and metabolic pathways in metal-reducing delta-proteobacteria. Genome Biol 5(11):R90.

Roe A J, McLaggan D, Davidson I, O'Byrne C, Booth I R. 1998. Perturbation of anion balance during inhibition of growth of *Escherichia coli* by weak acids. J Bacteriol 180(4):767-72.

Roos J W, Mclaughlin J K, Papoutsakis E T. 1985. The effect of pH on nitrogen supply, cell-lysis, and solvent production in fermentations of *Clostridium acetobutylicum*. Biotechnol Bioeng 27(5):681-694.

Saier M H, Jr., Tran C V, Barabote R D. 2006. TCDB: the Transporter Classification Database for membrane transport protein analyses and information. Nucleic Acids Res 34(Database issue):D181-6.

Sakuraba H, Satomura T, Kawakami R, Yamamoto S, Kawarabayasi Y, Kikuchi H, Ohshima T. 2002. L-aspartate oxidase is present in the anaerobic hyperthermophilic archaeon *Pyrococcus horikoshii* OT-3: characteristics and role in the de novo biosynthesis of nicotinamide adenine dinucleotide proposed by genome sequencing. Extremophiles 6(4):275-81.

Satish Kumar V, Dasika M S, Maranas C D. 2007. Optimization based automated curation of metabolic reconstructions. BMC Bioinformatics 8:212.

Schilling C H, Covert M W, Famili I, Church G M, Edwards J S, Palsson B O. 2002. Genome-scale metabolic model of *Helicobacter pylori* 26695. J Bacteriol 184(16):4582-93.

Schleifer K H, Kandler O. 1972. Peptidoglycan types of bacterial cell walls and their taxonomic implications. Bacteriol Rev 36(4):407-77.

Schomburg I, Chang A, Ebeling C, Gremse M, Heldt C, Huhn G, Schomburg D. 2004. BRENDA, the enzyme database: updates and major new developments. Nucleic Acids Res 32(Database issue):D431-3.

Schreier H J, Smith T M, Bernlohr R W. 1982. Regulation of nitrogen catabolic enzymes in *Bacillus* spp. J Bacteriol 151(2):971-975.

Schuster S, Fell D A, Dandekar T. 2000. A general definition of metabolic pathways useful for systematic organization and analysis of complex metabolic networks. Nat Biotechnol 18(3):326-32.

Schwarz W H. 2001. The cellulosome and cellulose degradation by anaerobic bacteria. Appl Microbiol Biotechnol 56(5-6):634-49.

Senger R S, Papoutsakis E T. 2008. Genome-scale model for *Clostridium acetobutylicum*. Part 1: Metabolic network resolution and analysis. submitted to Biotechnol. Bioeng.

Senger R S, Phisalaphong M, Karim M N, Linden J C. 2006. Development of a culture sub-population induction model: signaling pathways synergy and taxanes production by *Taxus canadensis*. Biotechnol Prog 22(6):1671-82.

Shlomi T, Eisenberg Y, Sharan R, Ruppin E. 2007. A genome-scale computational study of the interplay between transcriptional regulation and metabolism. Mol Syst Biol 3:101.

Sohling B, Gottschalk G. 1996. Molecular analysis of the anaerobic succinate degradation pathway in *Clostridium kluyveri*. J Bacteriol 178(3):871-80.

Song H, Kim T Y, Choi B K, Choi S J, Nielsen L K, Chang H N, Lee S Y. 2008. Development of chemically defined medium for *Mannheimia succiniciproducens* based on its genome sequence. Appl Microbiol Biotechnol.

Stephanopoulos G, Aristidou A A, Nielsen J. 1998. Metabolic engineering. Principles and methololgies. San Diego: Academic Press.

Sun J, Lu X, Rinas U, Zeng A P. 2007. Metabolic peculiarities of *Aspergillus niger* disclosed by comparative metabolic genomics. Genome Biol 8(9):R182.

Tedeschi G, Negri A, Mortarino M, Ceciliani F, Simonic T, Faotto L, Ronchi S. 1996. L-aspartate oxidase from *Escherichia coli*. II. Interaction with C4 dicarboxylic acids and identification of a novel L-aspartate: fumarate oxidoreductase activity. Eur J Biochem 239(2):427-33.

Tegner J, Yeung M K, Hasty J, Collins J J. 2003. Reverse engineering gene networks: integrating genetic perturbations with dynamical modeling. Proc Natl Acad Sci USA 100(10):5944-9.

Teusink B, Wiersma A, Molenaar D, Francke C, de Vos W M, Siezen R J, Smid E J. 2006. Analysis of growth of *Lactobacillus plantarum* WCFS1 on a complex medium using a genome-scale metabolic model. J Biol Chem 281(52):40041-8.

Thomas R, Mehrotra S, Papoutsakis E T, Hatzimanikatis V. 2004. A model-based optimization framework for the inference on gene regulatory networks from DNA array data. Bioinformatics 20(17):3221-35.

Thomas R. Paredes C J, Mehrotra S, Hatzimanikatis V, Papoutsakis E T. 2007. A model-based optimization framework for the inference of regulatory interactions using time-course DNA microarray expression data. BMC Bioinformatics 8(1):228.

Thormann K, Feustel L, Lorenz K, Nakotte S, Durre P. 2002. Control of butanol formation in *Clostridium acetobutylicum* by transcriptional activation. J Bacteriol 184(7):1966-73.

Tomas C A, Alsaker K V, Bonarius H P, Hendriksen W T, Yang H, Beamish J A, Paredes C J, Papoutsakis E T. 2003. DNA array-based transcriptional analysis of asporogenous, non-solventogenic *Clostridium acetobutylicum* strains SKO1 and M5. J Bacteriol 185(15):4539-47.

Tomas C A, Alsaker K V, Bonarius H P, Hendriksen W T, Yang H, Beamish J A, Paredes C J, Papoutsakis E T. 2003. DNA array-based transcriptional analysis of asporogenous, nonsolventogenic *Clostridium acetobutylicum* strains SKO1 and M5. J Bacteriol 185(15):4539-47.
Tomas C A, Beamish J, Papoutsakis E T. 2004. Transcriptional analysis of butanol stress and tolerance in *Clostridium acetobutylicum*. J Bacteriol 186(7):2006-18.
Tummala S B, Junne S G, Paredes C J, Papoutsakis E T. 2003. Transcriptional analysis of product-concentration driven changes in cellular programs of recombinant *Clostridium acetobutylicum*strains. Biotechnol Bioeng 84(7):842-54.
Urbanczik R. 2006. SNA—a toolbox for the stoichiometric analysis of metabolic networks. BMC Bioinformatics 7:129.
Vasconcelos I, Girbal L, Soucaille P. 1994. Regulation of carbon and electron flow in *Clostridium acetobutylicum* grown in chemostat culture at neutral pH on mixtures of glucose and glycerol. J Bacteriol 176(5):1443-50.
Vo T D, Greenberg H J, Palsson B O. 2004. Reconstruction and functional characterization of the human mitochondrial metabolic network based on proteomic and biochemical data. J Biol Chem 279(38):39532-40.
Voellmy R, Leisinger T. 1975. Dual role for N2-acetylornithine 5-aminotransferase from *Pseudomonas aeruginosa* in arginine biosynthesis and arginine catabolism. J Bacteriol 122(3):799-809.
Vollherbst-Schneck K, Sands J A, Montenecourt B S. 1984. Effect of butanol on lipid composition and fluidity of *Clostridium acetobutylicum* ATCC 824. Appl Environ Microbiol 47(1):193-4.
Wiback S J, Famili I, Greenberg H J, Palsson B O. 2004. Monte Carlo sampling can be used to determine the size and shape of the steady-state flux space. J Theor Biol 228(4):437-47.
Wilkinson S R, Young D I, Morris J G, Young M. 1995. Molecular genetics and the initiation of solventogenesis in *Clostridium beijerinckii* (formerly *Clostridium acetobutylicum*) NCIMB 8052. FEMS Microbiol Rev 17(3):275-85.
Xie T, Sheng Q H, Ding D F. 2000. Reconstruction of ABC Transporter Pathways of Archaea and Comparison of Their Genomes. Sheng Wu Hua Xue Yu Sheng Wu Wu Li Xue Bao (Shanghai) 32(2):169-174.
Yang Y T, Bennett G N, San K Y. 2001. The effects of feed and intracellular pyruvate levels on the redistribution of metabolic fluxes in *Escherichia coli*. Metab Eng 3(2):115-23.
Zhao J, Ding G H, Tao L, Yu H, Yu Z H, Luo J H, Cao Z W, Li Y X. 2007. Modular co-evolution of metabolic networks. BMC Bioinformatics 8:311.
Zhao Y, Hindorff L A, Chuang A, Monroe-Augustus M, Lyristis M, Harrison M L, Rudolph F B, Bennett G N. 2003. Expression of a cloned cyclopropane fatty acid synthase gene reduces solvent formation in *Clostridium acetobutylicum* ATCC 824. Appl Environ Microbiol 69(5):2831-41.
Zhao Y, Tomas C A, Rudolph F B, Papoutsakis E T, Bennett G N. 2005. Intracellular butyryl phosphate and acetyl phosphate concentrations in *Clostridium acetobutylicum* and their implications for solvent formation. Appl Environ Microbiol 71(1):530-7.

We claim:

1. A method of optimizing a genome-scale metabolic network model for a cell, comprising the steps of:
   obtaining the genome-scale metabolic network model for the cell;
   determining the pH of the extracellular environment of the cell;
   determining a specific proton flux as a function of the total extracellular hydrogen ion concentration, wherein the total extracellular hydrogen ion concentration is the sum of the free proton concentration and the concentrations of protonated weak acids, wherein the weak acids comprise butyric acid, acetic acid, lactic acid, carbonic acid, ammonium ion, monobasic potassium phosphate, and dibasic potassium phosphate; and
   optimizing with a computer the genome-scale metabolic network model by limiting the number of possible solutions to a flux balancing equation based on the determined pH of the extracellular environment of the cell and the determined specific proton flux, whereby an optimized genome-scale metabolic network model is generated on the computer.

2. The method of claim 1, wherein the obtaining step comprises:
   identifying with the computer one or more errors in genome-scale metabolic network information of the cell by reverse engineering the genome-scale metabolic network information;
   determining at least one solution to at least one of the one or more errors in the genome-scale metabolic network information; and,
   correcting with the computer the at least one of the one or more errors in the genome-scale metabolic network information by substituting the at least one solution for the at least one of the one or more errors.

3. The method of claim 1, further comprising predicting with the computer growth of the cell when a constraint set is applied to a plurality of reactions of the cell.

4. The method of claim 1, further comprising predicting with the computer production of biomass of the cell when a constraint set is applied to a plurality of reactions of the cell.

5. The method of claim 1, further comprising predicting with the computer production of a metabolite by the cell when a constraint set is applied to a plurality of reactions of the cell.

6. The method of claim 5, wherein the metabolite is selected from the group consisting of acids, solvents and intracellular intermediates of the metabolism of the cell.

7. The method of claim 6, wherein the acid is selected from the group consisting of acetate, butyrate, lactate, formate, propionic acid and acids of the TCA cycle.

8. The method of claim 6, wherein the solvent is selected from the group consisting of acetone, butanol and ethanol.

9. The method of claim 1, further comprising predicting with the computer utilization of a substrate by the cell when a constraint set is applied to a plurality of reactions of the cell.

10. The method of claim 9, wherein the substrate is selected from the group consisting of hexoses, pentoses, oligosaccharides, and complex carbohydrates.

11. The method of claim 10, wherein the complex carbohydrate is selected from xylans and celluloses.

12. The method of claim 1, wherein the cell is anaerobic bacterial cell.

13. The method of claim 1, wherein the cell is a *Clostridium* species.

14. The method of claim 1, wherein the cell is a solventogenic butyric-acid *clostridium*.

15. The method of claim 1, wherein the cell is *Clostridium acetobutylicum* (ATCC 824).

* * * * *